(12) United States Patent
Andrews et al.

(10) Patent No.: US 12,253,308 B1
(45) Date of Patent: Mar. 18, 2025

(54) DISPOSABLE FOR A SPRAY DRYING SYSTEM

(71) Applicant: Velico Medical Inc., Beverly, MA (US)

(72) Inventors: Robert R. Andrews, Norfolk, MA (US); Herman E. Snyder, W. Lafayette, IN (US); William J. Merritt, Danvers, MA (US); Evan P. Ordway, Salem, MA (US); Clair Strohl, Emmaus, PA (US); Russell Barron, Boston, MA (US)

(73) Assignee: Velico Medical Inc., Beverly, MA (US)

( * ) Notice: Subject to any disclaimer, the term of this patent is extended or adjusted under 35 U.S.C. 154(b) by 0 days.

(21) Appl. No.: 18/747,011

(22) Filed: Jun. 18, 2024

Related U.S. Application Data

(63) Continuation of application No. 18/496,766, filed on Oct. 27, 2023, now Pat. No. 12,092,397, and a
(Continued)

(51) Int. Cl.
*F26B 3/12* (2006.01)
*A61K 35/16* (2015.01)

(52) U.S. Cl.
CPC ............... *F26B 3/12* (2013.01); *A61K 35/16* (2013.01)

(58) Field of Classification Search
CPC ................................. F26B 3/12; A61K 35/16
(Continued)

(56) References Cited

U.S. PATENT DOCUMENTS 2,362,025 A 1/1943 Price
2,411,152 A 11/1946 Folsom
(Continued)

FOREIGN PATENT DOCUMENTS

AU 2010234607 10/2010
CA 1182411 A 2/1985
(Continued)

OTHER PUBLICATIONS

Lea, et al. "The Reaction between Proteins and Reducing Sugars in the "Dry" State" Department of Pathology, University of Cambridge; Jun. 5, 1950; pp. 626-629.
(Continued)

*Primary Examiner* — Stephen M Gravini
(74) *Attorney, Agent, or Firm* — Antoinette G Giugliano; Antoinette G Giugliano PC

(57) ABSTRACT

The present invention includes a spray drying disposable device for use in a spray drying system. The disposable has a spray drying head and a plasma drying chamber. The head has a spray dry nozzle assembly in fluid communication with the plasma source and the pressurized aerosol gas source. The pressurized gas flows in a vortex pattern that atomizes plasma droplets in the chamber. The head also includes a plenum has uniform air pressure of the drying gas. A baffle plate forms the floor of the plenum having drying gas jets that supply drying gas to the chamber. The atomized plasma droplets evaporate in the presence of the drying gas emitted from the jets to obtain dried plasma particles and humid air. A capture filter captures the dried plasma particles and allows the humid air to pass. The humid air passes through the gas outlet and the exhaust port.

27 Claims, 46 Drawing Sheets

Related U.S. Application Data continuation of application No. 17/945,124, filed on Sep. 15, 2022, now Pat. No. 11,841,189.

(58) Field of Classification Search
USPC .................................................. 34/372
See application file for complete search history.

(56) References Cited

U.S. PATENT DOCUMENTS

| | | | |
|---|---|---|---|
| 2,528,476 A | 10/1950 | Roos et al. | |
| 2,575,175 A | 11/1951 | Kronisch | |
| 3,228,838 A | 1/1966 | Rinfret et al. | |
| 3,230,689 A | 1/1966 | Hussmann | |
| 3,449,124 A | 6/1969 | Lipner | |
| 3,507,278 A | 4/1970 | Werding | |
| 3,644,128 A | 2/1972 | Lipner | |
| 3,654,705 A | 4/1972 | Smith et al. | |
| 3,693,886 A | 9/1972 | Conrad | |
| 3,735,792 A | 5/1973 | Asizawa et al. | |
| 3,945,574 A | 3/1976 | Polnauer | |
| 4,187,617 A | 2/1980 | Becker, Jr. et al. | |
| 4,251,510 A | 2/1981 | Tankersley | |
| 4,347,259 A | 8/1982 | Suzuki et al. | |
| 4,358,901 A | 11/1982 | Takabatake et al. | |
| 4,376,010 A | 3/1983 | Gauvin | |
| 4,378,346 A | 3/1983 | Tankersley | |
| 4,380,491 A | 4/1983 | Joy | |
| 4,422,900 A | 12/1983 | Bordelon | |
| 4,597,868 A | 7/1986 | Watanabe | |
| 4,600,613 A | 7/1986 | Yoshida | |
| 4,645,482 A | 2/1987 | Yoshida | |
| 4,705,612 A | 11/1987 | Shimomura et al. | |
| 4,725,355 A | 2/1988 | Yamamoto et al. | |
| 4,735,832 A | 4/1988 | Ishikawa et al. | |
| 4,743,375 A | 5/1988 | Seita et al. | |
| 4,774,019 A | 9/1988 | Watanabe et al. | |
| 4,787,154 A | 11/1988 | Titus | |
| 4,845,132 A | 7/1989 | Masuoka et al. | |
| 4,861,632 A | 8/1989 | Caggiano | |
| 4,966,699 A | 10/1990 | Sasaki et al. | |
| 5,096,537 A | 3/1992 | Bergquist et al. | |
| 5,139,529 A | 8/1992 | Seita et al. | |
| 5,145,706 A | 9/1992 | Hagi et al. | |
| 5,167,763 A | 12/1992 | Sakamoto | |
| 5,181,415 A | 1/1993 | Esvan et al. | |
| 5,227,017 A | 7/1993 | Tanaka | |
| 5,244,578 A | 9/1993 | Ohnishi et al. | |
| 5,252,221 A | 10/1993 | van Dommelen | |
| 5,254,248 A | 10/1993 | Nakamura | |
| 5,257,983 A | 11/1993 | Garyantes et al. | |
| 5,267,646 A | 12/1993 | Inoue et al. | |
| 5,279,738 A | 1/1994 | Seita et al. | |
| 5,309,649 A | 5/1994 | Bergmann et al. | |
| 5,372,811 A | 12/1994 | Yoder | |
| 5,447,077 A | 9/1995 | Lautenschlager | |
| 5,499,768 A | 3/1996 | Tanaka | |
| 5,522,156 A | 6/1996 | Ware | |
| 5,523,004 A | 6/1996 | Tanokura et al. | |
| 5,529,821 A | 6/1996 | Ishikawa et al. | |
| 5,547,576 A | 8/1996 | Onishi et al. | |
| 5,562,919 A | 10/1996 | Doty et al. | |
| 5,567,238 A | 10/1996 | Long, Jr. | |
| 5,575,999 A | 11/1996 | Yoder | |
| 5,581,903 A | 12/1996 | Botich | |
| 5,582,794 A | 12/1996 | Hagiwara et al. | |
| 5,624,530 A | 4/1997 | Sadykhov | |
| 5,647,142 A | 7/1997 | Andersen et al. | |
| 5,657,555 A * | 8/1997 | Milojevic ............... F26B 21/02 | |
| | | | 34/271 |
| 5,680,712 A * | 10/1997 | Kiyokawa ............... F26B 5/048 |
| | | | 34/267 |
| 5,610,170 A | 11/1997 | Inoue et al. | |
| 5,727,333 A | 3/1998 | Folan | |
| 5,924,216 A | 7/1999 | Takahashi | |
| 5,993,804 A | 11/1999 | Read et al. | |
| 6,004,576 A | 12/1999 | Weaver et al. | |
| 6,060,323 A | 5/2000 | Jina | |
| D430,939 S | 9/2000 | Zukor et al. | |
| 6,148,536 A | 11/2000 | Lijima | |
| 6,197,289 B1 | 3/2001 | Wirt et al. | |
| 6,223,455 B1 * | 5/2001 | Chickering, III ........ B01D 1/18 |
| | | | 34/582 |
| 6,284,282 B1 | 9/2001 | Maa et al. | |
| 6,299,906 B1 | 10/2001 | Bausch et al. | |
| 6,308,434 B1 | 10/2001 | Chickering, III et al. | |
| 6,308,826 B1 | 10/2001 | Merrell | |
| 6,345,452 B1 | 2/2002 | Feuilloley et al. | |
| 6,463,675 B1 | 10/2002 | Hansen et al. | |
| 6,523,276 B1 | 2/2003 | Meldrum | |
| 6,526,774 B1 | 3/2003 | Lu et al. | |
| 6,560,897 B2 | 5/2003 | Chickering, III et al. | |
| 6,569,447 B2 | 5/2003 | Kisic et al. | |
| 6,582,654 B1 | 6/2003 | Kral et al. | |
| 6,723,497 B2 | 4/2004 | Wolkers et al. | |
| 6,762,336 B1 | 7/2004 | Macphee et al. | |
| 6,893,412 B2 | 5/2005 | Saito et al. | |
| 7,005,857 B2 | 2/2006 | Stiene et al. | |
| 7,007,406 B2 | 3/2006 | Wang et al. | |
| 7,074,582 B2 | 7/2006 | Fischer et al. | |
| 7,089,681 B2 | 8/2006 | Herbert et al. | |
| 7,094,378 B1 | 8/2006 | Goodrich, Jr. et al. | |
| 7,297,716 B2 | 11/2007 | Shanbrom | |
| 7,361,306 B2 | 4/2008 | Bole | |
| 7,399,637 B2 | 7/2008 | Wright et al. | |
| 7,419,682 B2 | 9/2008 | Campbell et al. | |
| 7,527,805 B2 | 5/2009 | Crenshaw et al. | |
| 7,648,699 B2 | 1/2010 | Goodrich et al. | |
| 7,931,919 B2 | 4/2011 | Bakaltcheva et al. | |
| 7,993,310 B2 | 8/2011 | Rosiello | |
| 8,322,046 B2 | 12/2012 | Wang et al. | |
| 8,398,732 B2 | 3/2013 | Turok et al. | |
| 8,407,912 B2 | 4/2013 | Hubbard et al. | |
| 8,434,242 B2 | 5/2013 | Hubbard et al. | |
| 8,449,520 B2 | 5/2013 | Pepper et al. | |
| 8,469,202 B2 | 6/2013 | Rosiello | |
| 8,518,452 B2 | 8/2013 | Bjornstrup et al. | |
| 8,533,971 B2 | 9/2013 | Hubbard et al. | |
| 8,533,972 B2 | 9/2013 | Hubbard et al. | |
| 8,595,950 B2 | 12/2013 | Hubbard et al. | |
| 8,601,712 B2 | 12/2013 | Hubbard et al. | |
| 8,968,879 B2 | 3/2015 | Inaba et al. | |
| 9,440,011 B2 | 9/2016 | Van Waeg et al. | |
| 9,453,676 B2 * | 9/2016 | Robinson ................. C08L 5/00 |
| 9,545,379 B2 | 1/2017 | Liu et al. | |
| 9,551,527 B2 | 1/2017 | Beetz | |
| 9,561,184 B2 | 2/2017 | Khan et al. | |
| 9,561,893 B2 | 2/2017 | Root et al. | |
| 9,863,699 B2 | 1/2018 | Corbin, III et al. | |
| 9,867,782 B2 | 1/2018 | Fischer et al. | |
| 9,915,473 B2 * | 3/2018 | Ilan ......................... F26B 7/00 |
| 10,022,478 B2 | 7/2018 | Anzai et al. | |
| 10,251,911 B2 | 4/2019 | DaCorta et al. | |
| 10,279,359 B2 | 5/2019 | Ackerman | |
| 10,376,614 B2 | 8/2019 | Kohama | |
| 10,376,809 B2 | 8/2019 | Nielsen | |
| 10,377,520 B2 | 8/2019 | Root et al. | |
| 10,539,367 B2 | 1/2020 | Corbin, III et al. | |
| 10,793,327 B2 | 10/2020 | Weimer et al. | |
| 10,806,665 B2 | 10/2020 | Murto | |
| 10,843,100 B2 | 11/2020 | Khan et al. | |
| 10,960,023 B2 | 3/2021 | DaCorta et al. | |
| 10,969,171 B2 | 4/2021 | Corbin, III et al. | |
| 11,052,045 B2 | 7/2021 | Liu et al. | |
| 11,213,488 B2 | 1/2022 | Fischer et al. | |
| 11,841,189 B1 * | 12/2023 | Andrews ............... F26B 21/004 |
| 11,913,722 B1 * | 2/2024 | Andrews .................. F26B 3/12 |
| 11,913,723 B1 * | 2/2024 | Andrews ................ F26B 21/12 |
| 11,975,274 B2 * | 5/2024 | Liu ........................... A61J 1/00 |
| 11,998,861 B2 | 6/2024 | Andrews | |
| 2002/0056206 A1 | 5/2002 | Pace | |
| 2002/0122803 A1 | 9/2002 | Kisic et al. | |
| 2002/0182195 A1 | 12/2002 | Marguerre et al. | |
| 2003/0037459 A1 | 2/2003 | Chickering, II et al. | |
| 2003/0099633 A1 | 5/2003 | Campbell et al. | |

(56) References Cited

U.S. PATENT DOCUMENTS

| | | |
|---|---|---|
| 2003/0103962 A1 | 6/2003 | Campbell et al. |
| 2003/0143518 A1 | 7/2003 | Luck et al. |
| 2003/0163931 A1 | 9/2003 | Beyerinck |
| 2003/0180283 A1 | 9/2003 | Batycky |
| 2003/0186004 A1 | 10/2003 | Koslow |
| 2003/0190314 A1 | 10/2003 | Campbell et al. |
| 2003/0209245 A1 | 11/2003 | Poole et al. |
| 2004/0058309 A1 | 3/2004 | Washizu |
| 2004/0086420 A1 | 5/2004 | MacPhee |
| 2004/0110871 A1 | 6/2004 | Perrut et al. |
| 2004/0146565 A1 | 7/2004 | Strohbehn et al. |
| 2004/0175296 A1 | 9/2004 | Opalsky et al. |
| 2004/0202660 A1 | 10/2004 | Campbell et al. |
| 2004/0247628 A1 | 12/2004 | Lintz et al. |
| 2005/0142208 A1 | 6/2005 | Yoo |
| 2005/0170068 A1 | 8/2005 | Roodink et al. |
| 2005/0186183 A1 | 8/2005 | DeAngelo et al. |
| 2005/0271674 A1 | 12/2005 | Campbell et al. |
| 2006/0045907 A1 | 3/2006 | Campbell et al. |
| 2006/0088642 A1 | 4/2006 | Boersen et al. |
| 2006/0130768 A1 | 6/2006 | Crenshaw et al. |
| 2006/0216687 A1 | 9/2006 | Alves-Filho et al. |
| 2006/0222980 A1 | 10/2006 | Makino et al. |
| 2007/0014806 A1 | 1/2007 | Marguerre et al. |
| 2007/0084244 A1 | 4/2007 | Rosenflanz et al. |
| 2007/0166389 A1 | 7/2007 | Bakaltcheva |
| 2008/0058469 A1 | 3/2008 | Abe et al. |
| 2008/0060213 A1 | 3/2008 | Gehrmann et al. |
| 2008/0119818 A1 | 5/2008 | Bakaltcheva et al. |
| 2008/0138340 A1 | 6/2008 | Campbell et al. |
| 2008/0145444 A1 | 6/2008 | Merchant et al. |
| 2008/0145834 A1 | 6/2008 | Ho |
| 2008/0213263 A1 | 9/2008 | Campbell et al. |
| 2008/0234653 A1 | 9/2008 | McCarthy et al. |
| 2008/0317640 A1 | 12/2008 | Mayer |
| 2009/0092678 A1 | 4/2009 | Marguerre et al. |
| 2009/0155410 A1 | 4/2009 | Crenshaw et al. |
| 2009/0113753 A1 | 5/2009 | Pepper et al. |
| 2009/0145783 A1 | 6/2009 | Forker |
| 2009/0223080 A1 | 9/2009 | McCarthy |
| 2010/0011610 A1 | 1/2010 | Bittorf |
| 2010/0108183 A1 | 5/2010 | Rosiello |
| 2010/0215667 A1 | 8/2010 | Campbell et al. |
| 2010/0233671 A1 | 9/2010 | Bakaltcheva |
| 2010/0273141 A1 | 10/2010 | Bakaltcheva |
| 2011/0142885 A1 | 6/2011 | Haley et al. |
| 2011/0282325 A1 | 11/2011 | Gregory |
| 2012/0027867 A1 | 2/2012 | Fischer et al. |
| 2012/0103536 A1 | 5/2012 | Hubbard, Jr. et al. |
| 2012/0167405 A1 | 7/2012 | Hubbard, Jr. |
| 2012/0222326 A1 | 9/2012 | Hubbard et al. |
| 2013/0000774 A1 | 1/2013 | Rosiello |
| 2013/0048225 A1 | 2/2013 | Hubbard et al. |
| 2013/0056158 A1 | 3/2013 | Hubbard et al. |
| 2013/0126101 A1 | 5/2013 | Hubbard, Jr. et al. |
| 2013/0129817 A1 | 5/2013 | Consigny |
| 2013/0209985 A1 | 8/2013 | Hoke |
| 2013/0243877 A1 | 9/2013 | Haley |
| 2013/0264288 A1 | 10/2013 | Hlavinka et al. |
| 2014/0083627 A1 | 3/2014 | Khan et al. |
| 2014/0083628 A1 | 3/2014 | Khan et al. |
| 2014/0088768 A1 | 3/2014 | Haley et al. |
| 2014/0221873 A1 | 8/2014 | Hayakawa et al. |
| 2014/0230266 A1 | 8/2014 | Luy et al. |
| 2015/0099866 A1 | 4/2015 | Kelleher |
| 2015/0158652 A1 | 6/2015 | Root et al. |
| 2015/0354894 A1 | 12/2015 | Corbin, III et al. |
| 2016/0015863 A1 | 1/2016 | Gupta et al. |
| 2016/0082043 A1 | 3/2016 | Khan et al. |
| 2016/0082044 A1 | 3/2016 | Liu |
| 2016/0084572 A1 | 3/2016 | Khan et al. |
| 2016/0113965 A1 | 4/2016 | DaCorta et al. |
| 2016/0223255 A1 | 8/2016 | Beetz |
| 2016/0362307 A1 | 12/2016 | Shiner |
| 2017/0100339 A1 | 4/2017 | Liu et al. |
| 2017/0113824 A1 | 4/2017 | Root et al. |
| 2017/0203871 A1 | 7/2017 | Murto et al. |
| 2017/0259186 A1 | 9/2017 | Khan et al. |
| 2017/0367322 A1 | 12/2017 | Liu et al. |
| 2018/0128544 A1 | 5/2018 | Corbin et al. |
| 2018/0153811 A1 | 6/2018 | Fischer et al. |
| 2018/0207654 A1 | 7/2018 | Phua |
| 2018/0229150 A1 | 8/2018 | Sorensen |
| 2019/0106254 A1 | 4/2019 | Weimer et al. |
| 2019/0223671 A1 | 7/2019 | Tomasiak |
| 2019/0241300 A1 | 8/2019 | Root et al. |
| 2019/0255455 A9 | 8/2019 | Sorensen |
| 2019/0298765 A1 | 10/2019 | DaCorta et al. |
| 2020/0022691 A1 | 1/2020 | Pollack |
| 2020/0298137 A9 | 9/2020 | Khan |
| 2021/0069607 A1 | 3/2021 | Khan et al. |
| 2021/0213057 A1 | 7/2021 | DaCorta et al. |
| 2021/0290545 A1 | 9/2021 | Lie et al. |
| 2022/0040110 A1 | 2/2022 | Lie et al. |
| 2022/0106357 A1 | 4/2022 | Patatanyan |
| 2023/0172849 A1 | 6/2023 | Zeki |
| 2024/0109000 A1 | 4/2024 | Liu |
| 2024/0131062 A1 | 4/2024 | Popovsky |
| 2024/0131236 A1 | 4/2024 | LaRocque |
| 2024/0131446 A1 | 4/2024 | Andrews |
| 2024/0159462 A1 | 5/2024 | Andrews |
| 2024/0191943 A1 | 6/2024 | Andrews |

FOREIGN PATENT DOCUMENTS

| | | |
|---|---|---|
| CA | 2065582 A1 | 10/1992 |
| CA | 2 472 028 | 8/2003 |
| CA | 2757961 | 10/2010 |
| CA | 2816090 A1 | 5/2012 |
| CH | 622683 A5 | 4/1981 |
| CN | 1315139 A | 10/2001 |
| CN | 102206273 A | 10/2011 |
| CN | 108005711 A | 5/2018 |
| CN | 111789867 B | 1/2022 |
| DE | 3507278 | 9/1986 |
| EP | 0058903 A1 | 9/1982 |
| EP | 0408801 A1 | 1/1991 |
| EP | 1050220 A1 | 8/2000 |
| EP | 2745922 A2 | 6/2014 |
| EP | 2745923 A2 | 6/2014 |
| EP | 2416790 | 5/2018 |
| EP | 3151662 B1 | 10/2020 |
| GB | 573500 | 11/1945 |
| GB | 886533 | 10/1962 |
| GB | 964367 | 7/1964 |
| GB | 975786 | 11/1964 |
| GB | 1188168 | 4/1970 |
| GB | 2003042 A | 3/1979 |
| HK | 1167098 | 8/2012 |
| JP | 56011903 | 2/1981 |
| JP | 63218201 | 9/1988 |
| JP | 01011618 | 1/1989 |
| JP | 03131302 | 6/1991 |
| JP | 03181301 | 8/1991 |
| JP | 5245301 | 9/1993 |
| JP | 525910 | 10/1993 |
| JP | H10182124 A | 7/1998 |
| JP | 3219828 B2 | 10/2001 |
| JP | 2002009037 | 1/2002 |
| JP | 2005191275 A | 7/2005 |
| JP | 2007216158 A | 8/2007 |
| JP | 6336419 | 6/2018 |
| KR | 911657 B1 | 8/2009 |
| KR | 2022079809 A | 6/2022 |
| MX | 2011010633 | 1/2012 |
| WO | WO1996015849 A1 | 5/1996 |
| WO | WO1996018312 A1 | 6/1996 |
| WO | WO1997038578 A1 | 10/1997 |
| WO | WO1999007236 A1 | 2/1999 |
| WO | WO1999007390 A1 | 2/1999 |
| WO | WO2000056166 A1 | 9/2000 |
| WO | WO2001072141 A2 | 10/2001 |
| WO | WO2002078741 A2 | 10/2002 |
| WO | WO2002078742 A2 | 10/2002 |

(56) References Cited

FOREIGN PATENT DOCUMENTS

| | | | | | |
|---|---|---|---|---|---|
| WO | WO2002083157 | A1 | 10/2002 | | |
| WO | WO2002092213 | A1 | 11/2002 | | |
| WO | WO2003030654 | A1 | 4/2003 | | |
| WO | WO2003030918 | A1 | 4/2003 | | |
| WO | WO-03037303 | A | 5/2003 | | |
| WO | WO2003063607 | A1 | 8/2003 | | |
| WO | WO2004075988 | A2 | 9/2004 | | |
| WO | WO2004078187 | A1 | 9/2004 | | |
| WO | WO2005079755 | A2 | 9/2005 | | |
| WO | WO2007036227 | A1 | 4/2007 | | |
| WO | WO-2008080167 | A2 | 7/2008 | | |
| WO | WO2008122288 | A1 | 10/2008 | | |
| WO | WO2008143769 | A1 | 11/2008 | | |
| WO | WO2010111132 | A2 | 9/2010 | | |
| WO | WO2010113632 | A1 | 10/2010 | | |
| WO | WO2010117976 | A1 | 10/2010 | | |
| WO | WO2011075614 | A2 | 6/2011 | | |
| WO | WO2012058575 | A3 | 5/2012 | | |
| WO | WO2013141050 | A1 | 9/2013 | | |
| WO | WO2016036807 | A1 | 3/2016 | | |
| WO | WO2016208675 | A1 | 12/2016 | | |
| WO | WO2019074886 | A1 | 4/2019 | | |
| WO | WO-2020065413 | A1 | 4/2020 | | |
| WO | WO2020111132 | A1 | 6/2020 | | |
| WO | WO2024059759 | A1 | 3/2024 | | |
| WO | WO2024059762 | A1 | 3/2024 | | |
| WO | WO2024059763 | A1 | 3/2024 | | |
| WO | WO2024059764 | A1 | 3/2024 | | |
| WO | WO2024059765 | A1 | 3/2024 | | |
| WO | WO2024059766 | A1 | 3/2024 | | |
| WO | WO2024059767 | A1 | 3/2024 | | |
| WO | WO-2024059768 | A1 * | 3/2024 | ............ | A61K 35/16 |
| WO | WO2024059769 | A1 | 3/2024 | | |
| WO | WO2024059770 | | 3/2024 | | |
| WO | WO2024059771 | A1 | 3/2024 | | |
| WO | WO-2024059772 | A1 * | 3/2024 | ............ | A61K 35/16 |
| WO | WO2024059774 | A1 | 3/2024 | | |

OTHER PUBLICATIONS

Carpenter, et al. "Rational Design of Stable Lyophilized Protein Formulations: Theory and Practice" Kluwer Academic/Plenum Publishers; 2002; pp. 109-133.

Schmid "Spray drying of protein precipitates and Evaluation of the Nano Spray Dryer B-90" PhD Thesis; 2011; 125 pages.

Shuja, et al. "Development and Testing of Low-Volume Hyperoncotic, Hyperosmotic Spray-Dried Plasma for the treatment of Trauma-Associated Coagulopathy" The Journal of Trauma; Mar. 2011; vol. 70; No. 3; pp. 664-671.

Bakaltcheva; et al. "Freeze-dried whole plasma: Evaluating sucrose, trehalose, sorbitol, mannitol and glycine as stabilizers" Thrombosis Research; 2007; vol. 120; pp. 105-116.

European Search Report, EP Application No. 14154366, mailed Aug. 29, 2014, pp. 1-3.

European Search Opinion, EP Application No. 14154366, mailed Aug. 29, 2014, pp. 1-3.

International Search Report and Written Opinion, PCT/US2010/049176, mailed Nov. 4, 2010, pp. 1-10.

International Search Report and Written Opinion, PCT/US2011/058358, mailed Jul. 4, 2012, pp. 1-9.

Answer, Affirmative Defenses, Counterclaims, Cross-Claims and Jury Demand, *Entegrion, Inc.* vs *Velico Medical, Inc.*, dated Dec. 3, 2012, pp. 1-47.

Civil Action Cover Sheet; *Entegrion, Inc.* vs *Velico Medical, Inc.*, dated Oct. 19, 2012, pp. 1-2.

Complaint including Exhibit A, B, and C; *Entegrion, Inc.* vs *Velico Medical, Inc.*, dated Oct. 19, 2012, pp. 1-29.

Mini Spray Dryer B-290-Application Note; www.buchi.com; Mar. 30, 2008, entire document; 1 page.

Nano Spray Dryer B-90; www.buchi.com; Jul. 18, 2011, entire document, 12 pages.

Mini Spray Dryer System Configuration; www.buchi.com; Jan. 8, 2007, entire document, 1 page.

Quick Operation Guide; Mini Spray Dryer B-290; www.buchi.com; Sep. 16, 2004, pp. 15-53.

Process Parameters; www.buchi.com; Nov. 21, 2008, pp. 1-2.

Training Papers Spray Drying; Version B; www.buchi.com; 19 pages; Oct. 29, 2002.

Mini Spray Dryer B-290; www.buchi.com; May 10, 2007, pp. 1-8.

Fischer M., et al., "Stability of African swine fever virus on spiked spray-dried porcine plasma," *Transboundary and Emerging Diseases*, 68(5): 2806-2811 (2021).

International Preliminary Report on Patentability, PCT/US2011/058358, mailed Apr. 30, 2013, pp. 1-7.

Edwards et al., The Preparation and Use of Dried Plasma for Transfusion; British Medical journal; vol. 1, No. 4131;Mar. 9, 1940; pp. 377-381.

Blazquez, E., et al., "Biosafety steps in the manufacturing process of spray-dried plasma: a review with emphasis on the use of ultraviolet irradiation as a redundant biosafety procedure," *Porcine Health Management*, 6(16): p., 78 refs. (2020), 9 pages.

Blazquez, E., et al., "Effect of spray-drying and ultraviolet C radiation as biosafety steps for CSFV and ASFV inactivation in porcine plasma," *PLoS One*, 16(4) (2021), entire document, 11 pages.

Entegrion's Reply to Counterclaims; *Entegrion, Inc.* vs *Velico Medical, Inc*; Dated: Jan. 14, 2013, entire document, 22 pages.

Entegrion's Motion to Dismiss Counts I, II, V, VI and XI of Velico Medical, Inc's Counterclaims and Memorandum in Support of Entegrion's Motion to Dismiss Counts I, II, V, VI, and XI of Velico Medical, Inc.'s Counterclaims; *Entegrion, Inc.* vs *Velico Medical, Inc*; Dated: Jan. 14, 2013, entire document, 3 pages.

International Preliminary Report on Patentability, PCT/US2010/049176, mailed Feb. 18, 2014, pp. 1-9.

Pusateri, Anthony E."Dried plasma: state of the science and recent developments" *Transfusion* 56: S128-S139 (Apr. 2016).

Pusateri, Anthony E."Comprehensive US government program for dried plasma development" *Transfusion* 56: S16-S23 (2016).

Popovsky, Mark A. "Spray-dried plasma: a post-traumatic blood "bridge" for life-saving resuscitation" *Transfusion*. 2021;61:S294-S300 (2021).

Flaumenhaft, Elissa J. et al., "Retention of Coagulation Factors and Storage of Freeze-Dried Plasma," *Military Med.* 186 (S1):400-407 (2021).

Parr, Ashely, "Coagulation Activity of Freeze-Dried Plasma is similar to that of Fresh Frozen Plasma" (May 16, 2018) entire document, 14 pages.

Peng, Henry T. "Ex vivo hemostatic and immune-inflammatory profiles of freeze-dried plasma" Transfusion 61: S119-S130 (2021).

Larry J. Dumont, et al., "The bioequivalence of frozen plasma prepared from whole blood held overnight at room temperature compared to fresh-frozen plasma prepared within eight hours of collection," *Transfusion* 55: 480 (2015), entire document, 9 pages.

Blazquez, E., et al., "Combined effects of spray-drying conditions and postdrying storage time and temperature on *Salmonella choleraesuis* and *Salmonella typhimurium* survival when inoculated in liquid porcine plasma," *Letters in Applied Microbiology*, 67(2): 205-211 (2018).

S. Suessner, et al., "Comparison of several complement and coagulation factor concentrations in different plasma products." *Transfusion Medicine and Hemotherapy*, 41 (supplement 1) Abstract No. PBK-V02: p. 36 (2014), 3 pages.

Cancelas, J. A., "A Phase 1, Single-Center, Partial Double-blind, Randomized, Controlled (Versus Fresh Frozen Plasma [FFP] in Cohort 3 Only) Clinical Study of the Safety of Ascending Doses of Autologous Freeze Dried Plasma (FDP) in Healthy Volunteers," Falls Church, VA: The Surgeon General, Department of the Army (2018), p. 1-128.

Polo, J., et al., "Neutralizing antibodies against porcine circovirus type 2 in liquid pooled plasma contribute to the biosafety of commercially manufactured spray-dried porcine plasma," *Journal of Animal Science*, 91(5): 2192-2198 (2013).

(56) References Cited

OTHER PUBLICATIONS

Blazquez, E., et al., "UV-C irradiation is able to inactivate pathogens found in commercially collected porcine plasma as demonstrated by swine bioassay," *Veterinary Microbiology*, 239 (2019), entire document, 2 pages.

Blazquez, E., et al., "Evaluation of the effectiveness of the SurePure Turbulator ultraviolet-C irradiation equipment on inactivation of different enveloped and non-enveloped viruses inoculated in commercially collected liquid animal plasma," PLoS One, 14(2) (2019), entire document, 17 pages.

Shen, E., et al., "Commercially produced spray-dried porcine plasma contains increased concentrations of porcine circovirus type 2 DNA but does not transmit porcine circovirus type 2 when fed to naïve pigs," *Journal of Animal Science*, 89(6): 1930-1938 (2011).

Pujols, J., and Segales, J., "Survivability of porcine epidemic diarrhea virus (PEDV) in bovine plasma submitted to spray drying processing and held at different time by temperature storage conditions," *Veterinary Microbiology*, 174(3/4): 427-432 (2014).

Blazquez, E., et al., "Evaluation of ultraviolet-C and spray-drying processes as two independent inactivation steps on enterotoxigenic *Escherichia coli* K88 and K99 strains inoculated in fresh unconcentrated porcine plasma," *Letters in Applied Microbiology*, 67(5): 442-448 (2018).

Pujols, J., et al., "No transmission of hepatitis E virus in pigs fed diets containing commercial spray-dried porcine plasma: a retrospective study of samples from several swine trials," *Virology Journal*, 11: p. 232 (2014), 8 pages.

Foddai, A., et al., "Probability of introducing porcine epidemic diarrhea virus into Danish pig herds by imported spray-dried porcine plasma," *Porcine Health Management*, 1: p. 18 (2015), 11 pages.

Gerber, P. F., et al., "The spray-drying process is sufficient to inactivate infectious porcine epidemic diarrhea virus in plasma," *Veterinary Microbiology*, 174(1/2): 86-92 (2014).

Patterson, A. R., et al., "Efficacy of experimentally produced spray-dried plasma on infectivity of porcine circovirus type 2," *Journal of Animal Science*, 88(12: 4078-4085 (2010).

Pujols, J., et al., "Commercial spray-dried porcine plasma does not transmit porcine circovirus type 2 in weaned pigs challenged with porcine reproductive and respiratory syndrome virus," *Veterinary Journal*, 190(2): 16-20 (2011).

Blazquez, E., et al., "Ultraviolet (UV-C) inactivation of Enterococcus faecium, *Salmonella choleraesuis* and *Salmonella typhimurium* in porcine plasma," *PLoS One*, 12(4) (2017), 11 pages.

Polo, J., et al., "Ultraviolet Light (UV) Inactivation of Porcine Parvovirus in Liquid Plasma and Effect of UV Irradiated Spray Dried Porcine Plasma on Performance of Weaned Pigs," *PLoS One*, 10(7) (2015), 12 pages.

Pujols, J., et al., "Lack of transmission of porcine circovirus type 2 to weanling pigs by feeding them spray-dried porcine plasma," *Veterinary Record*, 163(18): 536-538 (2008).

Opriessnig, T., et al., "Porcine Epidemic Diarrhea Virus RNA Present in Commercial Spray-Dried Porcine Plasma Is Not Infectious to Naïve Pigs," *PLoS One*, 9(8) (2014), 10 pages.

Polo, J., et al., "Efficacy of spray-drying to reduce infectivity of pseudorabies and porcine reproductive and respiratory syndrome (PRRS) viruses and seroconversion in pigs fed diets containing spray-dried animal plasma," *Journal of Animal Science*, 83(8): 1933-1938 (2005).

Perez-Bosque, A., et al., "Spray dried plasma as an alternative to antibiotics in piglet feeds, mode of action and biosafety," *Porcine Health Management*, 2: p. 16 (2016) 10 pages.

Moreto, M., et al., "Dietary supplementation with spray-dried porcine plasma has prebiotic effects on gut microbiota in mice," *Scientific Reports*, 10(1): p. 2926 (2020), 13 pages.

Hulst, M. M., et al., "Study on inactivation of porcine epidemic diarrhoea virus, porcine sapelovirus 1 and adenovirus in the production and storage of laboratory spray-dried porcine plasma," *Journal of Applied Microbiology*, 126(6): 1931-1943 (2019).

Pasick, J., et al., "Investigation into the Role of Potentially Contaminated Feed as a Source of the First-Detected Outbreaks of Porcine Epidemic Diarrhea in Canada," *Transboundary and Emerging Diseases*, 61(5): 397-410 (2014).

Duffy, M. A., et al., "Impact of dietary spray-dried bovine plasma addition on pigs infected with porcine epidemic diarrhea virus," *Translational Animal Science*, 2(4): 349-357 (2018).

Cottingim, K. M., et al., "Ultraviolet irradiation of spray-dried porcine plasma does not affect the growth performance of nursery pigs when compared with nonirradiated bovine plasma," *Journal of Animal Science*, 95(7): 3120-3128 (2017).

Gebhardt, J. T., et al., "Determining the impact of commercial feed additives as potential porcine epidemic diarrhea virus mitigation strategies as determined by polymerase chain reaction analysis and bioassay," *Translational Animal Science*, 3(1): 28-37 (2019).

Champagne C. P., et al., "Effect of bovine colostrum, cheese whey, and spray-dried porcine plasma on the in vitro growth of probiotic bacteria and *Escherichia coli*," *Canadian Journal of Microbiology*, 60(5): 287-295 (2014).

Perez-Bosque, A., et al., "The Anti-Inflammatory Effect of Spray-Dried Plasma Is Mediated by a Reduction in Mucosal Lymphocyte Activation and Infiltration in a Mouse Model of Intestinal Inflammation," *Nutrients*, 8(10) (2016), p. 1-13.

Prabhu, B., et al., "Effects of spray-dried animal plasma on the growth performance of weaned piglets—a review," *Journal of Animal Physiology and Animal Nutrition*, 105(4): 699-714 (2021).

Santos, D., et al., "Spray Drying: an Overview," *Biomaterials*, (2017), p. 1-29.

USAMRMC military plasma article "Advanced Development Products," (Second Edition). U.S. Army Medical Research and Materiel Command (2017), p. 521-529.

GovTribe, "Definitive Contract H9222216C0081", [online], [retrieved on Mar. 20, 2020], Retrieved from https://govtribe.com/award/federal-contract-award/definitive-contract-h9 22216c0081, entire document, 3 pages.

Noorman, F. et al. "Lyophilized Plasma, an Alternative to 4 degrees C Stored Thawed Plasma for the Early Treatment of Trauma Patients with (Massive) Blood Loss in Military Theatre," *Transfusion* 55A (2012), p. 1-2.

Bux, J., et al., "Quality of freeze-dried (lyophilized) quarantined single-donor plasma," *Transfusion*, 53: 3203-3209 (2013).

Noorman, F., "Comparison of a single Spray dried plasma product with standard Sanquin and MBB frozen, thawed (coldstored) plasma," (Final Report). Utrecht, Netherlands: Military Blood Bank (2021), p. 1-7.

Sailliol, A., et al., "The evolving role of lyophilized plasma in remote damage control resuscitation in the French Armed Forces Health Service," *Transfusion*, 53: 65S-71S (2013).

Zaza, M., et al. "Dried Plasma," *Damage Control Resuscitation: Identification and Treatment of Life-Threatening Hemorrhage*, 145-162 (2019).

Wataha, K., et al., "Spray-dried plasma and fresh frozen plasma modulate permeability and inflammation in vitro in vascular endothelial cells," *Transfusion*, 53: 80S-90S (2013).

Wang, H.H., et al., "Effect of gallbladder hypomotility on cholesterol crystallization and growth in CCK-deficient mice," *Biochim Biophys Acta*, 1801(2): 138-146 (2010).

Gadeela, N., et al., "The Impact of Circulating Cholesterol Crystals on Vasomotor Function. Implications for No-Reflow Phenomenon," *J Am Coll Cardiol Int*, 4: 521-529 (2011).

Abela, G.S., et al., "The Effect of Ethanol on Cholesterol Crystals During Tissue Preparation for Scanning Electron Microscopy," *J Am Coll Cardiol* 1: 93 (2012), 1 page.

Li, H., et al., "Synthesis of β-cyclodextrin conjugated superparamagnetic iron oxide nanoparticles for selective binding and detection of cholesterol crystals," *Chem Commun*, 48(28): 3385-3387 (2012).

Elizabeth, A., et al., "Growth and micro-topographical studies of gel grown cholesterol crystals," *Bull Mater Sci*, 24(4): 431-434 (2001).

Kroll, M.H., et al., "Effect of Lyophilization on Results of Five Enzymatic Methods for Cholesterol," *Clin Chem*, 35(7): 1523-1526 (1989).

(56) References Cited

OTHER PUBLICATIONS

Mughal, M.M., et al., "Symptomatic and asymptomatic carotid artery plaque," *Expert Rev Cardiovasc Ther*, 9(10): 1315-1330 (2011).

Morales, J., and Gonzalez, E., "Cholesterol Crystal Embolization," *Blood Purif*, 24: 431-432 (2006).

Walton, T.J., et al., "Systemic cholesterol crystal embolisation with pulmonary involvement: a fatal combination after coronary angiography," *Postgrad Med J*, 78: 288-289 (2002).

Oe, K., et al., "Late Onset of Cholesterol Crystal Embolism after Thrombolysis for Cerebral Infarction," *Inter Med*, 49: 833-836 (2010).

Warren, B. A., and Vales, O., "The ultrastructure of the stages of atheroembolic occlusion of renal arteries," *Br J Exp Pathol*, 54(5): 469-478 (1973).

Warren B. A., Vales, O., "Electron microscopy of the sequence of events in the atheroembolic occlusion of cerebral arteries in an animal model," *Br J Exp Pathol*, 56(3):205-215 (1975).

Warren, B. A., and Vales, O., "The ultrastructure of the reaction of arterial walls to cholesterol crystals in atheroembolism," *Br J Exp Pathol*, 57(1), 67-77 (1976).

Steiner, T.J., et al., "Cholesterol crystal embolization in rat brain: a model for atheroembolic cerebral infarction," *Stroke*, 11: 184-189 (1980).

Nozari A., et al., "Microemboli may link spreading depression, migraine aura, and patent foramen ovale," *Ann Neurol*, 67(2):221-229 (2010).

Duewell, P., et al., "NLRP3 inflammasomes are required for atherogenesis and activated by cholesterol crystals," *Nature*, 464,7293: 1357-1361 (2010).

Samstadt, E. O., et al., "Cholesterol crystals induce complement-dependent inflammasome activation and cytokine release," *J Immunol*, 192(67): 2837-2845 (2014).

Grebe, A., and Latz, E., "Cholesterol Crystals and Inflammation," *Curr Rheumatol Rep*, 15: 313 (2013) 7 pages.

Sheedy, F., et al., "CD36 coordinates NLRP3 inflammasome activation by facilitating intracellular nucleation of soluble ligands into particulate ligands in sterile inflammation," *Nat Immunol*, 14: 812-820 (2013).

Ness, M. V., et al., "Neutrophils Contain Cholesterol Crystals in Transfusion-Related Acute Lung Injury (TRALI)," *Am J Clin Pathol*, 140(2): 170-176 (2013).

Sheffield, W. P., et al., "Retention of hemostatic and immunological properties of frozen plasma and COVID-19 convalescent apheresis fresh-frozen plasma produced and freeze-dried in Canada," *Transfusion*, 62: 418-428 (2021).

Garrigue, D., et al., "French lyophilized plasma versus fresh frozen plasma for the initial management of trauma-induced coagulopathy: a randomized open-label trial," *J Thrombosis and Haemostasis*, 16:481-489 (2017).

Van, P. Y., et al., "Lyophilized Plasma Reconstituted With Ascorbic Acid Suppresses Inflammation and Oxidative DNA Damage," *J Trauma*, 71(1) :20-24 (2011).

Medical Countermeasures, "BARDA continues partnership with Velico Medical for development of their FrontlineODP spray-dry plasma system to prepare for a radiological or nuclear emergency," [online], [retrieved on Sep. 20, 2021], Retrieved from https://www.medicalcountermeasures.gov/newsroom/2021/velico-medical/ entire document, 20 pages.

Burnouf, T., et al., "Assessment of complement activation during membrane-based plasmapheresis procedures," *J Clin Apheresis*, 19: 142-147 (2004).

Ohta, R., et al., "Serum concentrations of complement anaphylatoxins and proinflammatory mediators in patients with 2009 H1N1 influenza," *Microbiology and Immunology*, 55: 191-198 (2011).

"French Lyophilised Plasma (FLYP)," Ministry of Defence, Armed Forces Health Service, Jean Julliard Armed Forces Blood Transfusion Service (Technical Notice and Summary of Product Characteristics) (2013), 2 pages.

Arun, R., "Freeze Dried Plasma Role in Emergency Resuscitation", Tirupati, India: Sri Venkateswara Institute of Medical Sciences, https://www.istm.net.in/transmedcon2016-presentations/99.%20Freeze%20Dried%20Plasma-Role%20in%20Emergency%20Resuscitation.pdf, downloaded on Jan. 16, 2021, entire document, 51 pages.

Pusateri, A.E., and Weiskopf, R.B. "Dried Plasma for Trauma Resuscitation," *Trauma Induced Coagulopathy*, 705-718 (2021).

Sunde, G.A., "Prehospital Plasma / TXA experience—FDP in Norwegian HEMS," Norway: Norsk Luftambulanse (2014), p. 1-24.

Acker, J. P., et al., "Quality Assessment of Established and Emerging Blood Components for Transfusion," *Journal of Blood Transfusion*, (2016) p. 1-29.

Warr, M., "Lyoplas reconstitution English," Deutsches Rotes Kreuz, [Youtube], [retrieved on Jan. 9, 2022], Retrieved from https://www.youtube.com/watch?y=Pdyd5tEygtk. Entire document.

"LyoPlas N—w A freeze-dried single donor plasma," Brochure, DRK-Blutspendedienst West, Hagen, Germany: Deutsches Rotes Kreuz (May 2012), entire document, 14 pages.

Mew, I., "Reconstituting Lyoplas (Freeze dried FFP)", [Youtube], [retrieved on Jan. 9, 2022], Retrieved from https://www.youtube.com/watch?v=RxpQDMwVK8Y.), entire document, 9 pages.

Cancelas, J. A., et al., "Characterization and first-in-human clinical dose-escalation safety evaluation of a next-gen human freeze-dried plasma," *Transfusion*, 62: 406-417 (2021).

"Mirasol Pathogen Reduction Technology System", TerumoBCT (2012), entire document, 13 pages.

Terumo BCT, "Terumo BCT Awarded $1.9 Million from the United States Government to Support Development of Freeze-Dried Plasma," [online], [retrieved on Mar. 20, 2020], Retrieved from https://www.terumobct.com/Pages/News/Press%20Releases/Terumo_BCT_Awarde_d_$1-9_Million_from_the_United_States_Government_to_Support_Development_of_Freeze-Dried_Plasma.aspx. , entire document, 2 pages.

Spinella, P. C., "Zero preventable deaths after traumatic injury: an achievable goal," *J Trauma Acute Care Surg*, 82:S2-S8 (2017).

Davis, J. S., et al., "An analysis of prehospital deaths: who can we save?," *J Trauma Acute Care Surg*, 77:213-218 (2014).

Shackelford, S. A., et al., "Association of prehospital blood product transfusion during medical evacuation of combat casualties in Afghanistan with acute and 30-day survival," *JAMA*, 318:1581-1591 (2017).

Gurney, J. M., and Spinella, P. C., "Blood transfusion management in the severely bleeding military patient," *Curr Opin Anesthesiol*, 31:207-214 (2018).

Moore, E. E., et al., "Plasma first in the field for postinjury hemorrhagic shock," *Shock*, 41(Suppl 1):35-38 (2014).

Maegele, M., et al., "Red-blood-cell to plasma ratios transfused during massive transfusion are associated with mortality in severe multiple injury: a retrospective analysis from the trauma registry of the deutsche Gesellshaft fur Unfallchirugerie," *Vox Sang*, 95:112-119 (2008).

Holcomb, J. B., et al., "Prehospital transfusion of plasma and red blood cells in trauma patients," *Prehosp Emerg Care*, 19:1-9 (2015).

Holcomb, J. B., et al., "The prospective, observational, multicenter major trauma transfusion (PROMMTT) study: comparative effectiveness of a time-varying treatment with competing risks," *JAMA Surg*, 148:127-136 (2013).

Holcomb, J. B., et al., "Damage control resuscitation: directly addressing the early coagulopathy of trauma," *J Trauma Acute Care Surg*, 62:307-310 (2007).

Holcomb, J. B., et al., "Transfusion of plasma, platelets, and red blood cells in a 1:1:1 vs 1:1:2 ratio and mortality in patients with severe trauma: the PROPPR randomized clinical trial," *JAMA*, 313:471-482 (2015).

Sperry, J. L., et al., "Prehospital plasma during air medical transport in trauma patients at risk for hemorrhagic shock," *N Engl J Med*, 379:315-326 (2018).

Zink, K. A., et al., "A high ratio of plasma and platelets to packed red blood cells in the first 6 hours of massive transfusion improves outcomes in a large multicenter study," *Am J Surg*, 197:565-570 (2009).

(56) References Cited

OTHER PUBLICATIONS

Saillol, A., et al., "The evolving role of lyophilized plasma in remote damage control resuscitation in the French armed forces health service," Transfusion, 53(Suppl 1): S129-S39 (2013).
Nuguyen, C., et al., "Use of French lyophilized plasma transfusion in severe trauma patients is associated with an early plasma transfusion and early transfusion ratio improvement," J Trauma Acute Care Surg, 84:780-785 (2018).
Shlaifer, A., et al., "Prehospital administration of freeze-dried plasma, is it the solution for trauma casualties?," J Trauma Acute Care Surg, 83:675-682 (2017).
Shlaifer, A., et al., "The impact of prehospital administration of freeze-dried plasma on casualty outcome," J Trauma Acute Care Surg, 86:108-115 (2019).
Bjerkvig, C.K., et al., ""Blood failure" time to view blood as an organ: how oxygen debt contributes to blood failure and its implications for remote damage control resuscitation," Transfusion, 56(Suppl 2):S182-S189 (2016).
White, N. J., et al., "Hemorrhagic blood failure: oxygen debt, coagulopathy, and endothelial damage," J Trauma Acute Care Surg, 82(6S Suppl 1):S41-S49 (2017).
Aird, W. C., "Endothelium and haemostasis," Hamostaseologie, 35:11-16 (2015).
Esmon, C. T., "Inflammation and the activated protein C anticoagulant pathway," Semin Thromb Hemost, 32(Suppl 1):49-60 (2006).
Tuma, M., et al., "Trauma and endothelial glycocalyx: the microcirculation helmet?," Shock, 46:352-357 (2016).
Kozar, R. A., and Pati, S., "Syndecan-1 restitution by plasma after hemorrhagic shock," J Trauma Acute Care Surg, 78(6 Suppl 1):S83-S86 (2015).
Rahbar, E., et al., "Endothelial glycocalyx shedding and vascular permeability in severely injured trauma patients," J Transl Med, 13:117 (2015), entire document, 7 pages.
Johansson, P. I., et al., "Traumatic Endotheliopathy: a prospective observational Study of 424 severely injured patients," Ann Surg, 265:597-603 (2017).
Wu, F., et al., "miR-19b targets pulmonary endothelial syndecan-1 following hemorrhagic shock," Sci Rep, 10:15811 (2020), 10 pages.
Johansson, P. I., et al., "Shock induced endotheliopathy (SHINE) in acute critical illness—a unifying pathophysiologic mechanism," Crit Care, 21:25 (2017), 7 pages.
Spronk, H. M., et al., "New insights into modulation of thrombin formation," Curr Atheroscler Rep, 15:363 (2013), 9 pages.
Dunbar, N. M., and Chandler, W. L., "Thrombin generation in trauma patients," Transfusion, 49:2652-2660 (2009).
Chandler, W. L., "Procoagulant activity in trauma patients," Am J Clin Pathol, 134:90-96 (2010).
Cardenas, J. C., et al., "Measuring thrombin generation as a tool for predicting hemostatic potential and transfusion requirements following trauma," J Trauma Acute Care Surg, 77:839-845 (2014).
Rourke, C., et al., "Fibrinogen levels during trauma hemorrhage, response to replacement therapy, and association with patient outcomes," J Thromb Haemost, 10:1342-1351 (2012).
Raza, I., et al., "The incidence and magnitude of fibrinolytic activation in trauma patients," J Thromb Haemost, 11:307-314 (2013).
Hayakawa, M., et al., "Disseminated intravascular coagulation at an early phase of trauma is associated with consumption coagulopathy and excessive fibrinolysis both by plasmin and neutrophil elastase," Surgery, 149:221-230 (2011).
Kaplan, A. P., and Ghebrehiwet, B., "The plasma bradykinin-forming pathways and its interrelationships with complement," Mol Immunol, 47:2161-2169 (2010).
Omar, M. N., Mann, K. G., "Inactivation of factor Va by plasmin," J Biol Chem, 262:9750-9755 (1987).
Marcos-Contreras, O. A., et al., "Hyperfibrinolysis increases blood-brain barrier permeability by a plasmin- and bradykinin-dependent mechanism," Blood, 128:2423-2434 (2016).

Chapman, M. P., et al., "Overwhelming tPA release, not PAI-1 degradation, is responsible for hyperfibrinolysis in severely injured trauma patients," J Trauma Acute Care Surg, 80:16-25 (2016).
Cardenas, J. C., et al., "Elevated tissue plasminogen activator and reduced plasminogen activator inhibitor promote hyperfibrinolysis in trauma patients," Shock, 41:514-521 (2014).
Moore, H. B., et al., "Acute fibrinolysis shutdown after injury occurs frequently and increases mortality: a multicenter evaluation of 2,540 severely injured patients," J Am Coll Surg, 222:347-355 (2016).
Shakur, H., et al., "Effects of tranexamic acid on death, vascular occlusive events, and blood transfusion in trauma patients with significant haemorrhage (CRASH-2): a randomised, placebo-controlled trial," Lancet, 376:23-32 (2010).
Peng, Z., et al., "Fresh frozen plasma lessens pulmonary endothelial inflammation and hyperpermeability after hemorrhagic shock and is associated with loss of syndecan 1," Shock, 40:195-202 (2013).
Diebel, L. N., "Microfluidics: a high-throughput system for the assessment of the endotheliopathy of trauma and the effect of timing of plasma administration on ameliorating shock-associated endothelial dysfunction," J Trauma Acute Care Surg, 84:575-582 (2018).
Yu, Q., et al., "Identification of fibrinogen as a key anti-apoptotic factor in human fresh frozen plasma for protecting endothelial cells in vitro," Shock, 53:646-652 (2020).
Wu, F., and Kozar, R. A., "Fibrinogen protects against barrier dysfunction through maintaining cell surface syndecan-1 in vitro," Shock, 51:740-744 (2019).
Wu, F., et al., "Fibrinogen activates PAK1/Cofilin signaling pathway to protect endothelial barrier integrity," Shock, 55:660-665 (2020).
Lopez, E., et al., "Antithrombin III contributes to the protective effects of fresh frozen plasma following hemorrhagic shock by preventing syndecan-1 shedding and endothelial barrier disruption," Shock, 53:156-163 (2020).
Deng, X., et al., "Adiponectin in fresh frozen plasma contributes to restoration of vascular barrier function after hemorrhagic shock," Shock, 45:50-54 (2016).
Rizoli, S. B., et al., "Clotting factor deficiency in early trauma-associated coagulopathy," J Trauma, 71(5 Suppl 1):S427-S434 (2011).
Pati, S., et al., "Lyophilized plasma attenuates vascular permeability, inflammation and lung injury in hemorrhagic shock," PLoS One, 13:e0192363 (2018), entire document, 13 pages.
Reineccius, G., "Flavor encapsulation, Chapter 7. Spray-drying of food flavors," United Kingdom: Taylor and Francis, 55-66 (1989).
"Considerations for the Development of Dried Plasma Products Intended for Transfusion", (Final Report). Food and Drug Administration (2019), entire document, 9 pages.
Liu, Q. P., et al., "Single-donor spray-dried plasma," Transfusion, 59:707-719 (2019).
Meledeo, M. A., et al., "Spray-dried plasma deficient in high-molecular weight multimers of von Willebrand factor retains hemostatic properties," Transfusion, 59:714-722 (2019).
Buckley, L., and Gonzales, R., "Challenges to producing novel therapies-dried plasma for use in trauma and critical care," Transfusion, 59:837-845 (2019).
Bercovitz, R., et al., "Microfluidic analysis of thrombus formation in reconstituted whole blood samples comparing spray-dried plasma versus fresh-frozen plasma," Vox Sang, 116:540-546 (2020).
Spinella, P. C., et al., "All plasma products are not created equal: characterizing differences between plasma products," J Trauma Acute Care Surg, 78:S18-S25 (2015).
Bomey, N., "Hurricane Maria halts crucial drug manufacturing in Puerto Rico, may cause shortages," USA Today, [online], [retrieved on Oct. 20, 2017] Retrieved from https://www.usatoday.com/story/money/2017/09/22/hurricane-maria-pharmaceutical-industry-puerto-rico/692752001/ (2017), entire document, 9 pages.
Robinson, R. A., "Barda Strategic Plan 2011-2016", Washington, D.C.: Biomedical Advanced Research and Development Authority. (2016), entire document, 20 pages.
Pusateri A.E., "Dried Plasma Development Update," Defense Health Agency (2015), entire document, 58 pages.

(56) References Cited

OTHER PUBLICATIONS

Downes, K. A., et al., "Serial measurement of clotting factors in thawed plasma stored for 5 days," *Transfusion*, 41: 570-570 (2001).
Runkel, S., et al., "The impact of whole blood processing and freezing conditions on the quality of therapeutic plasma prepared from whole blood," *Transfusion*, 55: 796-804 (2015).
Kelley, D., "Update on Plasma and Cryoprecipitate Transfusion," (Issue 1). *Institute for Transfusion Medicine* (2004), entire document, 2 pages.
Parsons, J. C., "Coagulation Hereditary bleeding disorders von Willebrand disease," [online], [retrieved on May 12, 2015], Retrieved from https://www.pathologyoutlines.com/topic/coagulationvonwillebranddisease.html, entire document, 5 pages.
ARUP Consult, "Von Willebrand Disease Testing," [online], [retrieved on May 12, 2015], Retrieved from https://arupconsult.com/sites/default/files/von_Willebrand_Disease_Testing_Algorithm.pdf, entire document, 1 page.
Heger, A., et al., "Biochemical quality of the pharmaceutically licensed plasma OctaplasLG® after implementation of a novel prion protein (PrPSc) removal technology and reduction of the solvent/detergent (S/D) process time," *Vox Sanguinis*, 97: 219-225 (2009).
Pusateri, A. E., et al., "Use of Dried Plasma in Prehospital and Austere Environments," *Anesthesiology*, 136: 327-335 (2022).
Pusateri, A. E., "Dried plasma: state of the science and recent developments," *Transfusion*, 56: S128-S139 (2016).
Chaffin, J., "Liquid Plasma," [online], [retrieved on Nov. 2, 2021], Retrieved from https://www.bbguy.org/education/glossary/g1104/, entire document, 2 pages.
Chaffin, J., "Thawed Plasma," [online], [retrieved on Nov. 2, 2021], Retrieved from https://www.bbguy.org/education/glossary/glt04/, entire document, 2 pages.
Barrows, E., "Freeze-dried Plasma The Trail Back to the Battlefield," *Defense AT&L Technology Transition*, pp. 16-19 (Sep.-Oct. 2006).
Martinaud, C., et al., "French Dried Plasma Program: Update on prehospital and emergency unit use for massive hemorrhage management," *French Military Blood Institute* (Jun. 27, 2017), entire document, 34 pages.
Martinaud, C., et al., "In Vitro Hemostatic Properties of French Lyophilized Plasma," *Anesthesiology*, 117: 339-346 (2012).
Sicard, B., et al., "Lyophilized Plasma in Out-of-Hospital Resuscitation: Risk Benefit Balance," *Ann Emerg Med*, S141:357 (2017).
Jost, D., et al., "Pre-hospital Administration of Lyophilized Plasma for Post-traumatic Coagulopathy Treatment (PREHO-PLYO)," [online], [retrieved on Apr. 25, 2022], Retrieved from https://clinicaltrials.gov/ct2/show/study/NCT02736812, entire document, 9 pages.
News 4 WOAI San Antonio, "Freeze-dried plasma saves special ops soldiers", [Youtube], [retrieved on Apr. 25, 2022], Retrieved from https://www.youtube.com/watch?v=rstOJjwnwkw, entire document, 6 pages.
Lee, T., et al., "The use of lyophilized plasma in a severe multi-injury pig model," *Transfusion*, 53: 72S-79S (2013).
Holcomb, J.B., et al., "Increased Plasma and Platelet to Red Blood Cell Ratios Improves Outcome in 466 Massively Transfused Civilian Trauma Patients," *Ann Surg*, 3: 447-458 (2008).
Gatnau, R., "Spray dried porcine plasma as a source of protein and immunoglobins for weanling pigs." Unpublished master's thesis, Iowa State University, Ames, Iowa. (1990), entire document, 95 pages.
Murad, M.H., et al., "The effect of plasma transfusion on morbidity and mortality: a systematic review and meta-analysis," *Transfusion*, 50(6): 1370-1383 (2010).
Buchi Mini Spray Dryer B-191; www.buchi.com; Dec. 19, 2000, entire document, 28 pages.
DSS "Powdered Blood? Synthetic Blood Trials Show Promising Result" https://www.discoveryscientificsolutions.com/item/73 (downloaded Dec. 22, 2022), entire document, 9 pages.
Hamilton GJ "Lyophilized plasma with ascorbic acid decreases inflammation in hemorrhagic shock." J Trauma, 71 (2):292-7 (2011).
Hawksworth, J.S et al., Evaluation of lyophilized platelets as an infusible hemostatic agent in experimental non-compressible hemorrhage in swine, Journal of Thrombosis and Haemostasis, Oct. 2009, vol. 7, No. 10, pp. 1663-1671.
Solheim B G et al., Improved Preservation of Coagulation Factors After Pre-Storage Leukocyte Depletion of Whole Blood; Transfus Apher Sci., Oct. 2003. 29(2): pp. 133-139.
Goto et al., Characterization of the Unique Mechanism Mediating the Shear-dependent Binding of Soluble von Willebrand Factor to Platelets, The Journal of Biological Chemistry, vol. 270, No. 40, Oct. 6, 1995, pp. 23352-23361, 1995.
Horn, R.G., Addition of a polarizing microscope to the Weissenberg Rheogoniometer, 1979 American Institute of Physics, Rev. Sci. Instrum. 50(50, May 1979, pp. 659-661.
Moake, et al., Involvement of Large Plasma von Willebrand Factor (vWF) Multimers and Unusually Large vWF Forms Derived from Endothelial Cells in Shear Stress-induced Platelet Aggregation, The American Society for Clinical Investigation, Inc., vol. 78, Dec. 1986, pp. 1456-1461.
Shuja et al., Development and Testing of Freeze-Dried Plasma for the Treatment of Trauma-Associated Coagulopathy, The Journal of Trauma Injury, Infection and Critical Care, Presented at the 38th Annual Meeting of the Western Trauma Association, Feb. 24-Mar. 1, 2008, vol. 65, pp. 975-985.
CardianBCT, INC "Mirasol Pathogen Reduction Technology", PN 306690-148, retrieved online Apr. 4, 2023 <URL: http://eurolambda.sk/shared/files/mirasol_plasma.pdf>, 2 pages. (Year: 2009).
Terumo BCT, INC "Mirasol Pathogen Reduction Technology System", PN 306690232, retrieved online Apr. 4, 2023 <URL: https://www.terumopenpol.com/wp-content/uploads/2019/12/306690232-1.pdf>, 7 pages. (Year: 2012).
Heger, Andrea "Frozen and Freeze-dried solvent/detergent treated plasma: Tow different pharmaceutical formations with comparable quality" *Transfusion* (62): pp. 2621-2630 (Sep. 11, 2022).
Highlights of Prescribing Information https://octaplasusa.com/wp-content/uploads/2021/03/20210202_pil_952_US_25_pdf Downloaded Apr. 11, 2023; Octapharma USA Inc, (Feb. 2021) pp. 1-9.
Operation Manual; Mini Spray Dryer B-290; Version G; www.buchi.com; Feb. 8, 2007, pp. 1-57.
Bulut, S. et al., "Effects of Combined Shear and Thermal Forces on Destruction of *Microbacterium lacticum*" *Appl Environ Microbiol*, vol. 65, No. 10, pp. 4464-4469 (Oct. 1999).
International Search Report and Written Opinion, Application No. PCT/US2023/074261 pp. 1-17 (Dec. 4, 2023).
Booth, Garrett S. et al., Spray: Single-Donor Plasma Product for Room Temperature Storage, *Transfusion*: 52: 828-833 (Apr. 2012) 6 pages.
Dickey et al., "Use of Dried Plasma in Prehospital Battlefield Resuscitation Apr. 2011", Defense Technical Information Center, Aug. 8, 2011, accessible online at: https://apps.dtic.mil/sti/citations/AD1034120 (8 pages) (Aug. 8, 2011).
Butler, Frank K. "Fluid Resuscitation in Tactical Combat Casualty Care: Yesterday and Today", Wilderness & Environmental Medicine, vol. 28, Issue 2, S74-S81, Jun. 2017, DOI: https://doi.org/10.1016/j.wer.2016.12.007 (8 pages).
WayBack Machine archive of https://apps.dtic.mil/sti/citations/AD1034120, WayBack Machine, Nov. 29, 2020 (2 pages).
Semantic Scholar Web page concerning Dickey et al. "Use of Dried Plasma in Prehospital Battlefield Resuscitation", accessed by Examiner Dec. 14, 2023, U R L: https://www.semanticscholar.org/paper/Use-of-Dried-Plasma-in-Prehospital-Battlefield-Dickey/b87005a2c7cd54f022b 1728a80de07 df3a 7f8e40 (3 pages).
International Search Report and Written Opinion, Application No. PCT/US2023/074274 pp. 1-16 (Jan. 18, 2024).
International Search Report and Written Opinion, Application No. PCT/US2023/074266, pp. 1-11 (Dec. 21, 2023).
International Search Report and Written Opinion, Application No. PCT/US2023/074265, pp. 1-17 (Feb. 6, 2024).
International Search Report and Written Opinion, Application No. PCT/US2023/074264, pp. 1-13 (Feb. 6, 2024).
International Search Report and Written Opinion, Application No. PCT/US2023/074267, pp. 1-12 (Feb. 6, 2024).

(56) References Cited

OTHER PUBLICATIONS

International Search Report and Written Opinion, Application No. PCT/US2023/074268, pp. 1-23 (Feb. 9, 2024).
International Search Report and Written Opinion, Application No. PCT/US2023/074269, pp. 1-16 (Feb. 9, 2024).
International Search Report and Written Opinion, Application No. PCT/US2023/074277, pp. 1-13 (Feb. 9, 2024).
International Search Report and Written Opinion, Application No. PCT/US2023/074270, pp. 1-21 (Mar. 5, 2024).
International Search Report and Written Opinion, Application No. PCT/US2023/074272, pp. 1-15 (Feb. 9, 2024).
International Search Report and Written Opinion, Application No. PCT/US2023/074273, pp. 1-16 (Mar. 1, 2024).
International Search Report and Written Opinion, Application No. PCT/US2023/074275, pp. 1-16 (Mar. 1, 2024).

* cited by examiner

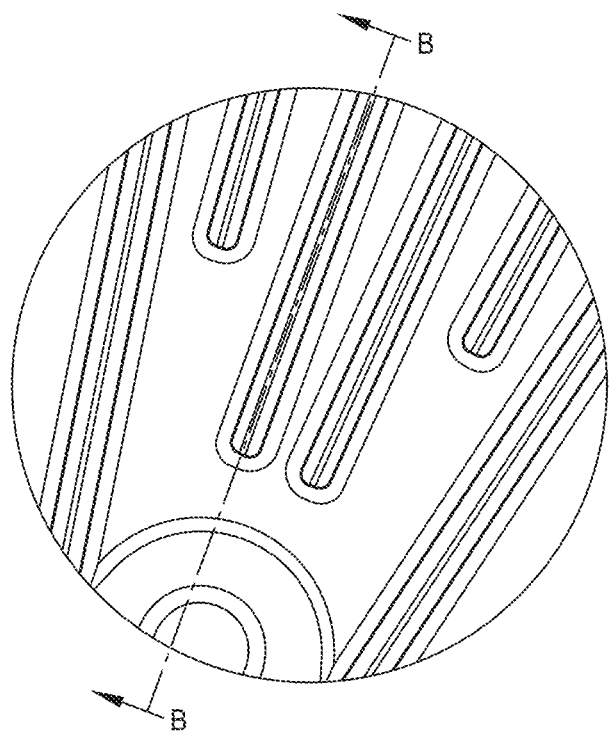
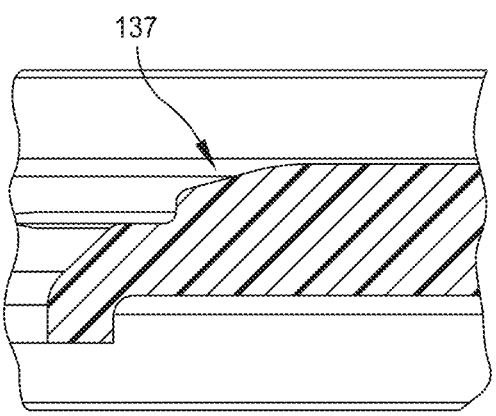
FIG. 2La
(CONTINUED)

Contours of static gas pressure inside aerosol gas passages, psig.

Contours of tangential velocity inside aerosol gas passages, m/s

Fig. 20

Velocity magnitude vectors inside aerosol gas passages, m/s

Fig. 2P

During evaporation droplets experience wet bulb temperatures

```
┌─────────────────────────────┐
│ Operator removes the lower  │
│ portion of the Spray Drying │
│ Disposable, leaving the middle│
│ portion of the Spray Drying │
│ Disposable with the dried plasma;│
│ the middle portion is the spray│
│ dried plasma unit; rotate shuttle to│
│ home position; the dried plasma│
│ unit is brought to the final│
│ packaging station           │
│           824               │
└─────────────────────────────┘
```

| Step | Description |
|---|---|
| 802 | Press the WAKE button and the finisher will automatically raise the shuttle to the load position or stay in the lowered position |
| 804 | Load the Spray Drying Disposable onto the shuttle by attaching the spray drying head to the spray drying head receiver |
| 806 | Press CONFIRM and the shuttle raises so operator can attach the gas outlet to gas outlet receiver |
| 808 | Press the CONFIRM button and RUN button to ready the finishing apparatus for the first seal and cut |
| 810 | The finisher will automatically lower, engage the impactor to move the dried plasma to the bottom of the Spray Drying Disposable; and cut the Spray Drying Disposable at the indicator, and air is evacuated; the finisher will automatically raise the shuttle |
| 812 | The operator inspects the first seal |
| 814 | Operator removes the upper portion of the Spray Drying Disposable, leaving the bottom portion of the Spray Drying Disposable with the dried plasma |
| 816 | Operator inverts the shuttle |
| 818 | Press the CONFIRM button and RUN button to ready the finishing apparatus for the second seal and cut |
| 820 | The finisher will automatically lower, engage the impactor to move the dried plasma to the bottom of the Spray Drying Disposable, cut the Spray Drying Disposable at the indicator, and air is evacuated; the finisher will automatically raise the shuttle |
| 822 | The operator inspects the second seal |

DISPOSABLE FOR A SPRAY DRYING SYSTEM

RELATED APPLICATION

This application is a continuation of U.S. application Ser. No. 18/496,766, entitled, "Disposable For A Spray Drying System" by Robert R. Andrews et al., filed Oct. 27, 2023, which is a continuation of U.S. application Ser. No. 17/945,124, entitled, "Disposable For A Spray Drying System" by Robert R. Andrews et al., filed Sep. 15, 2022.

GOVERNMENT SUPPORT

This invention was made with Government support under contract Nos. HHSO100201200005C and 75A50121C00059 awarded by the Biomedical Advanced Research and Development Authority (BARDA). The Government has certain rights in the invention.

The entire teachings of the above applications are incorporated herein by reference.

BACKGROUND OF THE INVENTION

The spray drying process, in general, is a well-known technology to dry a variety of liquid compositions for applications including cosmetics, animal feed, pharmaceuticals and others. Unfortunately, until the present invention, spray drying of blood plasma for transfusion has not been commercially feasible and generally spray drying has been an industrial or laboratory specialty involving complex, difficult to operate and often large machinery for manufacturing cosmetics, pharmaceuticals, animal feed and the like. Often, the aforementioned devices and methods have suffered from being impractical for use by a wide range of operators with little training or for aseptically manufacturing end products for human or animal medical use. These apparatuses are intended for use by highly skilled, experienced operators and not intended for use in environments or with personnel associated with the manufacture of human plasma for transfusion in blood centers and elsewhere.

With respect to plasma, transfused human blood plasma is often crucial to bleeding control and wound treatment in trauma victims and in surgery. Unfortunately, plasma is not readily available in many circumstances world-wide including battlefield, first responder, and rural settings remote from large hospitals, and in the second and third world.

The principal reason human plasma is not available as widely as needed is that in general blood plasma could only be stored frozen for long periods or as a liquid for very short periods. Accordingly, if a large amount of plasma is needed (e.g., such as in a mass casualty event), it may not be available in such quantities, or if plasma is needed in an emergency, it may not be available in time since it has to be thawed which can take 30-45 minutes or more.

The spray drying plasma process involves drying liquid plasma, a biological component, into a dried powder plasma. Maintaining the integrity of the plasma drying chamber of the disposable during spray drying and of the plasma unit assists in preventing a breach of the biological component and its exposure to pathogens.

Hence, a need exists to increase safety for a plasma spray drying system, the disposable and its dried plasma product. A need exists for a disposable for a spray dryer for use by a wide range of operators with little training or for aseptically manufacturing end products for human or animal medical use. A further need exists to design a spray drying system in which the spray drying plasma chamber and related components aseptically provides a dried plasma unit. Yet a further need exists for a spray drying system that provides a dried plasma unit from the spray dry chamber of a disposable used in the system to maintain system integrity. A further need exists for dried plasma to be readily available and able to rehydrate in a few minutes.

SUMMARY OF THE INVENTION

The present invention relates to a spray drying disposable device that has a spray drying head and a drying chamber. The spray drying disposable device is for use in a spray drying system that has a drying gas source, a plasma source and a pressurized aerosol gas source. In an embodiment, spray drying disposable device dries a single unit of donor plasma into a single unit of dried plasma. If desired, pooled plasma can also be prepared using the apparatus and process of the present invention.

The spray drying head includes a spray dry nozzle assembly in fluid communication with the plasma source and the pressurized aerosol gas source, wherein the pressurized aerosol gas flows in a vortex pattern, wherein, when in use, the pressurized aerosol gas atomizes the plasma entering the drying chamber to obtain atomized plasma droplets. The spray drying head also includes a plenum having a drying gas inlet in communication with the drying gas source, wherein, when in use, the drying gas resides in the plenum with uniform air pressure, wherein the plenum supports the nozzle assembly. The spray drying head further includes a baffle plate forming the floor of the plenum having one or more drying gas jets, wherein drying gas jet provides drying gas to the drying chamber.

The drying chamber of the spray drying disposable device is attached to the baffle plate in which atomized plasma droplets evaporate in the presence of the drying gas emitted from the one or more drying gas jet to thereby obtain dried plasma particles and humid air. The drying chamber further includes a capture filter, residing in the drying chamber, wherein the capture filter captures the dried plasma particles and allows the humid air to pass. The drying chamber also includes a gas outlet, wherein the gas outlet is attached to the exhaust port of the spray drying system during operation, wherein the humid air flows through the gas outlet.

In an embodiment, the spray dry nozzle assembly includes a cannula. The cannula, in an aspect, has an inner diameter in a range between about 0.010 inches and about 0.040 inches and an outer diameter between about 0.030 inches and about 0.060 inches.

In another embodiment, the spray drying disposable device further includes a vortex generator in communication with the pressurized aerosol gas. In an aspect, the vortex generator has a plurality of channels and a plurality of pads to create the vortex pattern of pressurized aerosol gas. The plurality of channels and the plurality of pads can be curved and/or the plurality of channels are curved and the plurality of pads have one or more curved edges.

In yet another embodiment, the nozzle assembly has an opening with a diameter. At this opening, the cannula emits the plasma and the pressurized aerosol gas. The nozzle opening has an inner surface. The cannula has an inner diameter and an outer diameter, and an outer surface. The opening emits pressurized aerosol gas in a vortex pattern. In particular, the vortex pattern of pressurized aerosol gas flows through the outer surface of the cannula and the inner surface of the opening. In an embodiment, the distance between the outer surface of the cannula and the inner surface of the opening is between about 0.015 inches and about 0.091 inches. In an aspect, the nozzle assembly extends past the plane defined by baffle plate into the plasma drying chamber.

In an embodiment, the drying gas inlet receives the drying gas source through a deflector that directs the drying gas to the inner side wall of the plenum. The drying gas inlet receives the drying gas source through a deflector that comprises a 90 degree elbow.

In yet another aspect, the plenum of the spray drying head further includes a baffle filter (e.g., 0.2 micron filter), through which the drying gas flows. In an embodiment, the baffle plate comprises one or more ribs on which the baffle filter rests. The baffle plate, in an aspect, has one or more channels of air flow communicating with the one or more drying gas jet. The one or more channels define one or more pie shaped air channels communicating with the one or more drying gas jet.

In an embodiment, the drying chamber of spray drying disposable device has a section that, after sealing and separation, becomes the dried plasma unit product. As such, this section further includes at least one or more ports for injecting reconstitution fluid or transferring the reconstituted plasma to a recipient, a slot for hanging the dried plasma unit, and a label. Along these lines, the drying chamber includes cut and seal locations that form the walls of the dried plasma unit.

In an embodiment, the drying chamber of spray drying disposable device has a separator at the capture filter, wherein the separator separates the capture filter from the inner wall of the spray drying chamber.

In yet another embodiment, the spray drying disposable device includes a locating arrangement for aligning the spray drying disposable device with the spray drying system.

The present invention includes methods of making spray dried plasma using the spray drying disposable device and spray drying system described herein and storing the spray dried plasma unit. The present invention further includes kits and systems having the spray drying disposable device and spray dried plasma unit described herein.

Advantageously, the present invention involves a spray drying system that has an easy-to-use spray dryer and a disposable that includes a drying chamber within it. A further advantage of the spray drying disposable is that, once the spray drying is completed, it converts into the spray dried plasma product that can be used in the field. The dried plasma of the present invention enables simplified storage, transport, and use options (e.g., refrigerated/ambient temperature storage) as compared to frozen plasma, the current standard for plasma. The present invention overcomes the inadequacies of the previous spray drying systems and permits the rapid, aseptic manufacture of small or single unit quantities of a wide range of materials by minimally trained operators of a wide range of statures. The applications of the present invention are wide and include dried human blood plasma. In particular, the present invention provides a process for moving the plasma into desired compartments of the disposable and sealing the disposable at certain locations to create a packaged, ready to use container for the dried material. The present invention is advantageously applicable to the aseptic manufacture of products for use in medicine such as pharmaceuticals or dried blood plasma. This plasma unit is rehydrated with sterile water and ready to use in minutes, providing easy and quick access to plasma.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2F is a schematic showing a front view of an embodiment of the angled edge cannula that is part of the spray dry nozzle assembly.

FIG. 2G is a schematic showing a perspective, top view of nozzle cap insert that guides the cannula and aerosolized air.

FIG. 2H is a schematic showing a perspective, bottom view of nozzle cap insert having the cannula inserted therein.

FIG. 2I is a schematic showing a top view of the nozzle cap.

FIG. 2Ia is schematic showing a bottom view nozzle cap of FIG. 2I with the cannular residing within the cap opening.

FIG. 2Ib schematic showing three possible vortex generator flow patterns that could be used with the nozzle cap insert of FIG. 2I.

FIG. 2Ic is a schematic showing a cross-sectional view of nozzle cap insert of FIG. 2H residing within nozzle cap of FIG. 2I.

FIG. 2J is a schematic showing a perspective, bottom view of the plenum of the spray drying head.

FIG. 2K is a schematic showing a partial front view of the spray dryer showing, in part, the drying gas deflector.

FIG. 2Ka is a model representation showing the modeled drying gas flow within the plenum chamber using a constant velocity magnitude surface of 15 m/s.

FIG. 2L is a schematic showing a perspective, top view of the baffle plate of the spray drying head.

FIG. 2La is a schematic showing a cut out section of the rib design of the baffle plate shown in FIG. 2L and a cut out section of another variation of the baffle plate rib design. FIG. 2La also shows a cross section of one of the ribs.

FIG. 2M is a schematic showing a perspective, bottom view of the baffle plate of the spray drying head.

Figure 2A:
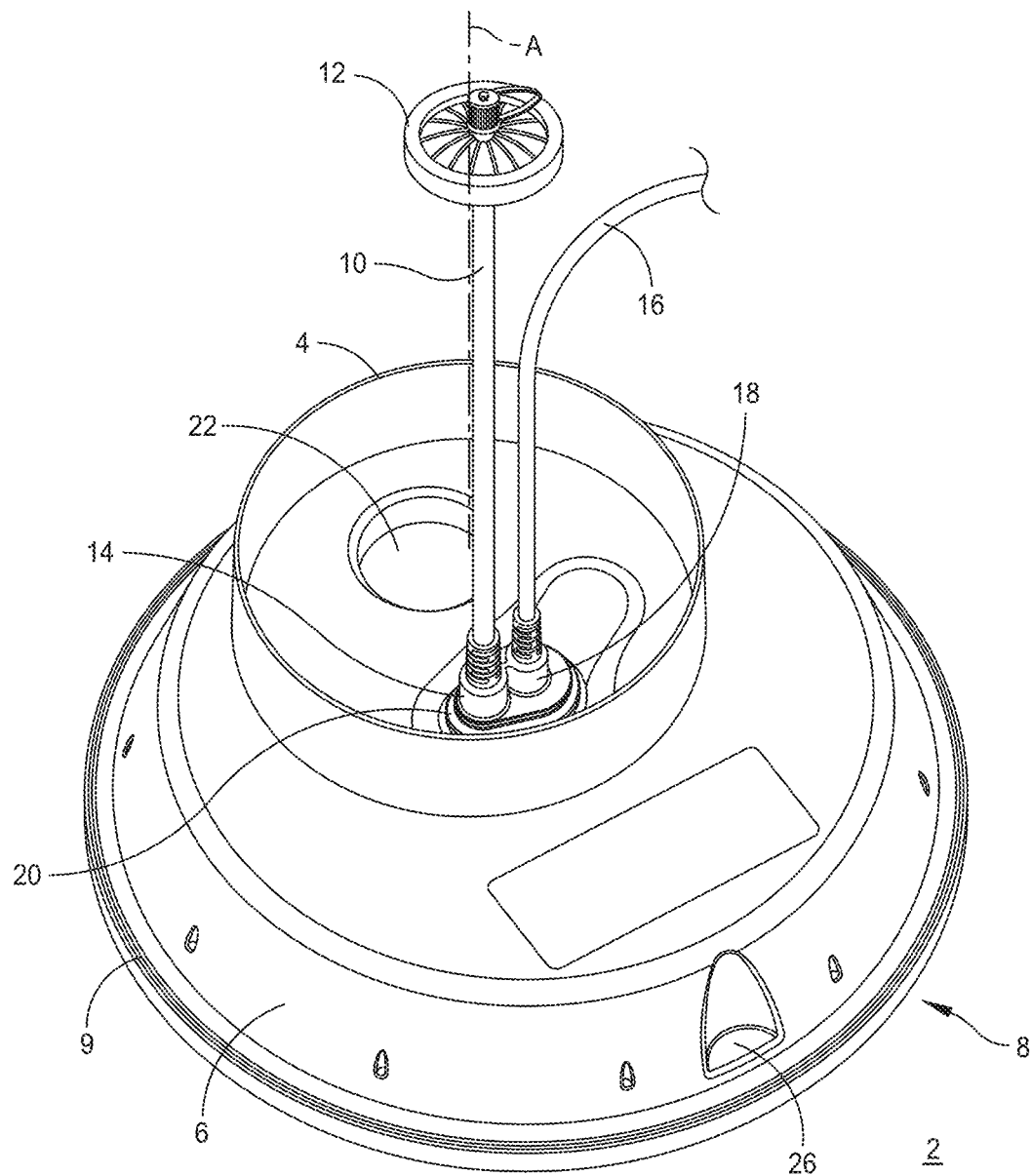
FIG. 2A is a schematic showing a perspective view of the spray drying head of the spray drying disposable device shown in FIG. 1A.
Figure 2B:
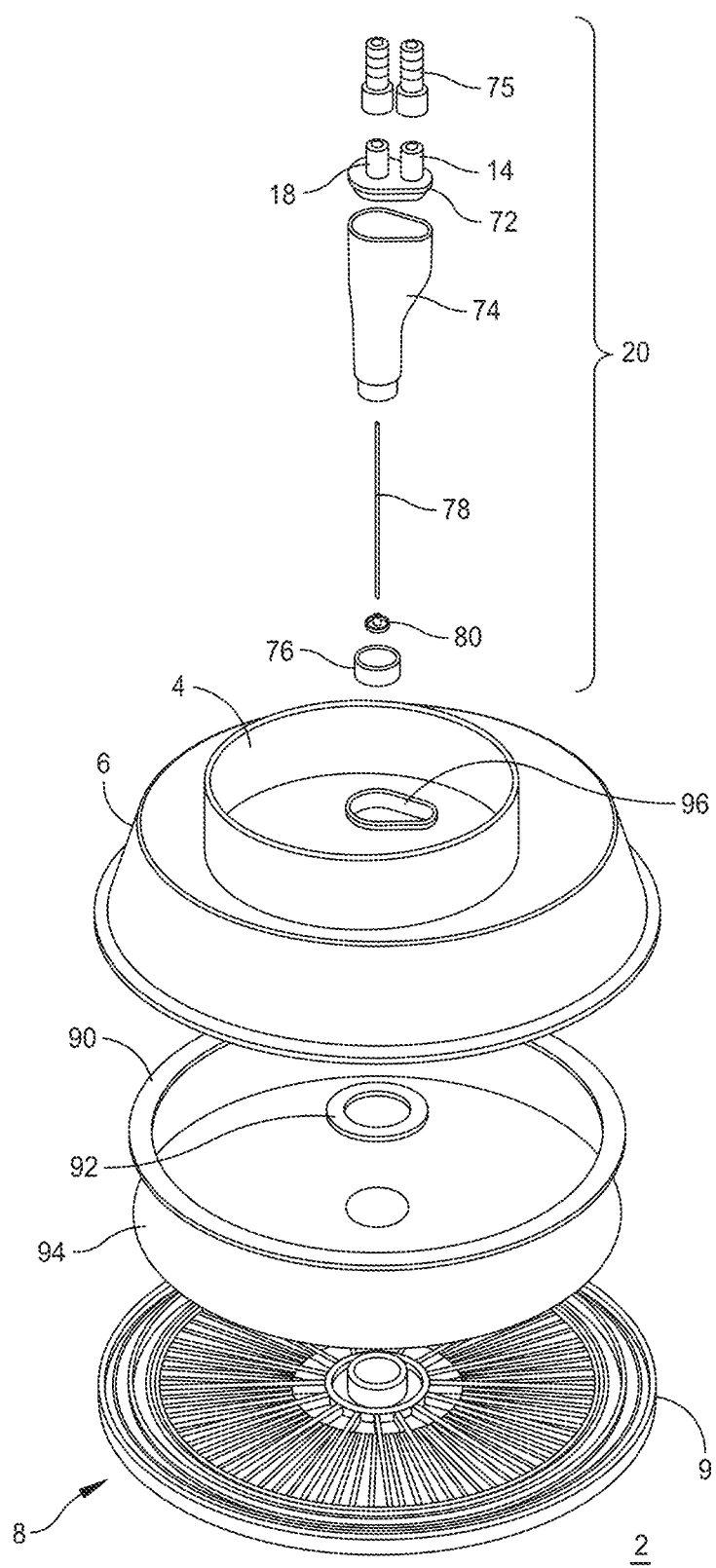
FIG. 2B is a schematic showing an exploding view of the spray dry nozzle assembly and the spray drying head of spray drying disposable device shown in FIG. 1A.
Figure 2C:
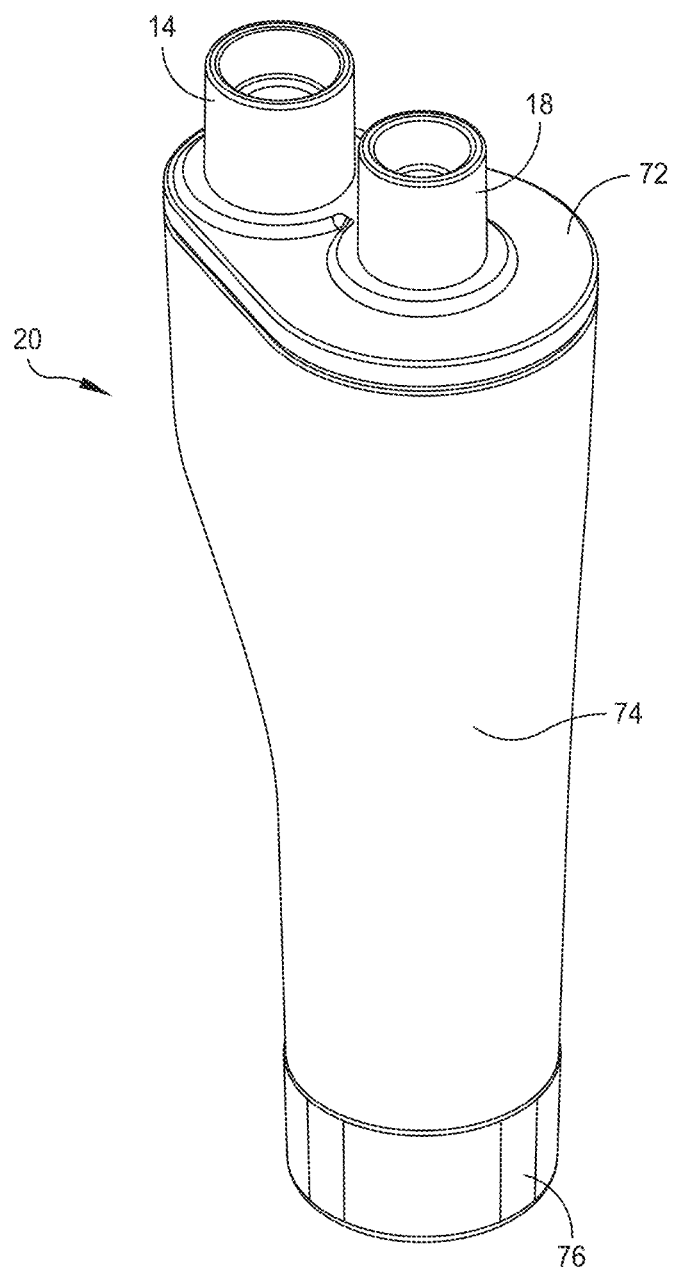
FIG. 2C is a schematic showing a perspective view of the spray dry nozzle assembly from the spray drying head of spray drying disposable device.
Figure 2D:
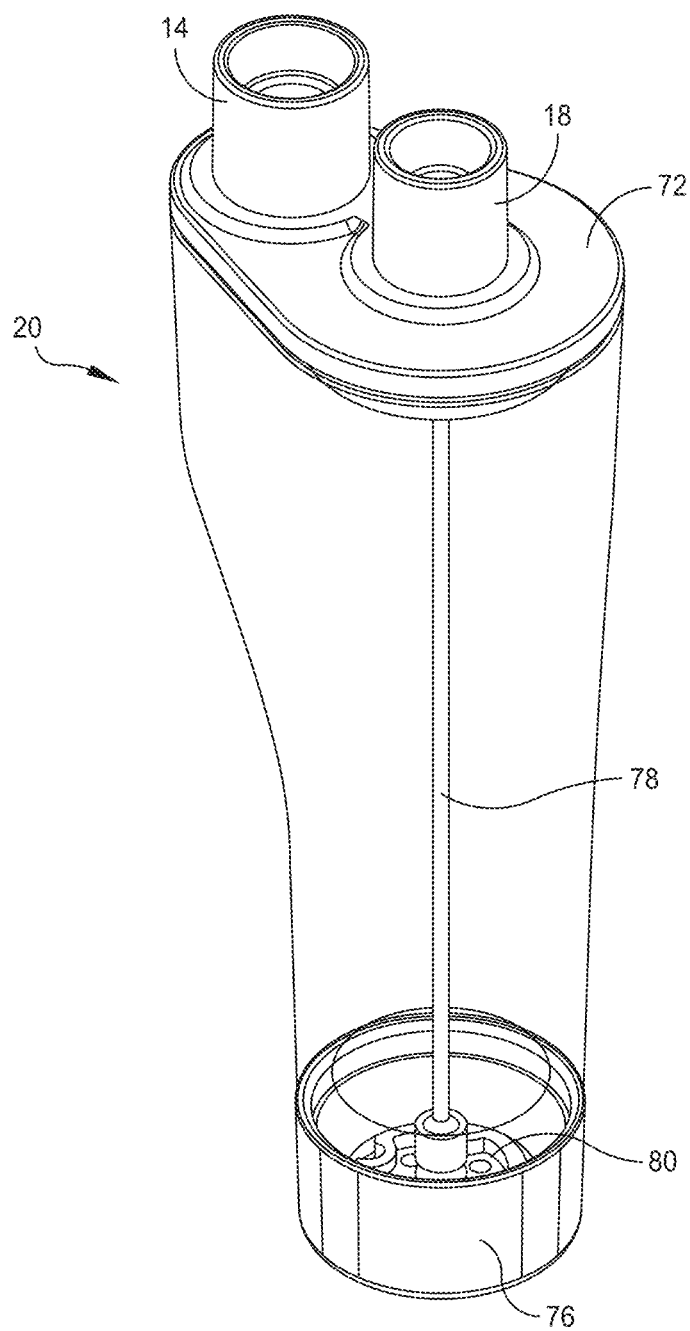
FIG. 2D is a schematic showing a perspective view of the spray dry nozzle assembly of FIG. 2 but with the aerosol reservoir housing being transparent to show the inner structures of the assembly.
Figure 2E:
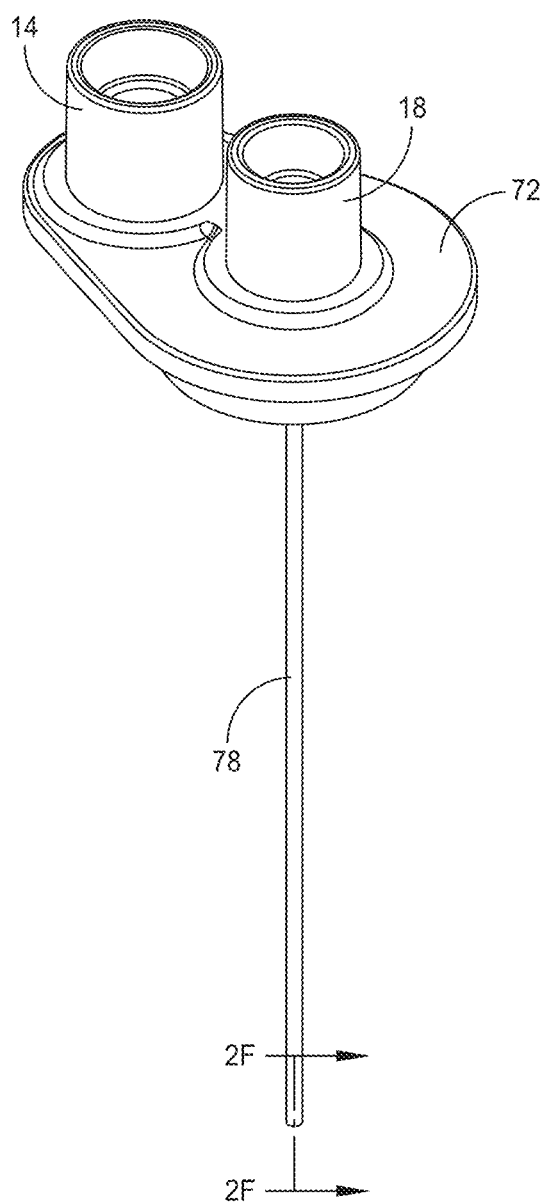
FIG. 2E is a schematic showing a perspective view of the spray dry nozzle assembly of FIG. 2 but with the aerosol reservoir housing, the nozzle cap and nozzle cap insert being removed and showing the manifold and the cannula.
Figure 2F:
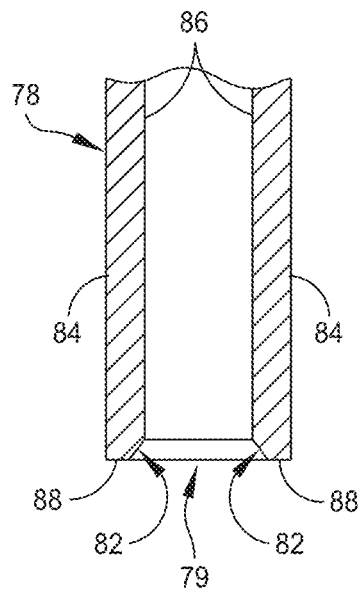
Figure 2G:
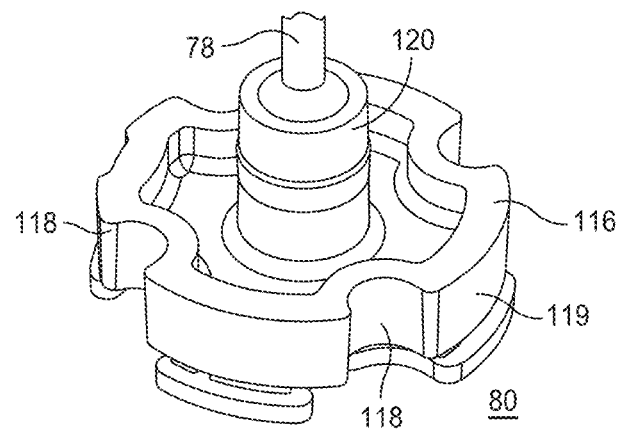
Figure 2H:
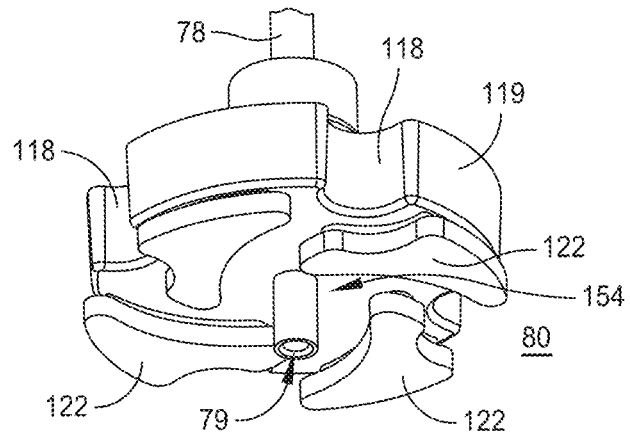
Figure 2I:
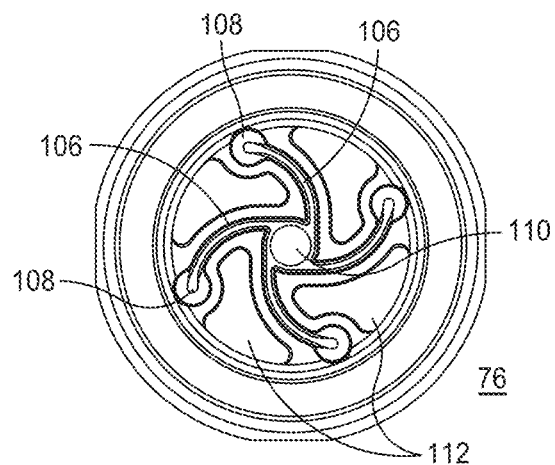
Figure 21A:
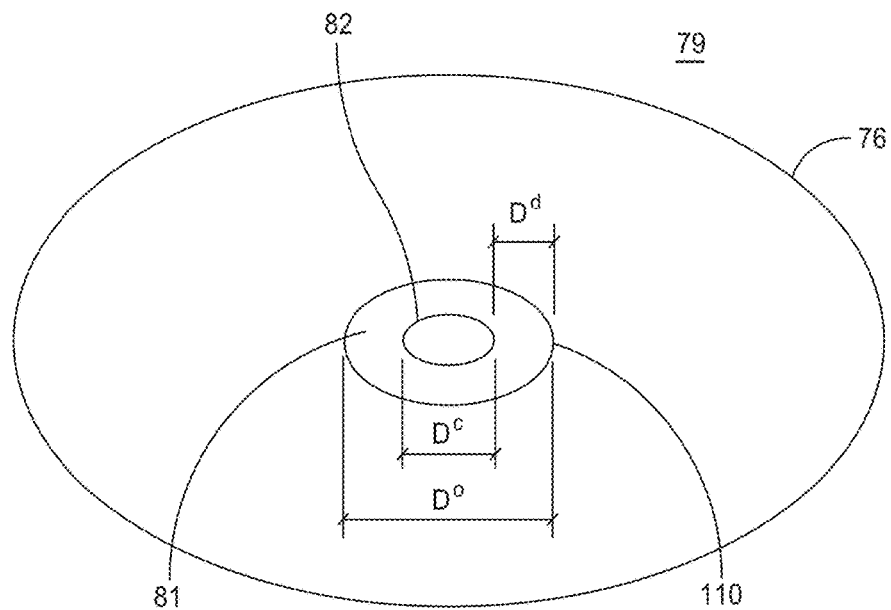
Figure 21B:
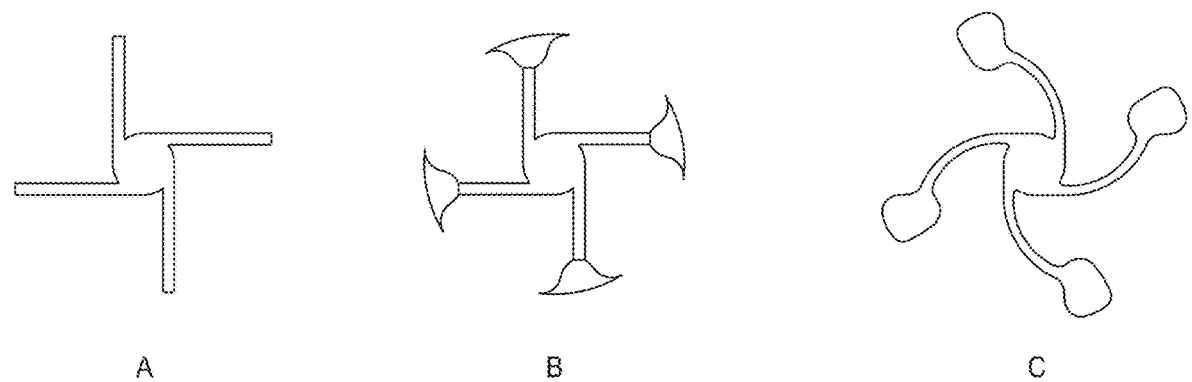
Figure 21C:
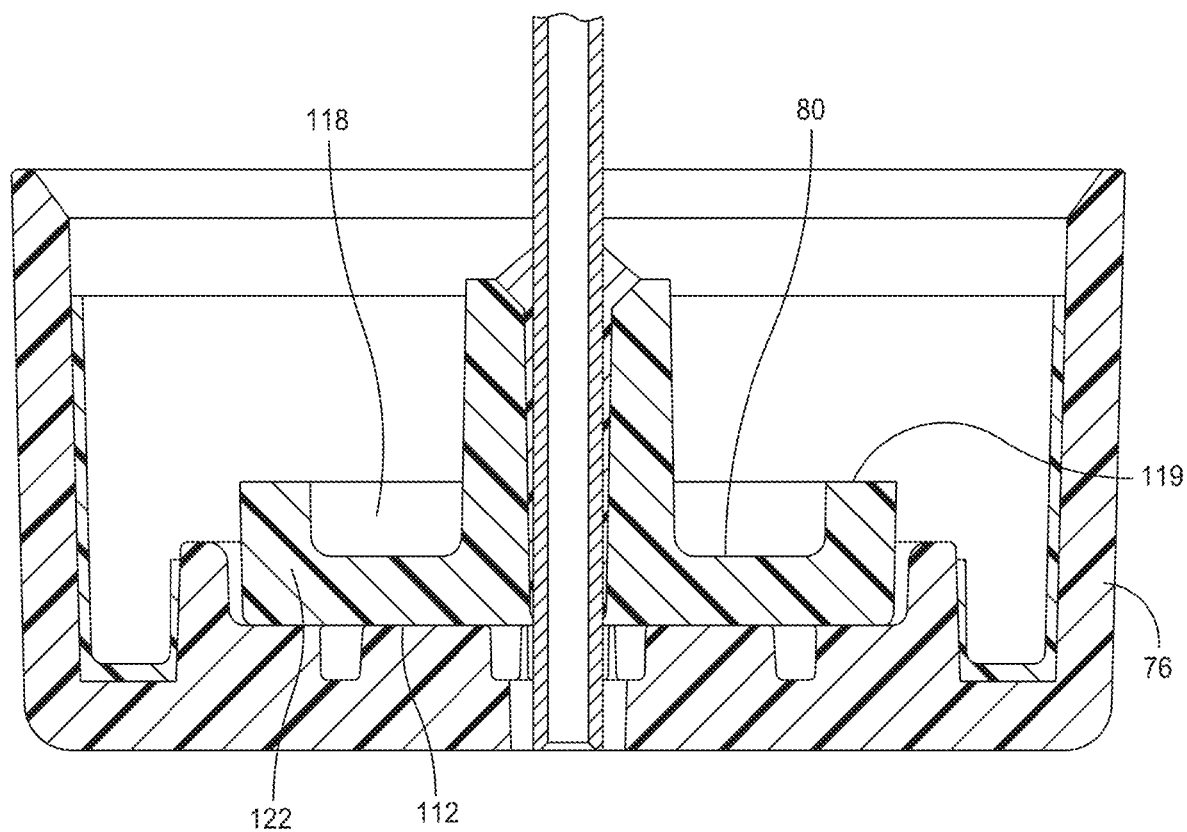
Figure 2J:
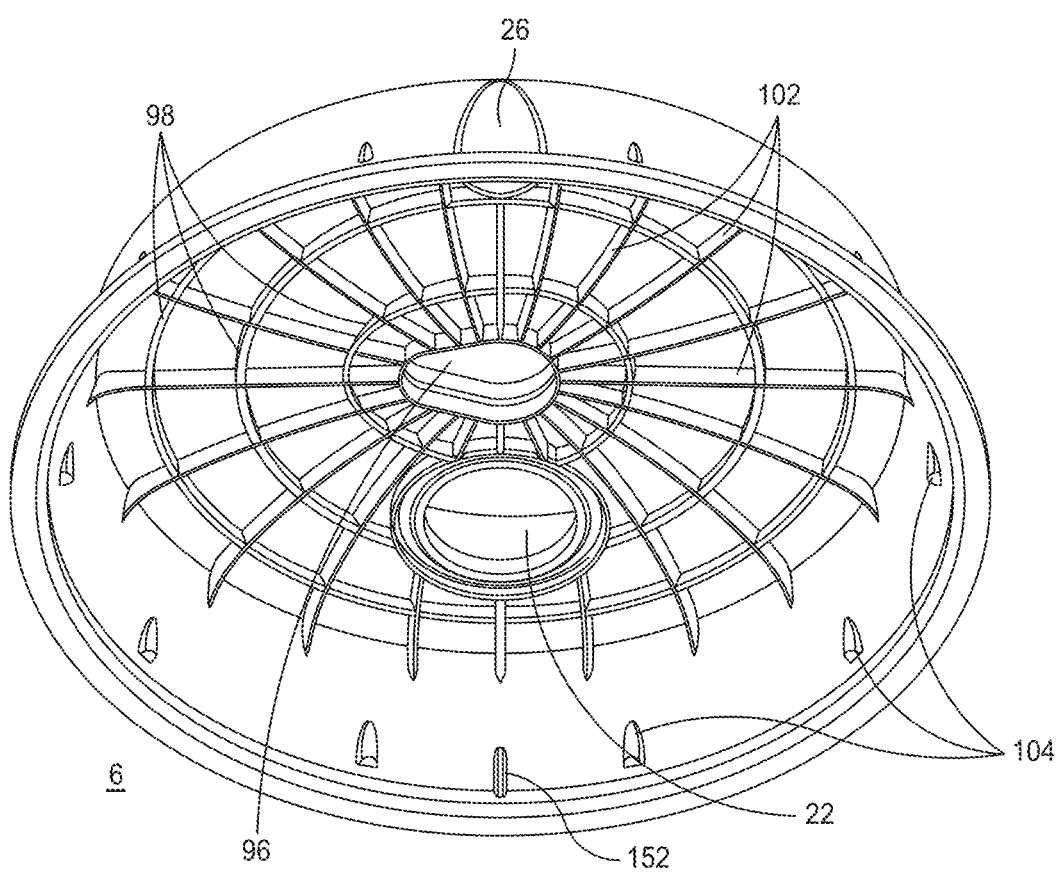
Figure 2K:
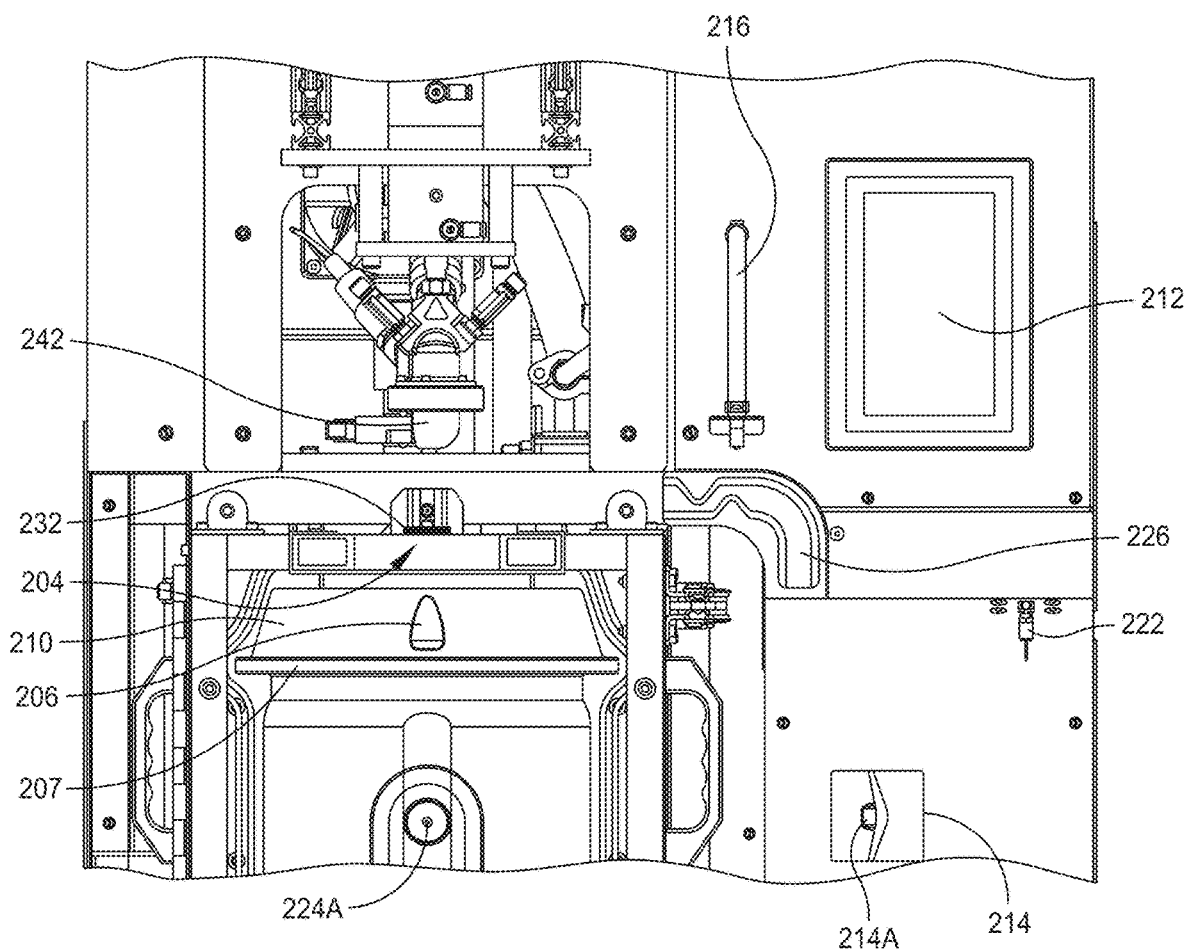
Figure 2K:
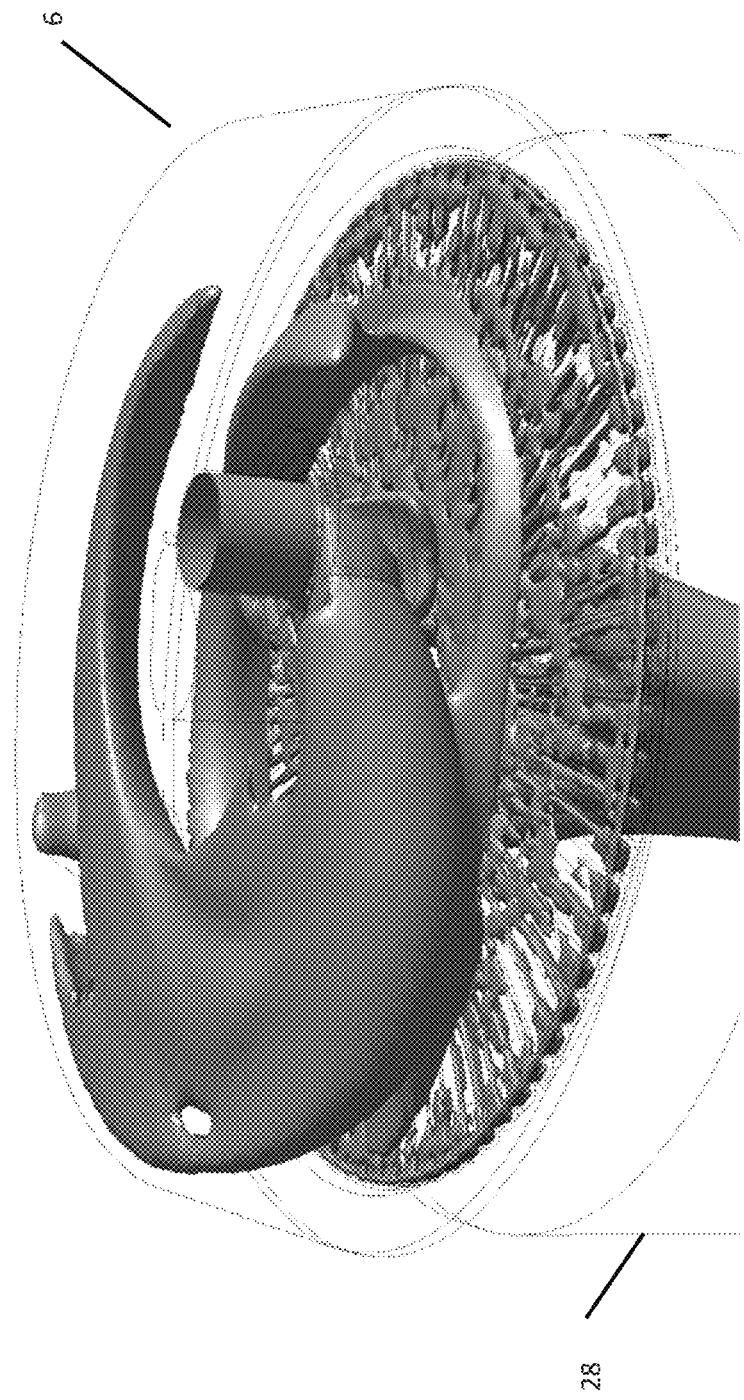
Figure 2L:
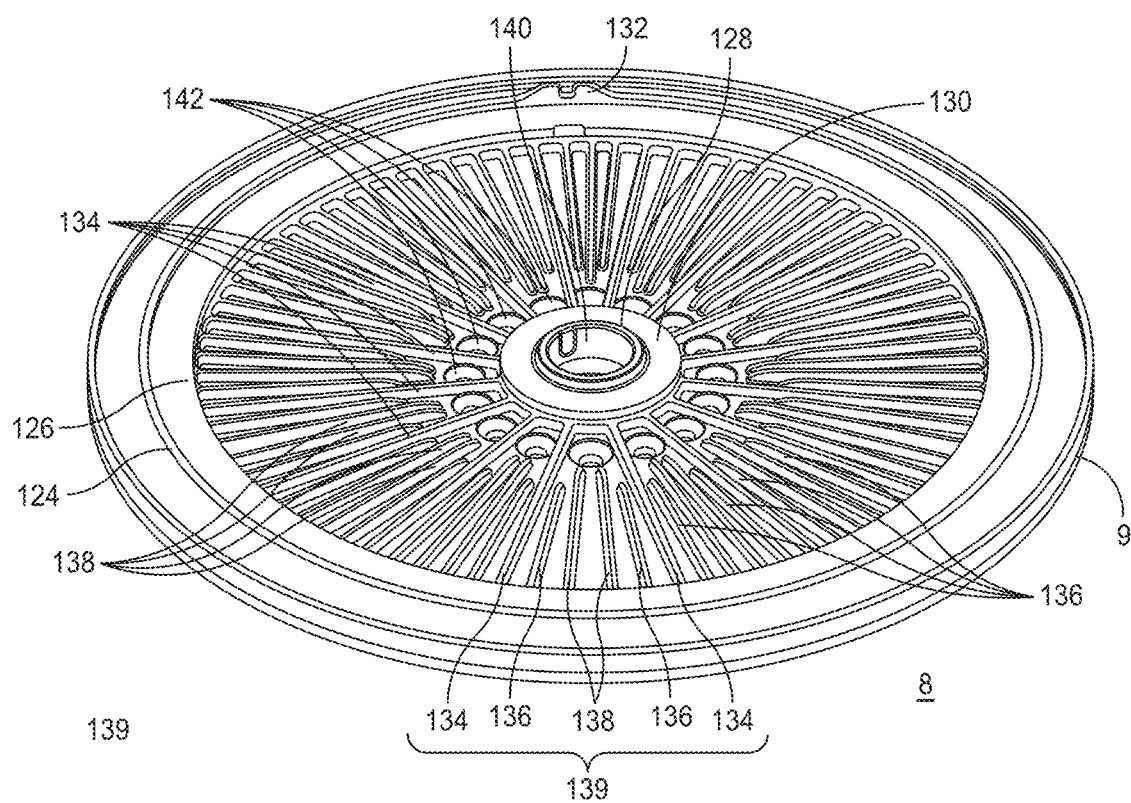
Figure 2L:
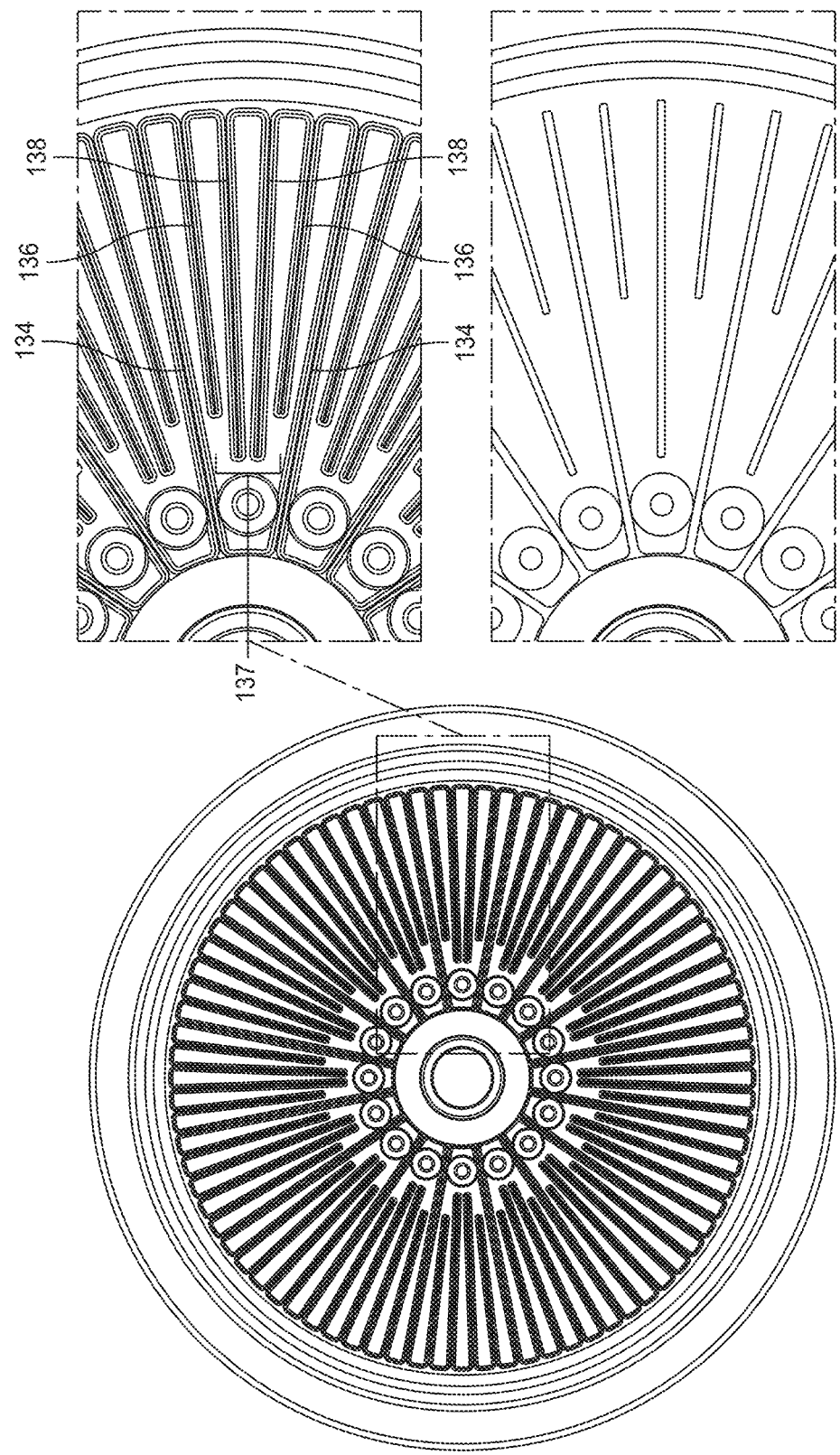
Figure 2M:
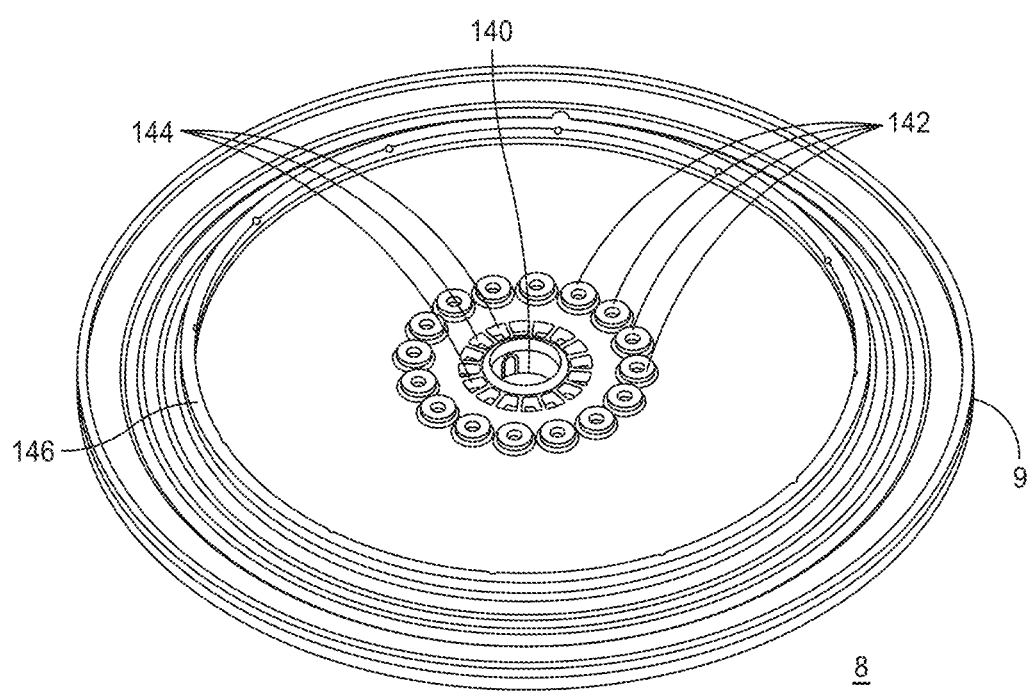
Figure 2M:
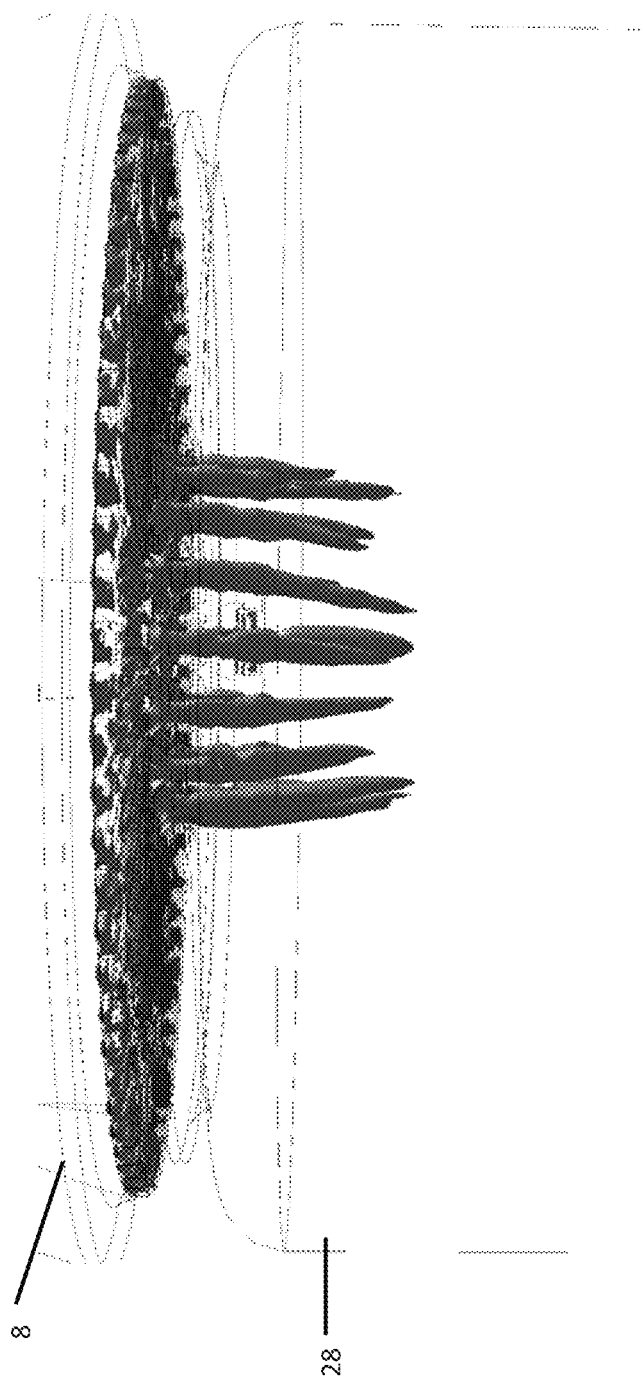

FIG. 2Ma is a model representation showing uniform jet penetration and drying gas distribution at constant velocity of 25 m/s and hence results in a circumferentially uniform introduction of the drying gas around the spray plume.

Figure 2N:
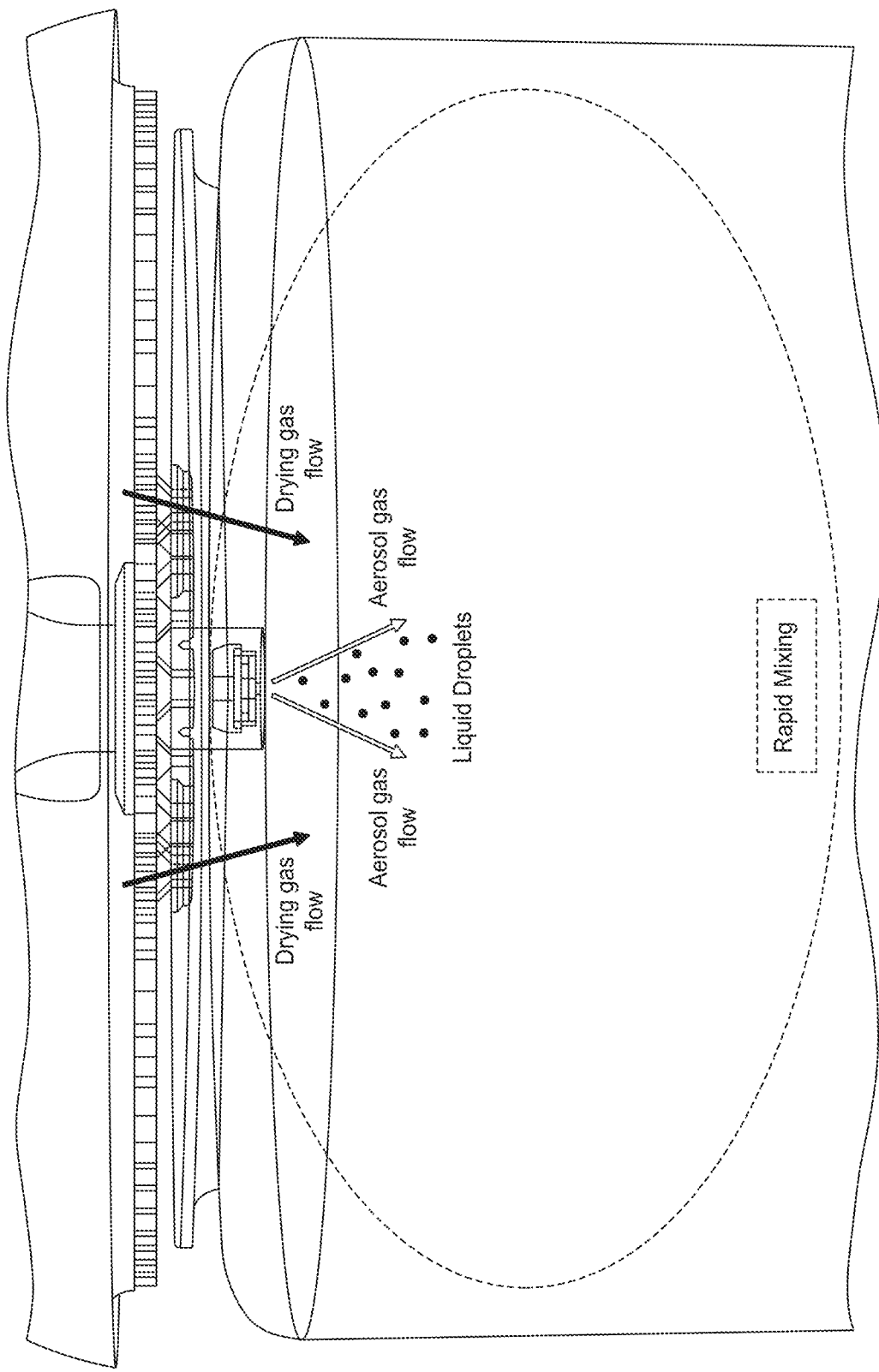
Figure 2N:
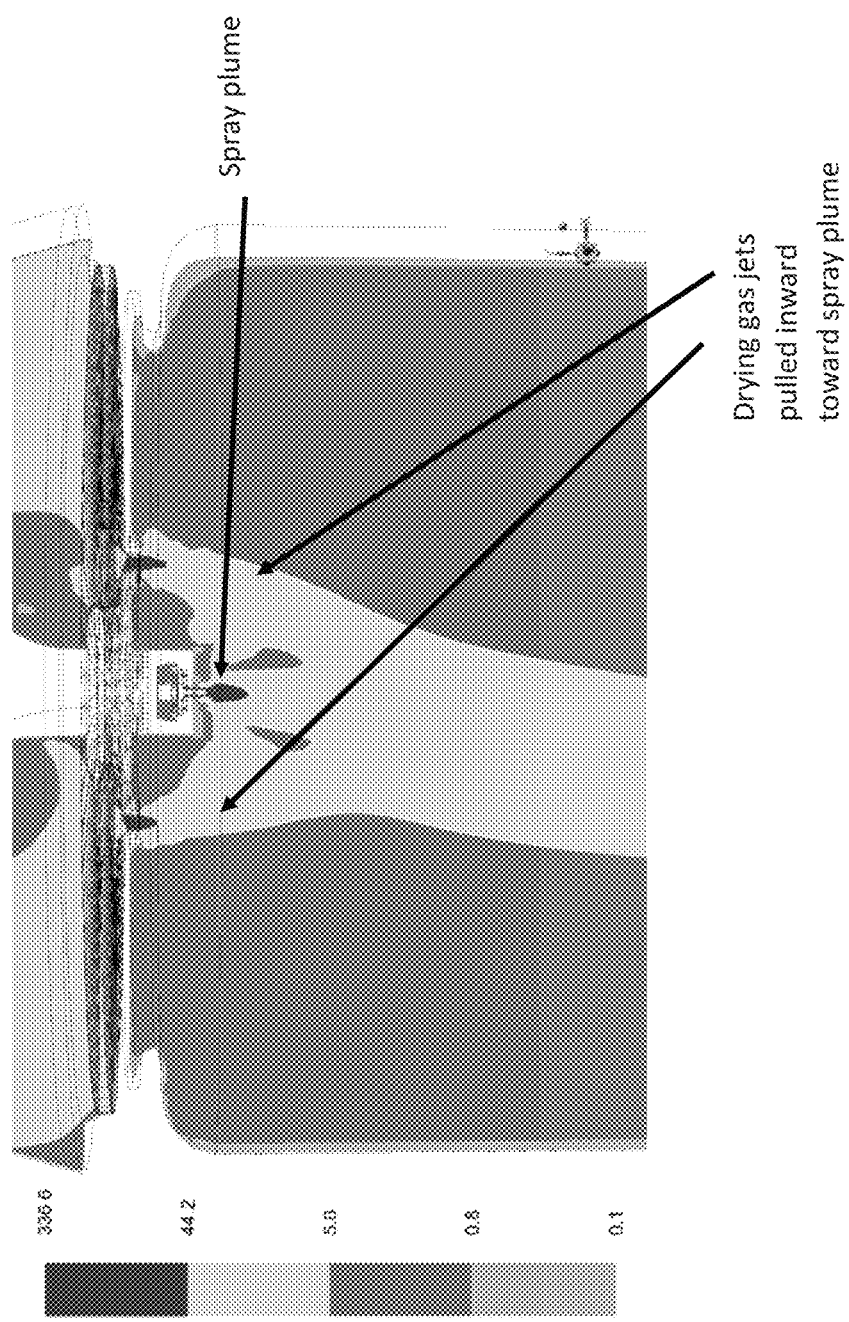

FIG. 2N is a schematic showing a schematic showing the droplet plume formation, aerosol gas flow and drying gas flow that promotes rapid mixing in the disposable of the present invention.

FIG. 2Na is a model representation displaying the gas velocity magnitude contours within the disposable's center plane indicating the drying jet penetration into the drying chamber and the effect of baffle plate flow channels and interaction with the high velocity spray plume which act to pull the drying gas jets radially inward to assist in the desired rapid mixing of the droplets and gas flows.

FIG. 2O is a model representation showing the gas pressure flow (psig) (top) and tangential velocity flow (m/s) (bottom) of the vortex generated in the nozzle insert and cap assembly.

FIG. 2P is a model representation showing gas velocity magnitude flow (m/s) in parts of the vortex generator.

Figure 2Q:
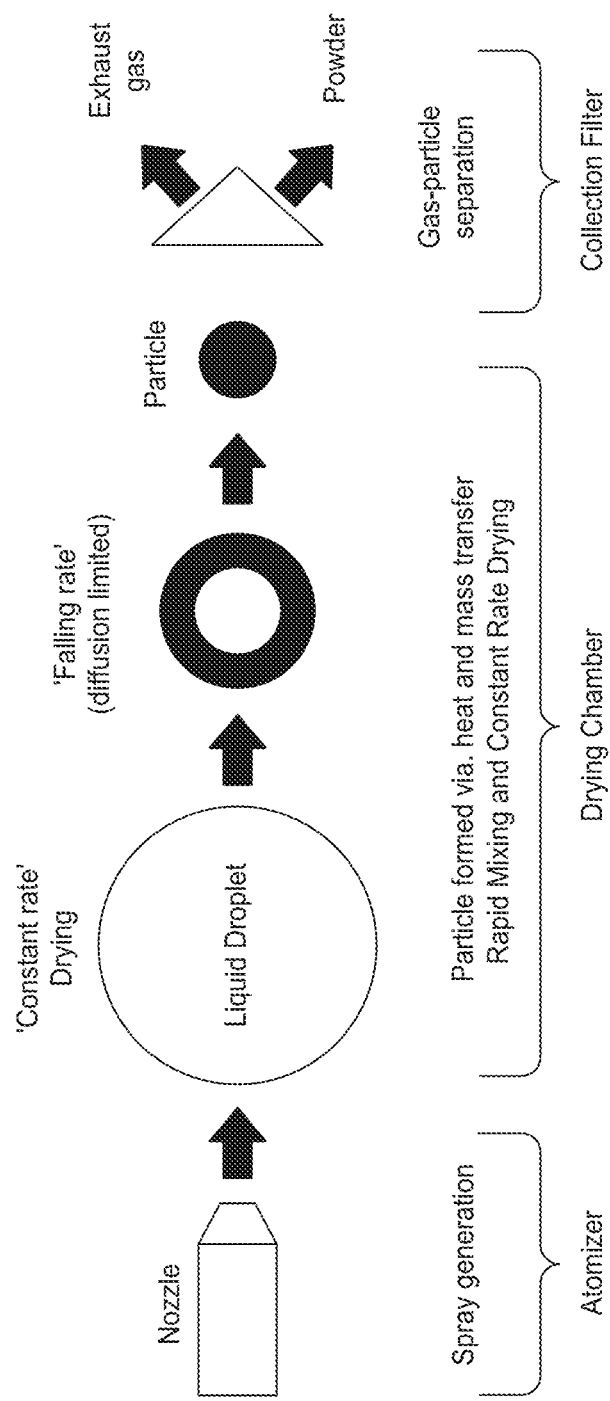

FIG. 2Q is a schematic showing the transformation of a liquid droplet to a dried particle using the disposable of the present invention.

Figure 2R:
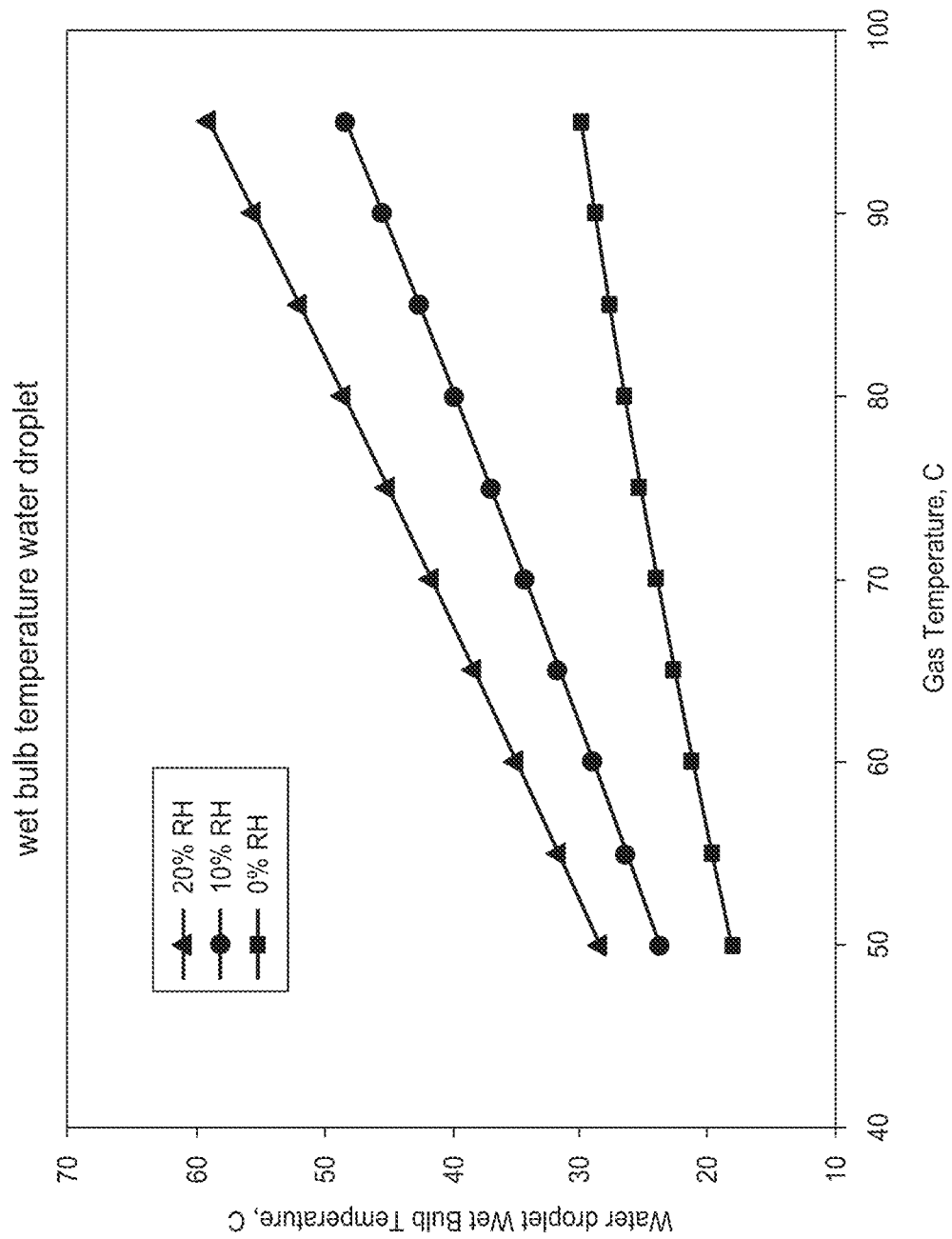

FIG. 2R is a line graph showing the droplet wet bulb temperature in ° C. and drying gas temperature in ° C. of water droplets dried to particles having 0% Relative Humidity (RH), 10% RH and 20% RH. This particular graph illustrates the concept but is not specific to plasma.

Figure 2S:
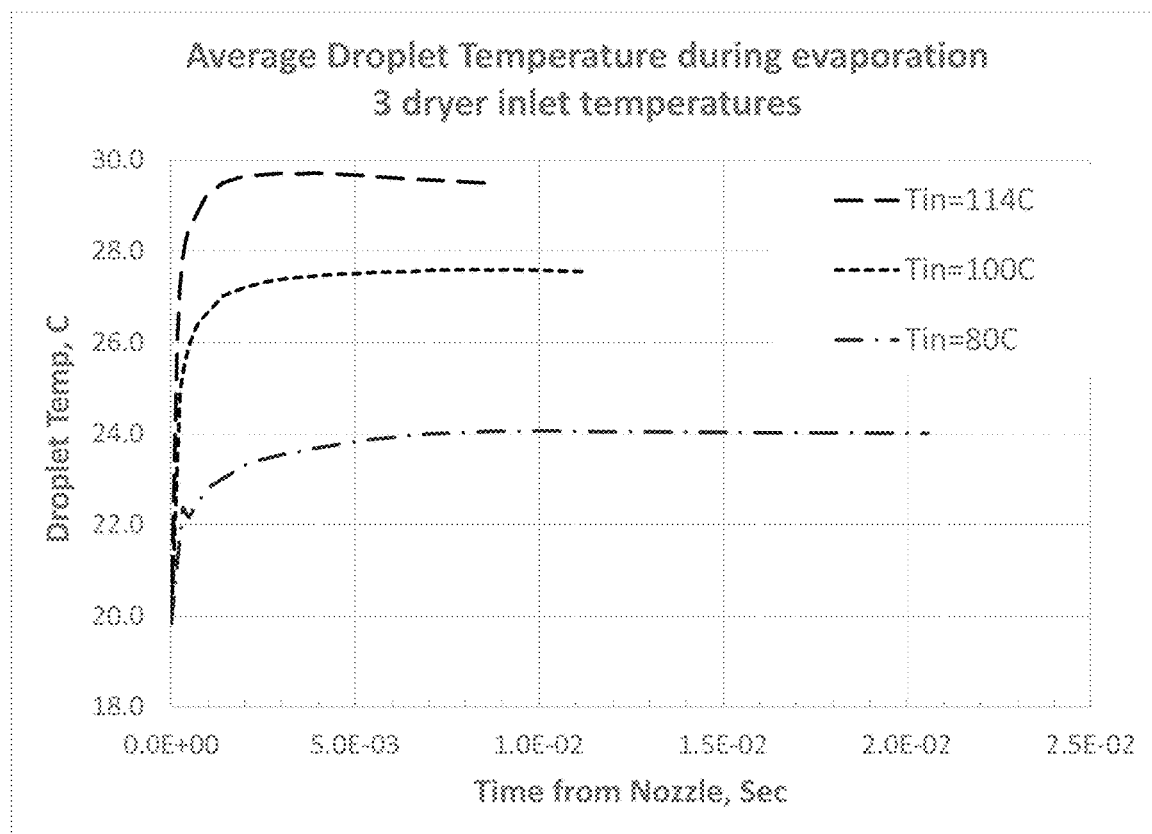
Figure 2S:
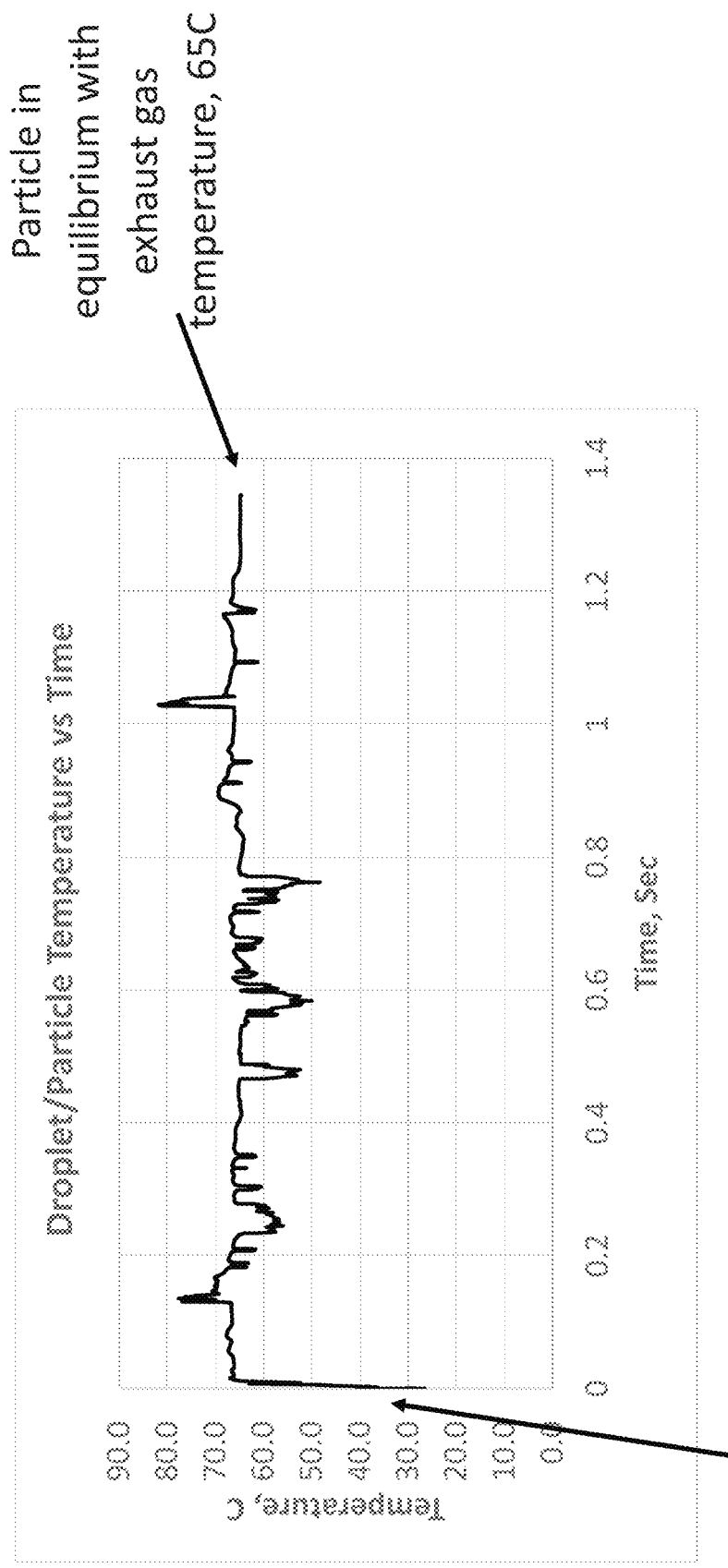

FIG. 2S is a line graph showing the evaporation mass transfer of droplet temperatures over time for all the averaged droplet trajectories average with three simulated drying gas inlet temperatures of 80° C., 100° C., and 114° C. in the model. Note the evaporation process cools the droplet to keep the delicate liquid protein below 30° C.

FIG. 2Sa is a line graph temperature in ° C. and time (seconds) of a plasma droplet as it becomes a particle in the model. Once the evaporation is complete, the protein encased in a solid particle is more tolerant of elevated temperature as it equilibrates with the dryer outlet temperature. In this case, evaporation occurs in less than fractions of a second (e.g., 0.01 to 0.05 seconds).

Figure 2T:
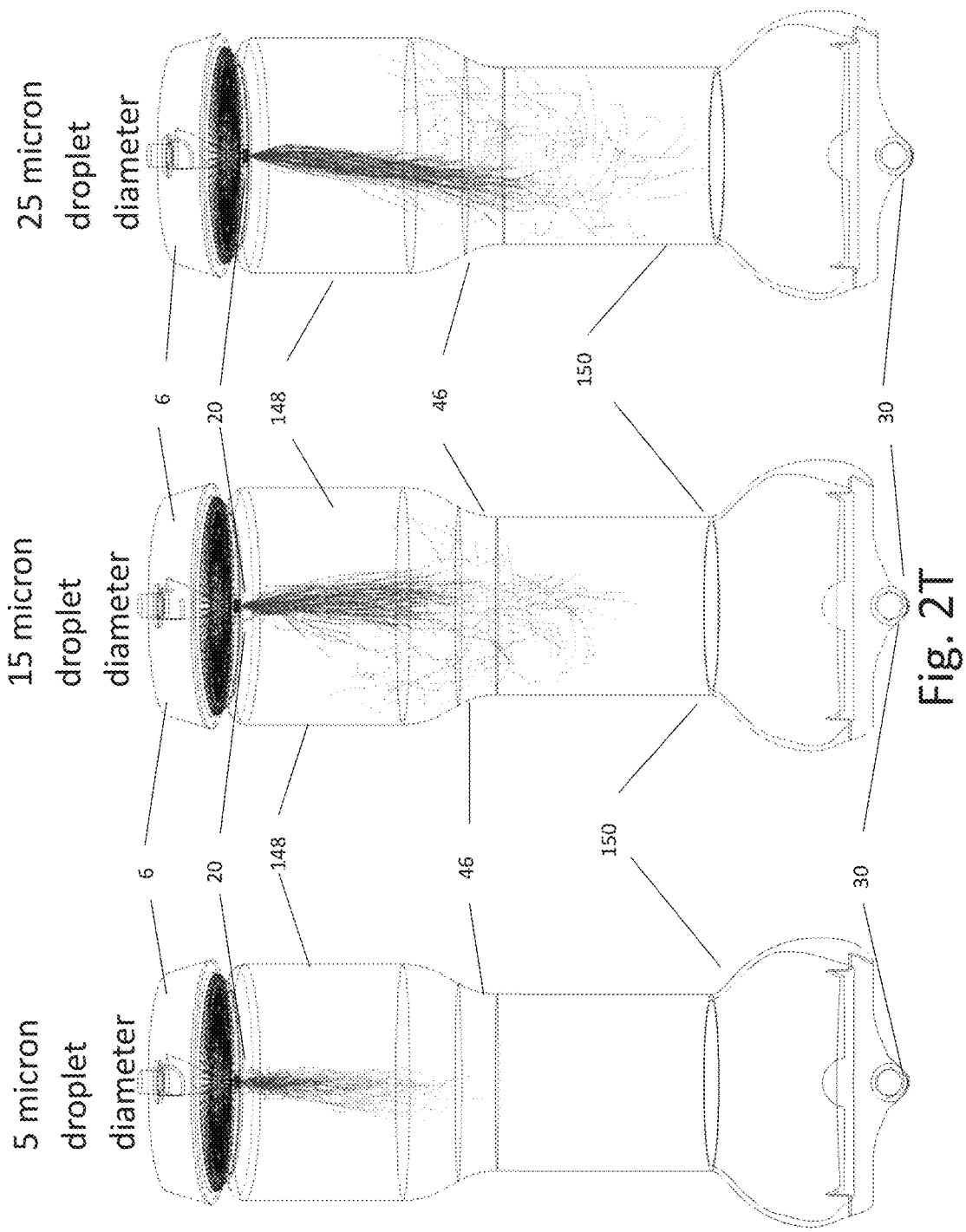

FIG. 2T is a model representation showing the path of droplets having a size of 5 microns, 15 microns and 25 microns, during evaporation, and the figure shows that smaller droplet size allows for more rapid evaporation mass transfer in a shorter path, enabling a physically smaller drying chamber.

Figure 1A:
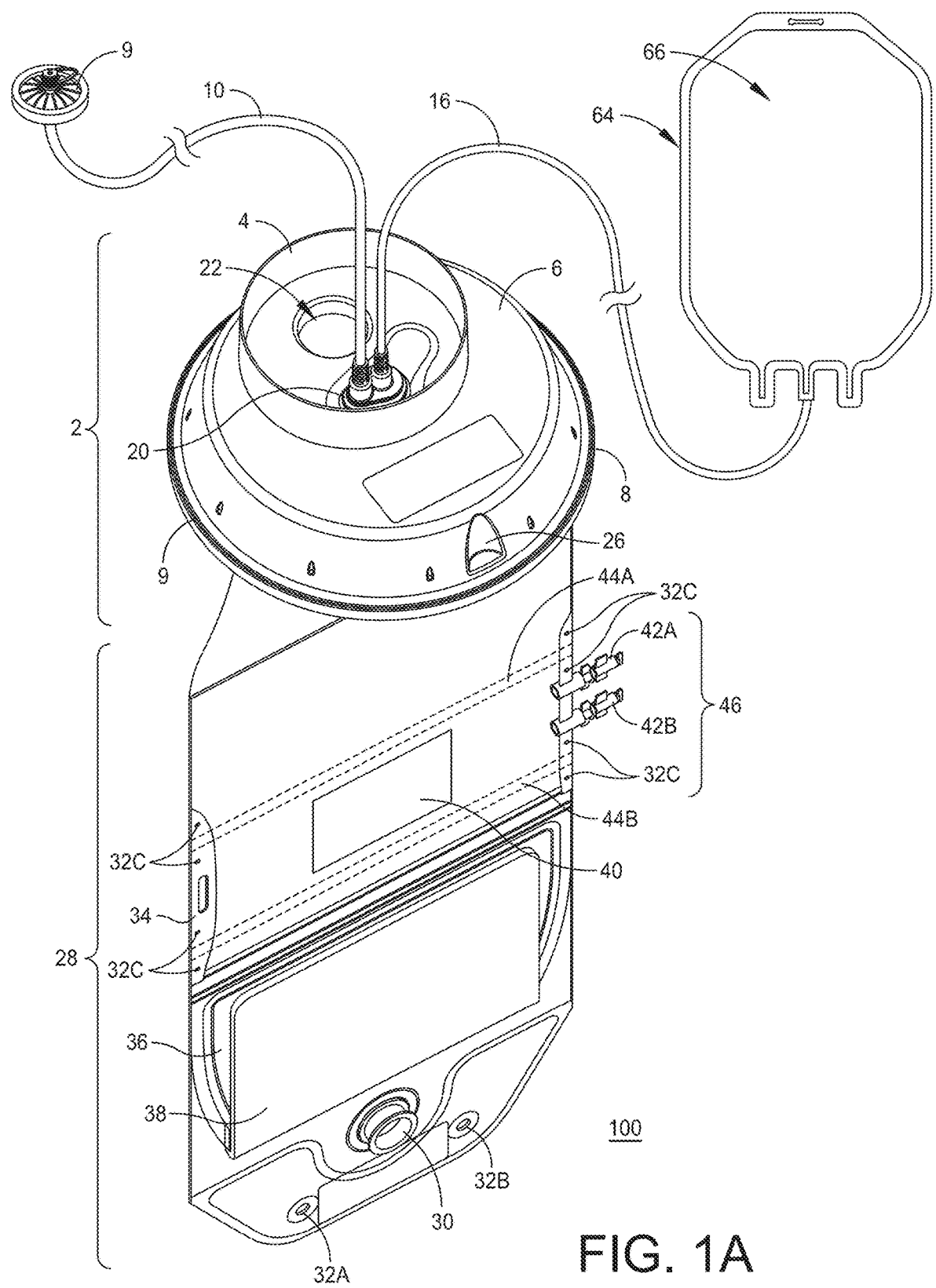
FIG. 1A is a schematic showing a perspective view of the spray drying disposable device, which includes the liquid plasma bag, spray drying head and spray drying chamber, wherein the disposable has alignment elements which allow it to align with a spray drying apparatus and a finishing apparatus.
Figure 3:
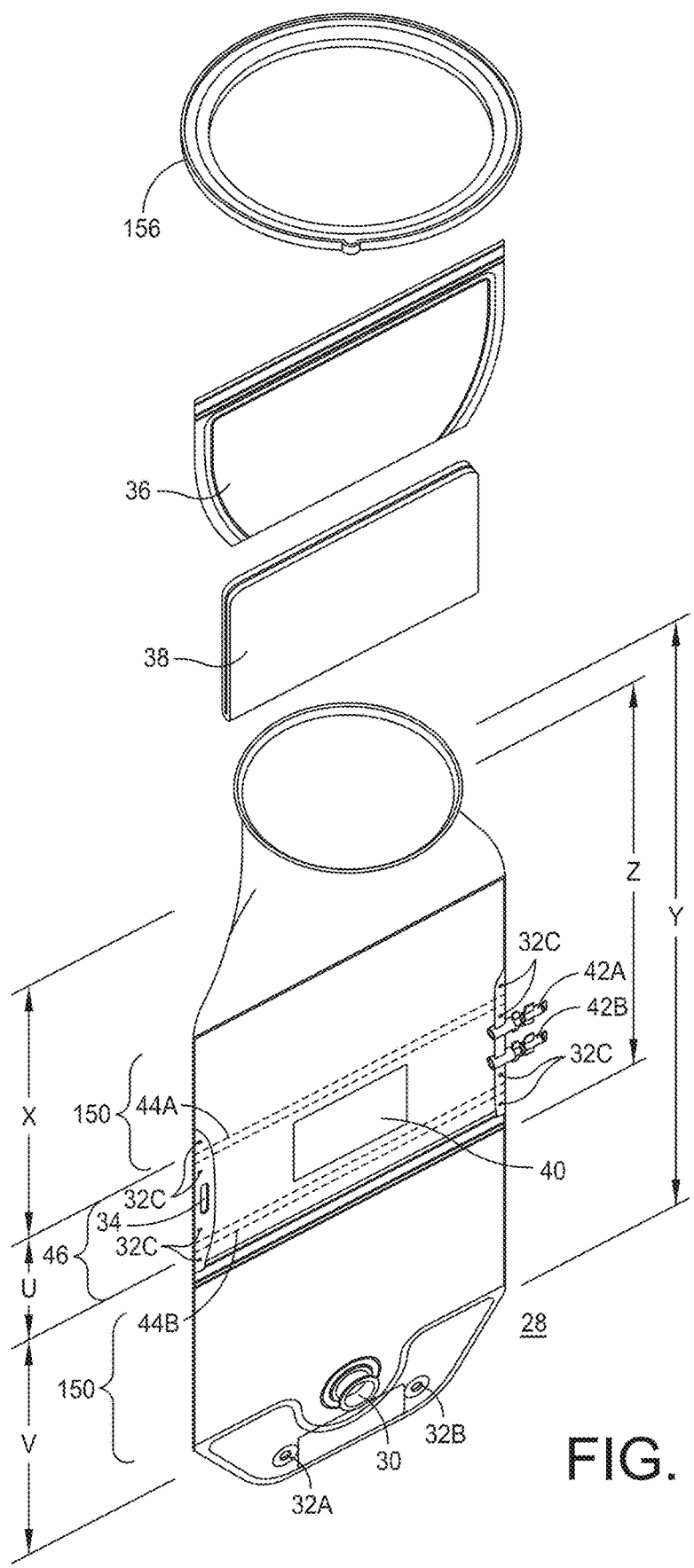

FIG. 3 is a schematic showing an exploding view of the drying chamber of the spray drying disposable shown in FIG. 1A.

Figure 4A:
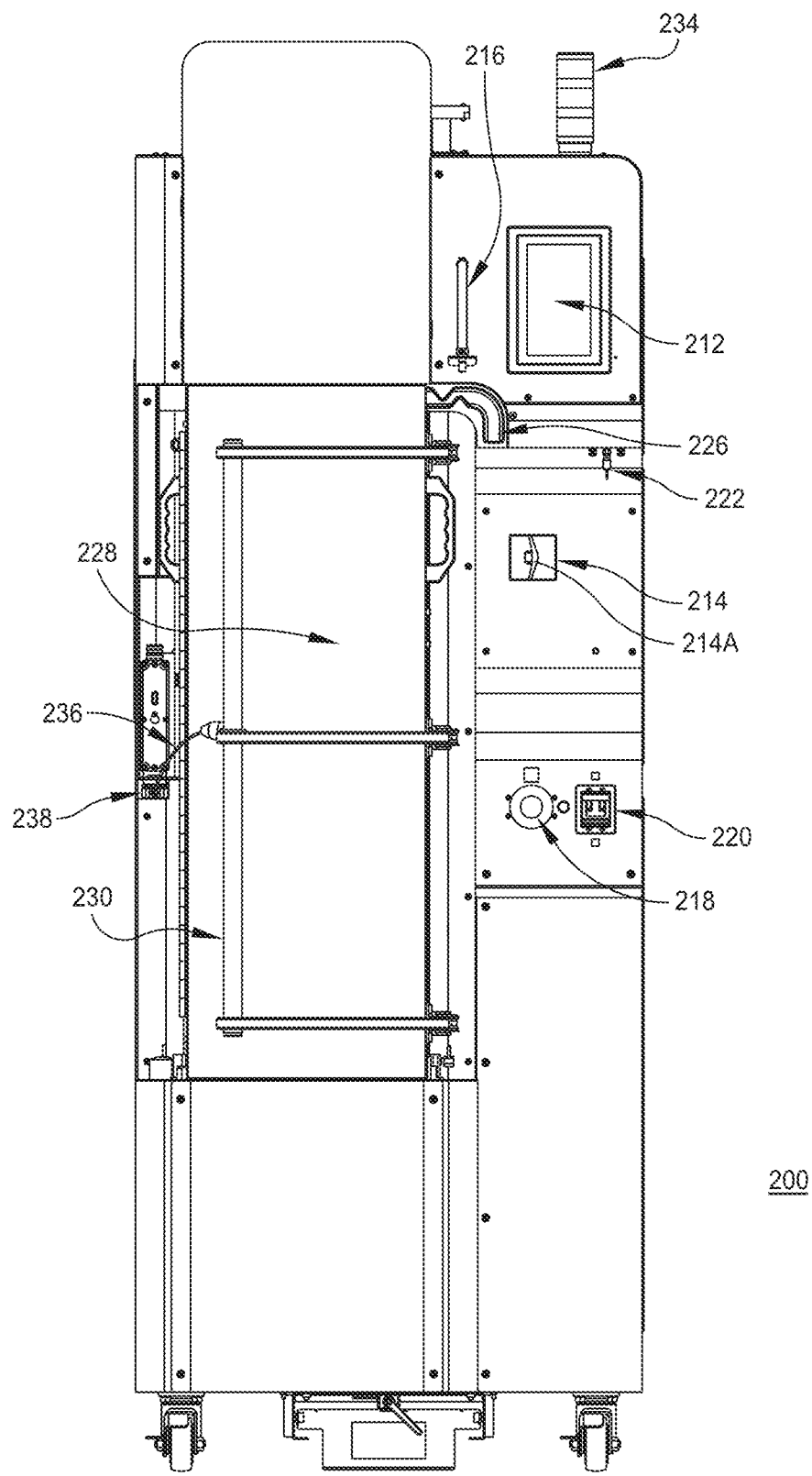

FIG. 4A is a schematic showing a front view of the spray drying apparatus with the door closed.

Figure 4B:
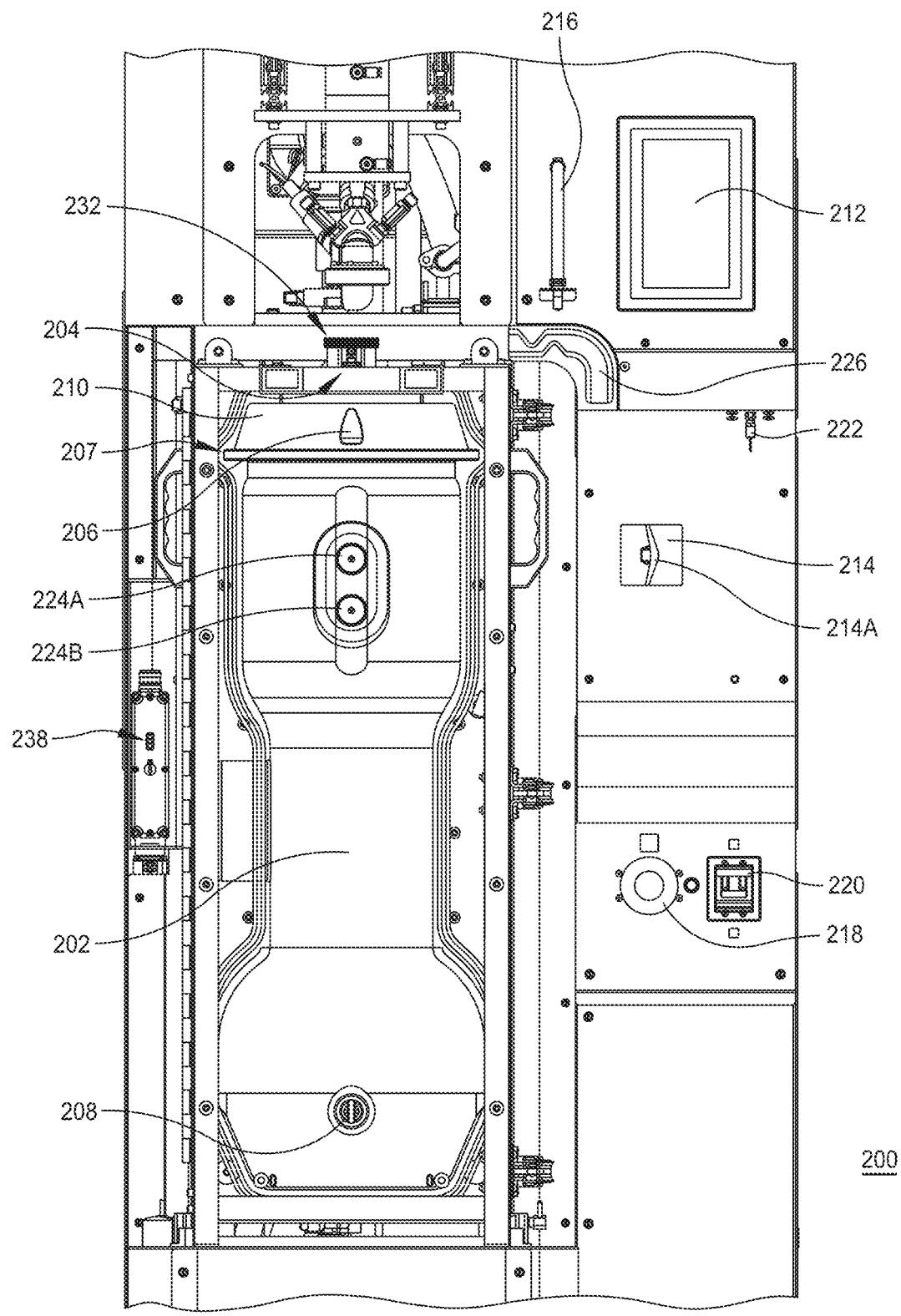

FIG. 4B is a drawing of a partial front view of the spray drying apparatus without the door to reveal the drying chamber housing having alignment elements that allow for alignment with the spray drying disposable device.

Figure 4C:
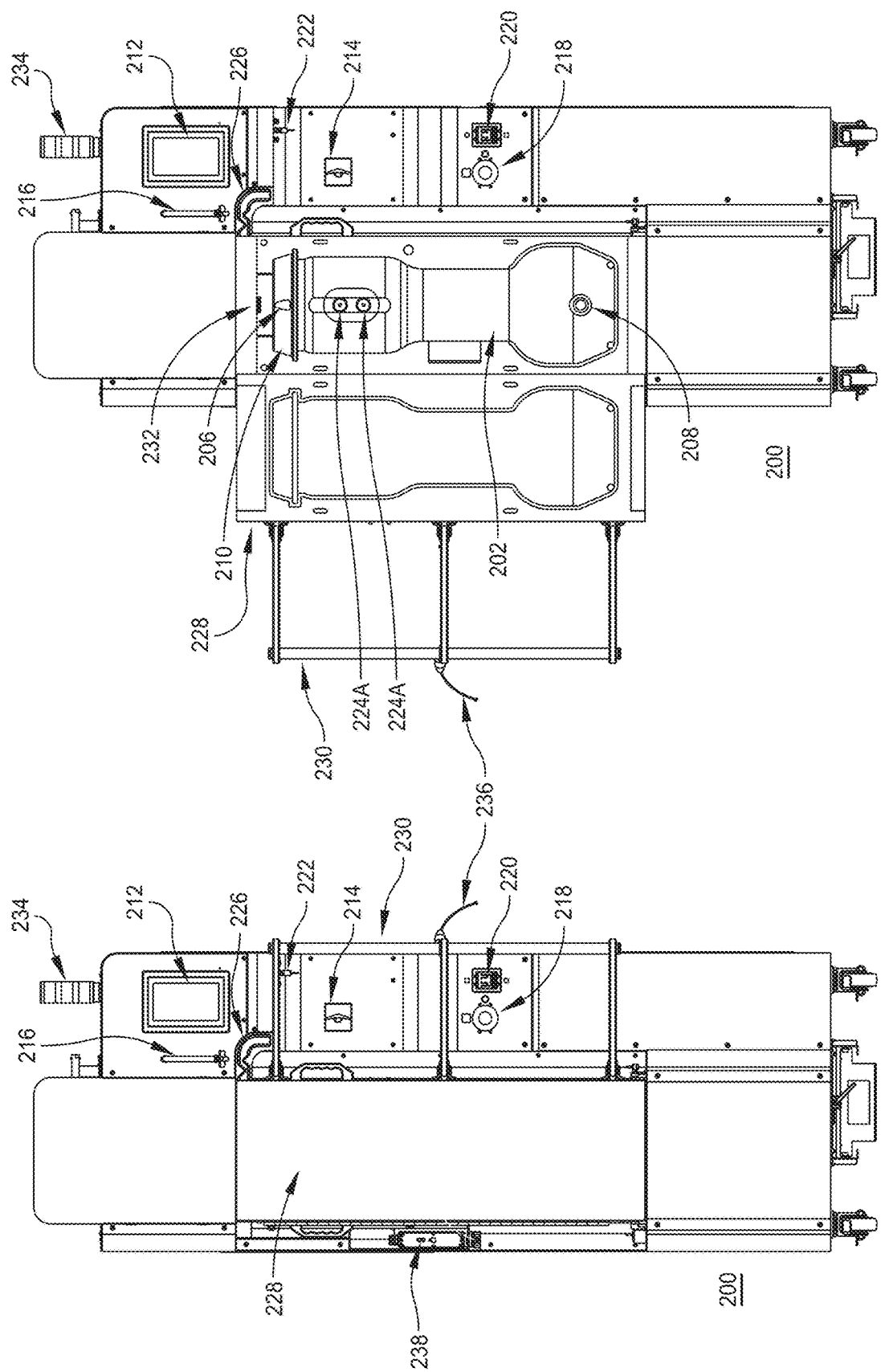

FIG. 4C is a schematic showing a front view of the spray drying apparatus with handle of the door being engaged and the door being opened.

Figure 5A:
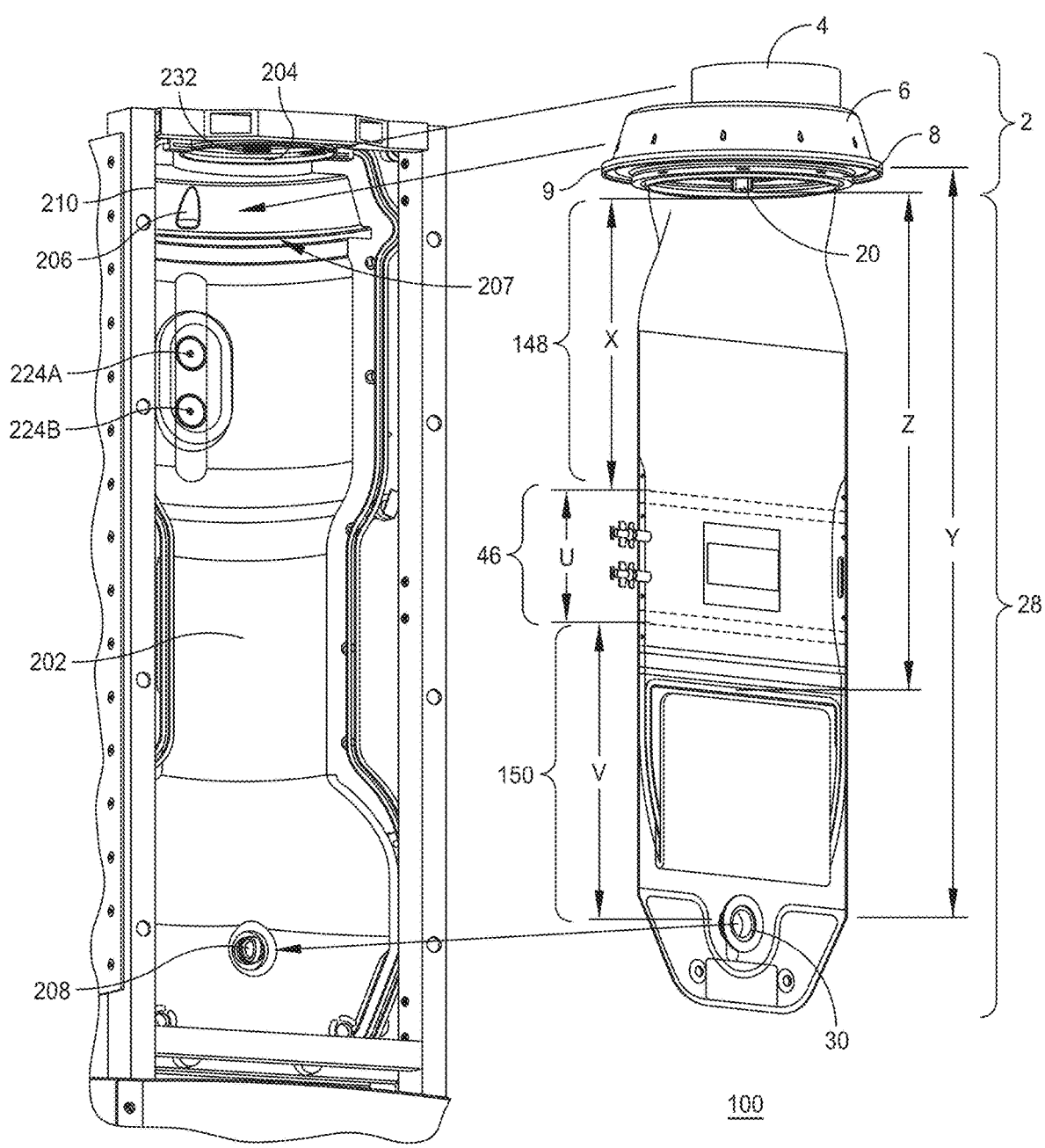

FIG. 5A is a schematic showing the alignment elements aligning the spray drying disposable device and the spray drying apparatus.

Figure 5B:
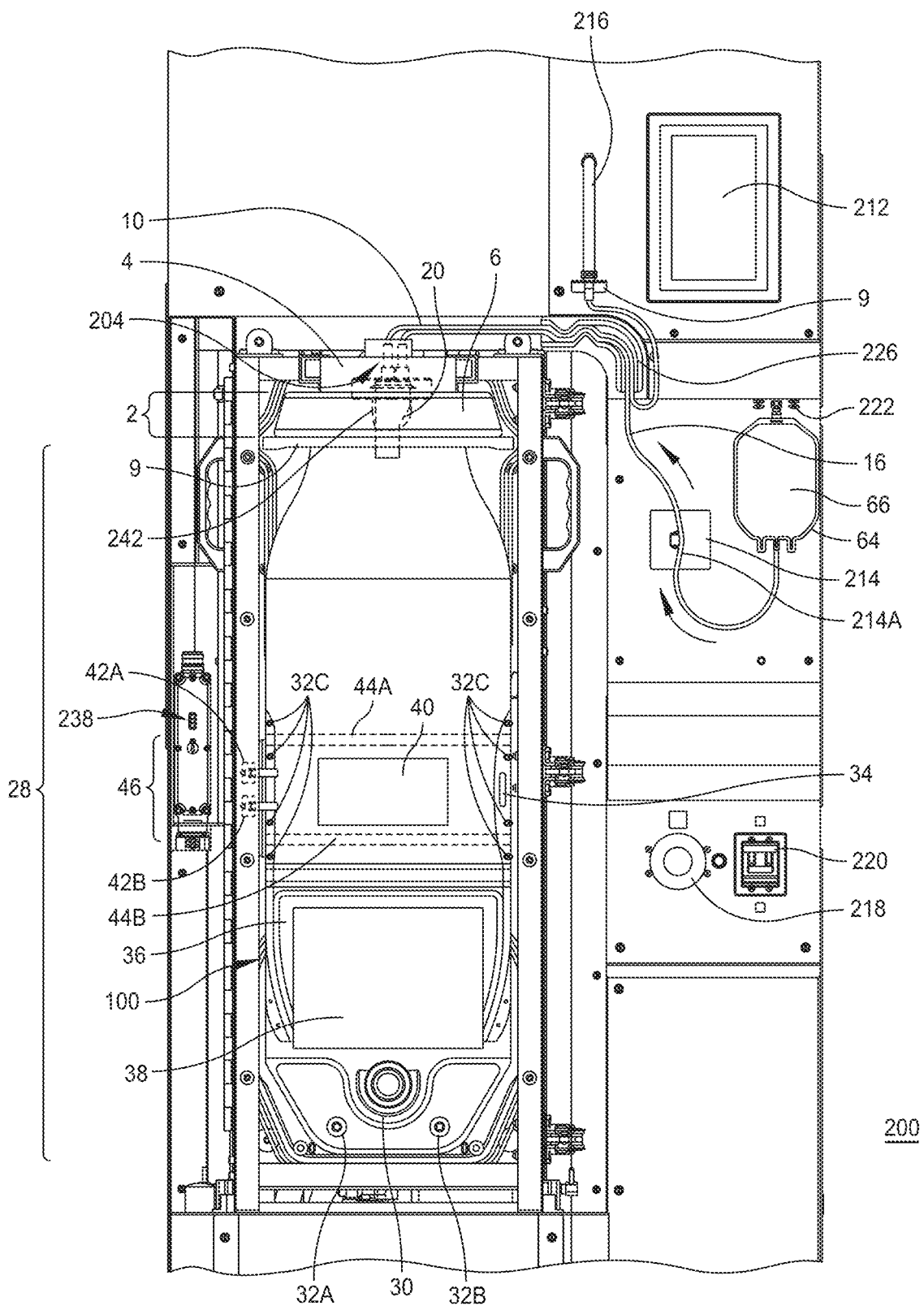

FIG. 5B is a schematic showing a partial front view of the spray drying apparatus without the door and with the spray drying disposable device installed and deflector engaged.

Figure 6A:
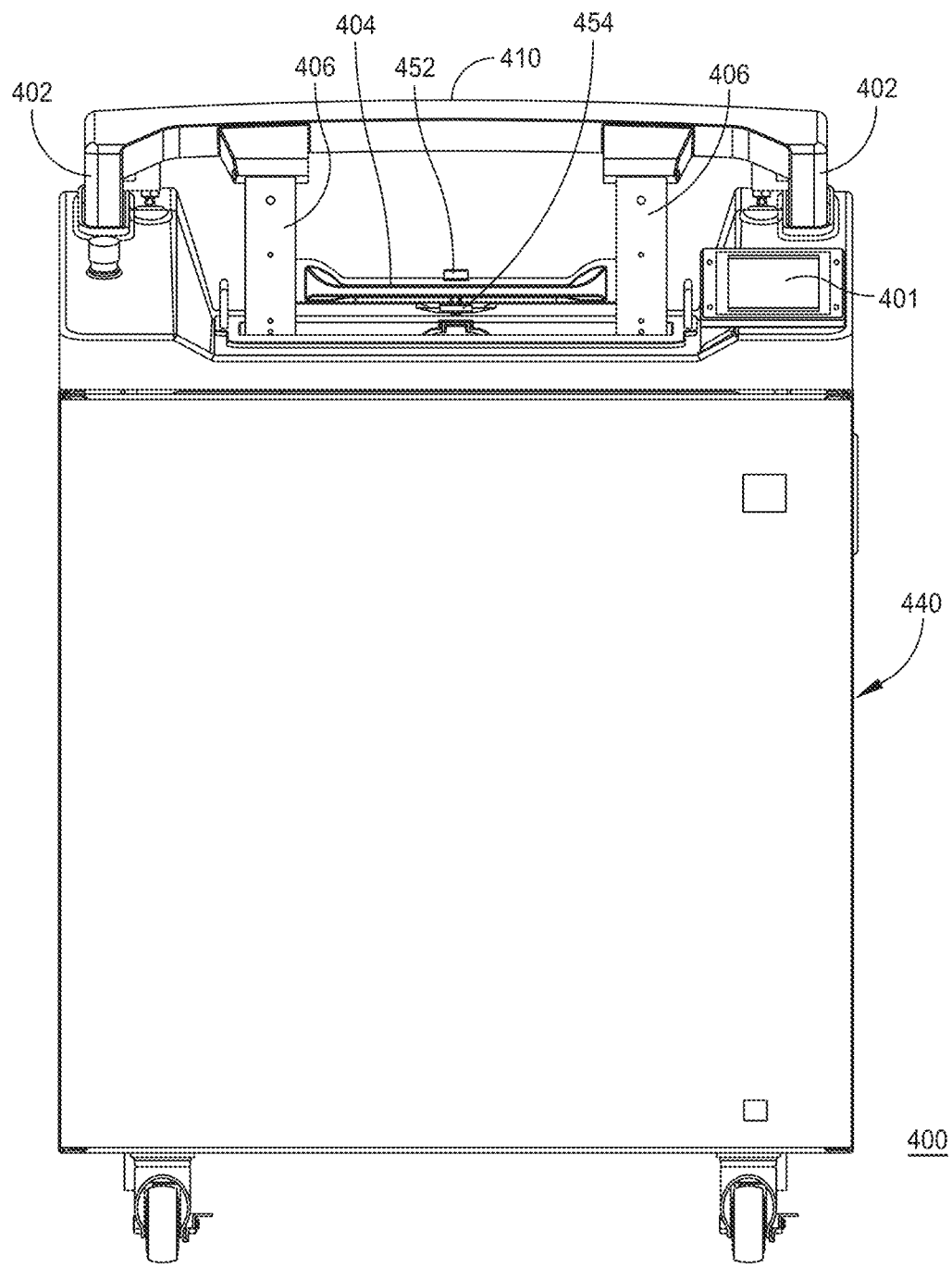

FIG. 6A is a schematic showing a front view of the finishing apparatus in the loading position and without the spray drying disposable attached.

Figure 6B:
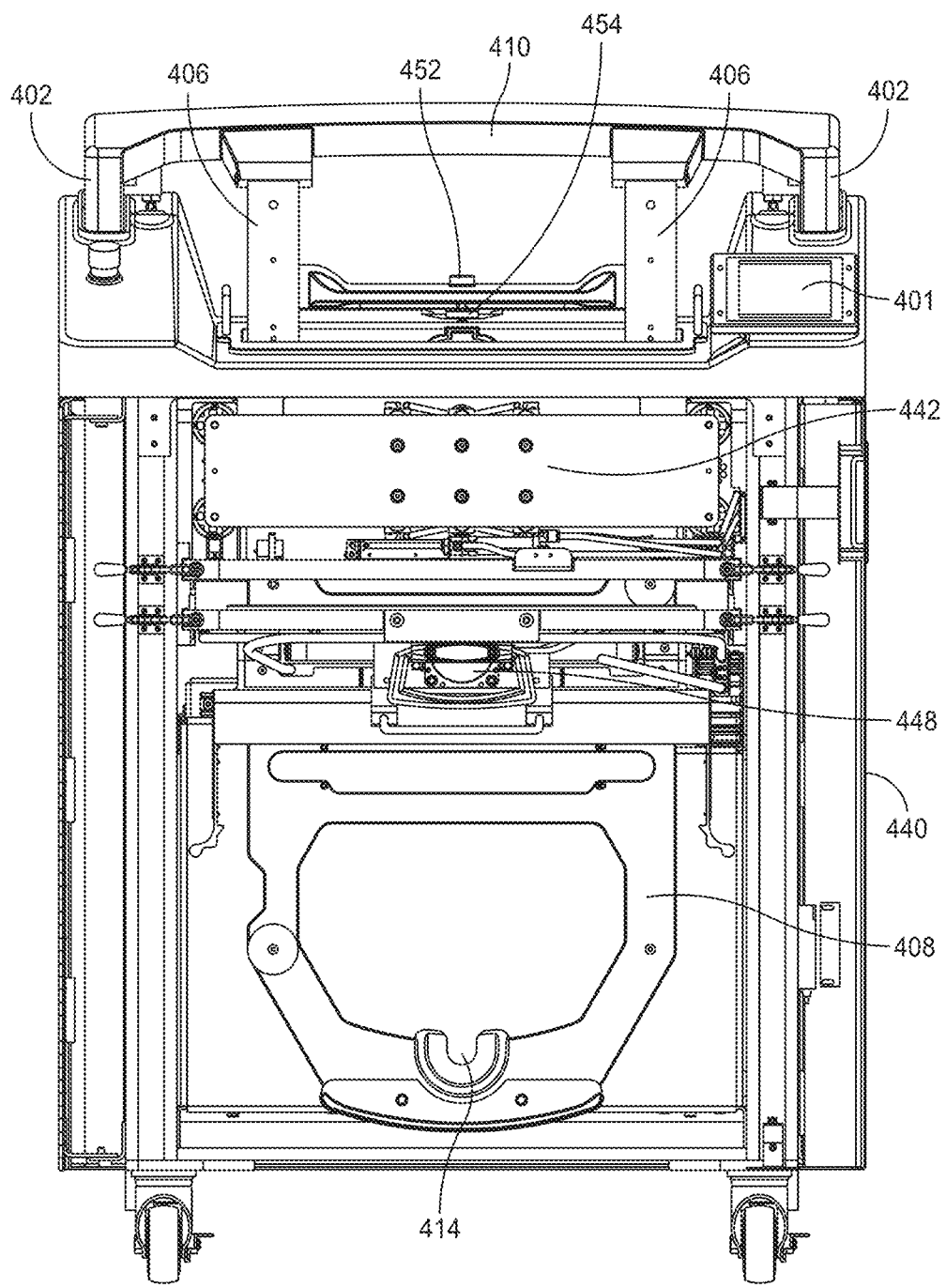

FIG. 6B is a schematic showing a front view of the finishing apparatus of FIG. 4A but without the front cover with the shuttle in the lowered position.

Figure 6C:
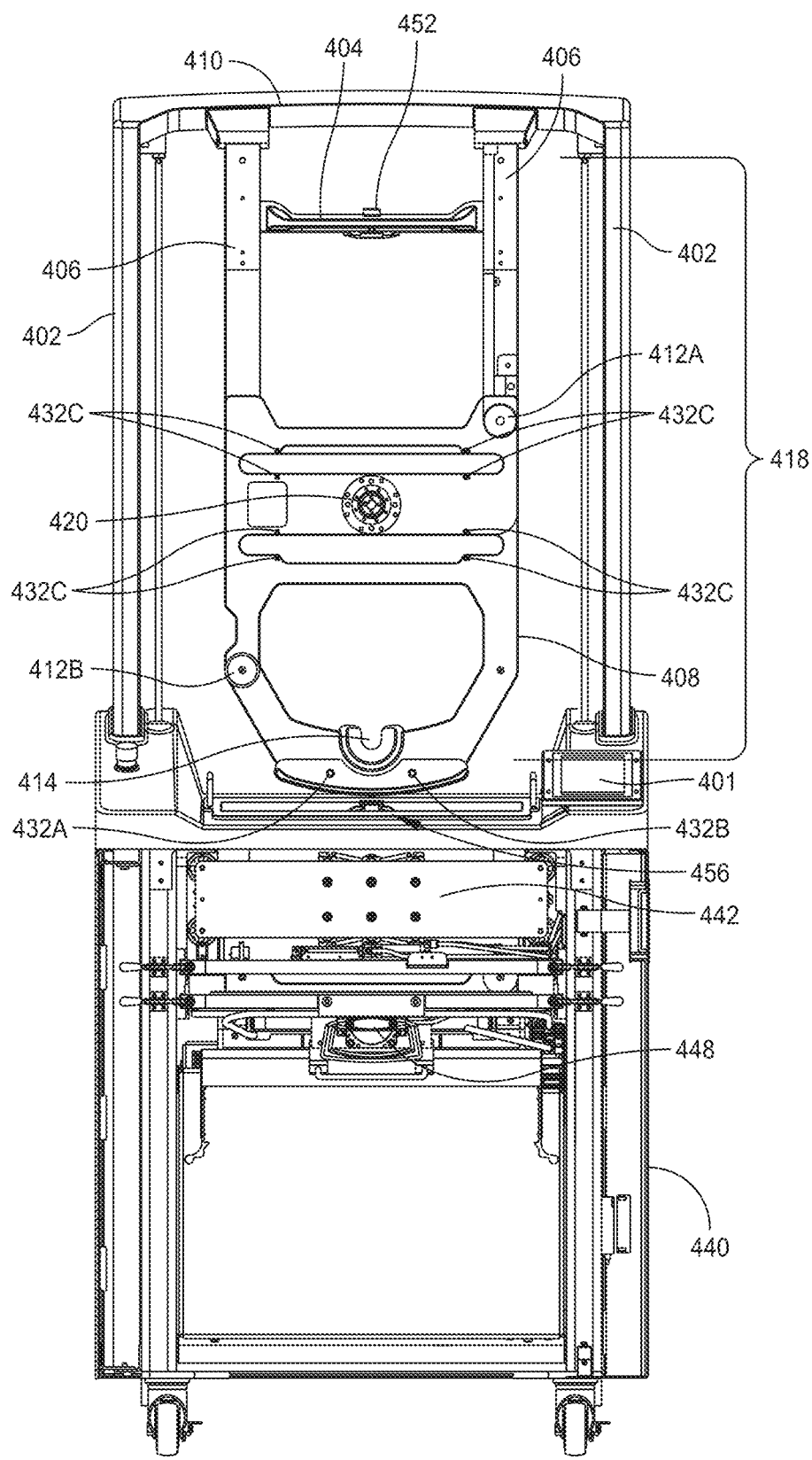

FIG. 6C is a schematic showing a front view of the finishing apparatus of FIG. 4B with the shuttle in the raised position and without the disposable attached.

Figure 7A:
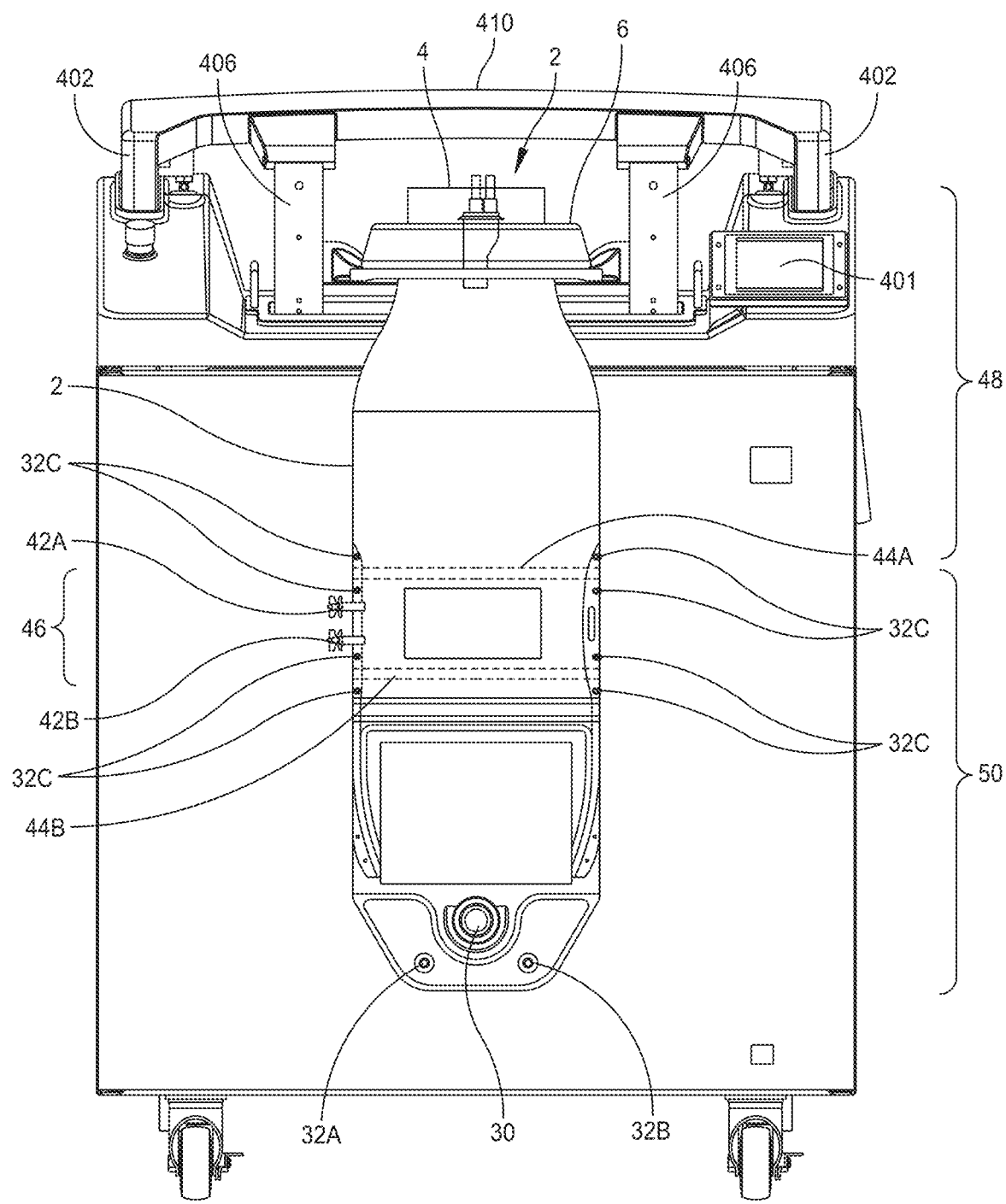

FIG. 7A is a schematic showing a front view of the finishing apparatus in the loading position with the spray drying head of the disposable signed thereto.

Figure 7B:
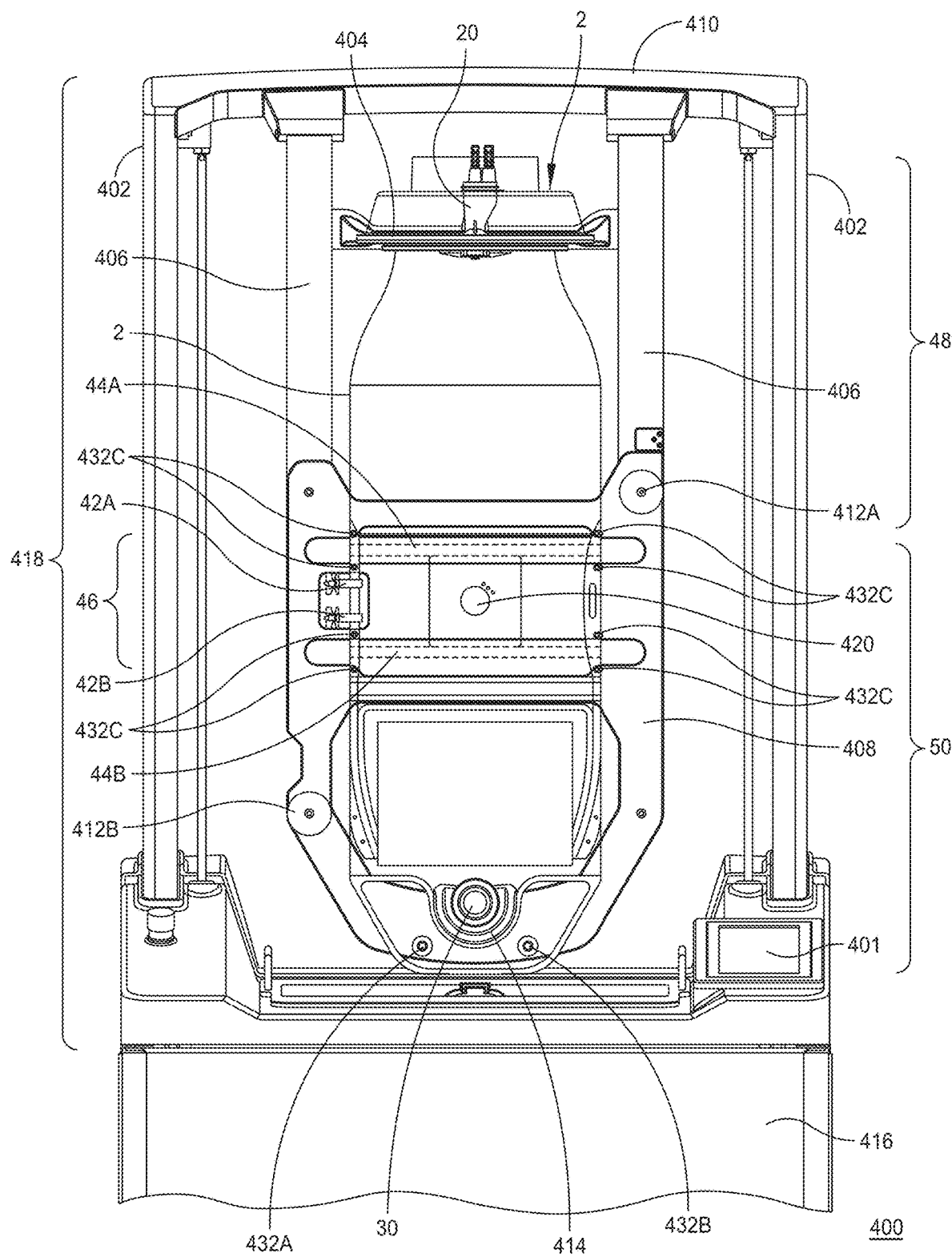

FIG. 7B is a schematic showing a front view of the finishing apparatus in the raised position with the disposable aligned thereto.

Figure 7C:
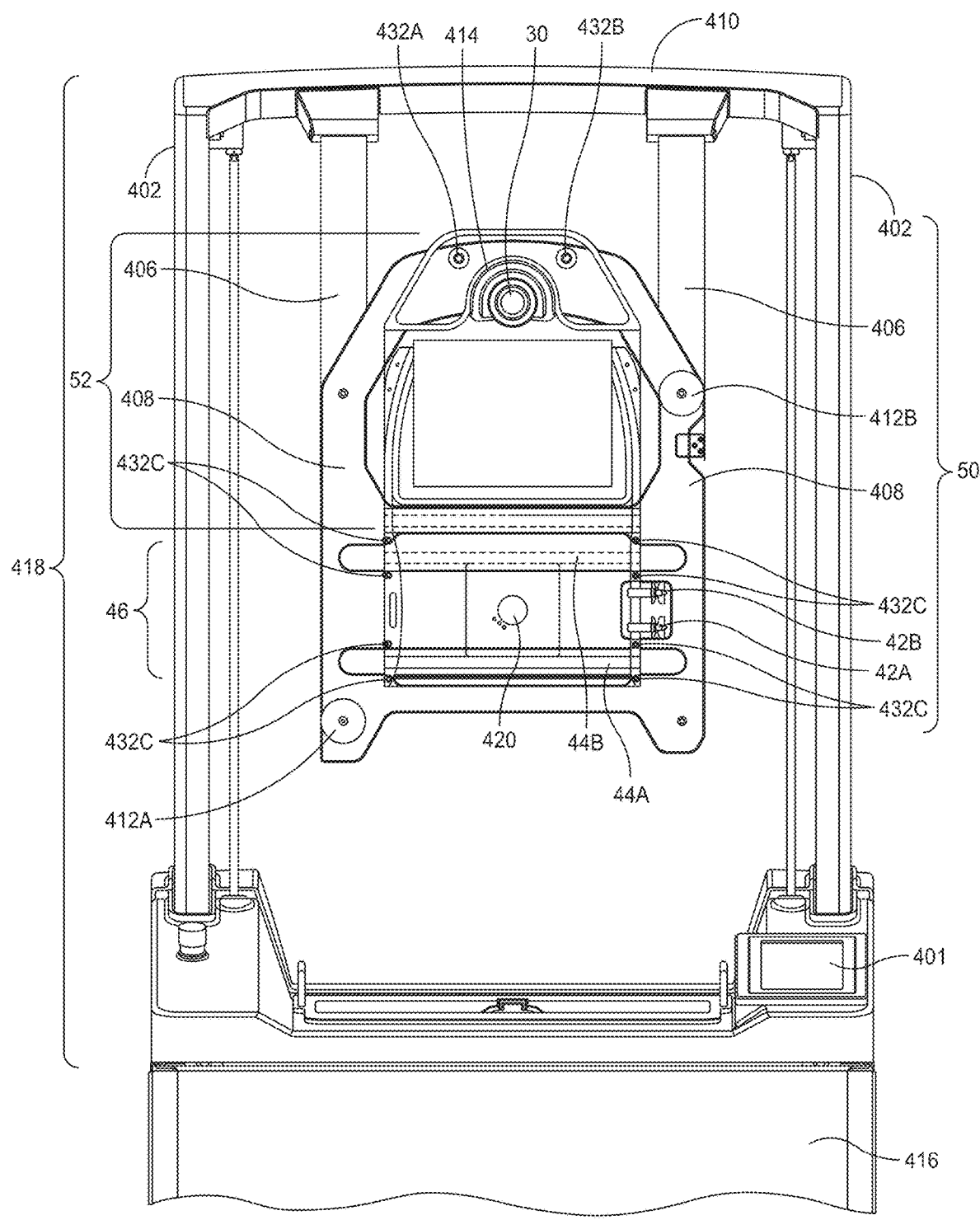

FIG. 7C is a schematic showing a front view of the finishing apparatus in the raised position with a portion of the disposable attached thereto, after the first seal and separate step is completed and the frame is rotated into position.

Figure 8:
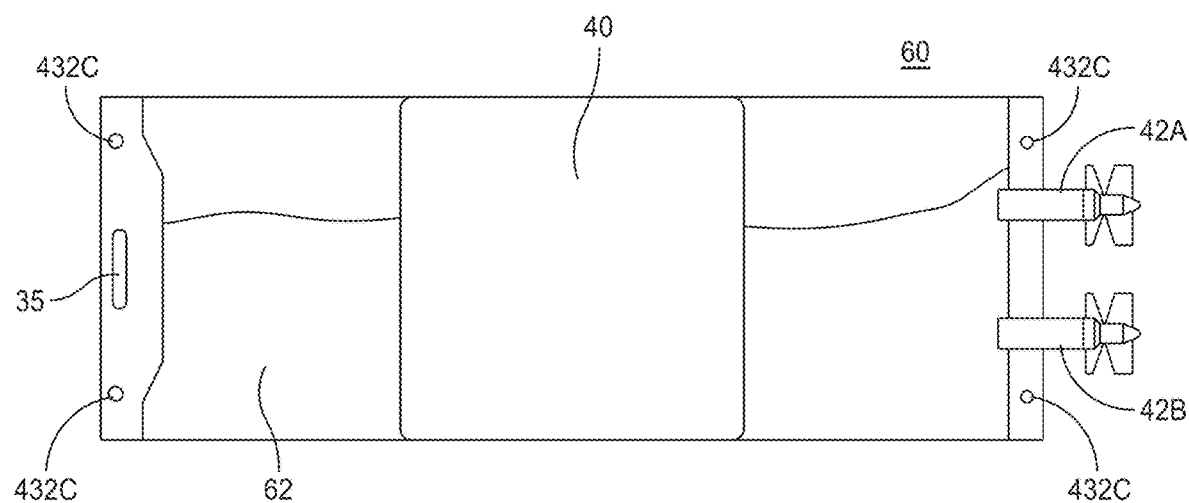

FIG. 8 is a schematic showing a front view of the spray dry plasma unit obtained from the spray drying disposable device after processed by the finishing apparatus.

Figure 9:
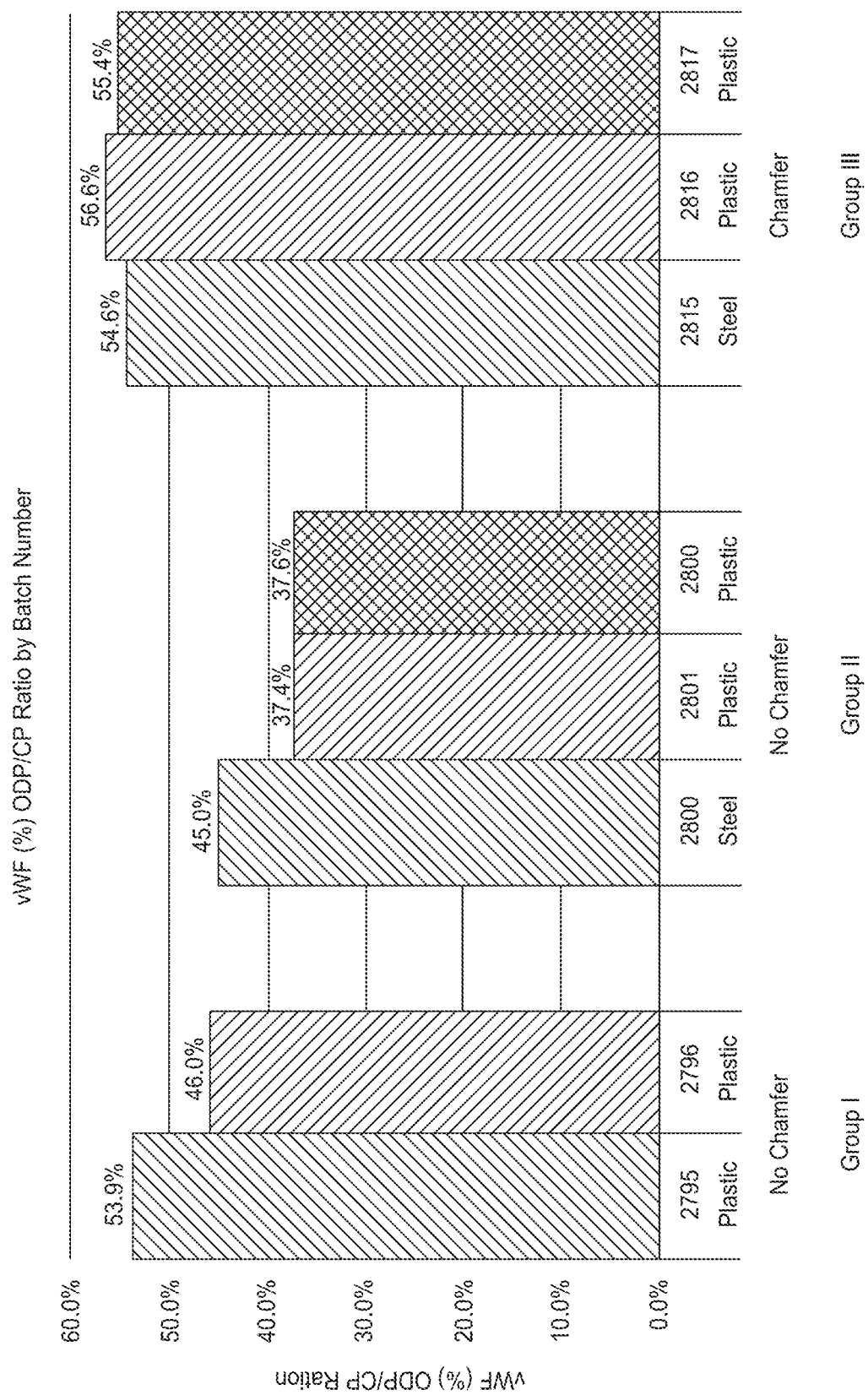

FIG. 9 is a bar graph comparing vWF % ratio of reconstituted plasma (to a never dried control aliquot) that was dried using disposable devices with composite nozzle assembly without a chamfer, with a chamfer and a benchmark stainless-steel nozzle.

Figure 10A:
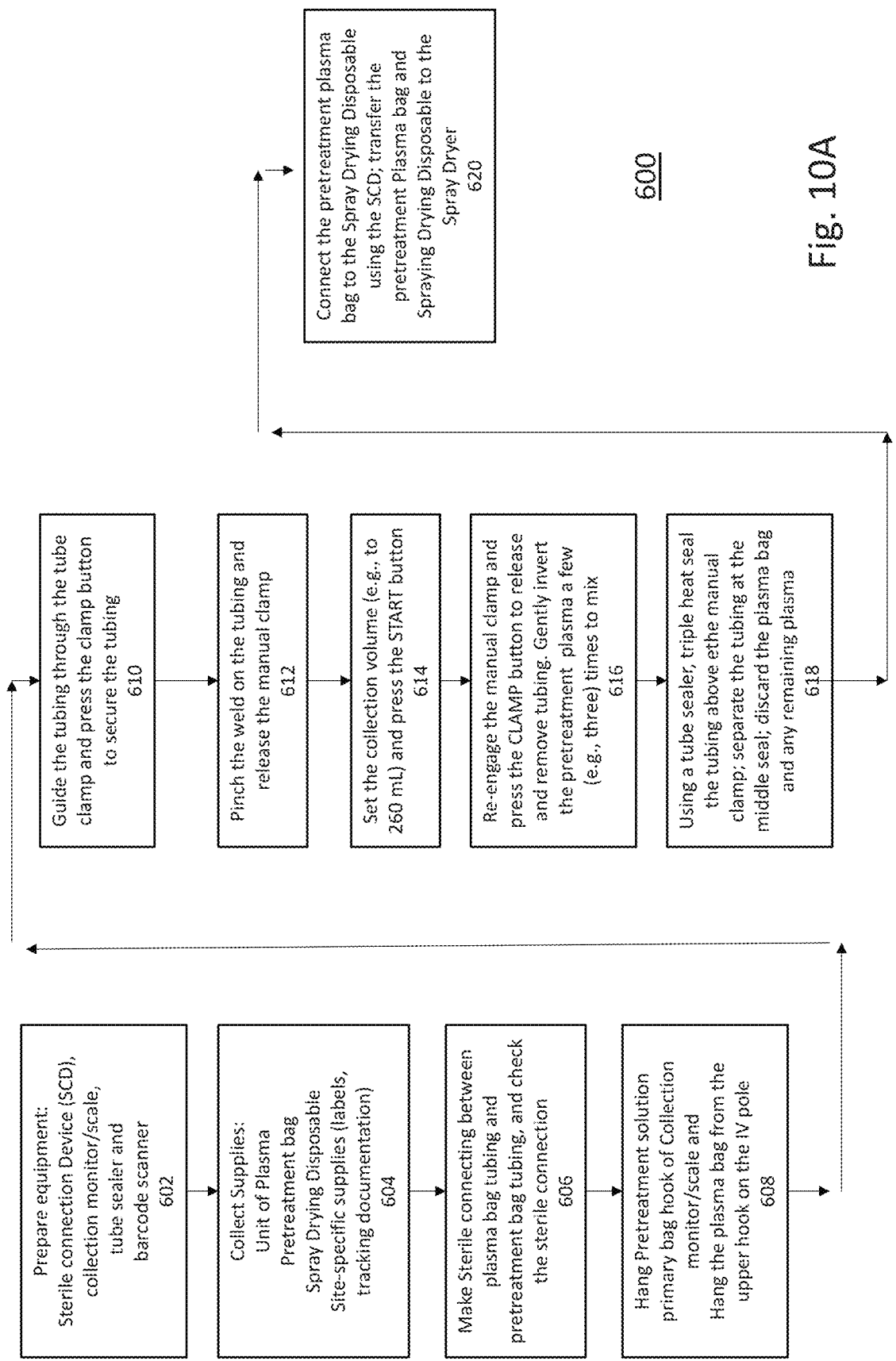

FIG. 10A is a flow chart showing the steps of the pretreatment methodology.

Figure 10B:
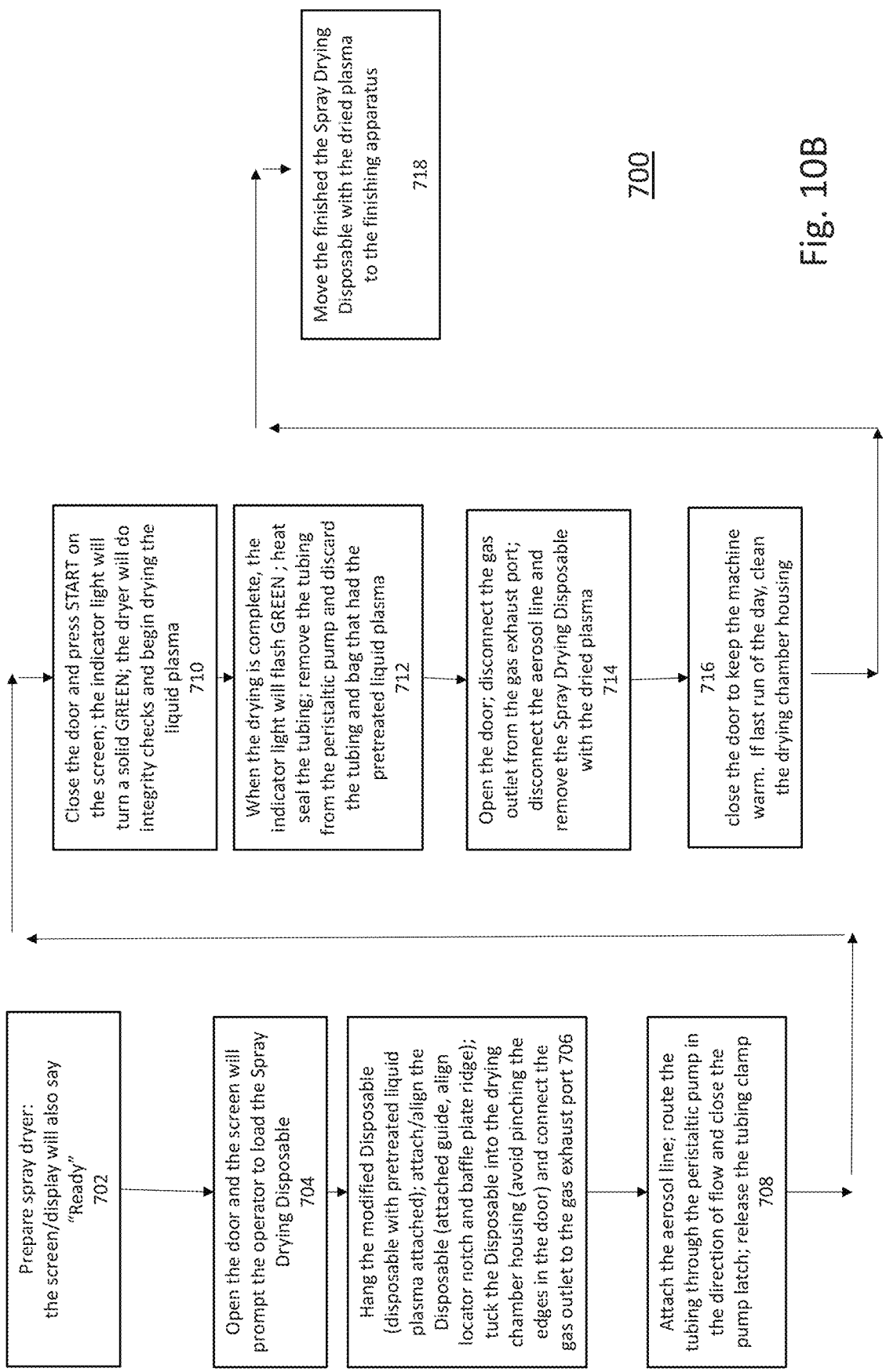

FIG. 10B is a flow chart showing the steps of the spray drying methodology employing the spray dryer and spray drying disposable.

FIG. 10C is a flow chart showing the steps of the finishing methodology employing the finisher and spray drying disposable to create a dried plasma unit.

Figure 10D:
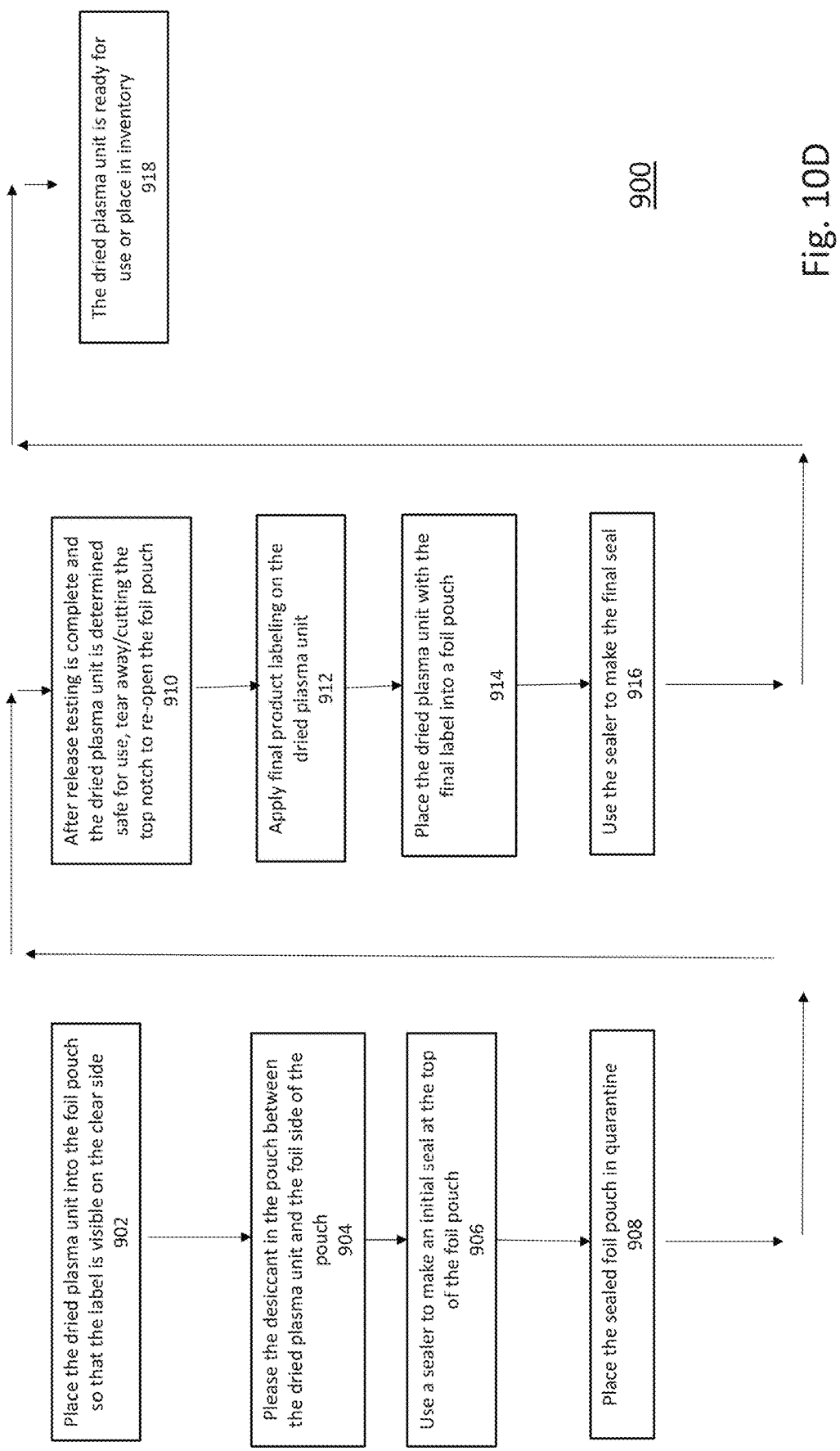

FIG. 10D is a flow chart showing the steps of the storage methodology once the spray dried unit is made.

Figure 11:
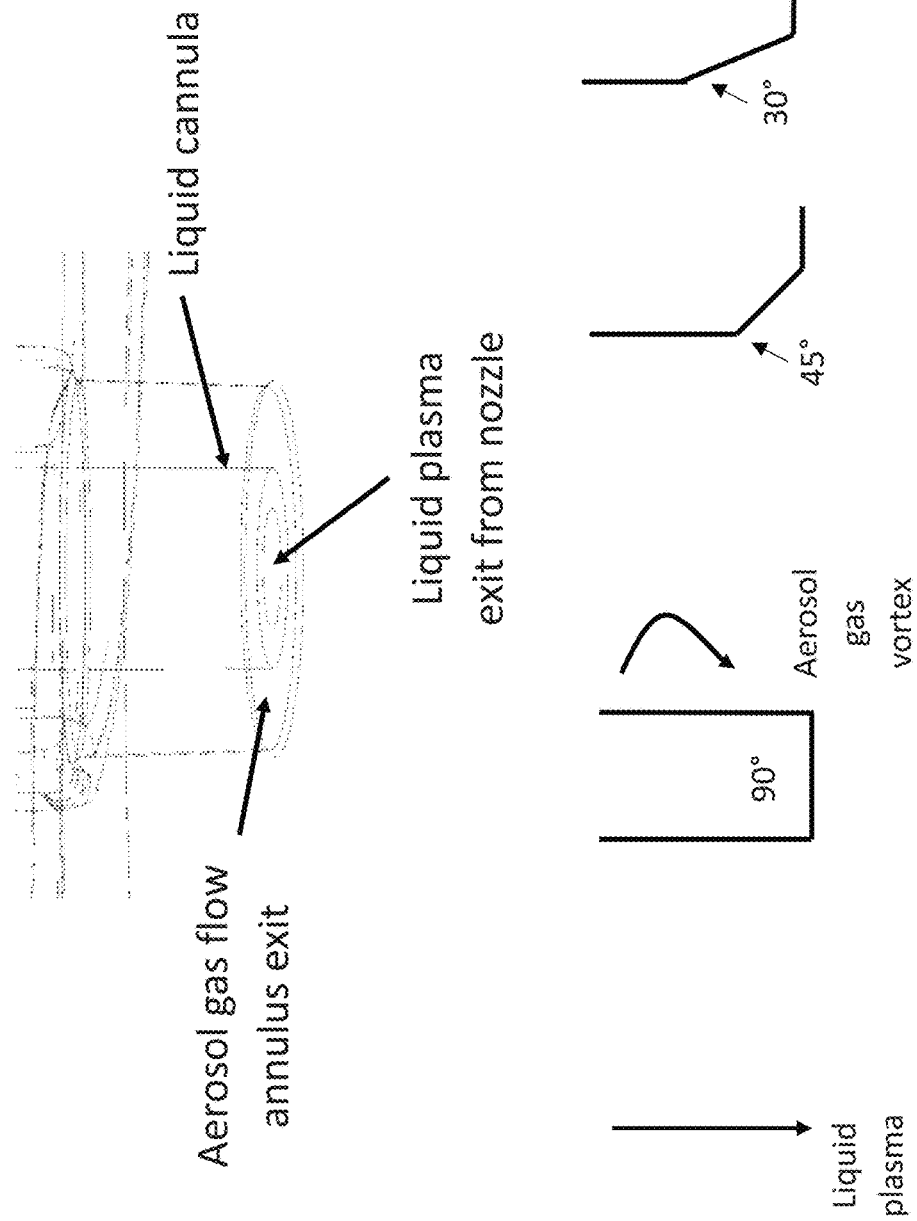

FIG. 11 is a schematic showing the geometry of the cannula to show sheer on vWF protein when exiting the cannula. The curved arrow shows the aerosol gas vortex direction within the annulus. In order to show the amount sheer impact on the liquid plasma at the exit area of the cannula, the figure shows the cannula edges at 90, 45 and 30 degrees and shows how the sheering contact of the cannula is reduced by the angled edge.

DETAILED DESCRIPTION OF THE INVENTION

A description of preferred embodiments of the invention follows.

The present invention relates to the components and system for using a spray drying disposable device. The spray drying system include a spray drying apparatus (hereinafter referred to as "drying apparatus," "machine," "spray dryer" or "dryer"), a spray drying finishing apparatus (hereinafter referred to as "finishing apparatus" "seal and separator," or "finisher") and a spray drying disposable device (hereinafter referred to as "disposable device" or "disposable"). The present invention includes a system that allows the spray drying disposable device having a liquid atomization nozzle and drying chamber that efficiently dries liquids including liquid human or animal blood plasma while protecting the active components such as plasma proteins. The spray drying disposable device is installed in the spray dryer that controls plasma flow, pressurized aerosol gas flow, drying gas flow, temperatures, pressures, etc. within the disposable. Once the spray drying process is complete, the disposable having dried plasma powder is aligned and processed by a spray drying finishing apparatus in which a portion of the disposable is sealed and separated to become the dried plasma unit. Moreover, the invention advantageously provides apparatuses for carrying out functions of spray drying and finishing products including dried human blood plasma.

The spray drying disposable of the present invention has compact drying chamber producing dried powder (<2% residual moisture) with a high powder production rate. The disposable is small, readily handled, and easy to use drying chamber with high performance. The drying systems of the present invention are a significant improvement providing a removable, disposable drying chamber for spray drying suitable for small batch size processing, such as individual blood units.

Certain older disposable drying chambers of the Applicant were quite long, being between 58" and 66" or more in length, to allow enough time (flight path) for the plasma to be dried to an acceptable residual moisture level. See U.S. Pat. Nos. 8,533,971, 8,595,950, 8,434,242, 8,601,712, 8,533,972, and 10,843,100. However, their length made those prior art disposables unacceptable in practice for use because they were difficult and inefficient to handle during installation in the spray dryer instrument. The shorter disposable of the present invention, as further described herein, is more easily handled than these prior art disposables which required reaching and stooping distances for users of over 6' and under 5' respectively. The shorter disposable makes the spray drying of human blood plasma practical in real world applications by real world people. Also, the disposable drying chamber of the present invention is a removable, disposable drying chamber that preserves quality and integrity of the plasma while improving processing time and product quality at reduced cost.

Several challenges were overcome to shorten the drying chamber of the present invention. For example, drying any product to a given degree of dryness involves exposing the material to be dried with enough heat energy to obtain the desired drying level while maintaining the functionality of the substance being dried. However, shortening the drying chamber also reduces the drying pathway.

The disposable drying chamber of the present invention is improved by:
Plasma being more efficiently manufactured;
Being considerably shorter;
Being readily usable by persons of a wide range of statures;
Drying material in less time;
Reducing the inlet air temperature;
Achieving a nozzle assembly and drying environment to obtain rapid mixing of the atomized droplets with the drying gas and rapid evaporation;
Achieving a lower level of residual dryness e.g., less than 2% residual moisture; and
Utilizing a specially designed, cost-efficient composite spray drying nozzle, as further described herein.

Overview of Spray Dry Disposable

In particular, disposable 100 has two general areas, the spray drying head 2 and the plasma drying chamber 28.

Spray Drying Head Overview

Spray drying head 2 of disposable 100 that has guide 4 that is offset as positioned on plenum 6, and baffle plate 8 having ridge 9 (FIGS. 1A and 2A). Plenum 6 has guide 4 on top of spray drying head 2. Within guide 4 is spray dry nozzle assembly 20 which has plasma flow inlet 18 connected to the liquid plasma via plasma tube 16 and aerosol pressurized gas inlet 14 connect to the pressurized gas via aerosol tube 10 and aerosol filter 12. Additionally, drying gas inlet port 22 is shown and is in communication with the drying gas source (not shown) which may be a source of air, nitrogen or other drying gas. Optionally, drying gas inlet port 22 may be covered by a removable cover such as a self-adhesive paper label or similar. This cover should be removed just prior to installation of disposable 100 into the spray dryer 200. The drying case source can optionally be in communication with a moisture reducing drying system. In one embodiment, the drying gas source is an Atlas-Copco SF 22+ compressor (Atlas Copco Nacka Municipality, Sweden) in conjunction with an Atlas-Copco CD45 desiccant drying system supplying clean dry air (CDA) to the spray dryer and heats air to the appropriate temperature for spray drying. In an embodiment, the drying gas flows through a filter from the CDA and, for example, is a Millipore Series 3000 0.2 micron filter CTGB71TP3 from Millipore Sigma of Danvers MA USA. The CDA supply is used, in an embodiment, for the supply for the drying gas and for the pressurized gas. In certain embodiments spray drying nozzle assembly 20 includes a "manifold" that coordinates the plasma and aerosol lines. When the plasma source, pressurized gas source, and drying gas source combine, the liquid plasma droplets are formed and dried into dried plasma (e.g., a fine, amorphous plasma powder). Plenum 6 has a notch, which is a locator referred to herein as locator 26 or a second locator, as further described herein.

Briefly, guide 4 fits into a receiver 204 of spray drying apparatus 200 which also properly aligns disposable 100 with drying apparatus 200 (FIGS. 4B and 4C). Guide 4 also aligns spray drying head 2 with respect to spray dryer 200 in a specific orientation such that drying gas inlet 22 receives the drying gas source (not shown). Ridge 9 fits into ridge receiver 207 of spray dryer 200 and provides support. Guide 4 along with ridge 9 allows alignment of disposable 100 with spray dryer 200 in a latitudinal orientation (e.g., in a plane defined by the top surface and bottom surface of the spray drying apparatus) which keeps the disposable secured so it does not move up and down within the spray drying chamber housing of the dryer. Additionally, ridge 9 of disposable 100 fits into receiver 404 of finisher 400 to secure disposable 100 to finisher 400 while finisher 400 is moving the plasma and sealing and separating the disposable to turn it into dried plasma unit 60. See FIGS. 5A-C. This alignment arrangement also provides for easy, universal attachment of the disposable to both the dryer and the finisher.

First locator, locator 206 (FIGS. 4B, 4C and 5A), is positioned on spray drying apparatus 200 and the second locator, locator 26 (FIGS. 1A and 2A) is positioned on spray drying disposable 100 such that the first and second locator engage during installation of disposable 100 into spray drying apparatus 200 to allow for alignment of the disposable with the spray drying apparatus. The same locator, locator 26 (the second locator), on the disposable also is used to align the disposable with a third locator, locator 452 (see FIGS. 6A-C), on spray drying finishing apparatus 400, the apparatus that directs the dried plasma into specific compartments of the disposable, seals and separates the dried plasma into a plasma unit having the dried plasma. This locating arrangement aligns the disposable to the spray drying apparatus axially, e.g., about an axis defined by the center of a receiver of guide 4 (see Axis A of FIG. 2A). This locating arrangement allows for easy universal attachment of the disposable to both the drying apparatus and the finishing apparatus.

As part of the disposable, spray drying head 2 includes nozzle assembly 20. This nozzle assembly allows the spray drying of the plasma to occur within the disposable. Overall, the design of the system has a spray dryer and disposable modified to have a nozzle as part of the disposable instead of the spray dryer so that spray drying occurs entirely within the disposable. This design helps keep the plasma in the disposable throughout the drying and finishing process, and out of the parts of the dryer or finisher which would require decontamination between each use. The design also minimizes external pathogen contamination by keeping the plasma within the disposable during the entire process. The nozzle assembly coordinates the plasma flow and the pressurized/aerosolized gas flow such that both are emitted at the proper rates and air flow to atomize the liquid plasma at tip of the nozzle where it is ready for rapid mixing with the drying gas. Spray drying head 2 of disposable 100 further includes plenum 6 and baffle plate 8 that guides the drying air for rapid mixing with aerosolized plasma and creates an air curtain to minimize buildup of dried plasma on the drying chamber wall.

Plasma Drying Chamber Overview

Drying chamber 28 is the area of the disposable where the plasma dries. The drying chamber is designed to capture the dried plasma while allowing the humid air to exit. The design of the drying chamber also allows the drying chamber to be sealed and separated in such a way as to form the commercial dried plasma unit.

Drying chamber 28 has three general areas, the upper portion defined by Dimension X (See FIGS. 3 and 5A), the mid-section defined by Dimension U, the area between locations 44A and 44B, and the bottom portion defined by Dimension V, the portion below location 44B, that includes filter 36 and a separator 38. The upper portion is a space in which the atomized liquid plasma hits the drying gas and evaporates the liquid within the droplet and dries. In particular, the atomized plasma rapidly mixes with the drying gas and dries, as further described herein. As the plasma rapidly mixes and dries, it circulates and moves in a downward direction toward the filter. Most of the evaporation occurs in the upper portion of drying chamber 28 (Dimension X) but it does continue to dry as the plasma falls into the midsection portion (Dimension U) and the lower portion (Dimensions V) of drying chamber 28.

Drying chamber 28 also includes midsection 46, defined by Dimension U, that has "seal and separate" locations 44A and 44B, label 40, spike ports 42A and 42B and hanging slot 34. Midsection 46 also includes locator pin openings 32C. The mid-section is later processed by the spray drying finishing apparatus which involves moving dried plasma into certain locations of the plasma drying chamber and sealing and separating at or near cut locations 44A and 44B. The section between locations 44A and 44B becomes dried plasma unit 60 that will eventually be rehydrated and transfused into patients.

Disposable 100 further includes a positioning arrangement to reversibly attach the outer wall of disposable 100 to finishing apparatus 400. Positioning openings 32A, 32B, and 32C are present on the outer edge of the wall of spray drying disposable device 100. (FIG. 1A, 7A). Positioning pins 432A, 432B and 432C are located on finishing apparatus 400 such that when positioning openings 32A, 32B, and 32C are placed around positioning pins 432A, 432B and 432C of finishing apparatus 400, drying chamber 28 of disposable 100 is aligned with on the finisher apparatus. See FIG. 6C, 7B, 7C.

The lower section of drying chamber 28 includes lower filter 36 (also referred to herein as a "capture filter"), lower filter separator 38, drying gas outlet port 30, and locator pin openings 32A and 32B. Optionally, gas outlet 30 may be covered by a removable cover such as a self-adhesive paper label or similar. In an embodiment, this cover should be removed just prior to installation of the drying chamber into the spray dryer 200. Briefly, the lower filter allows for separation of the dried plasma from the humid air and the separator acts as a spacer between the drying chamber wall and the filter to allow air to more easily pass and prevent pressure buildup. Humid air refers to the air traveling through the drying chamber and includes the combination of the drying gas, the aerosolized gas and the moisture that has been removed from the plasma droplets. During the drying of the plasma, the humid air passes through lower filter 36 and lower filter separator 38, through air flow channels, and out of gas outlet 30 leaving dried plasma in lower filter 36.

Disposable 100 further includes another alignment arrangement that relates to gas outlet 30 of disposable 100 and gas exhaust port 208 of dryer 200. The spray drying apparatus has gas exhaust port 208 to allow the drying gas to exit and the bottom portion of disposable 100 has gas outlet 30 that fits into the exhaust port 208 of dryer 200. (FIGS. 4B, and 5A). Additionally, spray drying finishing apparatus 400 has receiver 414 for the drying gas outlet 30 to secure the bottom of disposable 100 to finishing apparatus 400. (FIG. 7B, 7C). Again, this drying gas arrangement allows for universal attachment of the disposable to both the drying apparatus and the finishing apparatus.

Additionally, the entire length of the disposable (as measured from the top of the spray drying head to the very bottom of the drying chamber) is limited to about 40 inches or less (e.g., about 40, 39, 38, 37, 36, 35, 34, 33, 32, 31, 30, 29, 28, 27, 26, 25, or 24 inches or less) and preferably about 34.8 inches. A disposable having a length of about 40 inches or less was difficult to achieve because the drying of the plasma occurs in a smaller space and smaller volume but does so gently without degrading plasma proteins. The disposable length, as measured from the bottom of spray drying head 2 or bottom of baffle plate 8 to bottom of filter 36, shown as dimension Y in FIG. 5A, is about 31 inches or less (e.g., about 31, 30, 29, 28, 27, 26, 25, 24, 23, 22, 21, 20, 19 inches or less) and in an embodiment preferably about 25.9 inches. In another aspect, the area of disposable 100 encompassed by Dimension Z, the length from the bottom of spray drying head 2 and the top of filter 36, is about 22 inches or less (e.g., about 22, 21, 20, 19, 18, 17, 16, 15, 14 inches) and preferably about 19.11 inches. In yet another, the length of Dimension X, the length between the bottom of spray drying head 2 and the top section 46, is less than about 16 inches (e.g., about 16, 15, 14, 13, 12, 11, 10, 9, 8 inches) and preferably about 12.14 inches. In an embodiment, the length of disposable can be modified or shortened. For example, the length of the disposable of the present invention can be further shortened along dimension X by about 1 inch to about 8 inches (e.g., by 1, 2, 3, 4, 5, 6, 7, or 8 inches) thereby reducing the overall length by the same amount. In other embodiments, the disposable can also be shortened anywhere along Dimension Y and Z by the same amount.

Computational Model

Figure 1B:
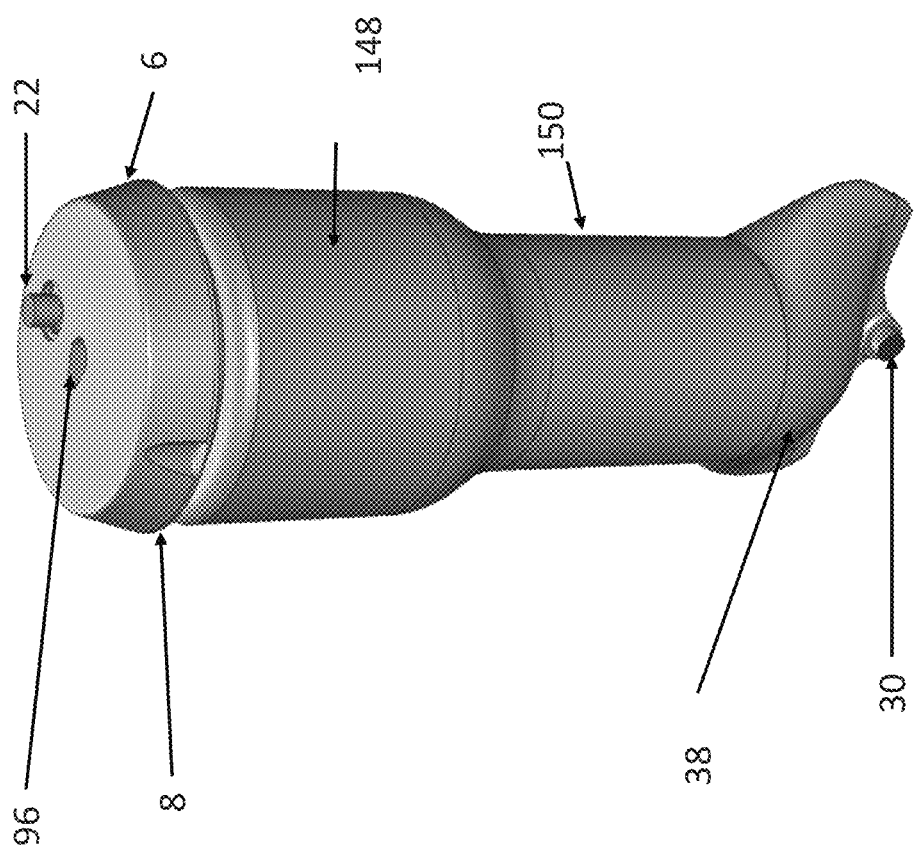
FIG. 1B is a model representation of the three-dimensional flow geometry of the flow model of the disposable during operation. This model is used to create the computer flow models described herein.

For some of the figures, a computational model was used to show flow paths, particle evaporation and the like. FIG. 1B shows the three-dimensional flow geometry of the disposable during operation that was used for the model.

The three-dimensional model showing in FIG. 1B was based on the disposable shown in FIG. 1A and the dryer shown in FIGS. 4A-C. These computer simulations show flows and mixing processes were created by first building the three-dimensional flow domain geometry. See FIG. 1B. This geometry was extracted from a computer aid design (CAD) model of the system hardware to create a high-fidelity representation of the flow region inside the ODP system. The flow domain of 0.0195 m³ volume was discretized into 3.3M spatial cells to generate a computational mesh using the commercially available Ansys-Gambit mesh meshing software. The flow model was calculated using a commercially available computer code; Ansys-Fluent version 2019-R1 running on an HPZ840 multi-processor workstation.

The simulation utilized a steady-state segregated solver assuming ideal gas properties, K-E turbulence model and the following:

Drying gas inlet temperature=114 C
Drying chamber exhaust temperature=65 C
System heat loss=0.18 kW
Drying gas flow=750 slpm
Atomizer aerosol gas flow=40 slpm
Feed rate=13.5 mL/min, and varies with exhaust gas temperature
- Liquid water droplets with 8.5% non-volatile mass, 5 micron diameter (monodispersed size)
- Exhaust port pressure=2.76 kPa (0.4 psig)

The inlet and product capture filters are modeled using a 'porous zone' function with flow resistance values set to match the measured pressure during operation in the drying gas manifold of 71.7 kPa (10.4 psig) and 27.6 kPa (4 psig) in the drying chamber at the start of a batch.

To calculate the average droplet diameter and temperature during the constant-rate evaporation period for a given set of process conditions, two customized c programs, "prsc_udf_multi_2017.c" and "processdata_multi_2017.c", are developed at PARSEC to obtain an averaged droplet drying pathway from a converged Fluent coupled dpm solution. The program "prsc_udf_multi_2017.c" is used to export droplet tracking data step by step for information interested. The program "prsc_udf_multi_2017.c" reads exported data file generated from the first program, and then get averaged pathway from all tracked particles. Its output file can be read into Excel file.

The data shown in FIGS. 1B, 2Ka, 2Ma, 2Na, 2O, 2P, 2S, 2Sa, and 2T were generated using this model.

Overview of Workflow

An overview of the process to use the disposable, spray dryer and finisher described herein, is as follows. The spray drying plasma methodology of the present invention includes pretreating a donated liquid plasma unit or defrosted previously frozen liquid plasma unit, drying the liquid plasma using a spray drying apparatus with the spray drying disposable device that results in a disposable having the dried plasma, finishing the disposable using the finishing apparatus that is designed to seal and separate the disposable, and transform the disposable into a dried plasma unit. The unit can be used or stored. When ready for use, the plasma unit is rehydrated and ready for transfusion into a recipient.

With respect to pretreatment, the pretreatment process involves adding biocompatible components (e.g., a spray dry stable acidic substance) to the liquid plasma (or defrosted fresh frozen plasma) that protect the plasma proteins during the spray drying process which involves high temperatures and pressures.

In an embodiment, making the pretreatment solution includes adding the following to a solvent, such as SWFI: between about 3.0 to about 7.0 (e.g., 3.0, 4.0, 4.5, 5.0, 5.5, 6.0, 6.5, and 7.0) mmol HCl and about 15 mmol and about 30 mmol glycine (e.g., about 15, 17, 20, 22, 25, 27, 30 mmol glycine) in 50 mL of solvent to obtain 260 mL of formulated plasma. In yet other words, glycine in an amount of about 440 mM, and HCl in an amount of about 106 mM is present in the pretreatment solution. In an embodiment between about 290 mM to about 570 mM (e.g., about 290, 300, 350, 400, 450, 500, 550, and 570) glycine and about 70 mM to about 140 mM (e.g., 70, 80, 90, 100, 110, 120, 130, 140 mM) HCl is present in the pretreatment solution. The pretreatment container is commercially available and can be formulated, filled and finished by e.g., Berkshire Sterile Manufacturing (Lee Massachusetts USA). In an embodiment the pretreatment solution has about 440 mM/50 ml of glycine and 106 mM/50 ml of hydrochloric acid. (The United States Pharmacopeial Convention ("USP") monograph (12601 Twinbrook Parkway Rockville, MD 20852-1790, USA)). The pretreatment solution, when combined with liquid plasma to form a formulated plasma, protects the plasma proteins during the drying process. The formulated plasma has a pH in a range between about 5.5 and about 7.2 which offsets spray drying impacts on pH to yield a final rehydrated product that is at normal physiologic pH, a pH range between about 6.7 and 7.8 (e.g., about 6.7, 6.8, 6.9, 7.0, 7.1, 7.2, 7.3, 7.4, 7.5, 7.6, 7.7, 7.8). pH lower than 6.7 or higher than 7.8, in certain instances, can be detrimental to the recipient. The resulting dried plasma product from the present invention is a plasma that retains its von Willebrand Factor and other blood proteins, and has fewer cholesterol crystals, less particles, less pathogens and a well-controlled pH with the aforementioned pretreatment step. Moreover, the resulting dried plasma has certain properties which are different from and superior to that of freeze-dried plasma.

In an embodiment, the methods of the present invention include methods for producing spray dried plasma by combining plasma with a pretreatment solution, wherein the pretreatment solution comprises glycine in an amount ranging between about 50 μmole/mL of plasma and about 110 μmole/mL of plasma (e.g., about 50, 60, 70, 80, 90, 100 110 μmole/mL of plasma), and hydrochloric acid (HCl) in an amount ranging between about 10 μmole/mL of plasma and about 30 μmole/mL of plasma (e.g., about 10, 15, 20, 25, and 30 μmole/mL of plasma), to thereby obtain formulated plasma. The method also includes drying the formulated plasma with a spray drying system to create spray dried formulated plasma, as described herein. In an embodiment, the pretreatment solution has glycine in an amount of about 84 μmole/mL of plasma and HCl in an amount of about 20 μmole/mL of plasma.

A sterile connecting device (SCD), as is known in the art, is used to connect the plasma unit to the pretreatment container and the liquid plasma and in an embodiment, a fixed volume of plasma is transferred utilizing, for example, a blood collection monitor/mixer. After the liquid plasma is transferred to the pretreatment container, in an embodiment, it is gently mixed in the pretreatment container by inversion. Other mixing methods such as rocking, shaking and agitating, can be used. Additionally, the mixing can be done by the operator or a device known in the art. The bag that contained the liquid plasma is tube sealed, separated, and discarded. Pretreatment container 64 having the pretreatment solution and the liquid plasma (i.e., formulated plasma 66) is then connected to the disposable device at plasma tube 16 utilizing an SCD, resulting in a modified spray drying disposable device, shown in FIG. 1A.

Spray drying disposable device 100 is a sterile, non-pyrogenic, single user container (e.g., about 35 inches long) which utilizes a pathogen retentive filter to filter air before it enters the drying chamber and as air exits the drying chamber. See FIG. 1A. The spray drying disposable is aseptically connected to the liquid plasma at the plasma tube, tube 16.

Briefly, the drying process is as follows. See FIGS. 4A-4C, 5A-5B. Pretreated plasma is aseptically spray dried in spray drying disposable device 100. See FIG. 4A-4C. During the process, in an embodiment, a positive airflow is maintained. Pretreated plasma is atomized using a nozzle contained within the single use spray drying disposable device creating fine plasma droplets. These droplets are then exposed to heated air. The resulting dried plasma particles are captured in filter 36 of the drying chamber 28. The spray drying disposable device is then undocked from the spray drying apparatus and taken to the finishing apparatus.

An overview of the finishing process is as follows. See FIGS. 6A-6C, 7A-C, 8. Once undocked from spray drying apparatus 200, disposable device 100 having dried plasma is transferred to finishing apparatus 400. Finishing apparatus 400 mechanically, acoustically or otherwise impacts or agitates the spray drying disposable device containing dried plasma to eventually consolidate dried plasma powder in the portion of the spray drying disposable device that becomes the spray dry plasma unit. The finishing apparatus utilizes an impactor to first assist the dried plasma in moving to the bottom of the disposable, and then in a second instance to the compartment that becomes spray dried plasma unit 60. Spray dry plasma unit 60 is sealed and separated from the rest of the disposable device utilizing impulse sealing. This step is the final closure step to create plasma unit 60. In an embodiment, the seals are visually inspected and excess portions of the disposable device are discarded and dried plasma unit 60 is produced (see FIG. 8).

With respect to an overview of the dried plasma storage process, dried plasma unit 60 is removed from the finishing apparatus and stored in a re-sealable moisture barrier foil pouch containing a desiccant. See U.S. Pat. No. 9,561,184. In an embodiment, the dried plasma unit is quarantined until completion of all required blood screening tests and stored at refrigeration. Upon meeting final release criteria, the pouch is opened and the dried plasma unit is relabeled for release. The dried plasma unit then placed in a resealable or other pouch, sealed, and stored following storage protocols.

In an embodiment, the dried plasma unit is compatible with commercially available fluid or other transfer sets for rehydration with sterile water for injection (SWFI). Dried plasma unit 60, once rehydrated, is also compatible with blood administration sets for transfusion. In a particular embodiment, spray dried plasma unit 60 is rehydrated within its existing container using an appropriate amount of sterile water (e.g., 200 mL, 208 mL) for injection prior to transfusion.

Detailed Description of Spray Dry Disposable
Detailed Description of the Spray Drying Head Referring to FIG. 1A, a perspective view of spray drying disposable device 100 is shown. As described above, the disposable has generally two portions, spray drying head 2 and drying chamber 28. The spray drying head includes plenum 6, guide 4, baffle plate 8, baffle filter 94, nozzle 20, and locator notch 26 (also referred to as a "second locator" herein).

In an aspect, the purpose of spray drying head 2 is, in part, to A) assist in securing disposable 100 to dryer 200, B) coordinate the flow of the drying air, the aerosolized pressurized gas and the plasma flow, C) house the nozzle assembly, and D) house the baffle filter.

With respect to securing disposable 100 to dryer 200, the system of the present invention includes an integrated and universal alignment system. In an embodiment, locator notch 26 on plenum 6 is shown in FIG. 2A. FIG. 2A also better shows plenum 6, guide 4, baffle plate 8 and ridge 9. Locator notch 26, also referred to as a second locator, aligns with locator projection 206 (shown in FIGS. 2K, 4B, 4C, and 5A), also referred to as a first locator, on spray drying apparatus 200. This locating arrangement allows for spray drying head 2 of disposable 100 to be aligned axially with spray drying apparatus 200. The locating arrangement can include any arrangement that attaches, fits, complements or otherwise communicates the locator on the disposable with the locator on the drying apparatus. Examples of locating arrangements can include a recess/projection arrangement, complementing shape arrangement, hook/receiver arrangement, channel and groove arrangement, a latch and catch arrangement, a magnetic arrangement, and the like. In FIG. 5A, the male locator is on the spray drying apparatus and a complementing female locator is on the disposable, but the arrangement can be reversed. The complementing nature of the arrangement allows for easy matchup and alignment by the operator and can prevent the door from closing unless the disposable is aligned in the spray drying apparatus. In an embodiment, the locating arrangement can include any arrangement that allows for alignment between the locator on the disposable and the locator on the drying apparatus and also allows for alignment between the disposable and the finishing apparatus. In another embodiment, the drying apparatus and the finishing apparatus have the same locator that fits the locator on the disposable to create a universal alignment. Having a universal arrangement reduces the training needed and increases muscle memory because the operator inserts the disposable into the spray dryer and the finisher in a similar way.

When the first locator of the spray drying apparatus and the second locator of the disposable are aligned, in an embodiment, the system of the present invention provides positive feedback to the operator. In an embodiment, spray drying apparatus 200 has spring clip 232 mounted to the top of the drying chamber housing and engages guide 4 when the disposable is aligned and secured in the spray drying apparatus. See FIG. 5A. In this case, the positive feedback to the operator is an audible "click". Such feedback can include an audible indicator (e.g., an audible click) or a visual indicator (e.g., a sensor providing a communication to the display indicating alignment). Retention clip 232 is an alignment element as well since it aligns with ridge 9, further described below.

FIG. 2A also shows guide 4 which is off set from the center of baffle plate 8. The off-set design of the guide on plenum 6 allows disposable 100 to be attached to the receiver 204 (shown in FIGS. 4B and 5A) of spray drying machine 200 in a specific orientation. Prior to inserting the disposable device into the dryer, the operator removes and discards the adhesive covers, if present, from the top, exposing drying gas inlet port 22, and the bottom, exposing gas outlet 30. In a preferred embodiment, the operator removes and discards the adhesive cover from drying gas inlet port 22 only and inserts spray drying head 2 into spray drying head receiver 404. The cover the drying gas outlet 30 at the bottom of the disposable can be removed later, just before it is ready to be attached to the gas exhaust port 208. The operator generally aligns and inserts ridge 9 formed by baffle plate 8 on spray drying head 2 of disposable 100 into groove 207 of spray dryer 200. See FIG. 5A. Once engaged, the operator can use his/her hands to further push spray drying head 2 inward and it will self-align with groove receiver 207 so long as notch locator 26 on spray drying head 2 is within about 30 degrees (e.g., within about 30, 25, 20, 15, 10, 5 degrees) with respect to alignment with projection locator 206 on dryer 200. The insertion and alignment of the spray drying head can be done rapidly e.g., within 10 seconds (2-5 seconds). Receiver 204 of guide 4 also serves as drying gas inlet on the spray dryer and provides the drying gas source (not shown). Ridge 9 of spray drying head 2 also provides support and fits complementarily into groove 207 of receiver 210. It also allows spray drying head 2 of the disposable 100 to be aligned latitudinally with respect to dryer 200.

In an embodiment, receiver 210 has groove 207, as shown in FIG. 4B. The ridge and groove arrangement between the spray drying head and the dryer can be any arrangement that allows the spray drying head to fit within the drying chamber housing 202 such that the arrangement provides support and latitudinal alignment. In addition to groove 207, the receiver can be a shelf, ledge, arm, stopper, base or other structure that engages the baffle plate and allows the spray drying head to remain stable throughout the spray drying process.

The operator then inserts the disposable device by placing the guide 4 into receiver 204 of the spray drying apparatus 200. Once inserted and aligned, the spray drying disposable can no longer move up and down. When using this guide and the locating arrangement, described above, they align the disposable so that it cannot move up and down and cannot move axially about the axis defined by the center of guide 4. As shown in FIGS. 4B and 5A, the guide fits into receiver 204 and does so such that the fit is snug or tight. In this embodiment, once the spray drying end is aligned and in an engaged position, then the operator can remove the bottom adhesive cover at drying chamber gas outlet 30 and attach it to the gas exhaust port 208, as further described herein.

When the locating arrangement (locators 26 and 206) is aligned, guide 4 is inserted into receiver 204, ridge 9 is inserted into groove receiver 207, and retention clip 232 is engaged, in an embodiment, spray drying head is inserted, secured and aligned. Specifically, in an embodiment, retention clip 232 engages ridge 9 to hold the spray drying head 2 in place. Retention clip 232 provides an audible indicator that the spray drying head is properly aligned and inserted. In the embodiment shown in FIGS. 4B, 4C and 5A, the retention clip is a spring clip. The retention clip can be any type of retainer that engages ridge 9 and include, for example, a fastener, pin, clasp, slide and the like. The retainer can be made from metal, plastic, rubber and the like. The retainer that engages the spray drying head is optional.

Although in the embodiment shown in FIGS. 4B, 4C, and 5A, a spring clip is used as an audible indicator to allow the operator to know that spray drying head 2 of disposable 100 is properly inserted and aligned with dryer 200, any type of indicator can be provided. The indicator can be audible, vision or tactile. In an embodiment, a sound indicator provides audible feedback mechanically or otherwise of correctly completed loading of spray drying head 2 of disposable 100. An audible indicator can be mechanical, like the sound of a spring clip locking into place, or can be generated by sensor (mechanical or pressure/contact sensor) that receives a signal of correct positioning of spray dry head 2 in dryer 200 and communicates with an actuator or processor that provides a visual indicator to the operator, for example, on display 212 or on indicator light 234. In an alternative embodiment, the sensor can send feedback to a processor that causes a sound indicator to a speaker to inform the operator of proper placement. In yet another embodiment, the feedback can be in the form of a tactile response, e.g., a vibration to inform the operator of incorrect or correct placement. Feedback can include an audible indicator (e.g., an audible click) or a visual indicator (e.g., a sensor providing a communication to the display indicating alignment).

FIG. 2B is an exploding view of spray drying head 2 and shows the parts of spray dry nozzle assembly 20 along with plenum 6, outer filter sealing ring 90, inner filter sealing ring 92, plenum filter 94 and baffle plate 8 having ridge 9. Nozzle assembly 20 includes, going from top to bottom in FIG. 2B, strain relief valve 75, plasma and aerosol pressurized gas manifold 72, aerosol reservoir 74, cannula 78 having opening 79, liquid nozzle cap insert 80, and nozzle cap 76. The nozzle cap 76 has opening 110 whose inner wall has a diameter, defined by Diameter $D^o$ (See FIG. 2Ia). FIG. 2Ia also shows cannula 78 that has an outer wall (outer diameter) defined by Diameter $D^c$. Diameter $D^o$ is slightly larger than Diameter Dc and the difference is defined by Distance $D^d$. The resultant difference in diameter, Distance $D^d$, creates annulus 81 through which pressurized air received from aerosol reservoir housing 74 forms a vortex and flows to the drying chamber 28 to facilitate the formation of small droplets of fluid to be dried. See Example 1.

Accordingly, the length of the cannula ranges between about 2 and about 5 inches, and in an embodiment, is 3.500 inches+/−0.005 inches.

More specifically, referring to FIG. 2A and FIG. 2B, spray dry nozzle assembly 20 has plasma flow inlet 18 connected to pretreated liquid plasma 66 (shown in FIG. 1A) via plasma tube 16 and aerosol pressurized gas inlet 14 connect to the pressurized gas source (not shown) via aerosol tube 10 and aerosol filter 12. Additionally, drying gas inlet port 22 is shown in FIGS. 1A and 2A and communicates with the drying gas source (not shown). When the plasma source, pressurized gas source, and drying gas source combine, the liquid plasma particles are formed under pressurized (aerosolized) gas and dried into a fine dried plasma (e.g., a plasma powder).

FIGS. 2C and 2D show a detailed perspective view of spray dry nozzle assembly 20. In particular, FIGS. 2B and 2J show where and how the spray dry nozzle assembly fits within assembly opening 96 of plenum 6 of spray dry head 2. Plasma and pressurized aerosol gas manifold 72 coordinates and directs the plasma source via inlet 18 and the pressurized aerosol gas source via inlet 14. Strain relief 75 fits and communicates with manifold 72 to provide support to tubes 10 and 16 and prevent them from collapsing under pressuring during packaging, transport and spray drying. Strain relief 75 also prevents the tubes from collapsing in the packaging and in transit. Spray dry nozzle assembly 20 includes aerosol gas reservoir housing 74 through which the pressurized aerosol gas is held and builds before being released through liquid nozzle cap insert 80 and nozzle cap opening 110 (shown in FIGS. 2G, 2H, 2I, 2Ia, and 2Ic). Nozzle assembly 20 is housed by aerosol gas reservoir housing 74 and secured by nozzle cap 76. Liquid nozzle cap insert 80 guides cannula 78 and holds the cannula in place during use. Annulus 81 is disposed between the outer surface of cannula 78 and inner surface of opening 110. The design of liquid nozzle cap insert 80 and nozzle cap 76 allow the pressurized aerosol gas to flow though annulus 81 in a vortex pattern to maximize aerosolization and promote rapid mixing of the aerosolized plasma droplets with the drying gas, as further described herein. The entire nozzle assembly 20 is secured to opening 96 of plenum 6 which includes baffle plate 8 having ridge 9, with filter 94 therebetween and sealed by inner filter sealing ring 92 and outer filter sealing ring 90. See FIG. 2B.

FIG. 2D shows the aerosol gas reservoir housing 74 as transparent so that cannula 78 and attachment to liquid nozzle cap insert 80 and nozzle cap 76 can be seen and FIG. 2E shows manifold 72 and cannula 78 with the aerosol gas reservoir housing 74, liquid nozzle cap insert 80 and nozzle cap 76 removed. FIG. 2F shows the bottom tip, the end opposite the manifold, of cannula 78 having outer wall surface 84, inner wall surface 86, flat edge 88, and beveled or angled edge 82 (e.g., a chamfer) at the bottom surface of the cannula.

It has been discovered that a cannula with an angled edge (e.g., chamfer) on the inside diameter, when used in spray drying to create the atomized plasma particles, assists or allows many of the proteins in the plasma to remain intact, functional, or both. Hence, the angled edge cannula of the present invention reduces the amount a protein degrades during spray drying because the angled edge cannula reduces shear on the passing liquid plasma film.

In a particular embodiment, a blood protein, vWF, was measured. vWF is considered a more fragile, easily degradable protein, as further described herein. In an embodiment, using spray dry nozzle with the angled cannula of the present invention, vFW recovery is maintained, as compared to a nozzle with a non-angled cannula. In fact, based on the data described in Example 2, using a composite nozzle with a chamfered cannula resulted in an increase in vFW recovery, as compared to both a composite nozzle having non-angled cannula and to a benchmark stainless steel nozzle (as Buchi Model no. 4244 Buchi Corporation of New Castle, Delaware United States). In an embodiment, using a nozzle with an angled cannula resulted in an increase in an amount at least ranging between about 1% and 25% (e.g., 1, 2, 3, 4, 5, 6, 7, 8, 9, 10, 11, 12, 13, 14, 15, 16, 17, 18, 19, 20, 21, 22, 23, 24, and 25%) in vFW recovery, as compared to a nozzle having non-angled cannula. In particular, as described in Example 2, the data show that spray drying with a chamfered cannula having an angle of 45 degrees and length of 0.005" increased the vWF RCO assay result by about 9%-22%, as compared to the same system operated with a composite nozzle having a cannula without the angled edge and, surprisingly, 3.7% better as compared to the benchmark control Buchi nozzle.

Among the plasma proteins maintained throughout the spray drying process using an angled-edge cannula, includes von Willebrand Factor (vWF). vWF is involved in clotting, repairing vascular injury and platelet adhesion. In particular, vWF is a large adhesive glycoprotein with established functions in hemostasis. It serves as a carrier for factor VIII and acts as a vascular damage sensor by attracting platelets to sites of vessel injury. The regulation of vWF multimeric size and platelet-tethering function is carried out by ADAMTS13, a plasma metalloprotease that is constitutively active. It is secreted into blood and degrades large vWF multimers, decreasing their activity. Unusually, protease activity of ADAMTS13 is controlled not by natural inhibitors but by conformational changes in its substrate, which are induced when vWF is subject to elevated rheological shear forces. This transforms vWF from a globular to an elongated protein. This conformational transformation unfolds the vWF A2 domain and reveals cryptic exosites as well as the scissile bond. To enable vWF proteolysis, ADAMTS13 makes multiple interactions that bring the protease to the substrate and position it to engage with the cleavage site as this becomes exposed by shear forces. ADAMTS 13 (a disintegrin and metalloproteinase with a thrombospondin type 1 motif, member 13), also known as von Willebrand factor-cleaving protease (vWFCP), is a zinc-containing metalloprotease enzyme.

Without being restricted to a theory of operation, it is believed that during spray drying, the plasma proteins are subject to considerable shear forces due to the spraying mechanism as the solutions are fluidized out of the end of a fine nozzle to form the droplets in contact with drying air. The process of unfurling multimeric vWF is expected to be triggered by the hydrodynamic forces of elevated shear stress during spray drying in combination with air-liquid interface stress. The shear-induced structural change of vWF, when combined with other physical factors associated with spray drying, such as high temperature and/or unfavorable pH as well as the air-liquid interface stress, may lead to protein denaturation (if unfolded vWF fails to refold properly post-spray drying) and proteolytic degradation (unfolded vWF exposes proteolytic sites for ADAMTS13), impairing the vWF activity in the spray dried plasma, as well as other proteins.

Spray drying system of the present invention can be optimized to reduce the protein damage caused by shear force and temperature and the specially designed cannula of the present invention helps to minimize shear and damage to the proteins include vWF.

The cannula of present invention, in an embodiment, has a bottom edge wherein at least a portion of the bottom edge is angled, referred to herein as an angled edge cannula. In an instance, the entire bottom edge can be angled or a portion of the bottom edge can be a flat edge (e.g., about a 90° angle from the outer wall surface or the inner wall surface). In another embodiment, a portion of the bottom edge of the cannula is a flat edge, like flat edge 88, (e.g., about 90° from the outer wall surface or inner wall surface) and a portion of the bottom edge of the cannula is angled, like angled edge 82, (e.g., 45° angle from the outer wall surface, or 135° angle from the inner side wall surface), as shown in FIG. 2F. This embodiment shown in FIG. 2F can edge having a flat edge (90° from the outer wall) from which a 45° angle is formed is referred to as a "chamfer" or as having a "chamfered edge."

In the case in which the cannula has a bottom edge and the entire bottom edge is angled from the outer wall to the inner wall, the angle as measured from the outer wall surface ranges from about a 30° angle to about a 60° angle (e.g., about a 30°, 35°, 40°, 45°, 50°, 55°, 60° angle) and as measured from the inner wall surface ranges from about a 120° angle to about a 150° angle (e.g., about 120°, 125°, 130°, 135°, 140°, 145°, 150° angle). The length of the angled bottom edge ranges between 0.001 inches and about 0.010 inches (e.g., about 0.001, 0.002, 0.003, 0.004, 0.005, 0.006, 0.007, 0.007, 0.008, 0.009, 0.010 inches).

In the case in which the cannula has a bottom edge having a portion that is a flat edge and a portion that is angled, the flat edge is about 90° angle (e.g., between about 85% to about 95%) from the outer wall surface. The angled edge has an angle, as measured from the outer wall surface (imagining that the angled edge intersects the outer wall surface) ranges from about a 30° angle to about a 60° angle (e.g., about a 30°, 35°, 40°, 45°, 50°, 55°, 60° angle), and in an embodiment, is 45°+/−5° and as measured from the inner wall surface ranges from about a 120° angle to about a 150° angle (e.g., about 120°, 125°, 130°, 135° 140°, 145°, 150° angle), and in an embodiment, is 135°+/−5° See FIG. 11 for an example of a 45° and a 30° angled edge. The length of the flat edge portion ranges between 0.001 inches and about 0.009 inches (e.g., about 0.001, 0.002, 0.003, 0.004, 0.005, 0.006, 0.007, 0.007, 0.008, 0.009 inches) and the length of the angled edge portion ranges between about 0.001 inches and about 0.009 inches (e.g., about 0.001, 0.002, 0.003, 0.004, 0.005, 0.006, 0.007, 0.007, 0.008, 0.009 inches), and in an embodiment, is 0.005+/−0.003. The ratio between the length of the flat edge and the length of the angle edge has a range between about 5 and about 500 percent. In an embodiment, the flat edge adjoins the outer wall surface and the angled edge adjoins the inner wall surface.

The angled edge cannula, accompanied with or without a flat edge, results in less stress/shear on the plasma droplet exiting the cannula, as compared to a non-angled cannula, having a 90° angle. While not being bound to any particular theory, it is believed that when a plasma droplet exits a 90° non-angled cannula edge, a portion of the plasma droplet or plasma film undergoes a shearing effect and, in the process, degrades a high percentage of the plasma proteins therein. In this case, the 90° non-angled cannula exerts a shearing force on the droplet, thereby degrading the proteins in the plasma. As the plasma droplet exits cannula having an angled edge, as in the present invention, less sheer on the plasma droplet is exerted. As the plasma is drawn out by the air flow of an angled edge cannula, it accelerates based upon the plasma feed rate and the plasma gets pulled around the cannula edge. Unlike a cannula having a 90° non-angled edge, the plasma is not forced to make a 90 degree turn. By softening the turn that the plasma makes as it exits the cannula by angling the edge of the cannula, less shear is exerted upon the liquid film as it is drawn out. The liquid plasma film that exits out of an angled cannula is thicker and accelerates more slowly thereby reducing shear exerted on the liquid.

The inner diameter of the cannula ranges between about 0.010 inches and about 0.040 inches, and in an embodiment, is 0.030 inches+/−0.002 inches and the outer diameter ranges between about 0.030 inches and about 0.060 inches, and in an embodiment, is 0.050 inches+/−0.0005 inches. The angled edge of the cannula impacts the size of the atomized droplet. When exiting an angled cannula, the droplet sizes in this range is between about 5 microns and about 35 microns and in an embodiment the droplet size is about 10 microns. Small droplet size which is defined in part by the angled edge of the cannula, promotes rapid mixing, faster evaporation and reduced drying time. See FIG. 2T which shows that the larger the droplet size the longer it takes for the droplet to evaporate with higher drying gas temperatures. The shape of the droplet is created by its surface tension dominates and creates a sphere after exiting the cannula. Droplet size is also primarily impacted by the pressurized gas rate ratioed to the liquid feed rate (ALR) and nozzle design.

The cannula of the present invention can be made from a stainless-steel material suitable for medical devices. Examples of the grade of stainless steel that can be used is grade 304 and 316 stainless steels. The stainless steel used for the cannula of the present invention is commercially available e.g., from Bergsen Metals (Santa Fe Springs, California, USA) or Fort Wayne Metals (Fort Wayne, Indiana, USA). The nozzle assembly (except for the cannula), nozzle insert, nozzle cap, plenum and baffle plate, outer filter ring, inner filter ring and the like can be made from plastic used in medical devices, such as a polycarbonate, polypropylene, polysulfone or combination thereof. Each aforementioned part can be made from the same material, from different materials or a combination thereof. Such plastic is commercially available and can be purchased from e.g., Covestro AG (Kaiser-Wilhelm-Allee 6051373 Leverkusen, Germany), Teknor Apex (Pawtucket, Rhode Island USA), Colorite Plastics of NJ Inc (101 Railroad Ave, Ridgefield, New Jersey USA), American RENOLIT Corporation (301 Berkeley Drive, Suite B, Swedesboro, New Jersey USA), and Exxon Mobile (Technology Centers, Baytown, TX USA 77520, United States), or molded from e.g., Egli Machine (Sidney, NY USA) Co, and Southwest Mold, Inc. (Tempe, AZ USA). Other materials now know or later developed can be used for the cannula and/or nozzle so long as when combined result in a maintenance or increase in vWF recovery in plasma after spray drying.

A stainless-steel nozzle, such as Buchi Model no. 4244 (Buchi Corporation of New Castle, Delaware United States), is often used in spray drying but it is expensive to manufacture or buy, especially for a disposable device that is discarded after each spray drying run. For example, a common Buchi stainless steel nozzle body, part No. 4244, costs between $1000 and $2000. The nozzle assembly of the present invention is a composite nozzle for use in spray drying and especially spray drying of delicate materials such as human blood plasma at a cost of less than $30.00, orders of magnitude less than stainless steel nozzles, such as the Buchi Model no. 4244. The described Buchi nozzle serves as a useful benchmark for a composite nozzle as it had been used by the applicant to make dried human blood plasma that preserved the proteins in blood plasma to a regulatorily acceptable level.

As indicated, most of the nozzle assembly, except for the cannula which is made from a stainless-steel material, is made from a less expensive plastic material, as described above. As such, the nozzle assembly is also referred to as a "composite nozzle" or "composite nozzle assembly" to refer to the two or more different types of materials used to make the nozzle assembly (e.g., a stainless-steel cannula and a polycarbonate nozzle insert and nozzle cap). Example 2 shows that a chamfered cannula of a composite nozzle assembly provides for improved vWF recovery as compared to one that has a unchamfered cannula, and vWF recovery about as good as an expensive stainless-steel nozzle.

When the plasma exits the tip of the cannula, it is exposed to the pressurized aerosol gas at nozzle cap 76. More particularly, the pressurized aerosol gas exits in a vortex pattern through the annulus 81 and hits the liquid plasma droplets flowing from the chamfer edge/angled edge 82 of cannula 78 and the plasma atomizes to form a plume. When the atomized plasma exits the spray dry nozzle assembly, it is exposed to the drying gas and dries into plasma powder in the drying chamber. In an embodiment, the tip of cannula 78 is flush with the distal end of opening 110.

Liquid nozzle cap insert 80 secures the bottom portion of cannula 78 and guides the pressurized aerosolized gas flow. FIG. 2G shows a perspective top view liquid nozzle cap insert 80. As can be seen, cap insert 80 has insert wall 116 and cannula anchor 120 which has an opening (not shown) through which cannula 78 extends. The top of insert wall 116 forms a ridge and the side of insert wall 116 defines a series of recesses 118 and projections 119. Cannula anchor 120 supports the tip of cannula 78 during plasma flow. Angled edge 82 of cannula 78 through which the plasma exits and annulus 81 through which the pressurized aerosol gas is emitted create the actual nozzle. Cannula anchor 120 is a hollow, cylindrical base but can be of any shape so long as the cannula is supported, and its position maintained during spray drying. The recesses of the wall, recesses 118, allow for the pressurized air to pass from the reservoir (defined by reservoir housing 74) to the area between nozzle cap insert 80 and nozzle cap 76 before exiting the center opening 110 of nozzle cap 76. When the pressurized air exits center cap opening 110, the air exists through annulus 81 defined by the outer wall of cannula 78 and inner wall of opening 110. More specifically, when the cap insert 80 is secured to cap 76 and cannula 78 resides within opening 110, the pressurized air exits through annulus 81. See FIG. 2Ia. As such, the diameter of opening 110 is greater than the outer diameter of cannula 78. In particular, opening 110 of nozzle cap 76 has an inner wall with a diameter, defined by Diameter $D^o$ (See FIG. 2Ia). FIG. 2Ia also shows cannula 78 that has an outer wall defined by Diameter $D^c$. Diameter $D^o$ is slightly larger than Diameter $D^c$ and the difference is defined by Distance $D^d$. The resultant difference in diameter, Distance $D^d$, creates annulus 81 through which pressurized air received from aerosol reservoir housing 74 forms a vortex and flows to the drying chamber 28 to facilitate the formation of small droplets of fluid to be dried. In an embodiment, the outer diameter of cannula 78, Diameter $D^c$, is between about 0.030 and about 0.070 inches (e.g., 0.030, 0.040, 0.050, 0.060, 0.070) and the diameter of opening 110 is between 0.075 and 0.100. For ease of use, "Distance $D^d$" is also referred to as the "radial distance of annulus 81." In an embodiment, the Diameter $D^c$ is 0.050+/−0.0005 inches and the Diameter $D^o$ is 0.082+/−0.001 inches. The radial distance between the outside surface of cannula 78 and the inner surface of opening 110, Distance $D^d$, is the space through which the rotating vortex of pressurized aerosol gas flows and assists in creation of small droplets of plasma to mix with the hot drying gas during spray drying. In an embodiment, $D^d$ has a range between 0.005 and 0.030 inches (e.g., 0.015 and 0.021 inches).

Along these lines, the data from Example 1 show that that the radial distance of annulus 81, $D^d$, has an impact on both the yield for dried product from the drying process and on the preservation of vWF. Yield is the ratio of starting solids in the to-be-dried liquid material by weight to dried material recovered by the drying process by weight.

Before the present invention, one source of loss of yield occurred when dried sprayed material that was not fully dried and retaining residual moisture above about 2.5% contacted and stuck to the interior structures of the drying disposable during drying without being recoverable.

Example 1 describes the reduction in the amount of material visibly stuck to the underside of baffle plate 8 after completion of the drying cycle. The data described in Example 1 show that overall yield by weight was increased by changing the radial distance of annulus 81 $D^d$ from 0.021" to 0.015". The yield was acceptable with the annulus dimension at 0.021". However, the yield percentage was improved by more than 2.2% by reducing the annulus width/diameter to 0.015". Other features of disposable 100 increase yield and include, in part, drying jets 142 that form an air wall within plasma drying chamber 28, as further described herein.

Example 1 also described in increase in the recovery of vWF as measured by Ristocetan (RCO) assay by changing the radial distance of annual 81 from 0.021" to 0.015." The vWF recovery was acceptable with the annulus dimension at 0.091". However, vWF recovery was increased by more than 2.0% by reducing the annulus width to 0.082". Other features of disposable 100 also increase vWF recovery and include, in part, the angled edge cannula 78, as described herein.

The space between nozzle cap insert 80 and nozzle cap 76 before exiting the center opening 110 of nozzle cap 76 is generally referred to herein as the "vortex generator" which includes a series of channels and curved pads, as further described below. Pressurized air passes through recesses 118 that act as openings in nozzle assembly 20 to allow air to enter and travel down the channels and between the curved pads. See FIGS. 2G, 2H, 2I and 2Ic.

Referring to FIG. 2H, the bottom of surface of cap insert 80 not occupied by pads 122 on the underside of projections 119/recesses 118 and will act as walls for the channels in the vortex generator. Pads 122 form a kidney-like shape that assists in locating recesses 118 for the vortex air flow pattern. The nozzle cap, cap 76, shown in FIG. 2I, has complementary receivers 112 to receive the pads from the cap insert 80. The complementary fit between nozzle insert 80 and nozzle cap 76 is shown in FIG. 2Ic (as a cross-section). Nozzle cap 76 also has nozzle cap channels 106 extending from bulbous head 108 and ending at opening 110. The surface of the bottom of cap insert 80 that is not occupied by pads 122 and further complemented by channels 106 of cap 76, is the space through which the pressurized air flows. The vortex generator includes the recesses 118 and the surface of the bottom of cap insert 80 that is not occupied by pads 122, bulbous heads 108 and channels 106 of cap 76, the shape and position of each cause the pressurized air to form a vortex air flow pattern. Bulbous head 108 receives the pressurized air flow through recess 118 and the curved ramp like surface of channel 106 provides a curved boundary for the air to flow. In other words, recesses 118 is an entrance port and feeds the air flow and channels 106 feeds the vortex. Channel 106 are arched and further accentuates the curved air flow and directs the tangential air flow toward opening 110 in which cannula 78 resides. These channels, channels 106, guide the air in a circular fashion from bulbous head 108 to nozzle cap opening 110, all working in concert to expel pressurized air as a vortex through opening 110. The design provides tangential momentum to provide an efficient generation of a vortex. Channels 106 are in the form of an arc or curve, and the radius of the curvature ranges from about 0.10 inches to about 0.25 inches, and in an embodiment about 0.140+/− 0.010 inches radius. The vortex generated includes 4 channels but can have between about 2 and 12 channels (e.g., 2, 3, 4, 5, 6, 7, 8, 9, 10, 11 or 12 channels). Other types of shaped channels can be used. FIG. 2I shows the design molded into nozzle cap 76. Designs A and B both show more linear channels but Design A have no equivalent of a bulbous head and Design B shows a bell-shaped head. Design C is similar to the design shown in FIG. 2I but with a lobe instead of a bulbous shape at the end. The present invention includes nozzle caps having Designs A and B but found the Design C appears to be a more efficient vortex generator. The various designs demonstrate that any combination of channels, heads and shapes can be used to generate a vortex in the annulus. Other types of channels include conical shaped channels including convert or divergent cone shapes and the like.

As the vortex is generated, pressure and velocity flow patterns are shown in FIGS. 2O and 2P. FIG. 2O shows the static gas pressure in psig at the top and tangential velocity contours in the aerosol pressurized gas flow in m/s at the bottom. As can be seen, there is an inverse relationship between pressure and velocity. In areas where the pressure is increased, the velocity is decreased and vice versa. In particular, at bulbous head 108 where the pressurized gas enters the vortex generator, there is higher relative static gas pressures (e.g., about $2.54 \times 10^1$ psig) and relatively low velocity flow rates (e.g., about $2.00 \times 10^1$ m/s). Conversely, at annulus 81, relatively low or negative gas pressures (e.g., about −2.24 psig) and higher velocity (e.g., between about −1.58×10² to about −3.75×10² m/s). As the pressurized aerosol gas travels along the curved nozzle cap channel 106, the pressure and velocity are at rates in between. As such, the vortex generator of the present invention has gas pressure of between about 2.54×10¹ psig to about −2.24 psig and velocity at a rate between about 2.00×10¹ m/s and about −3.75×10² m/s. In an embodiment, any vortex generator can be used with the present invention so long as gas pressure and velocity are produced in these ranges. Similarly, FIG. 2P shows a more detailed velocity pattern that occurs in annulus 81. The pressurized gas moves between exits of channels 106 as it integrates into the vortex. The pressurized gas accelerates when it enters annulus 81 and becomes a vortex.

The vortex generator in this embodiment includes a curved pad/ramp, a bulbous head to receive the pressurized air flow and curved channels extending to the exit opening. The present invention can include other vortex generator elements such as wings, edges, wedges, vanes and the like. Other shaped channels can also be employed to create a vortex generator. One of skill in the art can utilize other vortex generators of residing within the insert and the cap of the nozzle assembly of the present invention so long as the pressurized air exits between the inner surface of opening 110 and the outer surface of the cannula 78 in a vortex.

The pressurized air circulates between the outer surface of cannula 78 and the inner surface of opening 110. Specifically, the pressurized gas exits through annulus 81. The plasma is pumped through cannula 78 by peristaltic pump 214 at approximately room temperature. The plasma travels down the inside of stainless-steel cannula 78 and is drawn out of cannula 78 by the pressurized aerosol air flow exiting annulus 81. The high-speed aerosolization air flow atomizes the liquid droplets. In an embodiment, the steady-state plasma feed rate is between about 6 and about 23 mL/min (e.g., 6, 7, 8, 9, 10, 11, 12, 13, 14, 15, 16, 17, 18, 19, 20, 21, 22, or 23). In a preferred embodiment, 13.5 mL/min is the steady-state feed rate after system is warmed-up, in thermal equilibrium.

In an embodiment, the plasma feed rate is related to or dependent on the outlet temperature. As the outlet temperature lowers, the system adjusts to lower the plasma feed rate. Conversely, as the outlet temperature increases, the system increases the plasma feed rate. The outlet temperature may be lower when the spray dryer is warming up or when time passes between spray drying runs, for example. In particular, in an embodiment, the plasma feed rate can be modulated as follows:

TABLE 1

| Dryer Inlet Temperature C. | System heat loss kW | Dryer Outlet Temperature C. | Dryer Outlet Relative Humidity % | Plasma feed rate mL/min | Reduction in feed rate % change |
|---|---|---|---|---|---|
| 114 | 0.18 | 65 | 11.7 | 13.5 | |
| 100 | 0.18 | 59.3 | 11.8 | 10.5 | 22.2% |
| 80 | 0.18 | 50 | 11.8 | 6.6 | 51.1% |

Chart values calculated based upon thermodynamic principles, assuming constant system heat loss, full droplet evaporation, and a dryer outlet relative humidity of <11.8%.

As such, when the outlet temperature is lower, the plasma feed rate lowers to maintain the target drying chamber outlet temperature needed to dry the plasma to a residual moisture of less than 2%. When the outlet temperature is higher within the range, the plasma feed rate can also be increased, and still maintain a residual moisture content of plasma of less than 2% only if the total gas flow can be increased and/or the drying chamber outlet temperature is allowed to increase to maintain target system relative humidity.

Just below the cannula there is negative pressure, while pressurized gas flow is at a high velocity. Generally, the velocity increases along a pathway of decreasing static pressure. The aerosol pressurized gas travels through the series of channels 106 and creates a vortex flow which both atomizes the plasma droplets and directs the initial droplet trajectory. Aerosol flow rate is between about 20 splm and about 60 slpm (e.g., about 20, 25, 30, 35, 40, 45, 50, 55, 60 slpm) and in an embodiment is about 40 slpm. This occurs with a pressure of between about 180 kPa to about 260 kPa (e.g., about 180, 190, 200, 210, 220, 230, 240, 250, 260 kPa) and in an embodiment about 227.5 kPa (33 psig). The aerosol flow acts to draw the liquid feed out of the cannula where it forms a film across the end. The expansion of the aerosol gas as it exits the opening locally cools the near nozzle gas field, which also acts to delay evaporation slightly by cooling the liquid droplets. Also, in an embodiment, the pressure just below the end of cannula is less than that inside the cannula and pressurized gas velocity is accelerating when traveling along the outside surface of the cannula. Upon exit, the spherical plasma droplets hit the pressurized gas to aerosolize and form a spray plume which is surrounded by a ring of drying gas jets, which are further described below. See FIG. 2N. The mixing of aerosol and drying gas sets the initial conditions for the evaporation process.

FIG. 2Q is a schematic that shows the liquid plasma droplet undergoing the drying process. The plasma droplet is atomized at the nozzle assembly cannula exit into the drying chamber and is generally spherical. The dried plasma particle is formed with heat and mass transfer. Drying takes place is two stages. These are: evaporative drying stage (constant rate) drying which occurs in the initial drying (e.g., in, less than 1 second) and falling rate drying (diffusion limited) which occurs after the evaporative drying stage and continues so long as the dried particle is subject to ambient relative humidity lower than its internal relative humidity.

The factors involved in the evaporative drying stage of the plasma droplet include the temperature of the plasma and the drying gas, the surface area of the droplet, the humidity in the drying gas and the air circulation within the plasma drying chamber. When initially exiting the nozzle assembly, the temperature of the drying gas is between about 90° C. to about 130° C. (e.g., between about 100° C. to about 114° C.) and the temperature of the plasma droplet is between about 20° C., and about 65° C. in the plume as shown in FIG. 2Sa. The heat flows from a point of higher temperature to that of a lower temperature, and in this case the drying gas heat flows to the plasma droplet. With respect to the surface area, the droplet is spherical thereby maximizing its surface area and the droplet size is very small so the mass and heat transfer can happen quickly. The relative humidity in the drying gas is very dry (e.g., about 0.1% RH) and therefore the low humidity of the surrounding drying gas promotes evaporation of the plasma particle. Finally, as described in more detail below, the drying gas is emitted using several drying gas jets in an angled and downward direction into the plasma drying chamber and into the plume of atomized droplets to initiate rapid mixing of the drying air and the atomized droplets, which increases the rate of evaporation of the liquid droplets. The drying rate is constant and as the liquid particle evaporates and loses moisture, the moisture transfers from the liquid plasma droplet to the drying gas, and the heat from the drying gas transfers to the plasma droplet making it into a dried particle. The plasma droplet enters the drying chamber essentially at room temperature and the temperature stays constant the majority of the evaporation period. See FIG. 2S. Once most all of the moisture leaves the particle, the temperature of the particle increases to equilibrate with the dryer chamber exit temperature of 65° C. During evaporation, the droplet is maintained at a lower temperature thereby protecting heat sensitive proteins such as vWF. See FIG. 2S. During the evaporation process, the temperature of the liquid droplet and the proteins therein experience a lower temperature, the thermodynamic wet bulb temperature, compared to the inlet drying gas temperature, thereby protecting the proteins. See FIG. 2R. Evaporation reduces protein temperature to near the thermodynamic wet bulb value and when the evaporation slows the particle temperature rises. See FIG. 2Sa.

The starting liquid droplet size produced by the nozzle assembly impacts the residence time in the drying chamber needed to complete evaporation. The larger the liquid droplet, the smaller the ratio of evaporation surface area to droplet mass and the slower the mass transfer rate from the droplet. This slower rate requires a greater distance between nozzle assembly 20 and the lower filter 36 to avoid overly wet particles depositing on the filter membrane of lower filter 36. An overly wet particle causes "plugging or blinding" of the porous filter membrane and the inability to complete the process as the chamber pressure would elevate excessively, preventing production of powder. See FIG. 2T.

Additionally, FIG. 2T shows that in all cases, the majority of the evaporation occurs in the upper portion of disposable 148. This is particularly seen when using a small droplet size, e.g., under 15 microns. As seen from FIG. 2T, the drying chamber can be shortened to that where the majority of the evaporation occurs while still allowing a dried particle to achieve less than 2.5% residual moisture before being deposited on lower filter 36. In other words, in an embodiment, drying chamber 28 can be shortened by an amount between about 8 inches and 1 inch when the droplet size is below about 15 microns and achieves a residual moisture of below about 2.5%.

Turning to the plenum, the functions of the plenum include 1) allowing for the introduction and flow of the drying gas to the disposable, 2) housing the nozzle assembly, and 3) provide support for the drying chamber during the spray drying process. The underside of plenum 6 is shown in FIG. 2J. Plenum 6 has two openings, opening 96 to receive nozzle assembly 20 and drying gas inlet port 22 to receive the drying gas.

Nozzle assembly receiver opening 96 is complementary in shape to the top of nozzle reservoir housing 74 and manifold 72. The top of nozzle assembly 20 is secured in opening 96. The length of nozzle assembly coincides with the height of plenum 6 such that the bottom of nozzle assembly 20 extends past baffle plate 8. See FIGS. 5A and 5B. In certain embodiments, the cannula is flush with the nozzle assembly and the baffle plate. Nozzle assembly 20 can be secured with adhesive, fasteners, or with an interlocking assembly (e.g., a spring latch, screw fit and the like).

The other opening of plenum 6 is drying gas inlet port 22 which receives the drying gas. The drying gas source (not shown) flows into the plenum through drying gas inlet deflector 242, which is shown in FIG. 2K. Once the disposable is secured and aligned, and the door to the spray dryer is closed and spray drying begins. Drying gas inlet deflector 242 lowers through drying gas inlet port 22 to provide the drying gas to plenum 6. Drying gas inlet deflector 242 has the shape of an elbow so that the drying gas flows toward the far inside side wall of the plenum creating a tangential mixture, as shown in FIG. 2Ka. The right angle of deflector 242 distributes the drying gas throughout plenum 6, creating a low velocity, highly uniform pressure reservoir. Uniformity is desired to create low velocity, uniform pressure of the drying gas as it exists each of drying jets 142. When the drying gas is not deflected off the side of plenum 6 but instead in a downward direction, the air pressure can be asymmetrical with drying jet closer to the drying gas inlet experiencing high pressures as compared to those farther away from the inlet. Accordingly, the present invention includes a drying gas inlet that is deflected to the side of plenum e.g., with a 90-degree elbow as is the case with deflector 242. Other geometries of deflector 242 can be employed to create a uniform air pressure in plenum 6. For example, the deflector can be angled at degree less than a 90-degree angle, as measured from the top surface of the plenum. For example, the deflector can have angle ranging between about 60 and about 110 degrees relative to the top surface of plenum 6 so that the drying gas pressure across the width of plenum 6 is substantially uniform. Alternatively, more than one drying gas inlet from opposing sides can be used to create a substantially uniform drying gas pressure across the width of plenum 6.

As shown in FIG. 2J, plenum 6 has concentric ribs 98 and radiating ribs 102. These ridges provide support for the structure of plenum 6. The additional support provided by the concentric and radiating ribs allow the plenum to withstand the pressure and heat of the spray drying process. Since the drying gas is a low velocity, uniform pressure air container, concentric ribs 98 and radiating ribs 102 do not contribute to or affect the drying gas air flow. Similarly, the projections on the inside side wall of the plenum, projections 104, are used in the injection molding process when making the plenum and are not involved in the drying gas flow.

Referring to FIGS. 2L, 2La, and 2M, the baffle plate has several functions as follows: A) serves as a support in securing disposable 100 when the disposable is aligned and inserted into spray dryer 200, B), creates drying gas air flow channels and releases the drying air into plasma drying chamber 28 of disposable 100, and C) supports baffle filter 94.

FIG. 2L shows the top, inside view of baffle plate 8. The inner surface of baffle plate 8 has baffle plate nozzle opening 140 through which a portion of nozzle assembly 20 resides. Baffle plate 8 also includes raised outer ring 124 with its base 126 and raised inner ring 128 with its base 130. Outer sealing ring 90 is placed around outer ring 124 and inner sealing ring 92 is placed round inner ring 128. The sealing rings prevent drying gas from flow out the edges of filter 94 and instead the drying gas flows through it. The inner side of baffle plate 8 further includes locator 132 for insertion of locator notch 26 of plenum 6. The plenum and baffle plate have locators to align one another. Baffle plate 8 has baffle locator 132 that receives plenum locator 152 on plenum 6.

Baffle plate ribs, 134, 136 and 138 provide support to baffle plate filter 94 (shown in FIG. 2L) while keeping most of the surface of filter 94 lifted off the baffle plate during use. The baffle plate ribs also act as a guide for the drying gas flow. It has been determined that if the baffle plate filter 94 lies flat on the inner side of baffle plate 8 without ribs, the drying gas flow slows and does not freely flow through the plurality of drying jets 142. To obviate that phenomenon, in particular, baffle plate 8 has radiating ribs 134 which connects inner ring base 130 with outer ring base 126. Each radiating rib 134 has a consistent profile throughout its length and allows the filter to sit in a raised position, as compared to resting directly on inner surface of the baffle plate. Radiating ribs 134 also form pie-shaped air channel 139 leading to drying jet 142. Radiating ribs 134 are the side walls of pie-shaped air channel 139. Baffle plate 8 has two types of ribs that extend from outer ring base 126 but do not connect with or reach inner ring base 130. Of these types of ribs, there is shorter radiating rib 136 and intermediate radiating rib 138. Both shorter radiating ribs 136 and intermediate radiating ribs 138 have a consistent profile in height as it proceeds from outer ring base 126 inward and then quickly tapers at tapered end 137. The tapered end 137 aids in supporting the filter without creating a corner on which the filter could be pierced. In particular, baffle filter 94 rests atop ribs 134, 136 and 138 and is pressed against the ribs during spray dryer operation by air pressure e.g., of about 11.5 psig. The tapered ends on ribs 136 and 138 reduce the stress placed on the baffle filter, prevents damage to the filter and reduces loss of filtration efficiency. See FIG. 2La. The ribs keep baffle filter 94 from adhering to the inner baffle plate surface. Connecting ribs and non-connecting ribs are interspersed on the baffle plate inner surface and in the embodiment shown in FIG. 2L form a pattern within pie-shaped air channel 139 (e.g., connecting rib, shorter non-connecting rib, two intermediate non-connecting ribs, shorter non-connecting rib, connecting rib, etc.). Each pie-shaped air flow channel 139 defined by two connecting ribs on either side. The connecting and non-connecting ribs can be any pattern so long as they provide support for baffle filter 94 while also allowing drying gas to flow through filter 94 and beneath filter 94 and through the air channels 139 to drying jets 142. For example, FIG. 2La show another arrangement of ribs 136 and 138.

In an embodiment, the pressure drops when the drying gas passes baffle filter 94. The input drying air pressure in plenum 6 before traveling through the filter into the pie-shaped air flow channel 139, during operation, is between about 8 and about 15 psig, and in an embodiment is approximately 10.4 psig, When the drying gas passes baffle filter 94, the pressure drops by about 40-60% or in an embodiment by approximately 6 psig, The pressure decrease across baffle filter 94 is utilized to aid the uniform distribution of drying gas being injected into the drying chamber as shown in FIG. 2Ma. This feature helps to minimize asymmetric drying within the chamber to enable the overall shorter length. The resultant pressure in the drying chamber 28 in area defined by Dimension Z ranges between about 4 psig and about 7 psig and in an embodiment is approximately 5.5 psig. Although further described later herein, lower filter 36 of disposable 100 causes a pressure drop by about 40-80% or in an embodiment by approximately 3.0-5.5 psig that increases as dried plasma accumulates on the filter resulting in exiting air pressure of approximately 1-2.5 psig. In an embodiment, the gas exhaust port 208 of spray dyer 200 is slightly constricted so that the exhaust gas leading to the outside is about 1.5 to about 3 psig. If there are valves, sensors or tubing length past the exhaust exit those will add a small pressure increase.

In an embodiment, the flow of drying gas passing through and over the baffle plate 8 is not restricted. In an aspect, the height and placement of the ribs 134, 136, 138 of baffle plate 8 are such that the baffle plate filter 96 does distort somewhat under the pressure of the drying air but has no material effect on the pressure drop. Note that baffle plate filter 96 does create a pressure drop as the drying gas passes through it, as described above, but not so with baffle plate 8 itself. The cross-sectional area of pie shape channels 139 is equal to or greater to the cross-sectional area of the opening of the drying gas inlet deflector 242. Or alternatively, the cross-sectional area of pie shape channels 139 are equal or greater to the sum of the cross-sectional area of sum of all of the openings of the drying gas jets 142.

The data shown in Example 3 show that that air flow channels 139 of baffle plate 8 shown in FIG. 2L does not impede the bacterial filtration efficiency (BFE) of baffle filter 94 permitting a greater than log 6 reduction of pathogens when challenged by *S. aureus* in BFE under American Society for Testing and Materials (ASTM) F2101-14 and does not damage the baffle filter 94 during operation of the spray dryer 200. See Example 3.

In an embodiment, baffle filter 94 is a 0.2 micron filter (e.g., 0.22 micron filter) that prevents pathogens that may be introduced into the drying gas from entering the drying chamber. The filter can be at least a 0.2 micron filter, e.g., a 0.1 micron filter or less so long as drying gas can flow through as described herein. The filter is strong enough to withstand heat and pressure of the spray drying process but flexible enough to not tear when pressed against the ribs as air flows through it. The baffle filter is such a filter and can be a 0.4-micron depth or membrane filter. The filter is commercially manufactured by Gore (231 East Oak Street Bozeman, Montana USA) Lydal (Rochester New Hampshire USA), Teijin (Chiyoda City, Tokyo, Japan), or Sabeu (Northeim, Germany). Any type of commercially available filter can be used so long as can prevent pathogens from being introduced into the drying chamber, but porous enough to allow drying gas to pass through it at the flow rates specified. The baffle filter and lower filter can be made from e.g., a polyethylene filter matrix. In an embodiment, baffle filter 94 is commercially available from Sabeu of Northeim Germany as Art. No. 063090.

Referring to FIG. 2M, the underside of the baffle plate can be seen. After the drying gas passes through baffle filter 94 it exits through a plurality of drying gas jets 142. In an embodiment, drying gas jets 142 have centerlines along their length that are parallel to one another and perpendicular to the baffle plate 8. Despite the mechanical structure described of jets 142 the drying gas air exiting from them does so in an inwardly angled manner toward the center line of drying chamber 28. FIG. 2N and FIG. 2Na shows the flow pattern of drying gas jets 142.

Drying gas jets 142 effectively create an "drying gas air wall," as shown in FIG. 2Ma, within plasma drying chamber 28 while promoting rapid mixing with the atomized plasma particles. The drying jet air flow are directed, in part, to the plume of atomized liquid plasma droplet for rapid mixing. The drying gas air wall minimizes build-up of dried plasma on the inner wall of plasma drying chamber 28.

A plurality of indentations 144 exists inside the plurality of drying gas jets 142. Indentations 144 are used to provide additional support to the structure so that plenum 6 and baffle plate 8 do not buckle during spray drying and are not involved in the air flow. Drying gas jets 142 are concentrically positioned in relation to indentations 144. In the embodiment shown in FIG. 2M, there are 16 drying jets 142. The present invention can have more or less drying jets, ranging from 2-32 jets.

Additionally, drying gas jets 142 are not flush with the baffle plate but extend past the plane of baffle plate, similar to the nozzle assembly. Extending nozzle assembly 20 and drying gas jets 142 past the plane of the baffle plate allows for drying of the plasma to occur away from the baffle plate surface so that the dried plasma build up is reduced on the baffle plate's outer surface and/or to the bottom surface of the nozzle assembly during the drying process.

In light of the structures above, the heated drying gas dries the atomized plasma droplet as follows. Heated drying gas is fed to the top of the plenum through deflector 242 at flow between about 500 slpm to about 1000 slpm (e.g., about 500, 550, 600, 650 700, 750 800, 850, 900, 950, 1000 slpm) and in an embodiment at about 750 slpm. Heated drying gas enters the plenum at a temperature between about 100° C. to about 130° C. (e.g., about 100, 105, 110, 115, 120, 125, 130° C.) and in an embodiment at about 114° C. Deflector 242 diverts gas 90 degrees to aid uniformity of the air flow within the plenum. Drying gas is forced through baffle filter 94 (e.g., a 0.2 micron, sterilizing rated filter) which sits on the top side of the baffle plate. As described above, baffle plate 8 is designed with channels to create pie shaped air channel 139 with the filter providing the top surface of the channels. Pie shaped ducts 139 direct the drying gas to the 16 individual drying gas jets 142. This flow structure creates jets which are directed inward, toward the atomizer to aid on the plume containment. The mixing of the heated drying gas, aerosol gas, liquid droplets and water vapor drive the evaporation to convert the plasma into dried powder. That process will largely be completed in less than one second at the present invention's spray drying process conditions, with individual particles formed in the upper portion, defined by Dimension X of drying chamber 28.

Inner concentric ridge 146 of on outer side of baffle plate 8 is the base for attachment of the wall of plasma drying chamber 28. Plasma drying chamber 28 can be attached to baffle plate 8 with a collar or ring, an adhesive, a fastener and the like. Plasma drying chamber 28 can also be attached to baffle plate 8 at ridge 146 by heating welding the chamber to baffle plate 8. A point of attachment can also be molded as part of the baffle plate. The drying chamber can be attached to the baffle plate in any number of ways that are commercially available.

Detailed Description of the Drying Chamber

As mentioned herein, the purpose of drying chamber 28 is: A) to allow for the drying of sprayed plasma while preserving proteins and their function, B) to capture the dried plasma while allowing the gas to exit, and C) to later transform into the commercial dried plasma unit without a filter. The drying chamber in an embodiment is a sterile, non-pyrogenic, single use dual purpose chamber, where the plasma is dried, collected and stored in a portion of the chamber for use.

Exploding FIG. 3 and FIG. 5A show drying chamber 28 which includes an upper section defined by length X, a midsection defined by length U and a lower section defined by length V.

Upper portion 148 is attached to baffle plate 8 via baffle plate ring 156 at outer concentric ring 146. Through baffle plate 8 protrudes nozzle assembly 20. As mentioned above, nozzle assembly 20 and dry gas jets 142 extend past the plane defined by baffle plate 8. As such the convergence of the atomized plasma occurs in upper portion 148 of plasma drying chamber 28. Most of the drying of the atomized plasma particle occurs in upper portion 148 although the plasma does continue to dry as it travels along the length of drying chamber 28. When the pressurized air is in the nozzle assembly, it is a vortex configuration. As the plasma film exits the cannula and the pressurized air exits the annulus as a vortex, the droplets aerosolize or atomize, and form a plume, and the vortex configuration weakens and widens as it travels downward, as shown in FIG. 2N. Meanwhile, drying gas jets 142 direct gas so that the flow is angled inwardly toward the plume to contain the plume and rapidly mix with the aerosolized plasma droplets. The combination of the weakened vortex and the flow from the angled drying gas flow dilute the spray plume of plasma droplets to get more drying gas around the plasma droplet to promote rapid mixing of the drying gas and the droplets. This action promotes efficient evaporation of the plasma droplet, which occurs nearly entirely in the upper portion of the drying chamber. When rapid mixing occurs, as it does with the present invention, the droplet evaporates and does so relatively quickly and at a lower temperature than the drying gas, which preserves the plasma proteins. See FIG. 2S. In contrast to freeze dried plasma, the rapid drying of the plasma of the present invention largely obviates the formation of crystals, especially undesirable cholesterol crystals in the dried plasma.

The gas flow from drying air jets 142 form an air curtain to impede the dried plasma particles from depositing on the inner side wall of the drying chamber. Additionally, the angled air wall formed from drying jets 142 also serve to direct the dried plasma particles in a downward direction toward lower filter 36.

Although most of the plasma undergoes evaporation and dries in upper section 148, drying of plasma continues in midsection 46, defined by Dimension U. Midsection 46 that has "seal and separate" locations 44A and 44B, label 40, spike ports 42A and 42B and hanging slot 34. "Seal and separate" locations 44A and 44B are the locations at which drying chamber 28 is cut to create dried plasma unit 60 (shown in FIG. 8). As described herein, a finishing apparatus, apparatus 400, moves the plasma within the disposable and seals and separates at locations 44A and 44B to isolate midsection 46 and remove upper portion 148 and lower portion 150 of the disposable to create the dried plasma unit. Spike ports 42A and 42B are for use with the dried plasma units. The spike ports can be used to reconstitute the dried plasma with a reconstitution solution or sterile water for injection (SWFI). Spike ports are plugging and/or connecting devices, and can be in the form of a "twist off" to expose the connecting port used for an aseptic environment. Other commercially available connectors and adaptors for spike ports can be used so long as it is appropriate for an aseptic environment. Hanging slot 34 is an opening that is used to attached plasma bag 64 to an IV (intravenous) pole. Spike ports 42A and 42B, and hanging slot 34, are made and used in the same way as those on IV medical bags. Midsection 46 also includes locator pin openings 32C. Locator pin openings 32C are used to secure disposable 100 to finishing apparatus 400 so that disposable 100 stays in place during sealing and separating, as further described herein.

Although most of the plasma undergoes evaporation and dries in upper section 148, the drying does continue in lower section 150, defined by Dimension V. Referring to exploding view of the disposable in FIG. 3, the lower section of drying chamber 28 includes lower filter 36, lower filter separator 38, drying gas outlet port 30, and locator pin openings 32A and 32B. The humid air (e.g., the drying gas, the aerosolized gas and removed moisture from the plasma aerosolized droplets) passes to the lower section 150 through lower filter 36, lower filter separator 38 and out gas outlet 30, which is secured to gas exhaust port 208. The humid air travels through the channel or space between filter 36 and the outer wall of drying chamber 28 and then out through gas exhaust port 208 and is filtered and emitted to outside air. When air is exhausted to the outside air, a filter is used to prevent contamination of plasma in the spray dryer in case of a breach. Such a filter can be a HEPA filter, a UPLA filter, and the like. A HEPA filter for filtering the exhausted air can be purchased commercially.

Lower/capture filter 36 separates the dried plasma from the humid air. In particular, lower filter 36 traps the dried plasma particles/powder while allowing the humid air to pass. The dried plasma builds up on the filter throughout the drying process. The goal of the drying process is to complete most of the evaporation (i.e., complete the mass transfer process) of the plasma droplet before the dried particle hits the filter surface. Effective evaporation occurs when rapid mixing of the drying air with an atomized plasma droplet size distribution having a size between about 1 microns and about 35 microns. Rapid mixing, as described herein, is enhanced by the vortex flow of pressurized air, the droplet size of the atomized plasma droplet and the drying gas flow. The length of the drying chamber is dependent on the atomized plasma droplet size. A shorter drying chamber provides less time for the droplet to complete the evaporation/mass transfer, and for a longer drying chamber, a larger the droplet can be used. The completion of the evaporation process of a particular droplet size depends, in part, on the drying chamber length. As the initial plasma particles gathers on the filter; subsequent dried plasma particles create a depth of powder that the air flow permeates across and pressure in the system does build but still allows humid air to effectively pass. When the dried plasma particle has a residual moisture of less than 2%, the humid air can pass through the dried plasma on the lower filter 36, through lower filter 36, and out gas outlet 30/gas exhaust port 208.

The dried plasma produced of the present invention is a fine, highly amorphous and quite dry (e.g., less than 2% residual moisture) powder so that little or no clogging of lower filter 36 occurs.

The initial powder when entering the lower filter is exposed to chamber outlet temperature for the duration of the batch, while subsequent powder has less residence time in the filter. The percent residual moisture in the plasma dried with the disposable and dryer of present invention is very low, e.g, below about 2.5%, 2%, 1%, preferably about 1.46% residual moisture, as measured by Karl Fischer moisture sensor, Model No. C30S Compact KF Coulometer (Mettler Toledo Billerica Massachusetts USA). This is a very low moisture level which is due to effective and efficient evaporation of the plasma droplet occurring in the upper portions of drying chamber 28 and the process conditions. In this aspect, powder moisture level is in equilibrium with chamber outlet air stream relative humidity. Plasma particles with higher moisture levels would build up on lower filter 36 and cause the humid air to pass through the filter at a slower rate thereby building up pressure within the chamber. Essentially, plasma particles with too much moisture and inefficient evaporation would clog the filter and prevent or severely reduce flow of the humid air. The present invention, however, has efficient evaporation thereby allowing humid air to pass through the captured dried plasma particles. Dried plasma with low moisture improves protein stability during storage.

In an embodiment, lower filter 36 is a 0.2 micron filter such that the pore size is small enough to prevent the plasma particle from passing through while allowing the humid air to pass with minimal pressure build-up. The filter can be at least a 0.2 micron filter, e.g., a 0.1 micron filter or less so long as humid air can flow through as described herein. Lower filter 36 is commercially available from Lydall Inc. of Rochester New Hampshire USA as model no. 70L02A.

Lower filter 36 is supported by a filter frame built in or attached to filter 36 and that can also be attached to the inner wall of plasma drying chamber 28. Filter 36 is attached to the entire circumference of the inner wall. In other words, the filter frame or the filter itself is attached all the way around the inner wall of drying chamber 28 such that there is no opening between the inner wall and the point of attachment of filter 36. The attachment of the filter to the inner wall in this fashion forms a barrier to the dried plasma particles and humid air which forces the plasma and humid air to move downward toward gas outlet 30 with filter 36 trapping the dried plasma while allowing the humid air to pass. Filter frame 37 is attached to inner surface of drying chamber 28 by heat welding. In other embodiments, the filter frame can be attached to the inner surface of drying chamber 28 by combined adhesive (e.g., UV adhesive) and RF welding e.g., by Dielectrics unit of UFP, Inc. of Chicopee Massachusetts USA.

Lower filter separator 38, as shown in FIG. 3, is positioned between filter 36 and the inner wall of drying chamber 28. Separator 38 acts in a similar way as the ribs of the baffle plate and lifts the filter away from the inner wall of drying chamber 28. The separating/lifting action prevents the filter from adhering to the inner wall of drying chamber 28 to allow the humid air to pass more easily and prevent pressure build-up. Lower filter separator 38 can be textured or ribbed to maintain space between filter 36 and the inner wall of drying chamber 28. In an embodiment, filter separator 38 is ribbed with a plurality of spacers. Any type of spacer or standoff can be used to maintain separation between filter 36 and the inner wall of drying chamber 28. Another example of a separator includes a flexible three-dimensional matrix of polymeric filaments. In the embodiment showing in FIG. 3, separator 38 surrounds most of filter 36. In other embodiments, separator 38 only need to surround enough of filter 36 to maintain a space between filter 36 and inner wall of drying chamber 28. Spacer/separator 38 is made from a material that can withstand the heat and pressure of the spray drying process and does not affect the plasma. In an embodiment, the separator is injection molded and can be made from olefins or thermoplastic elastomers such as polyester or polypropylene. In the embodiment shown in FIG. 1A, separator 38 is Baltex NPD 88 grade with a width is 8.750 in+/−0.65, height is 13.000 in+/−0.65, thickness is about 0.197 inches. The material used for this embodiment is 100% Polyester Spacer Mesh Fabric. During the drying of the plasma, the humid air passes through lower filter 36 and lower filter separator 38 and out of gas outlet 30 leaving dried plasma in lower filter 36.

Another important aspect relates to the length of disposable 100. In earlier versions, the disposable was about 66 inches long. The longer disposable allows for more time, space and heat to dry the plasma particle. However, the longer disposable was difficult for an operator to install and use, cumbersome and difficult to handle. See Example 7 and 8. In fact, a 66-inch-long disposable is longer than the height of many operators such as a US female of 5'6" height who is in the $79^{th}$ percentile, according to CDC MHANES 2015-2016 data. Males of 5'6" and shorter comprise the $14^{th}$ percentile for the US according to the same data which is still sizable number of potential operators of the present invention.

Shortening the disposable to that shown in FIG. 1A posed several challenges. A shorter disposable means that there is a shorter drying chamber. A shorter drying chamber means that the plasma particle had to be evaporated and dried in less distance, in a smaller volume, and in less time and all without damaging the proteins in the plasma. In other words, the plasma had to dried gently but faster and in less space.

Despite these obstacles, the present invention includes disposable 100 having a length of about 40 inches or less (e.g., about 40, 39, 38, 37, 36, 35, 34, 33, 32, 31, 30, 29, 28, 27, 26, 25, or 24 inches or less) and preferably about 34.8 inches. At 34.8" in length the disposable 100 is readily handled, installed in and removed from the dryer and other portions of the processing equipment by minimally trained personnel in the range of heights from the $5^{th}$ (4'11") to the $99^{th}$ (6'6") percentile of men and women according to data for the United States. See Examples 7-10.

The disposable length, as measured from the bottom of spray drying head 2 or bottom of baffle plate 8 to top of the bottom filter 36, shown as dimension Y in FIG. 3, is about 31 inches or less (e.g., about 31, 30, 29, 28, 27, 26, 25, 24, 23, 22, 21, 20, 19 inches or less) and in an embodiment preferably about 25.90 inches. In another aspect, the area of disposable 100 encompassed by Dimension Z, the length from the bottom of spray drying head 2 and the top of filter 36, is about 22 inches or less (e.g., about 22, 21, 20, 19, 18, 17, 16, 15, 14 inches) and preferably about 19.11 inches. In yet another, the length of Dimension X, the length between the bottom of spray drying head 2 and the top section 46, is less than about 16 inches (e.g., about 16, 15, 14, 13, 12, 11, 10, 9, 8 inches) and preferably about 12.14 inches.

In fact, when comparing the earlier developmental version of the disposable, having the length of the disposable was about 66 inches and Dimension Z was about 48 inches, to the disposable of the present invention, the difference in the overall length is about 30 inches or a 46% reduction and the difference in Dimension Z is about 29 inches or a 60% reduction. The significant difference can be accomplished by shortening the entire length of disposable or along Dimensions X, Y, and/or Z. In another embodiment, the length of the present invention can be further shortened along dimension X by about 1 inch to about 8 inches (e.g., by 1, 2, 3, 4, 5, 6, 7, or 8 inches) thereby reducing the overall length by the same amount. In an embodiment, length X ranges between about 30 and about 37 inches. In other embodiments, the disposable can also be shortened anywhere along Dimension Y and Z by the same amount.

This shorter disposable, disposable 100, dries liquid plasma that retains protein function of even the most fragile proteins such as von Willebrand's factor and other proteins. The spray drying system of the present invention and that shown in the figures meets FDA vWF requirements.

Shortening the length of the disposable 100, which includes spray dry head 2 and plasma drying chamber 28, of the present invention results in a system that is significantly more usable by operators of a variety of statures than that of the prior art. For example, the height of the upper loading slot for the prior art dryer using the described 66" inch disposable was 72.5 inches (over 6') as compared to only 54" for dryer 200 shown in FIGS. 4 and 5. The lower (exhaust), bending or stooping, loading height of the prior art dryer using the 66" disposable described here was a mere 16" above the floor while that of disposable 100 in dryer 200 described here is a much more comfortable 27.5". Multiple episodes of human factors testing (see Examples 7-10) demonstrated that the shorter disposable permits unencumbered installation of disposable 100 into the spray dryer 200 by an operator in the $5^{th}$ percentile (4'11") to $95^{th}$ (6'6") percentile of height in the US. The shorter disposable allows for easier reaching and stooping or bending actions required by the operator to install the disposable in the spray dryer to and to safely and effectively mount and dismount the disposable before and after spray dryer operation.

The plasma drying chamber tubing, baffle plate ring 156, exhaust port, and the like are made from blown or flat polyvinyl chloride (PVC) and are heat welded to form the drying chamber. The baffle plate ring 156 which is heat welded to disposable and once heat welded, the disposable can be attached to the baffle plate with an adhesive, for example. The drying chamber, in an embodiment, when in use, expands to take on the shape of the enclosure, the spray drying chamber housing of the dryer. Other commercially available materials and other vinyl materials can be used to make the plasma drying chamber of the present invention. Sheets of PVC material are molded by injection molding and/or heat welded to form the spray drying chamber and then sterilized.

The plasma drying chamber of the present invention, in an embodiment, functions as a single use chamber where spray drying occurs. Sterilization by gamma or X-ray irradiation provides Plasma Drying Chamber's sterility. The drying chamber development and manufacturing occurs under ISO 13485 design controls. Certification of the materials contacting the drying air or donor plasma within the drying chamber assembly provides lot traceability. Certification provides the toxicity testing and certification for human use.

The overall size of the spray dryer is generally much smaller than other manufacturing-type spray dryers which are often quite large and inappropriate for use in a blood center, military field medical unit or similar location. The spray drying system of the present invention is designed to fit and be used in a blood component lab, whereas other manufacturing spray dryers are used generally in a large industrial scale facility.

As discussed above and in co-pending application Ser. No. 17/945,129, entitled "Usability Of A Disposable For A Spray Drying Plasma System", filed on even date herewith, the entire teachings are incorporated herein by reference), the spray dryer of the present invention is largely automated and usable by persons with limited training. This in contrast to high training and skill demands associated with industrial spray drying or laboratory spray drying as, for instance, by the spray dryers sold by Buchi Corporation (19 Lukens Drive, Suite 400 New Castle, DE 19720 United States, Model No. 4244).

As further described in a co-pending related patent application (application Ser. No. 17/945,126), the liquid plasma pretreated before undergoing the spray drying process. The pretreatment solution protects plasma clotting factors during the spray drying process. A fixed volume of never frozen or frozen plasma (e.g., about 260 ml) is transferred to a plasma pretreatment container, which contains a spray dry stable acidic substance (SDSAS) e.g., 50 mL of glycine and hydrochloric acid solution. In an embodiment, single donor plasma expressed from collected whole blood or by apheresis which has never been frozen and is less than 24 hours old from collection is desirably utilized for this process. The plasma is collected from blood by standard techniques known to those of ordinary skill in the art, as described herein. Plasma is collected through a process call plasmapheresis. Plasmapheresis refers to a procedure in which the plasma is separated from the blood either by centrifugation or membrane filtration. The system process is also usable with pooled plasma if such is desired and with starting blood plasma material made with any currently available anti-coagulation system such as those known as CPD, CP2D, ACD-A and ACD-B. A sterile, non-pyrogenic, single-use container with SDSAS e.g., a 50 ml solution glycine and hydrochloric acid packaged in a 500 ml container within an overwrap pouch. In an embodiment, the process of the present invention includes converting a single donor unit of plasma which is collected by standard procedures into a single unit of spray dried plasma.

The in vitro characterization data demonstrate that the spray drying process effects of the system are comparable between units spray dried with different starting materials. Units manufactured from apheresed plasma (ACD-A anti-coagulation treatment) showed similar percent change due to manufacturing effects on the starting material as compared to units spray dried from whole blood derived plasma (CPD anti-coagulation treatment). A statistical analysis (ANOVA) was performed on the percent change pre and post manufacturing between the two starting materials across 20 assays including clotting times, coagulation function, and activation markers. Of the 20 assays, total protein concentration, PT, TT, and Factor VIII and XIII activities were determined to be statistically significantly different, however, the mean percent change is similar, and the mean values are all within the clinical reference range. In summary, the in vitro test results support the conclusion that the manufacturing impact on both apheresed and whole blood plasma is comparable, and the coagulation profile is within ±20% of their paired control or within the normal reference range.

Detailed Description of Spray Dryer

Spray dryer 200 provides the pressurized aerosol gas, flow for the plasma, and drying gas to disposable 100 and an exhaust for humid air. Disposable 100 is placed within the dryer and is fed the pressurized gas, plasma and drying gas so that the drying can occur within the disposable.

FIG. 4A is a front view of spray drying apparatus 200 with the door closed and FIG. 4B shows the spray drying apparatus 200 without the door so that the inner portions of the dryer can be seen. The disposable is placed in the dryer for spray drying. FIG. 4B shows first locator, projection locator 206, which receives notch locator 26 of disposable device 100. Additionally, receiver 204 (see FIGS. 4B and 4C and 5A), above projection locator 206, allows the disposable to be easily received such that it is aligned. FIGS. 4B and 4C also show spray drying head receiver 210 to receive the spray drying head 2 including the baffle 6.

At the top, spray drying apparatus 200 includes aerosol line 216 that provides a pressurized spray gas source (not shown) which, in an embodiment, provides clean dry air with a dew point of minus 40° C. such as the Atlas-Copco SF 22 oil free scroll compressor combined with an Atlas-Copco CD45 desiccant dryer (Atlas Copco Manufacturing company, Nacka Municipality, Sweden). The pressurized gas source need not be located contiguously with the spray dyer 200 but may be located at a distance and in a different space. Such devices are intended to be and are readily connected to the device receiving the pressurized air. Spray drying apparatus 200 heats air from the source to the appropriate temperature (e.g., in a range between about 100° C. to about 120° C. (e.g., about 100, 105, 110, 115, 120° C.) and in an embodiment at about 114° C.). See FIG. 4A-4C. In an embodiment, there are redundant in-line filters (e.g., 0.2 μm or smaller commercially available filters) in the drying gas line and aerosolizing gas line, in addition to the filter in the spray drying disposable device.

Display 212 provides instructions and information to the operator. The aerosol line 216 is in close proximity to installed spray drying head 2 in dryer 200. Aerosol line 216 has a Luer lock that attaches to aerosol filter 12 (which can also be a luer lock). In an embodiment, they screw together. Aerosol line 216 is in close proximity to aerosol filter 12 and aerosol tube 16 when spray drying head 100 is installed into dryer 200. In an embodiment, the aerosol line 216 exits the face of drying head 2 between about 4 and 10 inches with about 6 inches being a desirable distance, as measured from the top of spray drying head 2. Additionally, aerosol line 216 is oriented downward with Luer lock filter at the bottom such that it is within easy reach for an operator to attach aerosol filter 12 to aerosol line 216 at about 4'6" and 5'6" above the floor with about 5' being a desirable distance.

Indicator light 234 (See FIG. 4A) is located above display 212 to provide color/visual information (e.g., green=go, red=problem, yellow=assistance needed) to the operator. Below display 212, is a peristaltic pump 214 that pumps the liquid plasma through guide 226 into the nozzle of spray drying head 2. The peristaltic pump 214 has a plump latch 214A used to secure plasma tube 16. Peristaltic pump 214 provides the plasma to the disposable at the rate described herein. Dryer 200 also includes hook 222 that hangs the plasma bag, and emergency off switch 218 and circuit breaker 220. See FIGS. 4A, 4B, 4C. Tubing guide 226 allows the user to easily place and align plasma tube 16 that leads to the pretreated liquid plasma bag 64 and the aerosol tube 10 that attaches to aerosol line 216. Aerosol tube 10 attaches to aerosol line 216, providing pressurized gas source (not shown). via aerosol filter 12 which has a screw lock (e.g., Luer lock or Luer taper).

FIG. 5B shows spray dry disposable 100 installed in dryer 200. In this figure, the positional relationship between aerosol filter 12 of disposable 100 aerosol line 216 is shown. The plasma/aerosol guide, guide 226, is provided to protect the path of the plasma tubing 16 and aerosol tubing 10. The plasma tubing provides a flow of liquid (to-be-dried) plasma 66 that travels from liquid plasma bag 64 through pump 214 and to disposable 100 during spray drying. The aerosol tubing 10 provides a continuous flow of pressurized air flow from aerosol line 216 to disposable 100. Continuous flow of the plasma and pressurized air is necessary to ensure continuous spray drying, thereby making this guide an important aspect of the present invention. Plasma/aerosol guide 226 allows for the tubes to be properly placed to ensure that the tubing does not kink or buckle during operation. Plasma/aerosol guide 226 is well placed between plasma bag hook 222 and plasma flow inlet 18 on the installed disposable and between aerosol tubing 10 and aerosol line 216 and aerosol inlet 14 on the installed disposable. The placement of plasma/aerosol guide 226 allows for easy threading of both plasma tubing 16 and aerosol tubing 10. Once disposable 100 is aligned, the operator threads tubing 10 and 16 through plasma/aerosol guide 226. In an embodiment, plasma/aerosol guide 266 has a retention notch to retain the plasma tubing and/or aerosol tubing within the plasma/aerosol guide during operation of the spray dryer. In an embodiment, plasma/aerosol guide 226 is immediately visible to an operator having a height between the $5^{th}$ and $95^{th}$ percentile when loading when standing in front of the dryer (e.g., about 2 feet from the dryer).

FIG. 5B also shows placement of aerosol line 216, which provides the pressurized gas source. Once the operator threads aerosol tube 10 through plasma/aerosol guide 266, the operator attaches aerosol filter 12 to aerosol line 216 by connecting the Luer lock or screw lock. In this embodiment, the connection is an easy connection to make and only involves the alignment and turning of the Luer lock/screw lock. The proximity of spray drying head 2, plasma/aerosol guide 226 and aerosol line 216 allows the operator to thread and attach the aerosol line quickly and easily.

Similarly, plasma tubing 16, once threaded through plasma/aerosol guide 226, is threaded through peristaltic pump 214 and latch 214A is closed over plasma tubing 16 to keep it in place during spray drying. Again, the proximity of the proximity of spray drying head 2, plasma/aerosol guide 226 and peristaltic pump 214 allows for quick and easy threading and securing.

The operator controls (e.g., display 212, pump latch 214A, tubing guide 226 aerosol line 216, door handle 230) are positioned to be readily viewable and operable by an operator of a wide range of statures. Operators of a shorter stature could not readily see display 212 in an earlier version. The problem was addressed with the present invention and now 99% of all persons of varying statures can easily see and access display 212. These controls are within about 12, 13, 14, 15, 16, 17, 18, 19, 20 inches of one another, and in an embodiment they are about 15 inches from one another. In an embodiment, the controls are immediately visible to an operator having a height between the $5^{th}$ and $99^{th}$ percentile when loading when standing in front of the dryer (e.g., about 2 feet from the dryer). Not only are the controls in close proximity to one another but are positioned to be in close proximity to the part to which they attached or are used. Additionally, the controls are oriented toward the direction of attachment of the respective part. Furthermore, the layout of the plasma/aerosol guide 226, pump latch 214A, and aerosol line 216 are logically placed in accordance with flow of air/plasma.

Similarly, emergency shut off 218 is positioned to be easily locatable by the operator but specifically positioned to be lower and away from the operator controls described above. The idea is to encourage the operator to make a deliberate decision to use it by placing emergency shut off 218 away from the main controls. Next to emergency shut off 218 is circuit braker 220. Emergency shut off 218 and circuit braker 220 provide two ways to turn off dryer 200 in case of emergency.

FIGS. 4A-4C also show spray drying apparatus 200 that includes exhaust port 208 that receives gas outlet port 30 of disposable device 100. The alignment arrangement of the present invention, in an embodiment, includes the attachment of gas outlet 30 of disposable 100 to the gas exhaust port 208 of spray dryer 200 or the gas outlet receiver 414 of finishing apparatus 400. (see FIGS. 5A-C and FIGS. 6A-C). During spray drying, the attachment of the gas outlet 30 of disposable 100 to gas exhaust port 208 of spray dryer 200 allows disposable 2 to stay in place during plasma drying process by anchoring the bottom portion of the disposable to the dryer. Similarly, finisher 400 is designed to receive gas outlet 30 of disposable 100 via gas outlet receiver 414 to keep the disposable in place during the process of shaking/impacting the plasma into place, removal of air, sealing and separating. Gas outlet 30 of the disposable device 100 is made from a strong, rigid plastic material and is a cylindrical outlet with a lip. Exhaust port 208 of spray dryer 200 has an O-ring and a gasket that allows the lipped cylindrical gas outlet 30 to be secured to create a firm attachment. Gas outlet receiver 414 of finishing apparatus 400 has a receiver that has a "U" shaped slot so that the gas outlet can be firmly attached to the finishing apparatus and remain attached during the finishing process. The gas outlet of the disposable, the gas exhaust port on the spray dryer and/or the gas outlet receiver can include any arrangement to attach the gas outlet of the disposable to stay intact during use of the apparatus or finisher to which it is attached. The gas exhaust port or gas outlet receiver can be made from stainless steel, plastic, rubber and the like.

Put another way, in an embodiment as shown in FIG. 5A, to align the spray dry disposable device 100 in spray drying apparatus 200, the operator should insert the off-set guide 4 of the disposable 100 into receiver 204 of the dryer 200, align the locating arrangement on the disposable and the dryer, thereby engaging the retention clip, and insert the gas outlet of the disposable into the exhaust gas port of the dryer. Once these alignment elements are engaged, the disposable is aligned into place and ready to be locked. After attaching the plasma source and the pressurized gas source, the operator can lock the door of the spray drying chamber housing and the spray drying process can begin. The operator locks door 228 by engaging handle 230 by swinging the handle right and then left, and locking it into place. See FIG. 4C. The operator can lock the door by inserting key 236 into keyhole 238. In another embodiment, one or any combination of these alignment arrangements can be engaged so that the disposable is aligned with the spray drying apparatus.

If the operator improperly aligns disposable 100 with the dryer 200 (e.g., inserts spray drying head 2 with locator notch 26 facing outward), then ridge 9 will not completely sit in groove 207 and spring clip 232 does not engage with spray drying head 2. In this case, when the operator attempts to close door 228, door 228 will not close. If door 228 is not fully closed and handle 230 cannot lock into place, then the dryer cannot proceed with drying. Preventing the drying when disposable 100 is not properly aligned and installed ensures safety of operation.

In another embodiment, the operatory may insert disposable 100 with locator notch 26 within 30 degrees (e.g., within 30, 25, 20, 15, 10, 5 degrees) of locator projection 206. In other words, the operator may come close but does not perfectly align the locator notch arrangement. In this case, when the operator closes door 228, spray dry head 2 self-aligns so that locator projection 206 inserts into locator notch 26. As door 228 closes, it applies force to spray drying head 2 and spray drying head 2 slides along receiver 210 in a circular fashion until locators 26 and 206 align, ridge 9 fully sits within groove 207 and spring clip 232 is engaged. Although aligning the spray drying head is an easy task that does not require much force and/or training, if operator incorrectly inserts spray drying head 2 where it is within about 30 degrees of properly locator notch alignment, the system will self-correct the spray drying head installation.

In an embodiment, dryer 200 automatically monitors and controls at least four processes (e.g., pretreated plasma flow, aerosol air flow, drying air flow, and exhaust air flow) as well as ensuring the drying process is completed within operating ranges. In an embodiment, dryer 200 contains an array of sensors and actuators that allow for the automated control of the spray drying process.

In an embodiment, the dryer can be run according to these parameters:

TABLE 2

| Process Parameters | | | | |
|---|---|---|---|---|
| Process Parameter | Permissible Range | Tolerance | Measurement Units | Description |
| Drying air flow rate | 750 slpm | ±10 slpm | Standard Liters per minute | Drying air flow rate into the spray drying chamber (independent parameter) |

TABLE 2-continued

Process Parameters

| Process Parameter | Permissible Range | Tolerance | Measurement Units | Description |
|---|---|---|---|---|
| Drying air inlet temperature | 110-120 | ±1° C. | Degrees Centigrade | Drying air temperature into the spray drying chamber (independent parameter) |
| Plasma feed rate | 5-20 mL/min | N/A controlled by exhaust temperature | Grams per minute | Plasma flow rate to the two-fluid nozzle (independent parameter) |
| Aerosol air rate1 | 30-50 slpm | ±1 slpm | Standard Liters per minute | Aerosol air flow rate to the two-fluid nozzle (independent parameter) |
| Exhaust air outlet temperature | 60-70° C. | ±1° C. | Degrees Centigrade | Air temperature leaving the Plasma Drying Chamber (dependent parameter) |

Detailed Description of the Finisher

Once the spray drying is complete, the disposable having the spray dried plasma is transferred to the finishing apparatus.

Referring to FIG. 6A-C, finishing apparatus 400 is shown. In particular, the purpose of the finishing apparatus is to move the plasma in the designated portion of the disposable, remove any excess air in the disposable, seal and separate to result in a plasma unit having dried plasma (dried plasma unit 60). Plasma unit 60 can later be rehydrated e.g., within 5 minutes or less and transfused into a patient. In particular, finishing apparatus 400 has base 440 and shuttle 418. Base 440 includes an electrical source, an impactor 442, heat sealer and separator 448, and an air extractor. The impactor, in the embodiment shown in FIG. 6B, includes magnets and springs. In an embodiment, the impactor can include any combination of elements that allow an impacting force to be applied to the disposable sufficient to move the dried plasma to the desired compartment, as further described herein. The sealer can be an impulse sealer, a heat sealer, electric heater, radio frequency sealer, and the like. The separator, in an aspect, is a cut wire but can be any device that can separate and cut the disposable once it is sealed. The sealer and separator can be the same device or two separate devices. FIGS. 6A and 6B show the finishing apparatus with the shuttle in a lowered position.

More specifically, the spray drying disposable device 100 is aligned in finishing apparatus 400 as follows. In an aspect, this is accomplished by inserting plenum 6 of spray drying head 2 (by aligning locator notch 26 and the ridge 9) into the spray drying head receiver 404, attaching gas outlet 30 of the disposable into gas outlet receiver 414, and securing positioning pin openings 32A-C around positioning pins 432A-C. See FIGS. 7A-7B. In an embodiment, when all three alignment elements are engaged, namely, the locator arrangement, the gas port arrangement and the positioning arrangement for the outer wall of the disposable, the disposable device is aligned in and secured to the finishing apparatus. In other embodiments, any combination of these alignment elements can be utilized so long as the disposable is aligned and secured to the finishing apparatus.

In a further embodiment, gas outlet receiver is positioned to accommodate any changes in the length of the disposable or the configuration of the disposable gas outlet 30 caused by the heat and pressure stresses of the spray drying process accomplished by the spray dryer apparatus. Similarly, the location of the positioning pins 432A-C are positioned to accommodate and changes in the length any changes in the length of the disposable or the configuration of the positioning pin openings 32A-C caused by the heat and pressure stresses of the spray drying process accomplished by the spray dryer apparatus.

As described above, the second locator, locator 26, on disposable 100 is aligned with third locator 452 in spray dry head receiver 404 during the finishing process. In an embodiment, the spray drying head 2 is inserted into spray dry head receiver 404 with the locators aligned when finisher 400 is in the loading position, as shown in FIGS. 6A, 6B and 7A (shown in loading position with spray dry head attached). In an aspect, the third locator of the finisher and the first locator of the spray dryer are the same shape and size and align with the locator on the spray drying disposable. As with the locating arrangement for the spray drying head, this locating arrangement axially aligns in the spray drying disposable with the finisher. The locating arrangement can include any arrangement that attaches, fits, complements or otherwise communicates with the locator on the disposable and the locator on the finishing apparatus. Examples of locating arrangements can include a recess/projection arrangement, complementing shape arrangement, hook/receiver arrangement, channel and groove arrangement, a latch and catch arrangement, a magnet arrangement, and the like. In the embodiment in FIG. 7A, the male locator is on the spray drying finishing apparatus and a complementing female locator is on the disposable, but the arrangement can be reversed.

Spray drying head receiver 404 also aligns spray drying head 2 latitudinally. Receiver 404 of the spray drying head allows spray drying head 2 of disposable 100 to be aligned latitudinally with respect to finisher 400. Spray dryer head retention clip 454 secures the spray dryer head 2 during the finishing process. See FIG. 6A. Ridge 9 of spray drying head 2 also provides additional support when inserted into receiver 404. Once inserted and aligned, spray drying disposable 100 can no longer move up and down. When using the receiver and the locating arrangement, they align the disposable so that it cannot move up and down and cannot move axially as defined by an axis through the center of the spray drying head once inserted into the finisher. As shown in FIG. 7A, the spray drying head fits into receiver 404 and does so such that the fit is snug or tight.

The positioning arrangement (e.g., the pins and openings arrangement 32A-C and 432A-C) is located preferably at each corner of the outer wall of the plasma unit-to-be and above and below seal and separation locations 44A and 44B. The positioning arrangement shown is a pin and opening arrangement but can be any arrangement that allows the side walls of the disposable to be secured properly to the finisher while the finisher is in use. Compare FIGS. 6C and 7B. In addition to a pin and opening arrangement, other examples of other positioning arrangements include a hook/receiver arrangement, channel and groove arrangement, a latch and catch arrangement and the like. In the embodiment, the pins are positioned on the finisher and the openings are positioned on the disposable, but these can be reversed.

Once the disposable device is aligned and secured to the finishing apparatus, as shown in FIG. 7B, shuttle 418 lowers into the finishing apparatus where spring magnets attached to plates apply repeated impacts to either side of the disposable. This "impact" action, or alternatively a shaking action, applied to the disposable allows dried plasma that may have adhered to the inner wall of the disposable or may be embedded in the filter to release and move into the lower portion of the disposable. In other embodiments, the impact action can be achieved pneumatically. For example, a combination of compressed air and plates can be used to create the impacting action against the disposable wall. In this embodiment, the compressed air can be obtained from the drying gas source and any suitable in line regulator or controller. In yet another embodiment, a shaking action can be applied using a vibration source (e.g., magnetic coil, or piezo crystal or the like) or source of sound waves that translate into mechanical movement (e.g., the shaking or impacting action). The impacting action can be achieved by other ways including, a traditional shaking action, vacuum action and the like.

At this time, once the dried plasma moves into to the bottom compartment e.g., defined by Dimension V, the finishing apparatus heat seals (e.g., using impulse sealer 448) and separates top portion of the bag at location 44A, i.e., disposable top portion 48. See FIG. 7A. This first seal and separation action effectively forms one of the side walls of the dried plasma unit 60. The remaining portion of the disposable device, bottom disposable portion 50 (i.e., defined by the combined Dimensions U and V), includes the bottom portion up to location 44A at which point the bag is cut and sealed. This disposable device with a single cut can also be referred to as the as a modified spray drying disposable device. Shuttle 418 will automatically or manually raise upwards once the first seal and separate is complete. The operator then inspects the seal checking for unsealed portions, voids, or wrinkles that extended throughout the entire width of the seal. Top disposable portion 48, the portion of the disposable from locator line 44A to spray drying head 2 can now be discarded.

As shown in FIG. 7C, the operator will then rotate or invert lower shuttle frame 408 using knobs 412A and 421B about pivot point 420 and secure it lower frame 408 so that it overlaps upper frame 406. In an embodiment, the operator grasps the knobs 412A and 412B and rotates the shuttle clockwise 180° until it is in place. This could also be done automatically or mechanically with the engagement of a switch or computer display. Since bottom disposable portion 50 is still attached to the lower frame of the finishing apparatus by the positioning arrangement and by the gas outlet arrangement, the bottom disposable portion (e.g., the portion from location 44A to gas outlet 30) also rotates and when locked into position. In an embodiment, sensors can be used to ensure that the frame is in the locked position. As shown in FIG. 7C, the disposable is now upside down with gas outlet 30 and gas outlet receiver 414 upward.

Once the operator indicates to the finishing apparatus that the bottom frame has been locked and superimposed over upper frame, the finishing apparatus repeats the impacting process to further shake or loosen the dried plasma that may be in the filter or surrounding area so that it falls into the section of the disposable that will become the dried plasma unit 60, i.e., plasma unit portion 46. The air extractor will engage with the disposable 100 and remove any remaining air through gas outlet 30 and the exhaust (not shown) of the finishing apparatus. In an embodiment, some air is left in the dried plasma unit 60 (e.g., less than about 15 mL in a plasma unit). In an embodiment, the finisher measures the vacuum level from about −4 psi to about −0.5 psi. The vacuum level is an indicator of the amount of air left in the plasma unit. In one aspect, when the vacuum level at −3 psi, less than about 15 mL of air left in plasma unit 60. The alignment elements of the present invention including the gas outlet/gas outlet receiver and the positioning arrangement allows the modified spray drying disposable device to remain aligned, even after its top portion having the spray drying head has been separated away. The finishing apparatus then performs a second seal and separate to the disposable at line location 44B, above port 42A. See FIG. 7C and Step 820, FIG. 10C. Once completed, the finishing apparatus raises shuttle 418 and the operator can discard disposable device filter portion 52, the portion having the gas outlet, lower filter and filter separator. Once completed, the finishing apparatus manually or automatically raises shuttle 418 and the operator will inspect the seal. The second seal and separate action effectively seal the entire disposable from the open air and forms the plasma unit 60. As shown in FIG. 8, portion 46 of the disposable, now that both sides have been sealed and separated, results in dried plasma unit 60 having dried plasma 62.

The finishing processes described here as performed by finisher 400 is a preferred embodiment but the process (moving the plasma to the desired compartment, and sealing the plasma drying chamber to create the dried plasma unit) can be done manually using readily available tools such as scissors and a heat sealer of the appropriate size and able to make the two described seals.

The sealing and separation of the unit of the preferred embodiment of the present invention described here is a multi-step, semi-automated process that takes place within finisher 400. Finisher 400 is responsible for monitoring and controlling at least five processes to create the unit: the consolidation of the dried plasma powder on the outlet filter, the sealing and removal of the upper portion of disposable 100, the inversion and consolidation of the dried plasma powder, removal of excess air, and the sealing and separation of the lower portion of disposable 100. Finisher 400 ensures the sealing processes are completed within certain operating ranges. Finisher 400 contains an array of sensors and actuators that allow for the automated control of the sealing process and provides for back-lit Operator visual inspection of each heat seal of the film.

Detailed Description of Workflow

Before spray drying liquid plasma, the operator should prepare the spray drying apparatus (FIGS. 4A-4C) and finishing apparatus (FIGS. 6A-C and 7A-C). The operator ensures that spray drying apparatus 200 and finishing apparatus 400 are on and ready. The operator should also, in one aspect, tap "WAKE" on display 212, and open the door to the spray dryer (e.g., pull large, hinged handle 230 out and to the right to unlatch door 228 and then pull handle 230 to the left). See FIG. 4C. Optionally, paper labels or other demountable closure may be attached over the inlet port 22 and the gas outlet port 30. In another embodiment, the operator can attach the appropriate part of the disposable to the dryer in an alternating fashion. For example, the operator can and attach guide 4 of spray dry head 2 to drying receiver 204 of the spray dryer 200, and then the operator can attach gas outlet 30 to gas exhaust port 208.

To pretreat the liquid plasma, referring to FIG. 10A, the operator follows the steps of pretreatment methodology 600. The operator starts with Step 602 and prepares the equipment (e.g., Sterile connection Device (SCD), collection monitor/scale, tube sealer and barcode scanner) and collects the supplies (e.g., Unit of Plasma, Pretreatment bag, Spray Drying Disposable, Site-specific supplies (labels, tracking documentation)) of Step 604. The operator then makes a sterile connection (Step 606) between the liquid plasma bag tubing and the pretreatment container tubing. See FIGS. 1A and 10A. Now the liquid plasma bag and the pretreatment container have a sterile connection. When doing so, in an embodiment, it is preferable that the total tubing length after the sterile connection is approximately between about 15 and 20 inches long to enable hanging of the plasma unit for transfer into the pretreatment container without tension so that the blood collection monitor can accurately control the transfer of the plasma to the pretreatment bag. The pretreatment container having the pre-treatment solution is properly labeled. In particular, the pretreatment solution is a glycine and hydrochloric acid solution having between about 15 mmol and about 30 mmol (e.g., about 15, 20, 25, and 30 mmol) of glycine and a range between 3 mmol and about 7 mmol (e.g., about 3, 4, 5, 6, and 7 mmol) of hydrochloric acid. The formulated plasma has a pH in a range between about 5.5 and about 7.2 which offsets spray drying impacts on pH to yield a final rehydrated product that is at normal physiologic pH, a pH range between about 6.8 and 7.6. In another embodiment, pretreatment of the plasma is optional.

In an embodiment, mixing the liquid plasma with the pretreatment solution is done by transferring the plasma to the pretreatment container. This can be accomplished by first hanging the liquid plasma bag from the upper bag hook of the collection monitor/scale and by hanging the pretreatment container on the lower hook. See Step 608 of FIG. 10A. The tubing is guided through the mechanical tube clamp (Step 610) on the collection monitor/scale and secured in place. The weld on the tubing is pinched and the Hemostat/manual clamp is released to ensure plasma flow. See Step 612.

The mixing of liquid plasma and the pretreatment container having the pretreatment solution (e.g., 50 mL) can be done manually or can be automated via a commercially available collection monitor, a tray shaped scale, or other similar device. In an embodiment, the process is automated, and the transfer volume is set to 260 mL (e.g., between 240 and 280 mL). Once the START button is pressed, the plasma is transferred. Step 614. When 260 mL of plasma has been transferred, in an embodiment, the mechanical clamp on the collection monitor will automatically close, stopping the flow of plasma. The tubing is removed from the collection monitor and the pretreated liquid plasma can be manually agitated, shook, rocked, or otherwise mixed as described in Step 616. This process can also be automated using a commercially available laboratory rocker, agitator or the like.

Using a tube sealer, the pretreatment container having the pretreated liquid plasma is separated from the rest of the tubing and original liquid plasma bag. In an embodiment, the operator, in Step 618, using a tube sealer, triple heat seals the tubing above the manual clamp; separates the tubing at the middle seal.

In another embodiment, the pretreatment solution can be added to the liquid plasma bag or the two can be mixed into a third bag.

In an embodiment, once the plasma has been transferred, it is be placed into the dryer for drying in 4 hours or less (e.g., about 4 hours, 3 hours, 2 hours, 1 hours, 30 minutes, 15 minutes, 10 minutes, 5 minutes or less).

The plasma pretreatment bag having the pretreated plasma is also referred to herein as a "plasma bag," "liquid plasma bag," or "pretreated plasma bag." The pretreated plasma bag is connected to the spray drying disposable device at the plasma inlet tube, tube 16, as described in Step 620 to thereby obtain the modified disposable. The tubing from the pretreated plasma bag is connected to the plasma inlet tube via a SCD connection. In an embodiment, the operator should make the connection long enough to fit the modified spray drying disposable in the dryer. In an aspect, the operator can make the SCD union about 1 to about 2 inches (e.g., about 2.54 cm to about 5.08 cm) from the distal end of the spray drying disposable device tubing to ensure the total tubing length, after the sterile connection, is approximately 43 inches (e.g. about 101.6 cm) long. This will facilitate installation in the spray dryer. After the connection is made, the operator can label the disposable to apply, for example, a matching blood center number or other identifier. The operator can then hang the modified disposable on the drying apparatus bag hook 222 and pinch the tubing to ensure the SCD weld is opened.

The spray drying apparatus is prepared. FIG. 10B shows a flow chart describing methodology 700, detailing the steps the operator takes to dry the plasma using the spray dryer. To prepare the spray drying apparatus, the operator, as shown in Step 702, will ensure that the spray drying apparatus 200 displays the READY screen by pressing WAKE if necessary. The screen will then prompt the user to load drying chamber 202. As described in Step 704 (FIG. 10B), the operator opens door 228 of spray drying apparatus 200 as shown in FIG. 4C. The operator pulls large, hinged handle 230 out and to the right to unlatch the door and then pulls the handle to the left to allow the entire door panel to open. See FIG. 4C. The operator hangs the pretreated plasma bag from plasma bag hook 222 and disposable device 100 is aligned and inserted into the spray drying machine 200, as described herein. See Step 706 of FIG. 10B and FIG. 5A.

Once guide 4 is attached to receiver 204 and the operator tucks the disposable device edges and ports into the spray drying apparatus. The ports are tucked into for the port receiver (not shown). The operator ensures that the drying chamber is fully installed and all edges are tucked into the drying chamber cavity. In accordance with the alignment shown in FIG. 5A, the operator connects gas outlet 30 at the bottom of disposable device 100 into exhaust gas port 208 of dryer 200. The operator removes aerosol filter cap, if present, from the aerosol filter and attaches the aerosol tube 10 to aerosol filter 12. This step connects aerosol tube 10 to aerosol line that leads to pressurized gas source 216 via filter 12.

Once the disposable device is aligned and connected to the drying gas source, the pressurized gas source, the plasma source and the exhaust port 208, the operator prepares peristaltic pump 214, which pumps the liquid plasma into the disposable device. This is done by opening the peristaltic pump latch 214A and routing the pretreated plasma bag tube 16 through peristaltic pump 214 and plasma/aerosol guide 226 in the direction of the flow (i.e., plasma will flow from the pretreated plasma bag to disposable device). Step 708, FIG. 10B. Once routed through the pump in the plasma flow direction, the operator closes the pump latch.

The operator closes the door and inserts the key 236 into the manual safety lock 238. Step 710, FIG. 10B. In an embodiment, key 236 is attached to handle 230 of the door and keyhole 238 is on the left of spray drying apparatus 200. This is a safety feature and the spray drying device will not allow the operator to progress to the next step until this step is performed. This is indicated on display 212. Once closed and locked, the screen prompts the user to unclamp the plasma line. The operator releases the plasma by unclamping any Hemostat or manual clamp. At this point, with the covers removed and the door closes, the disposable is no longer exposed to open air/environment. In this case, the time from when the operator removes the first adhesive cover to close the door ranges between about 30 to 90 seconds.

Once the door is closed and the key is inserted, the operator confirms that this step is completed by utilizing the interactive display and pressing "CONFIRM", the spray drying apparatus will automatically run integrity checks. See Steps 710-712, FIG. 10B.

If there are no issues, the drying apparatus will automatically begin the drying process; the screen displays the estimated time remaining until completion. In an embodiment, the drying beacon, an indicator on the machine, remains a solid green as the normal operation of the instrument continues. The typical drying process time approximately 35 minutes but can range from about 20 minutes to 60 minutes (e.g., about 20, 25, 30, 25, 40, 45, 50, 55, 60 minutes).

Put another way, in an embodiment as shown in FIGS. 4A-C and 5A, to align the spray dry disposable device 2 in spray drying apparatus 200, the operator should insert the off-set guide 4 of the disposable 100 into the receiver 204 of dryer 200, align the locating arrangement on the disposable and the dryer, insert the gas outlet of the disposable into the exhaust gas port of the dryer. Once these three alignment elements are engaged, the disposable is aligned into place and ready to be locked. After attaching the plasma source and the pressurized gas source, the operator can lock the door of the spray drying chamber housing and the spray drying process can begin. In another embodiment, any combination of these alignment arrangements can be engaged so that the disposable is aligned with the spray drying apparatus.

The parameters for drying are described herein.

Once drying completes, the screen prompts the operator to clamp and remove the plasma pretreatment container, which should be hanging from hook 222 outside of the closed door. Indicator light 234 indicates that the drying process is complete by changing the flashing color or pattern, and in an embodiment the indicator light will flash green. Step 712, FIG. 10B.

To remove the disposable device, the operator re-engages the clamp on the plasma tube and seals and separates the plasma tubing after or up flow from the pump. Step 712, FIG. 10B. This step prevents any residual liquid plasma in the pretreatment plasma bag to enter the disposable device. Once the plasma tubing 16 is sealed and cut then the operator can open the door to spray drying apparatus 200. The operator opens latch 214A on peristaltic pump 214 and removes the plasma tubing from peristaltic pump 214 and can then discard the tubing and pretreatment plasma bag 64 which had formulated plasma 66.

Once the operator communicates with the spray drying apparatus that this step is completed by e.g., pressing CONFIRM on the interactive display, the operator can then remove the disposable device. Removing the disposable device involves unlatching the manual safety lock using the key and engaging the door handle to unlock and open the door.

Once the door of the spray drying is opened, the operator disconnects gas outlet 30 of the disposable device from gas exhaust port 208 of the spray drying apparatus. Step 714, FIG. 10B The operator then disconnects the aerosol line 10 from the pressurized gas source 216. The disposable device having the dried plasma can be removed from the spray drying apparatus. In an embodiment, the operator closes the door of the spray drying apparatus to keep the machine warm and ready for the next drying run. Step 716, FIG. 10B. The operator is now ready to move the spray drying disposable with the dried plasma to the finishing apparatus. Step 718, FIG. 10B.

The next part of the process, the finishing process, involves sealing and separating portions of the disposable device having the dried plasma to turn it into a spray dried plasma unit. Finishing methodology 800 of FIG. 10C refers to the steps needed to convert the spray drying disposable 100 having the spray dried plasma into spray dried plasma unit 60.

Also, referring to FIGS. 6A-6C and FIGS. 7A-7C, finishing apparatus 400 is shown. As described herein, FIGS. 6A-C show finishing apparatus 400 without disposable device 100 attached and FIGS. 7A-FIG. 7C show finishing apparatus 400 with disposable device 100 attached. Specifically, FIG. 6A shows finishing apparatus 400 in the lowered position ready to be loaded, FIG. 6B shows the inside of base 440 when apparatus 400 is in the lowered position, and FIG. 6C shows finishing apparatus 400 in the raised position without disposable 100 attached.

The screen 401 of finishing apparatus 400 will display the phrase "STANDING BY." When the operator communicates to the finishing apparatus e.g., by tapping "WAKE," the screen 401 will prompt the operator to load the plenum 6 of the disposable device 100 onto the spray dry head receiver 404 in the lower position. See Step 802, FIG. 10C. The finisher can have additional positions for loading, rotating the frame, inspecting seals and/or for removing the finished product. In an embodiment, the finisher can have two or three additional positions. In the embodiment when there are two positions, the lower position is the loading and processing position and the upper position is for inspection, rotating the frame and removal of the dried plasma unit. In the embodiment when there are three positions, then one position is an intermediate position for loading, one position is down for processing the disposable and the upper position is for inspection, frame rotation and removal of the dried plasma unit.

The operator loads the disposable device having dried plasma onto shuttle 418, as shown in FIG. 7A by inserting plenum 6 of the disposable device into the cap mounting clip, also referred to herein as spray dry head receiver 404, at the top of the shuttle. See Step 804 of FIG. 10C. The operator can coil the remaining tubing and insert it into guide 4 of the spray drying head 2.

As described herein, the second locator, locator 26, on the disposable is aligned with third locator 452 in spray dry head receiver 404 during the finishing process.

Once the spray drying head of the disposable is attached to the finisher as shown in FIG. 7A, the operator communicates this to the finishing apparatus e.g., by pressing CONFIRM. See Step 806 of FIG. 10C. The shuttle raises, as shown in FIG. 7B, to allow the operator to secure the rest of the disposable device having dried plasma. See Step 806 of FIG. 10C. This is the raised position (FIG. 7B). When in the raised position, the gas outlet 30 is attached to the bottom of the shuttle by inserting the exhaust outlet downward into 'U' shaped exhaust outlet receiver 414.

In particular, the finisher is designed to receive gas outlet 30 of the disposable to keep the disposable in place during the process of moving the plasma into place, removal of air, sealing and separating. Gas outlet receiver 414 of the finishing apparatus has a receiver that has a "U" shaped slot so that the gas outlet can be solidly attached to the finishing apparatus and remain attached during the finishing process.

The operator then attaches the disposable device having dried plasma using the positioning arrangement. The positioning arrangement (e.g., the pin and opening arrangement, or pin and grommet arrangement) is located preferably at each corner of the outer wall of the plasma unit-to-be (see positioning openings 32C) and above and below location lines for seal and separation 44A and 44B. Positioning openings 32A and B are located on either side of the outlet port and attached to positioning pins 432A and B. The positioning arrangement shown is a pin and opening arrangement but can be any arrangement that allows the side walls of the disposable to be secured to the finisher while the finisher is in use. In addition to a pin and opening arrangement, other examples of other positioning arrangements include a hook/receiver arrangement, channel and groove arrangement, a latch and catch arrangement and the like. In the embodiment, the pins are positioned on the finisher and the openings are positioned on the disposable but these can be reversed.

When the disposable device is aligned and securely loaded, the operator communicates this to the finishing apparatus e.g., by press CONFIRM. The operator then instructs the finishing apparatus to proceed with the finishing process e.g., by pressing RUN. See Step 808, FIG. 10C. Shuttle 418 having the disposable aligned and secured thereto will automatically begin to lower. In the embodiment shown in FIGS. 6A-C and FIGS. 7A-C, finishing device 400 has shuttle 418 and sliding frame 402, upper frame 406, and lower frame 408 raise and lower into position, as described herein. In another embodiment, the frame 402 is stationary and upper frame 406, and lower frame 408 move along rails. A rail system that allows upper frame 406 and lower frame 408 to move can include a chain, strap, lead screw and any other mechanism that allows the frames to move up and down. In the embodiment of using a rail system and lead screw, the lead screw moves up and down with precision.

Finishing apparatus 400 automatically initiates plasma consolidation and executes the first sealing and separating process. Step 810 of FIG. 10C. In an embodiment, the screen displays the estimated remaining time until completion. Shuttle 418 lowers into the finishing apparatus and finisher 400 moves the dried plasma powder e.g., by the impacting action, as described herein. The first seal and separate action seals top disposable portion 48 (see FIG. 7A).

Once the shuttle has risen to the top and stopped moving, the screen will prompt the user to Inspect Seal #1 and an inspection light will illuminate. Step 812 of FIG. 10C. The operator inspects the seal to ensure that the seal is fully formed and uniform. The operator, optionally, can tilt the shuttle outward by hinge (not shown) as needed obtain a better view of the seal for inspection purposes. Upon inspection, the seal, in an aspect, should not contain a channel (gap or unsealed area) that runs through the full width of a weld or seal. Ideally, a plasma unit that contains a wrinkle on the interior of the unit bag but is flat welded at the seal with no channel is acceptable. Discoloration and small gaps or wrinkles that do not run the entire width of the weld are acceptable.

If the seal is acceptable, the operator can indicate this to the finisher e.g., by pressing "ACCEPT" and continue with the process. If the seal is not acceptable, then the operator can also indicate this e.g., by pressing REJECT, discard the entire Plasma Drying Chamber, and press CONFIRM.

Once the operator deems the seal to have been properly made by the finisher, the operator can discard the disposable top portion 48, from location 44A to the spray drying head 2. See FIG. 7B and Step 814, FIG. 10C. This first seal and separation action effectively forms one of the side walls of the dried plasma unit and the seal is located above port 42A. The top disposable portion 48, the portion of the disposable from location 44A to spray drying head 2 can now be discarded.

As shown in FIG. 7C, the operator will then rotate or invert lower shuttle frame 408 using knobs 412A and 421B about pivot point 420 and secure lower frame 408 so that it overlaps upper frame 406. See Step 816, FIG. 10C.

Once the operator indicates that the bottom frame has been locked and superimposed over upper frame, e.g., by pressing "CONFIRM" and then "RUN", the finishing apparatus lowers. See Step 818, FIG. 10C. In an aspect, the screen will flash a warning notification and the shuttle will automatically begin to lower. As further described herein, finishing apparatus 400 automatically initiates the impactor to allow for plasma consolidation, air evacuation, and executes the second seal at location 44B above port 42B (in the inverted position show in FIG. 7C). In an embodiment, the screen displays the estimated time remaining until completion.

Once the shuttle has risen to the top and stopped moving, the screen, in an embodiment, will prompt the operator to inspect the second seal and an inspection light will illuminate. See Step 822, FIG. 10C. Again, the operator can optionally tilt the shuttle outwards as may be necessary to properly inspect the second seal. The seal is located above the rehydration ports. If the seal is acceptable, the operator can inform the finishing apparatus e.g., by pressing "ACCEPT" to continue with the process. Again, if the seal is not acceptable, the operator can inform the finishing apparatus by e.g., pressing "REJECT", discard the entire Plasma Drying Chamber.

Once the seal is accepted, in an embodiment, the screen will display "RUN COMPLETE" or similar indicator on the finishing apparatus' screen. The operator can discard disposable device filter portion 52, the portion having the gas outlet, lower filter and filter separator. See Step 824, FIG. 10C. As shown in FIG. 8, the remaining portion, portion 46 of the disposable, now that both sides have been sealed and separated, results in dried plasma unit 60 having dried plasma 62. See Step 824, FIG. 10C. In an embodiment the operator, will rotate the shuttle 418 back to the home position, or original position as shown in FIGS. 6C, and 7B. See Step 824, FIG. 10C.

Dried plasma unit 60 is then stored. In an embodiment, storage includes two stages, storage methodology 900 of FIG. 10D. The first stage is storage until testing of the plasma is competed and cleared for use (e.g., referred to as "quarantine storage") and the second stage involves storage of the unit after clearance but prior to transfusion into a recipient.

For the first stage storage or quarantine storage, the operator places dried plasma unit 60 in a storage pouch so that the label on the plasma unit is visible through the clear side. Step 902, FIG. 10D. The storage pouch in an embodiment has a clear side and a foil side. A desiccant is placed in the storage pouch, between the plasma unit and the foil side of the pouch. Step 904, FIG. 10D. The operator then makes an initial seal at the top of the pouch. Step 906, FIG. 10D. A commercially available pouch sealer can be used to make a more permanent seal sufficient for longer term storage. An example of a commercially available pouch sealer is the Midwest Pacific Impulse Heater Sealer model No. MP-12 from PackCo Inc. of Lake Ozark Missouri USA. The operator ensures the storage pouch sealer is turned on and places the pouch across the welding plane. The operator closes the welding arm and holds the arm in place for a period of time sufficient to make the weld e.g., between about 1 and 60 seconds and in an embodiment less than 10 seconds. An acceptable weld is one, for example, that contains no channel (gap or unsealed area running thru the full width of a weld) and has no discoloration. A weld that contains a wrinkle on the interior of the storage bag but is flat welded at the seal with no channel is also acceptable. However, a weld is unacceptable if the weld contains a channel (gap or unsealed area running thru the full width of a weld), has discoloration, or contains a wrinkle on the interior of the storage pouch that continues through the full width of the welded area creating a channel.

Once an acceptable weld is achieved, the operator then places the sealed dried plasma unit in quarantine. Step 908, FIG. 10D. In an embodiment the sealed dried plasma unit stored in quarantine during the first stage at a temperature in a refrigerated range between about 1° C., and about 6° C. In another aspect the dried plasma unit can be stored at room temperature (e.g., between about 18 to 25° C.).

After release testing is complete and the product is determined safe for use, then the dried plasma unit can be stored until it is ready to be used for transfusion. This is the second storage stage.

The operator opens the sealed outside pouch e.g., using a scissors and the point of cutting away the seal can be marked with a notch. Step 910, FIG. 10D.

The operator can then apply final product labeling on the dried plasma unit and place the unit with the final label into the same storage pouch. Step 912 & 914, FIG. 10D. The storage pouch sealer is again used to make a final seal on the on the pouch containing the dried plasma unit that has been approved for use. Step 916, FIG. 10D. The criteria for an acceptable seal are described above. The process described for the initial seal is repeated and the seal is completed. The dried plasma unit is ready for use or placed in inventory. Step 918, FIG. 10D.

The spray dried plasma unit that has been tested, approved and sealed in a pouch is then stored for a period of time ranging from about 1 minute to about 30 months at a temperature ranging between about 1° C., and about 45° C. In an embodiment, spray dried plasma of the present invention can be stored at room temperature for about 1 hour to about 12 months. In an embodiment, spray dried plasma of the present invention can be stored at refrigerated temperature for about 1 hour to about 24 months. In an aspect, refrigerated temperatures are between about 1° C., and about 6° C., and room temperatures are between about 20 and about 25° C.

In an embodiment, plasma unit 60 is packaged in a pouch, a high moisture barrier bag consisting of an opaque Polyethylene Terephthalate (PET) aluminum foil laminate on one side and a transparent PET double layer laminate on the other. In this embodiment, a 10-gram molecular sieve desiccant packet is placed in the pouch before sealing. Plasma unit 60 can be packaged in the overwrap pouch with a desiccant such that the label is visible through the transparent laminate. Such pouches are commercially available from e.g., Technipaq Inc. (Crystal Lake, IL USA).

The methods of the present invention further include reconstituting the dried plasma using a reconstitution solution. The reconstitution solution can be mixed with the dried plasma using one of spike ports 42A or 42 B of the dried plasma unit 60. In a preferred embodiment, sterile water for injection is used for the reconstitution solution. In other embodiments, the reconstitution solution includes distilled water, or in the case where pre-treatment step is not performed, the reconstitution solution could be, for example, an amino acid (e.g., glycine), and/or a buffered solution (e.g., an acid such as hydrochloric acid or citric acid). The amount of reconstitution solution used to rehydrate the dried plasma is in a range between about 218 ml and about 200 ml. Additionally, once the reconstitution solution is added, a step of the method includes shaking the reconstitution plasma unit to ensure the mixing and uniformity of the reconstitution solution and dried plasma. The reconstituted plasma is ready for transfusion into a recipient. A recipient can be human, primate, animal and the like.

The methods further include transfusing a recipient in need thereof. The reconstituted plasma unit is administered the same as any plasma. In an embodiment, the method includes transfusing the recipient intravenously with the reconstituted plasma Detailed Description of Methods and Parameters Overall, in an embodiment as shown in FIGS. 6A-C and 7A-C, to align the spray dry disposable device 2 to finishing apparatus 400, the operator should employ the apparatus described to align the locating arrangement and ridge on the disposable with the finisher, insert the gas outlet of the disposable into the gas port receiver of the finisher and position the openings of the bag over the positioning pins on the finisher. Once these alignment elements are engaged, the disposable is aligned into place and ready to be processed. In another embodiment, one or any combination of these alignment or positioning arrangements can be engaged so that the disposable is aligned with the finisher.

The alignment and positioning arrangements described herein can be used independently or in any combination with one another.

In addition to securing, aligning and/or positioning the spray drying disposable device within the spray drying apparatus using one of more of the alignment elements described herein, the methods of spray drying plasma further include providing plasma to a spray drying apparatus; engaging the spray drying apparatus to spray dry the plasma to form dried plasma powder, and engaging the finisher to create a dried plasma unit. The methods further include storing the dried plasma unit until ready for rehydration and transfusion.

In addition to aligning/securing the spray drying disposable device within the spray drying finisher using one of more of the alignment elements described herein, the methods of finishing the process (e.g., transforming the disposable having dried plasma into a plasma unit having dried plasma) further include engaging the finisher to lower the shuttle so that the finisher impacts and seals and separates the spray dry disposable at a first point. Once the shuttle raises, the operator discards the upper portion of the disposable, as described herein, and rotates the lower frame such that the lower frame is superimposed over the upper frame. The shuttle having the superimposed frame lowers and the finisher impacts and seals and separates the modified disposable at a second point to thereby create the plasma unit having dried plasma. The methods further include storing the dried plasma unit until ready for rehydration and transfusion.

In some embodiments, spray drying the plasma includes: directing plasma to a spray nozzle at a plasma flow rate; directing a heated drying gas to a drying chamber at an inlet temperature and a drying gas flow rate, directing a spray gas to the nozzle at a pressurized aerosol gas flow rate; combining the plasma and pressurized aerosol gas at the nozzle to atomize the plasma and dry the plasma; and combining the atomized plasma and drying gas to dry the atomized plasma.

Some embodiments include, during the spray drying, maintaining the plasma at a temperature between about 55° C., and about 85° C. The average temperature to which the plasma particle is exposed is about 65° C.

In some embodiments, the inlet temperature of the spray dryer is in the range of 100-130° C. (e.g., 114° C.). In an embodiment, the exhaust temperature of the spray dryer is between 55° C., and 85° C. (e.g. about 65° C.)

In some embodiments, the plasma flow rate is in the range of about 2 mL/min to about 50 mL/min (e.g., in an embodiment in a range from about 6 and about 23 mL/min) at a temperature of 15° C., and 35° C. (e.g., at ambient temperature). In some embodiments, the drying gas flow rate is in the range of about 500 L/min and about 1000 L/min at a temperature of between about 100° C., and 130° C. (heated). In some embodiments, the pressurized aerosol gas flow rate is in the range of about 25 L/min and about 65 L/min (e.g., 40 L/min).

In an embodiment, the exhaust rate of the air in the disposable during the finishing process is about 790 slpm. In an embodiment, the exhaust temperature of the air in the disposable during the finishing process is between about 63.5° C., and about 66.5° C.

Certain embodiments, the reconstitution solution includes at least one selected from the list consisting of distilled water, and saline solution. In some embodiments, especially when pretreatment is not performed, the reconstitution fluid is a buffered solution, has an amino acid (e.g., glycine) or both. In a preferred embodiment, Sterile Water For Infusion (SWFI) is used as a reconstitution solution.

Methods of spray drying plasma can be found in U.S. Pat. Nos. 8,533,971, 8,595,950, 8,434,242, 8,601,712, 8,533,972, and 10,843,100, the entire teachings of which are incorporated herein by reference.

Kits and Systems

The present invention further includes a kit or system having the components described herein. In an embodiment, the kit of the present invention includes the spray drying disposable device, and/or parts thereof, as described herein including those having the alignment elements described herein. In an embodiment, a kit of the present invention includes the disposable device, rehydration solution (e.g., SWFI), clamps, tubing and the like. In a preferred embodiment the SWFI is provided in a pre-measured container supplied as part of a kit with the other components of the system. However, if needed, SWFI from any source can be substituted for the pre-packed SWFI of the kit so long as the amount of SWFI used in the rehydration is the same as that specified. In an embodiment, the single use container is 200 mL of sterile water for injection (SWFI) is packaged in a 250 mL bag within an overwrap pouch. The kit can further include a rehydration Tubing Set e.g., a commercially approved standard sterile fluid transfer set (e.g. Fenwal Plasma Transfer Sets with Two Spikes 4C2243 or equivalent) to transfer the SWFI into the unit. Additionally, a Transfusion Tubing Set can also be included to transfuse rehydrated plasma into a patient. An example is a commercially approved standard sterile transfusion set/administration set (e.g. Fenwal Blood Component Recipient Set with Standard Blood Filter and Luer Adapter 4C2160 or equivalent). The system of the present invention includes the spray drying disposable device, the spray drying apparatus and the spray drying finishing device, and/or parts thereof, each with one or more of alignment elements described herein.

Clean Dry Air System Used with the Spray Dryer

In an embodiment, the drying gas source is an Atlas-Copco SF 22+ compressor (Atlas Copco Nacka Municipality, Sweden) in conjunction with an Atlas-Copco CD45 desiccant drying system supplying clean dry air (CDA) to the spray dryer and heats air to the appropriate temperature for spray drying. The CDA supply is used, in an embodiment, for the supply for the drying gas and for the pressurized gas. In certain embodiments spray drying nozzle assembly 20 includes a "manifold" that coordinates the plasma and aerosol lines. In an embodiment, there are redundant in-line 0.2 μm commercially available sterilizing grade hydrophobic filters in the drying gas line and pressurized aerosol gas line. A unidirectional positive airflow is maintained at the dryer aerosol gas and drying gas outlet ports during the spray drying process.

Numerous filters exist to filter air going in and out of the system. For example, the drying gas supply or source is filter with a 0.2 micron filter (e.g., Millipore Series 3000 0.2 micron filter CTGB71TP3 from Millipore Sigma of Danvers MA USA). Similarly, the pressurized/aerosol gas source also has a 0.2 micron filter (e.g., Millipore Series 3000 0.2 micron filter CTGB71TP3 from Millipore Sigma of Danvers MA USA). Both the consumable exhaust line and enclosure exhaust line to the outside air are filtered in an embodiment by a 0.1 micron filter (e.g., consumable exhaust line to outside air—Saint Gobain 1000 SLPM 0.1 micron filter LI2F010NTCTC from Saint Gobain Performance Plastics of Worcester MA USA; and enclosure exhaust line to outside air—Saint Gobain 50 SLPM 0.1 micron filter LI2F010NCTC from Saint Gobain Performance Plastics of Worcester MA USA).

The spray dryer of the present invention utilizes, in an embodiment, a source of clean, oil-free, dry air to provide a minimum of 790 standard liters per minute (SLM) of Clean Dry Air (CDA) to the Frontline Dryer including the Plasma Drying Chamber. The air is dried to −40° F. dew point. An acceptable CDA is available e.g., from Atlas-Copco although blood centers or other users may source alternative systems which meet the same or similar specifications.

The Atlas-Copco 30 HP Model SF22 System has three primary elements:

a. Oil Free Air Compressor—Atlas Copco 30 HP Model SF22+ Oil Free, multicore, rotary scroll air compressor package. The SF22+ contains four (4) 7.5 HP scroll compressors controlled by a microprocessor that will rotate their operation and even the wear hours over time. The package produces 100% oil free air and is extremely quiet (65 dB(A)). The full load capacity of the SF22+ package is 86.4 CFM @100 PSIG.

b. Heatless Desiccant Air Dryer—The Atlas Copco CD50+ desiccant air dryer is rated to dry the full capacity of the SF22+ package to the −40° F. pressure dewpoint continuously. The dryer is provided with optional demand dew point purge control which will conserve compressed air and increase efficiency by constantly monitoring the net delivered dew point and delaying the switch/purge cycle until needed based on the load. A coalescing pre-filter 0.1 μm/0.01 ppm and dust removal after filter (1 μm) for desiccant dust are included.

c. 240 Gallon Air Receiver Tank—A vertical 240-gallon air receiver is provided to serve as a reserve buffer of clean dry air for the spray drying application. A pressure gauge kit and safety relief valve are included.

This CDA can drive up to two dryers of the system of this preferred embodiment of the present invention.

This CDA system air purity has received ISO 8573-1 Class 2.2.1 certification, Edition 3 2010. The tubing segments connecting all elements are stainless steel with mechanical (not welded) connections. The pressure and mass flow controlled CDA output, flow through a 0.2 μm filter, before entering the dryer.

Sterile Water for injection (SWFI)

The SWFI supplied with the system kit is nominally 200 mL of sterile water for injection packaged in a 250 mL polyolefin bag, in an overwrap pouch and terminally sterilized by steam. Optionally, the pre-measured SWFI can be a different size (e.g., 208 mL) to account for example for evaporative loss of SWFI during storage. In normal circumstances the clinician/end user rehydrates a unit with a unit of the supplied system SWFI. The plasma unit receives the SWFI transfer via spike ports using off the shelf tubing sets (e.g. Fenwal Inc (Deerfield, IL USA) Plasma Transfer Sets with Two Spikes 4C2243 or equivalent). The amount of SWFI provided may be adjusted as needed to account for water that does not transfer to dried plasma in practical application.

In exigent circumstances 200 ml of SWFI supplied by the user may be substituted for the pre-measured, supplied system SWFI.

In an embodiment, all materials used in the assembly that directly contact the drying air or the donor plasma meet the ISO 10993 biocompatibility guidelines for an external communicating device, blood path indirect, limited contact duration.

The present invention may be utilized in a wide variety of fields including but not limited to veterinary, drug processing, preservation of microbes, animal feed manufacture, ceramics and any other in which spray drying is applicable.

The present invention can be utilized in a wide variety of environments including blood center component processing laboratories as may be found in the United States and Canada, blood component laboratories in other countries, and adverse environments such as battlefields or areas of unrest and regions of natural disaster or extreme weather conditions.

Additionally, the present invention can be utilized by personnel with very limited training or supervision.

EXEMPLIFICATION

Example 1: Impact of Nozzle Annulus Radial Distance $D^d$ on Plasma Yield and Quality Purpose: Compare plasma protein concentration yield and residual moisture of recovered dried plasma obtained by the composite nozzle assembly of the present invention with an annulus diameter of $D^o$ of 0.091" and that of 0.082", a cannula outside diameter $D^c$ of 0.050" and a resulting annulus radial distances, $D^d$, of 0.021" and 0.015" at an aerosol flow rate of 40 L/min and 114° C. drying gas inlet temperature.

Methods and Materials

Pre-production spray dryer (Model No. Wall-E3) by Velico Medical Inc. (Beverly Massachusetts USA)

9 Pre-production disposable devices (Model: V2.0 from Velico Medical Inc.) with a nozzle annulus radial distance of 0.021"

8 Pre-production disposable devices (Model V3.0 from Velico Medical Inc.) with a nozzle radial distance width of 0.015"

17 units for PF24 (Plasma frozen within 24 hours after phlebotomy) human blood plasma Laboratory balance scale Model No. AB204 from Mettler-Toledo, LLC in Columbus Ohio, United States of America Protein meter Model no. 1000 from ThermoFisher Scientific Inc. in Waltham, Massachusetts, United States of America Total protein measurement was determined with NanoDrop 1000. Utilizing the absorbance at 280 nm (A280), protein concentration (c) was calculated by the instrumentation using the Beer-Lambert equation A280=c*ε*b (ε is the wavelength-dependent protein extinction coefficient, b is the pathlength). Total protein measurement was done according to the NanoDrop 1000 specification.

Residual moisture in dried plasma was determined according to specification of Karl Fischer moisture sensor, Model No. C30S Compact KF Coulometer (Mettler Toledo Billerica Massachusetts USA). In this approach, the reagent and solvent were combined in the titration cell. When a sample was introduced into the titration cell and dissolved, reagent was released by the induction of an electrical current. The amount of current required to convert the water was the determinant of the amount of moisture.

vWFrco assays (model no. 23044717) from Siemens Healthineers, ThermoFisher Scientific Inc. in Waltham, Massachusetts, United States of America.

von Willebrand Factor ristocetin cofactor (vWF:RCo) activity assay was performed by determining the amount of reagents and samples required by using the information in the subsequent sections. The dead volume of each of the reagents for the BCS XP is as listed below.

TABLE 3

| Item | Volume μL |
| --- | --- |
| GW 5 Reagent Bottle | 150-200 |
| GW 5 Reagent Bottle | 2000 |
| GW 15 Reagent Bottle | 300-350 |
| Behring Coagulation Cup | 250-300 |

One vWF:RCo assay requires the amounts of sample and reagents listed below.

TABLE 4

| Item | Volume Required μL | Volume/ Bottle (mL) | Container |
| --- | --- | --- | --- |
| Sample | 20 | N/A | Behring Coagulation Cup |
| Sodium Chloride | 40 | N/A | GW 15 |
| BC vWF Reagent | 300 | 4 | GW 5 |

Reagent Preparation:

Always initial and date (including time) a vial when opened or reconstituted. Always write the expiration date on the label.

BC vWF Reagent: Reconstitute BC vWF Reagent with 4.0 mL of DI water. Mix on high with a vortex mixer twice for five seconds. Drop a small Teflon magnetic stir bar into the BC vWF Reagent Bottle. Once prepared, the BC vWF Reagent can be stored on board for 8 hours in a position with stirring marked with yellow in rack lanes 1-5 or for 2 days at 2-8° C. Swirl gently before use.

Control Plasma N and Control Plasma P: Obtain a vial of Control Plasma N and Control Plasma P and reconstitute each vial with 1.0 mL of DI water. Swirl gently without causing any foam formation to dissolve lyophilized powder. Let stand at 15-25° C. for at least fifteen minutes. Once reconstituted, Control Plasma N and Control Plasma P can be stored on board for eight hours in rack lanes 5-14. Swirl gently without causing any foam formation before use.

0.9% Sodium Chloride Solution: Obtain a GW15 bottle from the BC vial kit with a sodium chloride barcode. Pour approximately 10 mL of sodium chloride solution into the vial. At the end of the day, throw out any unused sodium chloride solution and rinse the vial with DI water.

SHP (Only if Calibration is Required): Obtain a vial of SHP and reconstitute with 1.0 mL of DI water. Swirl gently without causing any foam formation to dissolve lyophilized powder. Let stand at 15-25° C. for at least 15 minutes. Once reconstituted, SHP can be stored on board for 4 hours in rack lanes 5-14. Swirl gently without causing any foam formation before use.

Loading Reagents into the BCS XP: Load reagents into the BCS XP by following: Load the BC vWF Reagent in any of the stirring positions in rack lanes 1-5. Load the SHP, Control Plasma N, and Control Plasma P in any position in rack lanes 5-14. Load Sodium Chloride Solution in any position in rack lanes 3-14.

Calibration for each assay is required every 6 months, when a new reagent lot is used, or at laboratory discretion as described in WI-00125. If calibration is required, prepare SHP. Select the assay vWF to calibrate. Run controls immediately after calibration has completed to verify the curve. If the controls are out of range, rerun the control and if it is still out of range, recalibrate.

Controls: Print reagent overview sheet, add the 0.9% Sodium Chloride Solution lot number, Run Control N and Control P before running assays on test samples. Check all controls are within range before running test samples.

Running Assays: Use the same reagent lot number when testing comparative samples. Load test samples in Behring Coagulation Cup into a sample rack and load in any rack lanes 5-14. Request the assay vWF. Samples with a measurement greater than 150% must be diluted in half using the 0.9% sodium chloride solution by adding 200 μL of the test sample to 200 μL of the 0.9% sodium chloride solution in a new sample cup. Mix thoroughly by pipetting up and down five to ten times. Any test result less than approximately 17% is below the measurement range and is not acceptable. (The lower limit may change slightly depending on the SHP used to generate the calibration curve for the assay.

Note: The ABO blood group has been known to exert a major quantitative effect on circulating vWF levels. Studies have consistently reported that blood group type O subjects have significantly lower plasma vWF levels than non-O individuals.

Note: VIII/vWF appears as a series of aggregates with different molecular weights therefore subjects with higher VIII levels tend to have higher vWF.

Characterization Studies: if either the dried plasma of the present invention or CP has a raw value of <40% then confirmation/rerun analysis was at the discretion of the reviewer/operator.

Exploration/Stability/Method Development Studies: Characterization study guidelines can be used to evaluate if any trends are present and/or establish the quality of the sample. Any deviation outside the characterization study guidelines would not be an indication for confirmation/rerun analysis due to the varying nature of exploratory studies.

17 units of plasma was spray dried using the pre-production spray dryer at 114° C. inlet temperature and aerosol gas flow rate of 40 L/min. with 9 disposable devices having a nozzle annulus radial distance of 0.021" and 8 disposable devices having a nozzle radial distance width of 0.015". Total plasma mass recovered was measured and compared. Inside of disposable devices were inspected for residual plasma deposits (loss) and weighed.

The protein concentration ratio (PCR) was determined as follows

PCR=Rehydrated dried plasma protein concentration/control protein concentration

Yield was determined as follows:

$$Yield=((dried\ plasma\ mass\ grams+200\ g\ rehydration\ water) \times PCR)/starting\ plasma\ mass\ in\ grams$$

Residual moisture in dried plasma was determined according to specification of Karl Fischer moisture sensor, Model No. C30S Compact KF Coulometer (Mettler Toledo Billerica Massachusetts USA).

vWFrco recovery assay result was determined by Siemens BCS XP System Model No. 23044717 from Siemens Healthineers, ThermoFisher Scientific Inc. in Waltham, Massachusetts, United States of America. von Willebrand Factor ristocetin cofactor (vWF:RCo) activity assay was performed. The amount of reagents and samples was determined by using the information in the subsequent section. The dead volume of each of the reagents for the BCS XP is as listed below.

TABLE 5

| Item | Volume μL |
| --- | --- |
| GW 5 Reagent Bottle | 150-200 |
| GW 5 Reagent Bottle | 2000 |
| GW 15 Reagent Bottle | 300-350 |
| Behring Coagulation Cup | 250-300 |

One vWF:RCo assay requires the amounts of sample and reagents listed below.

TABLE 6

| Item | Volume Required μL | Volume/Bottle (mL) | Container |
| --- | --- | --- | --- |
| Sample | 20 | N/A | Behring Coagulation Cup |
| Sodium Chloride | 40 | N/A | GW 15 |
| BC vWF Reagent | 300 | 4 | GW 5 |

Reagent Preparation:

Always initial and date (including time) a vial when opened or reconstituted. Always write the expiration date on the label.

BC vWF Reagent: Reconstitute BC vWF Reagent with 4.0 mL of DI water. Mix on high with a vortex mixer twice for five seconds. Drop a small Teflon magnetic stir bar into the BC vWF Reagent Bottle. Once prepared, the BC vWF Reagent can be stored on board for 8 hours in a position with stirring marked with yellow in rack lanes 1-5 or for 2 days at 2-8° C. Swirl gently before use.

Control Plasma N and Control Plasma P: Obtain a vial of Control Plasma N and Control Plasma P and reconstitute each vial with 1.0 mL of DI water. Swirl gently without causing any foam formation to dissolve lyophilized powder. Let stand at 15-25° C. for at least fifteen minutes. Once reconstituted, Control Plasma N and Control Plasma P can be stored on board for eight hours in rack lanes 5-14. Swirl gently without causing any foam formation before use.

0.9% Sodium Chloride Solution: Obtain a GW15 bottle from the BC vial kit with a sodium chloride barcode. Pour approximately 10 mL of sodium chloride solution into the vial. At the end of the day, throw out any unused sodium chloride solution and rinse the vial with DI water.

SHP (Only if Calibration is Required): Obtain a vial of SHP and reconstitute with 1.0 mL of DI water. Swirl gently without causing any foam formation to dissolve lyophilized powder. Let stand at 15-25° C. for at least 15 minutes. Once reconstituted, SHP can be stored on board for 4 hours in rack lanes 5-14. Swirl gently without causing any foam formation before use.

Loading Reagents into the BCS XP: Load reagents into the BCS XP by following WI-00125 Section 8.12. Load the BC vWF Reagent in any of the stirring positions in rack lanes 1-5. Load the SHP, Control Plasma N, and Control Plasma P in any position in rack lanes 5-14. Load Sodium Chloride Solution in any position in rack lanes 3-14.

Calibration for each assay is required every 6 months, when a new reagent lot is used, or at laboratory discretion as described in WI-00125. If calibration is required, prepare SHP. Select the assay vWF to calibrate. Run controls immediately after calibration has completed to verify the curve. If the controls are out of range, rerun the control and if it is still out of range, recalibrate.

Controls: Print reagent overview sheet, add the 0.9% Sodium Chloride Solution lot number, Run Control N and Control P before running assays on test samples. Check all controls are within range before running test samples.

Running Assays: Use the same reagent lot number when testing comparative samples. Load test samples in Behring Coagulation Cup into a sample rack and load in any rack lanes 5-14. Request the assay vWF. Samples with a measurement greater than 150% must be diluted in half using the 0.9% sodium chloride solution by adding 200 μL of the test sample to 200 μL of the 0.9% sodium chloride solution in a new sample cup. Mix thoroughly by pipetting up and down five to ten times. Any test result less than approximately 17% is below the measurement range and is not acceptable. (The lower limit may change slightly depending on the SHP used to generate the calibration curve for the assay.

Note: The ABO blood group has been known to exert a major quantitative effect on circulating vWF levels. Studies have consistently reported that blood group type O subjects have significantly lower plasma vWF levels than non-O individuals.

Note: VIII/vWF appears as a series of aggregates with different molecular weights therefore subjects with higher VIII levels tend to have higher vWF.

Characterization Studies: if either the dried plasma of the present invention or CP has a raw value of <40% then confirmation/rerun analysis was at the discretion of the reviewer/operator.

Exploration/Stability/Method Development Studies: the reviewer/operator will have discretion to request a confirmation/rerun analysis at any time. Characterization study guidelines can be used to evaluate if any trends are present and/or establish the quality of the sample. Any deviation outside the characterization study guidelines would not be an indication for confirmation/rerun analysis due to the varying nature of exploratory studies.

Results

Data
0.021 Dd 0.015 Dd
Yield 76.2% 77.9%
vWFrco 49.0% 50.0%
Moisture 1.8% 1.0%

The pre-production disposable drying chambers (V3.0) with nozzle annulus distance $D^d$ of 0.015" provided a 2.2% greater yield percentage improvement as compared to those with nozzle Dd of 0.021". Both yields are sufficient for purposes of spray drying human blood plasma.

The disposable drying chambers with 0.015" annulus radial distance Dd yielded 1.0% residual moisture as compared to 1.8% residual moisture for disposable drying chambers with 0.021 annulus radial distance $D^d$. Again, for purposes of use for spray drying purposes, a residual moisture of less than 2% is sufficient.

vWF recovery of the 0.015" annulus radial distance nozzle compared to the 0.021" annulus radial distance nozzle was improved by 1 percentage point. While 49% or 50% vWF recovery as measured by the vWFrco assay is acceptable per FDA guidance per Meeting ID #BQ150234 (Mar. 14, 2018), the importance of VWF to clotting performance in vivo is so great that optimizing vWF recovery is of paramount importance.

Conclusion

Reduction of annulus radial distance improves dried plasma and VWFrco yield and reduces residual moisture in the dried plasma.

Example 2: Impact of Chamfered Cannula on vWFrco Recovery

Purpose: To study vWF recovery ratio by VWFrco assay of plasma dried with a composite nozzle assembly having a chamfered cannula, as compared to one with an unchamfered cannula. Specifically, an expensive Buchi stainless-steel nozzle assembly with unchamfered cannula (no chamfered cannula nozzle is known to be available commercially) used during development to produce regulatorily acceptable dried plasma was used a benchmark against which to judge the performance of a significantly less expensive composite nozzle of the present invention suitable for use in a disposable drying chamber for spray drying human blood plasma. The study also determined vWF recovery of less expensive chamfered and unchamfered plastic nozzle assemblies as compared to stainless steel nozzle benchmark.

Methods and Materials

Spray dryer test bed (Beta model, Velico Medical Inc, Beverly Massachusetts US)
8 plasma drying disposables
1 control Buchi Model No. 4244 stainless steel spray drying nozzle 1 pre-production composite nozzle with an unchamfered cannula (Velico Medical Inc. Beverly Massachusetts USA)

1 pre-production composite nozzle with chamfered cannula of 45 Degrees and 0.03" length, as shown in FIG. 2F (Velico Medical Inc, Beverly Massachusetts USA)

8 units of PF24 plasma vWF rco assays as needed ((model no. 23044717) from Siemens Healthineers, ThermoFisher Scientific Inc. in Waltham, Massachusetts, United States of America) for control plasma and test samples The units were grouped to three studies. Groups I and II used stainless steel and an unchamfered composite nozzle assembly and Group III used a chamfered composite nozzle assembly. The unchamfered stainless steel cannula was made with a polycarbonate plastic assembly (i.e., nozzle cap, nozzle insert, nozzle reservoir and the like), the chamfered stainless-steel cannula was made with a polycarbonate plastic assembly (i.e., nozzle cap, nozzle insert, nozzle reservoir and the like), and the stainless-steel nozzle assembly was made from stainless-steel (i.e., cannula, nozzle cap, pressurized air outlet and the like).

The control for each group was obtained by mixing each unit prior to spray drying. The control liquid plasma was not spray dried.

One unit from each of the (units 2795, 2800 and 2815) was spray dried with the control stainless steel nozzle. One unit from Group I (unit 2796) and two units from Group II (units 2801 and 2802) were spray dried with pre-production composite nozzle with an unchamfered cannula. Two units (2816 and 2817) from Group III were spray dried with pre-production composite plastic nozzle with a chamfered cannula.

The spray dried plasma was reconstituted with 200 ml Sterile Water for Injection. vWF rco assays were performed on the control samples and the reconstituted plasma dried as described above.

Results

The results are shown below:

As shown in FIG. 9, vWF recovery ratio of the chamfered cannula composite nozzle of the present invention was 3.7% greater as compared to the stainless-steel control nozzle. It is surprising to have any increase in vWF recovery ratio over the expensive stainless steel benchmark nozzle. The chamfered cannula used in the composite nozzle assembly of the present invention is less expensive and performs just as well or better than the expensive stainless-steel version or the unchamfered composite nozzle.

Conclusion

The chamfered cannula results in improved vWF recovery in spray drying of human blood plasma.

Example 3: Impact of Baffle Plate Configuration on BFE (Bacterial Filtration Efficiency) Performance of Baffle Plate Filter of Disposable Purpose: To determine the BFE of the baffle plate filter. Specifically, the purpose was to determine ASTM BFE log reduction value (LRV) for the tapered ribbed baffle plate of the present invention. The results determined that there is improved LRV resulting from the use of the tapered ribbed baffle plate.

Methods and Materials

ASTM 2101-14 Bacterial Filter Efficiency BFE test fixture 10 baffle plate plasma drying chamber upper sections with tapered ribs as shown in FIG. 2L and FIG. 2La.

*S. aureus* challenge organism

Nelson Laboratories facility of Biosciences Laboratories, LLC in Salt Lake City Utah USA The 10 pre-production plasma drying chamber upper sections with tapered ribs and an inlet filter (Model No. from Lydall Performance Materials Rochester, NH 03867 USA) were sterilized using gamma radiation. The filter was supported by tapered rib baffle plate and subjected to ASTM2101-14 bacterial filtration efficiency testing with *S.*

TABLE 7

CP is control plasma that is pumped through the cannula but not dried

| Group | Nozzle Assembly | Batch | Nozzle Type | Chamfer | vWF (%) | vWF (%) dried plasma/CP Ratio |
|---|---|---|---|---|---|---|
| Group I | N/A | 2795/2796 CP | N/A | N/A | 97.4% | N/A |
| | | 2795 | Steel | No | 51.1% | 52.5% |
| | Steel | 2795 | Steel | No | 52.5% | 53.9% |
| | | 2796 | Plastic Nozzle #1 | No | 42.4% | 43.5% |
| | Unchamfered Plastic | 2796 | Plastic Nozzle #1 | No | 44.8% | 46.0% |
| Group II | N/A | 2800/2801/2802 CP | N/A | N/A | 149.4% | N/A |
| | Steel | 2800 | Steel | No | 67.3% | 45.0% |
| | Unchamfered Plastic | 2801 | Plastic Nozzle B01 | No | 55.9% | 37.4% |
| | Unchamfered Plastic | 2802 | Plastic Nozzle B02 | No | 56.1% | 37.6% |
| Group III | N/A | 2815/2816/2817 CP | N/A | N/A | 73.1% | N/A |
| | Steel | 2815 | Steel | No | 39.9% | 54.6% |
| | Chamfered Plastic | 2816 | Plastic Nozzle B6 | Yes | 41.4% | 56.6% |
| | Chamfered Plastic | 2817 | Plastic Nozzle A1 | Yes | 40.5% | 55.4% |

*aureus* CFU challenge loading conditions sufficient to demonstrate log 6 reduction (LRV) per the test protocol of Nelson Laboratories.

The filter was inspected for evidence of filter tearing.

Results 9 of the 10 test samples resulted in no CFU's recovered, a Filtration Efficiency of 99.999987 and an LRV of >6.9.

1 of the test samples exhibited 3 CFU's recovered, a filtration efficiency of 99.99961 and an LRV of 6.4.

No filter tearing was noted.

Conclusion

The tapered rib baffle plate of the present invention successfully enables LRV's of 6.0 or greater when tested under ASTM 2102-14 and does not tear the filter.

Example 4: Increasing Aerosol Flow Rate Increases Yield

Purpose: It was determined that aerosol flow rate of 40 L/min increased yield by 7.5%

Methods and Materials

Plasma yield by weight was compared using aerosol flow rates of 35 L/min and 40 L/min. Two liquid plasma units were spray dried using the dryer of the present invention at an aerosol flow rate of 35 L/min and two at 40 L/min. Dried plasma units were weighed in the disposables and compared.

- pre-production spray dryer of the present invention
- 4 late pre-production drying chambers of the present invention
- 4 units PF24 human plasma
- laboratory balance scale Result Yield percentage by weight at 35 L/min. was 82.75%.

Yield percentage by weight at 40 L/min was 86.4%.

Conclusion

Increased aerosol flow rate to 40 L/min increases plasma yield.

Example 5: Spray Drying of Plasma Showing Consistency Across Three Spray Dryers of the Present Invention Summary The in vitro characterization of pooled spray dried plasma manufactured on the three (3) different spray dryer of the present invention, as described herein and referred to as FRONTLINE™ spray drier system from Velico Medical Inc's (Beverly, MA USA). FRONTLINE™ Dryers demonstrated that there is no statistically significant difference in percent change between the paired controls and the spray dried plasma unites manufactured on three (3) FRONTLINE™ Dryers in support of a lack of inter-instrument variability. The results also demonstrate minimal impact of the manufacturing process on spray dried plasma units, as compared to the starting plasma (prior to drying). Spray dried plasma processed by the FRONTLINE™ spray drier is referred to herein as FRONTLINEODP™. The plasma was dried using the disposable of the present invention, as described herein and shown in FIG. 1A.

The same 20 pooled plasma units were spray dried on three (3) FRONTLINE™ Dryers. The resulting 60 spray dried plasma units were characterized across 20 assays. A one-way analysis of variance (ANOVA) was completed for spray dried plasma units manufactured by the three (3) FRONTLINE™ Dryers for the characterization assays comparing the percent change from pre-(paired control plasma) and post-manufacture spray dried plasma unit. All p-values were greater than 0.05, indicating that there was no statistically significant difference between the percent change of spray dried plasma units manufactured across the three (3) FRONTLINE™ Dryers. The study demonstrated the robustness of the spray drying process and that there is no statistically significant variability in percent change of units manufactured between the different FRONTLINE™ Dryers.

TABLE 8

ANOVA Results for mean comparison of percent changes across three (3) Frontline Dryers

| | | Percent Change | | | |
|---|---|---|---|---|---|
| | Assay | Dryer 1 | Dryer 2 | Dryer 3 | p-value |
| General Properties | Total Protein g/dL | −2% ± 3% | −2% ± 3% | −2% ± 3% | 0.897 |
| | Osmolality (mOsm/kg) | 24% ± 5% | 24% ± 3% | 24% ± 5% | 0.893 |
| Global Tests | aPTT (s) | 11% ± 6% | 12% ± 6% | 11% ± 6% | 0.77 |
| | Prothrombin Time (s) | 11% ± 3% | 10% ± 2% | 11% ± 4% | 0.939 |
| | Thrombin Time (s) | 29% ± 6% | 32% ± 7% | 29% ± 5% | 0.053 |
| Coagulation Factors | Factor V (%) | −10% ± 5% | −11% ± 5% | −9% ± 6% | 0.689 |
| | Factor VII (%) | −12% ± 6% | −13% ± 5% | −13% ± 6% | 0.678 |
| | Factor VIII (%) | −21% ± 8% | −19% ± 8% | −22% ± 7% | 0.259 |
| | Factor XIII Activity (%) | −11% ± 7% | −11% ± 7% | −10% ± 8% | 0.965 |
| | Factor XIII Antigen (%) | −12% ± 4% | −12% ± 3% | −11% ± 4% | 0.735 |
| | Fibrinogen (mg/dL) | −11% ± 6% | −10% ± 6% | −12% ± 7% | 0.333 |
| Anticoagulant Proteins | Protein C (%) | −6% ± 4% | −6% ± 3% | −6% ± 3% | 0.941 |
| | Protein S (%) | −13% ± 4% | −15% ± 3% | −12% ± 4% | 0.185 |
| | Antithrombin III (%) | −9% ± 4% | −9% ± 3% | −9% ± 4% | 0.917 |
| vWF | von Willebrand Factor Antigen (%) | 1% ± 5% | 1% ± 5% | 1% ± 5% | 0.967 |
| | von Willebrand Factor Ristocetin Cofactor (%) | −58% ± 5% | −59% ± 4% | −59% ± 5% | 0.572 |

TABLE 8-continued ANOVA Results for mean comparison of percent changes across three (3) Frontline Dryers

| | | Percent Change | | | |
|---|---|---|---|---|---|
| | Assay | Dryer 1 | Dryer 2 | Dryer 3 | p-value |
| Complement Protein Activation Markers | C5a (ng/mL) | 397% ± 145% | 434% ± 149% | 354% ± 117% | 0.215 |
| | Prothrombin Fragment F 1 + 2 (pmol/L) | 8% ± 16% | 7% ± 13% | 10% ± 22% | 0.77 |
| | Thrombin-Antithrombin Complex (TAT) (μg/L) | 11% ± 25% | 18% ± 33% | 5% ± 14% | 0.244 |

Method

Spray dried plasma, obtained using the methods of the present invention, were manufactured from pooled single donor plasma pre-treated with a solution containing 440 mM glycine and 106 mM hydrochloric acid which were added to SWFI. Plasma combined with the pre-treatment solution is referred to as formulated plasma. The pretreatment solution was made using the following table:

TABLE 9

Pretreatment formulation

| Conc. (mM) | 250 mL | 500 mL | 1000 mL | 2000 mL | 4000 mL |
|---|---|---|---|---|---|
| HCl (mL) 106 | 2.18 ± 0.11 | 4.36 ± 0.22 | 8.72 ± 0.44 | 17.44 ± 0.87 | 34.88 ± 1.74 |
| Glycine (g) 440 | 8.26 ± 0.41 | 16.52 ± 0.83 | 33.08 ± 1.65 | 66.16 ± 3.31 | 132.32 ± 6.62 |

The spray drier used in processing spray dried plasma is described herein and is FRONTLINE™ spray drier system from Velico Medical Inc's (Beverly, MA USA). The study was limited to a sample size of n=60. Plasma units are produced from 20 pooled plasma samples processed on three different spray driers. Each pool is equally divided, treated with the pre-treatment solution and spray dried using one of the three instruments.

Sixty (60) units of blood plasma blood type A (27 units), blood type O (27 units), and blood type B (6 units) were pre-treated with the pre-treatment solution, pooled and spray dried on spray dried on three separate spray drying systems (i.e., FRONTLINE™ Systems (Velico Medical Inc, Beverly MA USA)) (n=20 pooled samples each) and tested.

The manufacturing effect of these spray drying system on the starting material was determined by calculating the change between the plasma unit having the pretreatment solution described herein and its paired control plasma (CP) for each of the assays.

$$\% \text{ Change} = \frac{FrontlineODP - CP}{CP} \times 100$$

Inter-instrument variability will be assessed across 20 assays outlined in the FDA panel including pH Materials ACCUMET® Benchtop pH Meter
Blood Collection Monitor
Calibrated timer
Clean Dry Air (CDA) System
Freezer
FRONTLINE™ System VEL 7000×3 and 1 Sealer ASY 30000S (Velico Medical Inc, Beverly MA, USA)
HELMER® Plasma Thawer
Instrumentation Laboratories ACL TOP 700 coagulation analyzer
Osmometer
Plate Reader
Plate Washer
Refrigerator
SELECTRA PRO M® Chemistry Analyzer
SIEMENS BCS XP® coagulation analyzer
Sterile Connection Device
Tubing Heat Sealer
Overwrap Sealer
Plasma Pretreatment Container having pretreatment solution having 16.8 mM HCl and 69.6 mM glycine and SWFI
Plasma Drying Chamber
Sterile Water for Injection (SWFI)
Never Frozen Plasma (NFP)
Fresh Frozen Plasma (FFP)
Plasma frozen within 24 hours (PF24)
3000 mL transfer pack
Reagents to complete panel per work instructions
5 mL Cryo-vials, P/N 01379

Results

Statistical analysis was performed using MINITAB® statistical software to determine if there was a statistically significant difference between the percent change of pre-treated spray dried plasma units including pH as compared to its paired control plasma made across the three (3) FRONTLINE™ Dryers. Method of analysis was one-way ANOVA with a two-sided confidence interval.

All ANOVA values were greater than 0.05 indicating that the null hypothesis was correct for each assay. There was no statistically significant difference between the three (3)

FRONTLINE™ Dryer's performance including the PH value across the three instruments of the resulting reconstituted spray dried plasma being in the range of 6.93 to 7.21 with a mean of 7.06.

TABLE 10

ANOVA Results for mean comparison of percent changes across three (3) Frontline Dryers

| | | Percent Change | | | |
|---|---|---|---|---|---|
| | Assay | Dryer 1 | Dryer 2 | Dryer 3 | p-value |
| General Properties | Total Protein g/dL | −2% ± 3% | −2% ± 3% | −2% ± 3% | 0.897 |
| | Osmolality (mOsm/kg) | 24% ± 5% | 24% ± 3% | 24% ± 5% | 0.893 |
| Global Tests | aPTT (s) | 11% ± 6% | 12% ± 6% | 11% ± 6% | 0.77 |
| | Prothrombin Time (s) | 11% ± 3% | 10% ± 2% | 11% ± 4% | 0.939 |
| | Thrombin Time (s) | 29% ± 6% | 32% ± 7% | 29% ± 5% | 0.053 |
| Coagulation Factors | Factor V (%) | −10% ± 5% | −11% ± 5% | −9% ± 6% | 0.689 |
| | Factor VII (%) | −12% ± 6% | −13% ± 5% | −13% ± 6% | 0.678 |
| | Factor VIII (%) | −21% ± 8% | −19% ± 8% | −22% ± 7% | 0.259 |
| | Factor XIII Activity (%) | −11% ± 7% | −11% ± 7% | −10% ± 8% | 0.965 |
| | Factor XIII Antigen (%) | −12% ± 4% | −12% ± 3% | −11% ± 4% | 0.735 |
| | Fibrinogen (mg/dL) | −11% ± 6% | −10% ± 6% | −12% ± 7% | 0.333 |
| Anticoagulant Proteins | Protein C (%) | −6% ± 4% | −6% ± 3% | −6% ± 3% | 0.941 |
| | Protein S (%) | −13% ± 4% | −15% ± 3% | −12% ± 4% | 0.185 |
| | Antithrombin III (%) | 9% ± 4% | −9% ± 3% | −9% ± 4% | 0.917 |
| vWF | vWF Antigen (%) | 1% ± 5% | 1% ± 5% | 1% ± 5% | 0.967 |
| | vWF:RCo (%) | −58% ± 5% | −59% ± 4% | −59% ± 5% | 0.572 |
| Complement Protein | C5a (ng/mL) | 397% ± 145% | 434% ± 149% | 354% ± 117% | 0.215 |
| Activation Markers | Prothrombin Fragment F 1 + 2 (pmol/L) | 8% ± 16% | 7% ± 13% | 10% ± 22% | 0.77 |
| | Thrombin-Antithrombin Complex (TAT) (μg/L) | 11% ± 25% | 18% ± 33% | 5% ± 14% | 0.244 |

The average characterization results are shown in Table 11. The characterization results for each instrument are shown in Tables 14-16.

TABLE 11

Summary of Results (Average of 20 FrontlineODP Units spray dried on three Frontline Dryer for a total of n = 60)

| | | Average of 3 Instruments | | | |
|---|---|---|---|---|---|
| | | FrontlineODP | | Change compared to Control | |
| | Assays | Mean ± SD | Range (min-max) | Mean ± SD | Range (min-max) |
| General Properties | pH | 7.06 ± 0.07 | (6.93-7.21) | −5% ± 1% | (−8%--3%) |
| | Total Protein g/dL | 5.44 ± 0.23 | (4.95-5.89) | −2% ± 3% | (−10%-4%) |
| | Osmolality (mOsm/kg) | 382 ± 14 | (343-404) | 24% ± 5% | (9%-31%) |
| Global Factors | aPTT (s) | 30.6 ± 2.1 | (27.0-34.7) | 11% ± 6% | (−1%-22%) |
| | Prothrombin Time (s) | 12.7 ± 0.5 | (11.8-13.8) | 11% ± 3% | (4%-19%) |
| | Thrombin Time (s) | 17.2 ± 1.2 | (14.9-21.8) | 29% ± 6% | (21%-47%) |
| Coagulation Factors | Factor V (%) | 94.0 ± 12.2 | (74.6-121.2) | −10% ± 5% | (−19%-5%) |
| | Factor VII (%) | 84.4 ± 9.9 | (63.1-105.2) | −12% ± 6% | (−25%-2%) |
| | Factor VIII (%) | 79.4 ± 14.7 | (51.0-126.2) | −21% ± 8% | (−32%-2%) |
| | Factor XIII Activity (%) | 112.7 ± 12.6 | (88.9-153.6) | −11% ± 7% | (−23%-6%) |
| | Factor XIII Antigen (%) | 101.6 ± 13.4 | (81.7-140.1) | −12% ± 4% | (−21%--3%) |
| | Fibrinogen (mg/dL) | 253 ± 25 | (213-314) | −11% ± 6% | (−27%-3%) |
| Anticoagulant Proteins | Protein C (%) | 100 ± 6 | (86-111) | −6% ± 4% | (−17%-2%) |
| | Protein S (%) | 93.5 ± 7.4 | (81.7-111.9) | −13% ± 4% | (−23%--3%) |
| | Antithrombin III (%) | 89 ± 6 | (75-101) | −9% ± 4% | (−17%-0%) |
| vWF | von Willebrand Factor Antigen (%) | 123.3 ± 22.0 | (94.3-187.8) | 1% ± 5% | (−14%-9%) |
| | von Willebrand Factor Ristocetin Cofactor (%) | 41.2 ± 8.8 | (27.2-61.9) | −58% ± 5% | (−67%--45%) |

TABLE 11-continued

Summary of Results (Average of 20 FrontlineODP Units spray dried on three Frontline Dryer for a total of n = 60)

Average of 3 Instruments

| | Assays | FrontlineODP Mean ± SD | Range (min-max) | Change compared to Control Mean ± SD | Range (min-max) |
|---|---|---|---|---|---|
| Complement Protein Activation Markers | C5a (ng/mL) | 33.45 ± 7.72 | (21.11-53.58) | 397% ± 145% | (197%-846%) |
| | Prothrombin Fragment F 1 + 2 (pmol/L) | 91.4 ± 23.7 | (51.3-171.8) | 8% ± 16% | (-47%-53%) |
| | Thrombin-Antithrombin Complex (TAT) (µg/L) | 2.04 ± 1.20 | (0.32-5.56) | 11% ± 25% | (-45%-137%) |

TABLE 12

Summary of Results for Frontline Dryer 1 (n = 20)

Instrument 1

| | Assays | FrontlineODP Mean ± SD | Range (min-max) | Change compared to Control Mean ± SD | Range (min-max) |
|---|---|---|---|---|---|
| General Properties | pH | 7.07 ± 0.06 | (6.98-7.21) | -5% ± 1% | (-6%--3%) |
| | Total Protein g/dL | 5.44 ± 0.22 | (5.07-5.89) | -2% ± 3% | (-10%-1%) |
| | Osmolality (mOsm/kg) | 383.36 ± 10.16 | (357-398) | 24% ± 3% | (16%-29%) |
| Global Factors | aPTT (s) | 30.77 ± 2.19 | (27-34.7) | 12% ± 6% | (1%-22%) |
| | Prothrombin Time (s) | 12.7 ± 0.47 | (11.8-13.3) | 10% ± 2% | (8%-15%) |
| | Thrombin Time (s) | 17.51 ± 1.48 | (15-21.8) | 32% ± 7% | (24%-47%) |
| Coagulation Factors | Factor V (%) | 93.31 ± 12.5 | (74.6-118.5) | -11% ± 5% | (-19%--2%) |
| | Factor VII (%) | 84.02 ± 9.99 | (63.1-105.2) | -13% ± 5% | (-25%--3%) |
| | Factor VIII (%) | 81.8 ± 16.65 | (51.25-126.2) | -19% ± 8% | (-32%-2%) |
| | Factor XIII Activity (%) | 112.7 ± 13.36 | (91-147) | -11% ± 7% | (-22%-1%) |
| | Factor XIII Antigen (%) | 101.81 ± 14.17 | (84.8-140.1) | -12% ± 3% | (-21%--7%) |
| | Fibrinogen (mg/dL) | 258.25 ± 27.54 | (213-314) | -10% ± 6% | (-19%-1%) |
| Anticoagulant Proteins | Protein C (%) | 99.7 ± 5.95 | (87-107) | -6% ± 3% | (-12%-2%) |
| | Protein S (%) | 92.22 ± 7.56 | (81.7-106.4) | -15% ± 3% | (-23%--9%) |
| | Antithrombin III (%) | 89.2 ± 6.07 | (75-101) | -9% ± 3% | (-15%--1%) |
| vWF | von Willebrand Factor Antigen (%) | 123.1 ± 22.59 | (99.4-187.8) | 1% ± 5% | (-14%-9%) |
| | von Willebrand Factor Ristocetin Cofactor (%) | 40.52 ± 8.07 | (28.1-56.6) | -59% ± 4% | (-67%--52%) |
| Complement Protein Activation Markers | C5a (ng/mL) | 35.89 ± 7.66 | (25-52.99) | 434% ± 149% | (200%-719%) |
| | Prothrombin Fragment F 1 + 2 (pmol/L) | 89.61 ± 19.54 | (58.37-122.76) | 7% ± 13% | (-17%-32%) |
| | Thrombin-Antithrombin Complex (TAT) (µg/L) | 2.1 ± 1.18 | (0.5-5.36) | 18% ± 33% | (-27%-137%) |

TABLE 13

Summary of Results for Frontline Dryer 2 (n = 20)

Instrument 2

| | Assays | FrontlineODP Mean ± SD | Range (min-max) | Change compared to Control Mean ± SD | Range (min-max) |
|---|---|---|---|---|---|
| General Properties | pH | 7.05 ± 0.07 | (6.93-7.16) | -5% ± 1% | (-7%--4%) |
| | Total Protein g/dL | 5.45 ± 0.2 | (4.95-5.85) | -2% ± 3% | (-8%-4%) |
| | Osmolality (mOsm/kg) | 382.51 ± 14.22 | (352.5-403.67) | 24% ± 5% | (14%-31%) |

TABLE 13-continued

Summary of Results for Frontline Dryer 2 (n = 20)

Instrument 2

|  | Assays | FrontlineODP Mean ± SD | Range (min-max) | Change compared to Control Mean ± SD | Range (min-max) |
|---|---|---|---|---|---|
| Global Factors | aPTT (s) | 30.37 ± 2.05 | (27.2-33.9) | 11% ± 6% | (1%-22%) |
|  | Prothrombin Time (s) | 12.73 ± 0.55 | (11.9-13.8) | 11% ± 4% | (5%-19%) |
|  | Thrombin Time (s) | 17.19 ± 0.92 | (14.9-18.8) | 29% ± 5% | (21%-39%) |
| Coagulation Factors | Factor V (%) | 94.69 ± 13 | (77.8-121.2) | −9% ± 6% | (−18%-5%) |
|  | Factor VII (%) | 83.82 ± 10 | (67.6-101.5) | −13% ± 6% | (−24%-2%) |
|  | Factor VIII (%) | 78.81 ± 12.75 | (58.65-106.9) | −22% ± 7% | (−31%--2%) |
|  | Factor XIII Activity (%) | 112.95 ± 12.01 | (88.9-136.6) | −10% ± 8% | (−22%-6%) |
|  | Factor XIII Antigen (%) | 102.12 ± 13.32 | (81.7-133.8) | −11% ± 4% | (−18%--4%) |
|  | Fibrinogen (mg/dL) | 250.25 ± 25.36 | (220-306) | −12% ± 7% | (−27%-3%) |
| Anticoagulant Proteins | Protein C (%) | 99.65 ± 6.34 | (87-110) | −6% ± 3% | (−11%-1%) |
|  | Protein S (%) | 94.85 ± 7.07 | (83.6-111.9) | −12% ± 4% | (−21%--3%) |
|  | Antithrombin III (%) | 89.2 ± 6.47 | (80-100) | −9% ± 4% | (−15%-0%) |
| vWF | von Willebrand Factor Antigen (%) | 123.56 ± 22 | (94.5-181.8) | 1% ± 5% | (−14%-7%) |
|  | von Willebrand Factor Ristocetin Cofactor (%) | 40.8 ± 8.85 | (27.2-61.8) | −59% ± 5% | (−67%--50%) |
| Complement Protein | C5a (ng/mL) | 30.83 ± 7.15 | (21.11-47.49) | 354% ± 117% | (204%-671%) |
| Activation Markers | Prothrombin Fragment F 1 + 2 (pmol/L) | 92.14 ± 23.38 | (57.18-134.34) | 10% ± 22% | (−47%-53%) |
|  | Thrombin-Antithrombin Complex (TAT) (μg/L) | 2.01 ± 1.3 | (0.36-5.56) | 5% ± 14% | (−27%-30%) |

TABLE 14

Summary of Results for Frontline Dryer 3 (n = 20)

Instrument 3

|  | Assays | FrontlineODP Mean ± SD | Range (min-max) | Change compared to Control Mean ± SD | Range (min-max) |
|---|---|---|---|---|---|
| General Properties | pH | 7.08 ± 0.08 | (6.93-7.2) | −5% ± 1% | (−8%--4%) |
|  | Total Protein g/dL | 5.42 ± 0.26 | (4.99-5.81) | −3% ± 4% | (−10%-3%) |
|  | Osmolality (mOsm/kg) | 381.12 ± 18.31 | (342.5-400.5) | 23% ± 6% | (9%-30%) |
| Global Factors | aPTT (s) | 30.55 ± 2.29 | (27-34.2) | 11% ± 7% | (−1%-22%) |
|  | Prothrombin Time (s) | 12.74 ± 0.51 | (11.9-13.6) | 11% ± 3% | (4%-16%) |
|  | Thrombin Time (s) | 16.9 ± 0.97 | (15-19.1) | 27% ± 5% | (21%-38%) |
| Coagulation Factors | Factor V (%) | 93.88 ± 11.55 | (79.5-118.5) | −10% ± 4% | (−18%--2%) |
|  | Factor VII (%) | 85.25 ± 10.01 | (66.9-99.1) | −11% ± 8% | (−23%-2%) |
|  | Factor VIII (%) | 77.6 ± 14.78 | (50.95-122.1) | −23% ± 7% | (−32%--4%) |
|  | Factor XIII Activity (%) | 112.35 ± 13.12 | (96.5-153.6) | −11% ± 7% | (−23%-3%) |
|  | Factor XIII Antigen (%) | 100.93 ± 13.36 | (83.8-138.7) | −13% ± 5% | (−18%--3%) |
|  | Fibrinogen (mg/dL) | 250.43 ± 21.24 | (213-302) | −12% ± 6% | (−23%--2%) |
| Anticoagulant Proteins | Protein C (%) | 99.3 ± 6.71 | (86-111) | −6% ± 4% | (−17%-0%) |
|  | Protein S (%) | 93.43 ± 7.57 | (83.3-111.8) | −13% ± 5% | (−22%--3%) |
|  | Antithrombin III (%) | 88.73 ± 6.5 | (78-99) | −9% ± 5% | (−17%--3%) |
| vWF | von Willebrand Factor Antigen (%) | 123.35 ± 22.63 | (94.3-182.7) | 1% ± 5% | (−12%-8%) |
|  | von Willebrand Factor Ristocetin Cofactor (%) | 42.18 ± 9.74 | (28.4-61.9) | −57% ± 5% | (−65%--45%) |
| Complement Protein | C5a (ng/mL) | 33.63 ± 7.85 | (24.68-53.58) | 402% ± 162% | (197%-846%) |
| Activation Markers | Prothrombin Fragment F 1 + 2 (pmol/L) | 92.46 ± 28.35 | (51.32-171.79) | 8% ± 10% | (−9%-25%) |
|  | Thrombin-Antithrombin Complex (TAT) (μg/L) | 2.02 ± 1.17 | (0.32-4.98) | 9% ± 23% | (−45%-72%) |

The percent change between the spray dried plasma units and its paired control on average is within ±20% for pH, aPTT, PT, Factor V activity, Factor VIII activity, Factor XIII activity, Factor XIII antigen, fibrinogen, Protein C, Protein S, Antithrombin III, von Willebrand Factor (vWF) antigen, Prothrombin Fragment 1+2 (PF1+2), Thrombin Anti-Thrombin (TAT), total protein. The mean von Willebrand ristocetin cofactor (vWF:RCo) levels of spray dried plasma units of 41.2% is ≥40%, meeting FDA's recommendation per Meeting ID #BQ150234 (Mar. 14, 2018). Decreased recovery of vWF:RCo activity was observed and is due to the shearing during the spray drying process. There was a 23% and 27% change with osmolality and thrombin time (TT), respectively, for spray dried plasma units compared to its paired control. The increase in osmolality in the spray dried plasma units is attributed to the hydrochloric acid and glycine in the Plasma Pretreatment Container. The European Pharmacopoeia specifies the pH as 6.5-7.6 and minimum osmolality of 240 mOsm/kg for Human Plasma (pooled and treated for virus inactivation). A previous internal study demonstrated that decreasing the pH of plasma induced a prolonged TT. The observed changes compared to the control for osmolality and TT are not clinically significant because the mean osmolality and pH are still within the acceptable ranges as indicated by the above-mentioned standard and the prolonged TT is an effect of the sample pH on the assay. The C5a in spray dried plasma unit is elevated compared to control plasma but the average of 33.45 ng/mL is acceptable because clinically acceptable values have been reported for apheresis plasma in the range of 4.9-74 ng/mL. The increase in levels for C5a are not considered clinically significant. Factor VIII had a mean change of −21% from spray dried plasma unit to control plasma across the three (3) instruments. This is acceptable however, because the average spray dried plasma characterization value of 79.4% is within the acceptable test ranges of 50%-200%. All spray drying manufacturing processes were within the stated acceptance criteria:

The starting mass recorded on Frontline Dryer was 348 g±32 g.
Total mass spray dried recorded on Frontline Dryer was 325 g±30 g
Drying gas inlet temperature: 115±3° C.
Drying gas flow rate: 750±10 L/min
Drying gas exhaust temperature: 65±2° C.
Aerosol gas flow rate: 40±1 L/min
Mean rehydrated ODP were within the acceptance criteria of:
pH within 6.69-7.37, where the actual value was 7.06.
Osmolality within 338-450 mOsm/kg, where the actual value was 382 mOsm/kg.
Protein concentration ODP normalized to control was within 0.88-1.17 on the Chemistry analyzer, where the actual value was 0.98.

Conclusion

The in vitro characterization of pooled spray dried plasma dried on the three (3) FRONTLINE™ Dryers demonstrated that there was no statistically significant difference between the performance of the three (3) FRONTLINE™ Dyers as determined by % change of the pretreated spray dried plasma units from their paired control across 20 characterization assays. This supports the lack of inter-instrument variability of the FRONTLINE™ Dryers including the PH value across the three instruments of the resulting reconstituted spray dried plasma being in the range of 6.93 to 7.21, with a mean of 7.06.

The characterization data show that reconstituted spray dried plasma units treated with a pre-treatment solution containing 16.8 mM HCl and 69.6 mM glycine intended for transfusion are comparable to the paired control plasma.

Example 6: Spray Drying with the System of the Present Invention Provides Functional Plasma Method This study compared spray dried plasma unit with paired control plasma to evaluate manufacturing effects of Velico Medical Inc's (Beverly, MA USA) the FRONTLINE™ spray drier system on the starting plasma, when using a pre-treatment solution to treat the starting plasma. The FRONTLINE™ spray drier system used in processing spray dried plasma is described herein. Spray dried plasma processed by the FRONTLINE™ spray drier is referred to herein as FRONTLINEODP™. Plasma combined with the pre-treatment solution is referred to as formulated plasma. The pre-treatment solution has 440 mM glycine and 106 mM hydrochloric acid which were added to SWFI.

The pretreatment solution was made using the following table

TABLE 15

| | | Pretreatment formulation | | | | |
|---|---|---|---|---|---|---|
| | Conc. (mM) | 250 mL | 500 mL | 1000 mL | 2000 mL | 4000 mL |
| HCl (mL) | 106 | 2.18 ± 0.11 | 4.36 ± 0.22 | 8.72 ± 0.44 | 17.44 ± 0.87 | 34.88 ± 1.74 |
| Glycine (g) | 440 | 8.26 ± 0.41 | 16.52 ± 0.83 | 33.08 ± 1.65 | 66.16 ± 3.31 | 132.32 ± 6.62 |

Summary

The in vitro characterization of spray dried plasma manufactured on the FRONTLINE™ System demonstrated that reconstituted formulated spray dried plasma units are comparable to the paired control plasma, including with regard to pH. Comparability of the in vitro tests supports that the manufacturing impact is acceptable resulting in formulated spray dried plasma units that meets the acceptance criteria for pH and coagulation factor activities profile within the normal reference range (n=60 pairs). The manufacturing effects of the FRONTLINE™ System on the starting material are comparable across blood type A, B, and O. The overall results demonstrate preservation of coagulation factors and analytes as evidence of comparability of reconstituted formulated spray dried plasma units to FFP and a resultant rehydrated plasma range of pH of 6.69-7.37 with a mean of 7.04.

The global assays aPTT and PT had a minimal change with the mean percent change of 2% and 7% respectively, between the reconstituted formulated spray dried plasma units and its paired control. TT was slightly prolonged and with a mean of 34% change for reconstituted formulated spray dried plasma units compared to paired controls. A previous study demonstrated that decreasing the pH of plasma induced a prolonged TT, therefore, the prolonged TT is due to the lowered sample pH from the pretreatment solution on the assay.

The intrinsic and extrinsic coagulation Factors II, V, VII, VIII, IX, X, XI, XII, XIII and fibrinogen activities had mean percent changes between the reconstituted formulated spray dried plasma units and paired controls within ±20%. The most labile factors, Factors V and VIII, had ≤5% and <20% change, respectively. Factors II, XI and fibrinogen were all within 10% change and Factors VII, IX, X and XIII activity had 15% change between reconstituted formulated spray dried plasma units and paired controls. All mean assay values were well within the clinical reference ranges.

Protease inhibitors C1 Esterase Inhibitor and Alpha 1 Proteinase Inhibitor have a change of ≤5% demonstrating minimal loss due to the FRONTLINE™ manufacturing process. The balance of pro- and anticoagulant activities is maintained following manufacture of reconstituted formulated spray dried plasma units. Of the anticoagulant protein assays, the mean percent change between the reconstituted formulated spray dried plasma unit and paired control for both Protein C and Antithrombin III is 9%, 14% for Protein S and 7% for Free Protein S. The mean change for procoagulant factors Plasminogen and Plasmin Inhibitor are 5% and 4%, respectively. All mean values are well within the clinical reference ranges.

The mean percent change in von Willebrand Factor (vWF) antigen assay is within ±20%. There is a 55% and 33% change with von Willebrand ristocetin cofactor (vWF:RCo) and vWF activity, respectively. Mean vWF:RCo of FrontlineODP Units is 41.8% meeting the FDA's recommendation of ≥40% per Meeting ID #BQ150234 (Mar. 14, 2018). vWF activity of 73.0±20.3% is within the normal reference range of 38.0-169.7%. Decreased recovery of vWF activity and vWF:RCo activity observed is thought to be due to the shearing during the spray drying process.

Complement protein assays have mean percent changes between the reconstituted formulated spray dried plasma units and paired controls of 31% and 659% for C3a and C5a, respectively. The C3a is slightly increased compared to control plasma, but the mean value of 300.2 ng/mL is within the clinical reference range of 55-486 ng/mL. Acid alone treatment resulted in improved recovery of vWF and the storage stability of spray dried plasma, but high levels of C5a (compared to NFP). Dual treatment with both acid and glycine brought down the C5a level (FIG. 29). The C5a level is not necessarily lower than NFP, but comparable to or not exceeding other FDA approved plasma products. C5a mean value is slightly increased in reconstituted formulated spray dried plasma units (33.9 ng/mL) compared to its paired control (7.6 ng/mL). The higher percent change pre- and post-manufacture occurs during the pretreatment process. This C5a value is within the reference range reported for apheresed plasma of 4.9-74 ng/mL and therefore does not reflect complement activation.

The activation marker assays, D-Dimer, Prothrombin Fragment 1+2 (PF1+2), and Thrombin Anti-Thrombin (TAT) all had mean percent changes between the reconstituted formulated spray dried plasma units and paired controls within ±20%.

For all chemistry assays, the mean percent change between reconstituted formulated spray dried plasma units and paired controls are within ±20% for total protein, cholesterol, LDL, HDL, Triglyceride, Albumin, Calcium, IgA, IgG, and IgM. There was a 22% change with osmolality for reconstituted formulated spray dried plasma unit compared to its paired control. The increase in osmolality in the reconstituted formulated spray dried plasma unit is attributed to the hydrochloric acid and glycine in the Plasma Pretreatment Container. The pH of reconstituted formulated spray dried plasma units (7.04) did not increase with uncorrected drying and was decreased compared to its paired control (7.44). The European Pharmacopoeia specifies the pH as 6.5-7.6 and minimum osmolality of 240 mOsm/kg for Human Plasma (pooled and treated for virus inactivation). The observed changes compared to the control for pH and osmolality are within the acceptable ranges as indicated by the above-referenced standard. The average moisture content is 1.46% (n=20).

The in vitro characterization results of 60 reconstituted formulated spray dried plasma units and paired controls demonstrate that the manufacturing impact of the FRONTLINE™ System on the starting material is acceptable and the characterization data is within the normal reference range, demonstrating preservation of coagulation factors, proteins, analytes and pH.

Materials

ACCUMET® Benchtop pH Meter
Blood Collection Monitor
Calibrated timer
Clean Dry Air (CDA) System
Freezer
FRONTLINE™ System VEL 7000×3 and 1 Sealer ASY 30000S (Velico Medical Inc, Beverly MA, USA)
HELMER® Plasma Thawer
Instrumentation Laboratories ACL TOP 700 coagulation analyzer
Osmometer
Plate Reader
Plate Washer
Refrigerator
SELECTRA PRO M® Chemistry Analyzer
SIEMENS BCS XP® coagulation analyzer
Sterile Connection Device
Tubing Heat Sealer
Overwrap Sealer
Plasma Pretreatment Container having pretreatment solution having 16.8 mM HCl and 69.6 mM glycine and SWFI
Plasma Drying Chamber
Sterile Water for Injection (SWFI)
Never Frozen Plasma (NFP)
Fresh Frozen Plasma (FFP)
Plasma frozen within 24 hours (PF24)
3000 mL transfer pack
Reagents to complete panel per work instructions
5 mL Cryo-vials, P/N 01379

Procedure:

27 blood type A (45%), 27 blood type O (45%), and 6 blood type B (10%) units of plasma were spray dried by the FRONTLINE™ system to represent the American blood type distribution of approximately 36% blood type A, 48% blood type O, 11% blood type B, and 5% blood type AB. "FAQs about Blood and Blood Donation," AABB, accessed Dec. 15, 2020. https://www.aabb.org/for-donors-patients/faqs-about-blood-and-blood-donation The spray dried plasma units obtained from FRONTLINE™ spray drier system were manufactured from thawed PF24. The paired control was refrozen at the time the spray dried plasma unit was manufactured and thawed prior to testing. Each was pre-treated with a pre-treatment solution described above.

The dried plasma units were spray dried and tested after a minimum of 7-day storage at refrigeration. The manufacturing effect of the FRONTLINE™ System on the starting material was determined by calculating the change difference between the dried plasma units and its paired control plasma (CP) for each of the assay.

$$\%\ \text{Change} = \frac{FrontlineODP - CP}{CP} \times 100$$

Results

Dried plasma unit characterization results (n=60) are shown in Table 16.

Factor VIII activity, Factor VIII antigen, Factor IX activity, Factor X activity, Factor XI activity, Factor XII activity, Factor XIII activity, Factor XIII antigen, and fibrinogen. Protease inhibitors C1 Esterase Inhibitor and Alpha 1 Pro-

TABLE 16

Summary of Results (n = 60, unless otherwise specified)

| Assays | Clinical Reference Range | Control Plasma Mean ± SD | FrontlineODP Mean ± SD | Percent Change compared to Control Mean ± SD | 95% Confidence Interval (Percent Change) |
|---|---|---|---|---|---|
| pH | (7.35-7.45) | 7.44 ± 0.08 | 7.04 ± 0.14 | — | — |
| Osmolality (mOsm/kg) | (280-296) | 309 ± 7 | 377 ± 17 | 22% ± 6% | (21%, 24%) |
| aPTT (s) | (22-35) | 30.0 ± 2.9 | 30.8 ± 4.0 | 2% ± 8% | (0%, 5%) |
| Prothrombin Time (s) | (10-14) | 11.7 ± 0.7 | 12.5 ± 0.8 | 7% ± 3% | (6%, 8%) |
| Thrombin Time (s) | (14.5-20.5) | 12.9 ± 1.2 | 17.2 ± 1.3 | 34% ± 9% | (31%, 36%) |
| Factor II Activity (%) | (70-120) | 98.1 ± 10.7 | 88.5 ± 10.3 | −10% ± 5% | (−11%, −9%) |
| Factor V Activity (%) | (50-200) | 95.0 ± 16.6 | 92.6 ± 15.9 | −2% ± 7% | (−4%, −1%) |
| Factor V Antigen (%) | (50-175) | 71 ± 14 | 66 ± 14 | −8% ± 9% | (−11%, −6%) |
| Factor VII Activity (%) | (50-200) | 90.1 ± 17.6 | 80.6 ± 16.2 | −11% ± 6% | (−12%, −9%) |
| Factor VII Antigen (IU/mL) | (0.7-1.46) | 1.01 ± 0.14 | 0.96 ± 0.15 | −4% ± 6% | (−6%, −3%) |
| Factor VIII Activity (%) | (50-200) | 95.3 ± 34.2 | 78.1 ± 28.9 | −18% ± 11% | (−21%, −15%) |
| Factor VIII Antigen (IU/mL) | (0.5-1.8) | 1.24 ± 0.30 | 1.18 ± 0.28 | −5% ± 5% | (−7%, −4%) |
| Factor IX Activity (%) | (50-200) | 104.1 ± 12.9 | 91.6 ± 12.2 | −12% ± 7% | (−14%, −10%) |
| Factor X Activity (%) | (50-200) | 91.4 ± 13.3 | 81.0 ± 13.7 | −12% ± 4% | (−13%, −10%) |
| Factor XI Activity (%) | (50-200) | 108.1 ± 18.2 | 98.3 ± 18.1 | −9% ± 9% | (−11%, −7%) |
| Factor XII Activity (%) | (50-200) | 124.0 ± 21.3 | 104.6 ± 18.7 | −16% ± 5% | (−17%, −14%) |
| Factor XIII Activity (%) | (57-192) | 122.1 ± 23.4 | 103.9 ± 20.9 | −15% ± 8% | (−17%, −13%) |
| Factor XIII Antigen (%) | (75.2-154.8) | 106.3 ± 21.8 | 94.0 ± 17.1 | −11% ± 6% | (−13%, −10%) |
| Fibrinogen (mg/dL) | (150-400) | 270 ± 57 | 241 ± 48 | −10% ± 8% | (−12%, −8%) |
| Plasminogen (%) | (70-150) | 92 ± 11 | 87 ± 12 | −5% ± 4% | (−6%, −4%) |
| Plasmin Inhibitor (%) | (85-156) | 103 ± 13 | 99 ± 12 | −4% ± 4% | (−5%, −3%) |
| C1 Esterase Inhibitor (%) | (70-130) | 104 ± 13 | 99 ± 14 | −5% ± 4% | (−6%, −4%) |
| Alpha 1-Proteinase Inhibitor (mg/dL) | (90-200) | 109.2 ± 11.2 | 104.8 ± 11.2 | −4% ± 4% | (−5%, −3%) |
| Protein C Activity (%) | (75-150) | 109 ± 17 | 100 ± 17 | −9% ± 4% | (−10%, −8%) |
| Protein S Activity (%) | (60-150) | 99.7 ± 14.5 | 85.6 ± 14.7 | −14% ± 6% | (−16%, −13%) |
| Free Protein S (%) | (57-155) | 100.8 ± 15.9 | 93.5 ± 16.6 | −7% ± 4% | (−9%, −6%) |
| Antithrombin III (%) | (80-120) | 100 ± 10 | 91 ± 10 | −9% ± 5% | (−10%, −8%) |
| von Willebrand Factor Activity (%)[a] | (50-200) | 112.5 ± 36.0 | 73.6 ± 20.1 | −33% ± 9% | (−36%, −31%) |
| von Willebrand Factor Antigen (%)[a] | (50-200) | 130.6 ± 40.2 | 125.9 ± 35.4 | −2% ± 8% | (−4%, 0%) |
| von Willebrand Factor Ristocetin Cofactor (%) | (50-200) | 95.6 ± 36.3 | 41.8 ± 14.5 | −55% ± 7% | (−57%, −53%) |
| C3a (ng/mL) | (55-486) | 233.0 ± 82.2 | 300.2 ± 114.9 | 31% ± 28% | (23%, 38%) |
| C5a (ng/mL) | (4.7-9.5) | 7.6 ± 6.3 | 33.9 ± 8.9 | 659% ± 992% | (408%, 910%) |
| D-Dimer (mg/L)[b,c] | (0-0.5) | 0.54 ± 0.64 | 0.55 ± 0.56 | 17% ± 26% | (10%, 24%) |
| Prothrombin Fragment PF 1 + 2 (pmol/L) | (91-137) | 153.2 ± 124.5 | 159.5 ± 144.0 | 14% ± 53% | (1%, 28%) |
| Thrombin-Antithrombin Complex (TAT) (µg/L)[d] | (0-4) | 5.07 ± 11.93 | 5.12 ± 12.18 | 10% ± 53% | (−4%, 23%) |
| Total Protein (g/dL) | (6-8.3) | 5.65 ± 0.37 | 5.42 ± 0.38 | −4% ± 4% | (−5%, −3%) |
| Cholesterol (mg/dL) | (0-200) | 150 ± 38 | 141 ± 35 | −6% ± 4% | (−7%, −5%) |
| LDL (mg/dL) | (0-100) | 93 ± 34 | 81 ± 27 | −13% ± 5% | (−14%, −12%) |
| HDL (mg/dL) | (35-100) | 41 ± 15 | 34 ± 10 | −14% ± 6% | (−16%, −13%) |
| Triglycerides (mg/dL) | (0-150) | 114 ± 65 | 111 ± 64 | −3% ± 4% | (−4%, −2%) |
| Albumin (g/dL) | (3.3-5) | 3.84 ± 0.22 | 3.62 ± 0.24 | −5% ± 3% | (−6%, −4%) |
| Calcium (mg/dL) | (8.6-10.3) | 6.40 ± 0.26 | 6.07 ± 0.29 | −5% ± 4% | (−6%, −4%) |
| IgA (mg/dL) | (69-309) | 186 ± 81 | 175 ± 76 | −6% ± 5% | (−7%, −5%) |
| IgG (mg/dL) | (614-1295) | 870 ± 235 | 829 ± 222 | −5% ± 5% | (−6%, −3%) |
| IgM (mg/dL) | (53-334) | 69 ± 42 | 64 ± 39 | −7% ± 4% | (−8%, −6%) |

The global assays aPTT and PT percent change between the FRONTLINEODP™ Unit and its paired control on average is within ±20%. There was a 34% change with TT for FRONTLINEODP™ Unit compared to its paired control. A previous study demonstrated that decreasing the pH of plasma induced a prolonged TT, therefore the prolonged TT is an effect of the sample pH on the assay. Of the coagulation factor assays, the percent change between the FRONTLINEODP™ Unit and its paired control on average is within ±20% for Factor II activity, Factor V activity, Factor V antigen, Factor VII activity, Factor VII antigen, teinase Inhibitor have a change of ≤5% demonstrating minimal loss due to the FRONTLINEODP™ manufacturing process. Of the anticoagulant protein assays, the mean percent change between the FRONTLINEODP™ Unit and paired control for both Protein C and Antithrombin III is 9%, 14% for Protein S and 7% for Free Protein S. The mean change for procoagulant factors Plasminogen and Plasmin Inhibitor are 5% and 4%, respectively. All mean values are well within the clinical reference ranges. The mean activation marker assays D-Dimer, Prothrombin Fragment 1+2 (PF1+2), and Thrombin Anti-Thrombin (TAT) for FRONT- LINEODP™ Units and paired control was above the normal reference range, however the percent change for all assays are between the FRONTLINEODP™ Unit and its paired control within ±20%. The mean percent change in von Willebrand Factor (vWF) antigen assay is within ±20%. There is a 55% and 33% change with von Willebrand ristocetin cofactor (vWF:RCo) and vWF Activity, respectively. The mean vWF:RCo levels of FRONTLINEODP™ units of 41.8% is ≥40%, meeting FDA's recommendation per Meeting ID #BQ150234 (Mar. 14, 2018). vWF activity of 73.0±20.3% is within the normal reference range of 38.0-169.7%. Decreased recovery of vWF activity and vWF:RCo activity was observed and is thought to be due to the shearing during the spray drying process. Complement protein assays have mean percent changes between the FRONTLINEODP™ Unit and its paired control of 31% and 659% for C3a and C5a, respectively. The C3a in FRONTLINEODP™ Units is slightly increased compared to control plasma, but the average of 300.2 ng/mL is within the clinical reference range of 55-486 ng/mL. C5a is elevated in FRONTLINEODP™ Units (33.9 ng/mL) compared to its paired control value (7.6 ng/mL) and is due to the pretreatment process. This value is within the range reported for apheresed plasma of 4.9-74 ng/mL and does not demonstrate complement activation. For all chemistry assays, the percent change between the FRONTLINEODP™ Unit and its paired control on average is within ±20% for total protein, cholesterol, LDL, HDL, Triglyceride, Albumin, Calcium, IgA, IgG, and IgM. There was a 22% change with osmolality, for FRONTLINEODP™ Unit compared to its paired control. The increase in osmolality in the FRONTLINEODP™ Unit is attributed to the hydrochloric acid and glycine in the Plasma Pretreatment Container. The pH of FRONTLINEODP™ Units (7.04) was decreased compared to its paired control (7.44). There was a 22% change with osmolality for FRONTLINEODP™ Unit compared to its paired control. The European Pharmacopoeia specifies the pH as 6.5-7.6 and minimum osmolality of 240 mOsm/kg for Human Plasma (pooled and treated for virus inactivation). The observed changes compared to the control for pH and osmolality are within the acceptable ranges as indicated by the above-mentioned standard.

Mean FRONTLINEODP™ Unit characterization results by blood type are shown in Table 17.

TABLE 17

Mean FRONTLINEODP ™ Unit characterization results by blood type (A, B, and O)

| Assays | Clinical Reference Range | Type A (n = 27) | Type B (n = 6) | Type O (n = 27) |
|---|---|---|---|---|
| pH | (7.35-7.45) | 7.05 ± 0.12 | 7.10 ± 0.10 | 7.03 ± 0.17 |
| Osmolality (mOsm/kg) | (280-296) | 376 ± 19 | 368 ± 9 | 379 ± 16 |
| aPTT (s) | (22-35) | 30.5 ± 5.0 | 28.4 ± 2.2 | 31.6 ± 2.9 |
| Prothrombin Time (s) | (10-14) | 12.5 ± 1.0 | 13.0 ± 0.5 | 12.4 ± 0.7 |
| Thrombin Time (s) | (14.5-20.5) | 17.4 ± 1.3 | 17.5 ± 1.4 | 17.0 ± 1.2 |
| Factor II Activity (%) | (70-120) | 89.2 ± 10.0 | 92.0 ± 8.7 | 87.0 ± 10.9 |
| Factor V Activity (%) | (50-200) | 92.4 ± 16.1 | 86.6 ± 6.2 | 94.1 ± 17.1 |
| Factor V Antigen (%) | (50-175) | 66 ± 14 | 62 ± 15 | 66 ± 14 |
| Factor VII Activity (%) | (50-200) | 80.9 ± 17.0 | 72.9 ± 14.6 | 81.9 ± 15.7 |
| Factor VII Antigen (IU/mL) | (0.7-1.46) | 0.98 ± 0.16 | 0.91 ± 0.15 | 0.96 ± 0.14 |
| Factor VIII Activity (%) | (50-200) | 84.3 ± 32.2 | 96.8 ± 29.8 | 67.7 ± 21.3 |
| Factor VIII Antigen (IU/mL) | (0.5-1.8) | 1.23 ± 0.30 | 1.47 ± 0.40 | 1.06 ± 0.16 |
| Factor IX Activity (%) | (50-200) | 91.2 ± 12.6 | 88.1 ± 9.2 | 92.7 ± 12.5 |
| Factor X Activity (%) | (50-200) | 81.9 ± 14.9 | 81.5 ± 13.9 | 80.0 ± 12.8 |
| Factor XI Activity (%) | (50-200) | 101.2 ± 16.9 | 104.3 ± 17.9 | 94.0 ± 18.9 |
| Factor XII Activity (%) | (50-200) | 109.5 ± 16.8 | 111.3 ± 13.2 | 98.1 ± 19.9 |
| Factor XIII Activity (%) | (57-192) | 102.7 ± 25.9 | 106.0 ± 15.0 | 104.5 ± 16.6 |
| Factor XIII Antigen (%) | (75.2-154.8) | 94.5 ± 21.2 | 93.6 ± 10.4 | 93.5 ± 13.9 |
| Fibrinogen (mg/dL) | (150-400) | 230 ± 49 | 210 ± 18 | 258 ± 46 |
| Plasminogen (%) | (70-150) | 88 ± 11 | 92 ± 9 | 86 ± 13 |
| Plasmin Inhibitor (%) | (85-156) | 100 ± 13 | 100 ± 10 | 98 ± 11 |
| C1 Esterase Inhibitor (%) | (70-130) | 98 ± 15 | 97 ± 13 | 100 ± 13 |
| Alpha 1-Proteinase Inhibitor (mg/dL) | (90-200) | 102.9 ± 12.8 | 104.8 ± 7.9 | 106.8 ± 10.1 |
| Protein C Activity (%) | (75-150) | 99 ± 15 | 101 ± 16 | 100 ± 19 |
| Protein S Activity (%) | (60-150) | 88.6 ± 16.1 | 83.6 ± 9.2 | 83.0 ± 14.0 |
| Free Protein S (%) | (57-155) | 97.4 ± 18.9 | 88.6 ± 11.1 | 90.7 ± 14.7 |
| Antithrombin III (%) | (80-120) | 92 ± 9 | 91 ± 9 | 89 ± 12 |
| von Willebrand Factor Activity (%) | (50-200) | 70.4 ± 29.8 | 81.2 ± 28.5 | 66.8 ± 19.6 |
| von Willebrand Factor Antigen (%) | (50-200) | 128.5 ± 46.6 | 150.1 ± 39.8 | 108.6 ± 32.1 |
| von Willebrand Factor Ristocetin Cofactor (%) | (50-200) | 45.7 ± 15.9 | 44.9 ± 15.8 | 37.1 ± 11.6 |
| C3a (ng/mL) | (55-486) | 306.1 ± 133.6 | 293.3 ± 34.8 | 295.7 ± 108.7 |
| C5a (ng/mL) | (4.7-9.5) | 33.5 ± 8.5 | 28.6 ± 5.7 | 35.5 ± 9.7 |
| D-Dimer (mg/L) | (0-0.5) | 0.46 ± 0.72 | 0.43 ± 0.21 | 0.49 ± 0.41 |
| Prothrombin Fragment F 1 + 2 (pmol/L) | (91-137) | 122.7 ± 52.4 | 121.8 ± 61.8 | 204.6 ± 199.3 |
| Thrombin-Antithrombin Complex (TAT) (µg/L) | (0-4) | 2.81 ± 4.56 | 2.88 ± 2.59 | 7.75 ± 17.21 |
| Total Protein (g/dL) | (6-8.3) | 5.45 ± 0.38 | 5.45 ± 0.34 | 5.39 ± 0.40 |
| Cholesterol (mg/dL) | (0-200) | 145 ± 30 | 157 ± 77 | 134 ± 23 |

TABLE 17-continued

Mean FRONTLINEODP ™ Unit characterization results by blood type (A, B, and O)

| Assays | Clinical Reference Range | Type A (n = 27) | Type B (n = 6) | Type O (n = 27) |
| --- | --- | --- | --- | --- |
| LDL (mg/dL) | (0-100) | 83 ± 24 | 94 ± 60 | 75 ± 19 |
| HDL (mg/dL) | (35-100) | 35 ± 9 | 29 ± 13 | 35 ± 10 |
| Triglycerides (mg/dL) | (0-150) | 114 ± 72 | 133 ± 67 | 103 ± 56 |
| Albumin(g/dL) | (3.3-5) | 3.67 ± 0.24 | 3.64 ± 0.31 | 3.57 ± 0.21 |
| Calcium(mg/dL) | (8.6-10.3) | 6.04 ± 0.29 | 6.12 ± 0.20 | 6.09 ± 0.31 |
| IgA (mg/dL) | (69-309) | 196 ± 67 | 156 ± 68 | 159 ± 83 |
| IgG (mg/dL) | (614-1295) | 800 ± 154 | 865 ± 169 | 850 ± 285 |
| IgM (mg/dL) | (53-334) | 69 ± 36 | 86 ± 47 | 54 ± 38 |

The manufacturing effects of the FrontlineODP System on the starting material are comparable across blood type A, B, and O.

All spray drying manufacturing process were within the acceptance criteria listed below.

Drying gas inlet temperature: 115±3° C.

Drying gas flow rate: 750±10 L/min

Drying gas exhaust temperature: 65±2° C.

Aerosol gas flow rate: 40±1 L/min

Mean rehydrated dried plasma of the present invention were within the acceptance criteria of:

pH within 6.69-7.37, where the average value was 7.04 SD+/−0.14.

Osmolality within 338-450 mOsm/kg, where the average value was 377 mOsm/kg.

Protein concentration dried plasma units normalized to control was within 0.88-1.17 on a Chemistry analyzer, where the average value was 0.96.

Conclusion

The characterization data of 60 samples show that reconstituted plasma units made from the FRONTLINE™ system which are intended for transfusion are comparable to the paired control plasma, including with regard to pH in the range of 6.69-7.37 with an average of 1.04 SD+/−0.14.

Comparability of the in vitro tests supports that the manufacturing impact of the FRONTLINE™ process is acceptable resulting in spray dried plasma units that meet the acceptance criteria with coagulation factor profile within the normal reference range and a pH range of 6.69-7.37 and a pH mean of 7.04 SD+/−0.14.

Example 7: Human Factors Study I

Method: observation/interview usability, human factors and heuristic evaluation compliant with FDA Guidance for Industry and Food and Drug Administration Staff, section 6.4.2 "Empirical Approaches to Identifying Critical Tasks" and section 6.3.2 "Heuristic Analysis" (2016), IEC 62366-1:2015, sections 5.1-5.6 "Usability Engineering Process" and section 5.7 "Establish User Interface Evaluation Plan" and IEC TR 62366-2:2016, sections 8.4 "Recommend Methods for Developing the Use Specification" and section 3.27 and section 16.2.2 "Conduct Heuristic Analysis" of IEC TR 62366-2 (2016)." Unpublished report from Ximedica Providence Rhode Island (USA).

Materials

1 VELICO® Alpha spray dryer (Velico Medical Inc, Beverly MA USA), the developmental version;

10 VELICO® Alpha disposables measuring about 66 inches in length;

7 participants selected as representative of end users and end user managers from blood centers in the United States;

3 trained observers;

2,163 photographs;

Multiple interviews and observations of each participant.

Methodology: Participants received training on the use of the VELICO® Alpha system consistent with that expectable in a blood center in the United States. Following that Alpha system was operated under observation followed up by interviews over a period of hours.

Results

Touch points on system outside of comfortable range of motion: bending required is too low; reaching required is too great; control screen too high for shorter users and too close to other controls, placement and directionality of disposable loading unintuitive.

Insufficient feedback provided to user: audible feedback expected; need confirmation that a given task has been performed properly in a noisy environment, too few clues that system preparation had been done properly.

Difficulty in feeding disposable tubing.

Emergency cut-off too close to other controls but still needed to be readily locatable.

Some disposable loading steps required too much force for smaller or weaker operators.

Disposable is too long.

Disposable slides out of place during loading.

Disposable must be tucked into place in processing chamber.

Insufficient information where to connect aerosol gas tubing.

Address physical abilities of 5% female to 95% male user

Example 8: Human Factors Study II

Human Factors Study 2 2019 ("Velico OnDemand Drying System Formative #2")

Method: Loring observation/interview usability, human factors and heuristic evaluation consistent with ISO 14971: 2007 "Application of Risk Management to Medical Devices"; IE 62366-1:2015 "Medical Devices: Part 1—Application of Usability Engineering to Medical Devices";

ANSI HE75:2009: Human Factors Engineering—Design of Medical Devices"; Applying Human Factors and Usability Engineering to Medical Devices: Guidance for Industry and Food and Drug Administration Staff." Unpublished report from Loring Human Factors, Inc. Westwood MA (USA).

Materials

4 VELICO® Beta Development Spray Dryer functional mockups (Velico Medical, Inc. Beverly MA USA). This beta disposable measured 34.2 inches in length.

Beta disposables as need.

12 blood center managers, and technicians selected to be representative of employees of US blood center. The participants ranged in height from 5'2" (female) to 5'10" (male)

A moderator, trained observers and a notetaker from Loring.

Three video cameras.

Multiple interviews and observations of each participant.

Methodology: Participants received training on the use of the then current Velico Beta development system mockups consistent with that expectable in a blood center in the United States including overhead guidance signage. Following that they operated the Beta system mockups under observation with interviews and discussion over a period of approximately 2 hours at intervals over 2 days.

Results

The disposable tubing length and threading was confusing;

The disposable too long for the space available in spray dryer apparatus chamber;

The disposable plenum would not slide into place easily;

None of the other concerns voiced in Human Factors Study 1 directed to the Velico Alpha spray dryer and disposable were repeated in Human Factors Study 2 directed to the Velico Beta spray dryer and disposable incorporating the instances of the present invention.

Example 9: Human Factors Study III (2021)

Method: See methodology from Example 8. Additionally, participants received training on the use of the VELICO® prototype commercial intent system consistent with that expectable in a blood center in the United States. Following that they each processed two units of plasma from start to finish—the first unit with coaching as needed and the second without assistance. The entire activity was conducted under observation with follow up interviews and discussion.

Materials

VELICO® prototype commercial intent spray dryers (Velico Medical, Inc. Beverly MA USA).

VELICO® prototype commercial intent disposables as needed.

4 Participants, two managers and two blood center technicians of height 5'2" to 5'9"

Loring trained moderator and videographer.

Results

The resultant report stated: "All the issues that arose during Formative #1 (i.e., Examples 7-8) appear to be sufficiently mitigated." The issues referred to in Formative #1 were rectified by the present inventions incorporated into the Velico commercial intent spray dryer and disposable.

Example 10 Human Factors Study IV (2022)

Purpose: To determine ease of use for users of the spray drying machine and disposable.

Methods and Materials: The subjects were provided with a 10 minute instruction on how to install the disposable device of FIG. 1A into the spray drying machine shown in FIG. 4A-C. The subjects were timed and observed. Three subjects, female, two having a height of 5'0" height and one of height 4'11" at a separate time. One subject, male, having a height of 6'9" which fell in the 99th percentile, respectively, according to Height calculator at "Height Percentile Calculator for Men and Women in the United States" https://dqydj.com/height-percentile-calculator-for-men-and-women/Don't Quit Your Day Job (2022). Subjects were interviewed as to ease of use.

Two guided training sessions (<5 minutes each) were provided for loading and unloading the disposable of the present invention into the spray dryer.

Disposable Device of FIG. 1
  Spray drying machine shown in FIG. 4A-C.
  2 subjects, female, 5'0" height, no observable or reported physical challenges or disabilities, no prior training or experience with spray dried plasma equipment
  1 subject, female, 4'11" height, no observable or reported physical challenges or disabilities, prior experience with spray dried plasma equipment
  1 subject, male, 6'9" height, no observable or reported physical challenges or disabilities, no prior training or experience with spray dried plasma equipment
  The same trainer was used as that in Example 9.

Results

Each subject was observed to be able to successfully load and unload the plasma drying chamber from the spray dryer without limitations or difficulty due to their stature or strength.

Conclusion

The disposable drying chamber of the present invention of about 34" in length can be readily loaded and unloaded into the spray dryer of the present invention without limitation or difficulty by subjects in the $5^{th}$ percentile to the $99^{th}$ percentile of height as reported by the CDC NHANES 2015-2016 survey. See Height calculator at "Height Percentile Calculator for Men and Women in the United States" https://dqydj.com/height-percentile-calculator-for-men-and-women/Don't Quit Your Day Job (2022).

Example 11 Computer Flow Modeling of Liquid Plasma Flow Exiting the Cannula of the Nozzle Assembly of the Present Invention A computer simulation of the liquid plasma as it exits the cannula should be used to calculate the difference in shear rate experienced by the plasma for different cannula end geometries. A transient simulation technique known as the 'Volume of Fluid' approach can be implemented using a two dimensional, axi-symmetric flow domain mesh. This is a feature available on the commercial computer code; Ansys-Fluent, version 2019-R1, and will be run on a dedicated HPZ840 multi-processor workstation.

This approach captures the physics across the air to liquid interface and effectively tracks the shape of liquid surface as it is being drawn out for the cannula.

Three different inner cannula edge geometries as shown in FIG. 11 will be simulated: 90/45/30 degrees with respect to cannula axis and the maximum shear rate in the liquid phase will be calculated and compared to the measured change in the vWF protein recovery. See FIG. 11.

It is expected that the 45 and 30 degree angle of the cannula will improve vWF recovery, as compared to a 90 degree cannula.

Example 12: Bacterial Filtration Efficiency (BFE) Performance of Baffle Filter and Capture Filters in the Disposable

Purpose

This was a study for the Bacterial Filtration Efficiency (BFE) of the baffle filter 94 and capture filter 36 used in disposable 100 to confirm these filters maintain their integrity after being subjected to the stress of the spray drying process.

Scope

The BFE test used for this study was modified from the standardized procedure listed in ASTM 2101-14 to increase the bacterial challenge density to greater than 106 colony forming units (CFU) to demonstrate a log 6 reduction value (LRV). Testing was conducted by Nelson Laboratories.

The study was limited to a sample size of n=40 (20 baffle filters/20 capture filters).

The single use filters were prepared after exposure to spray drying cumulative stresses of temperature and pressure and then tested.

Equipment

Clean Dry Air (CDA) System VMI EQ #0503, 0504, 0505 and 0506
Spray Dryer described herein and shown in FIGS. 4 and 5, model VEL7000
Sealer, ASY-300005
Sterile Connection Device (SCD) VMI EQ #0261
Tubing Heat Sealer VMI EQ #0035 or equivalent
Overwrap Sealer, VMI EQ #0541
A-Z Hot Knife, TC-20, S/N: 54691
Elix Water Purification, VMI EQ #0311

Supplies

Disposable 100, VEL9100
600 mL transfer pack, P/N 10016
Tyvek overwrap, P/N 10459
Microtome Blade
Steel hole punch, 2⅞" diameter

Procedure

Test unit numbers for this study are the following: 3362, 3364 through 3371, and 3373 through 3383.
Preparation of Filters
Filled a 600 mL transfer pack with 310 mL of Type II water, assigned a test batch number to each bag of water, recorded on the 'Introduction sheet' and saved the file description.

Connected each water filled transfer pack to a disposable by SCD and spray dried on a Dryer to expose the filters to spray drying process.

Recorded the Date, Time and Initials for each run.
Baffle Filter Extraction Process:

Cut the disposable bag from the plenum below the baffle plate ring and cut off the tubing just above the strain relief.

Flipped the Plenum upside down and used a hot knife to cut around the Plenum.

Put the top cap on the plenum/baffle plate outer rim and used the hot knife to cut around the aerosol reservoir. Removed the cut section to expose the baffle filter 94.

Used a microtome blade to cut around the Inner and outer filter ring.

Inspected the cut around the Inner Filter Ring and Outer Filter Ring for sections of tearing. Sections with a tear were used as a location to cut from the inner filter ring to the outer filter ring.

Removed the baffle filter 94 from the top cap and used a 2⅞" hole punch to outline the two sample areas. Selected an area large enough to fit the 2⅞" BFE Filter test fixture and with no visible damage/tearing.

Used a microtome blade to cut around the outlines to create two samples, one for testing and one backup in case of shipping damage.

Sealed the samples into separate compartments of a TYVEK™ Pouch and labeled with filter location, batch number, date of extraction, and test protocol number. Kept the remaining baffle filter section for posterity.
Capture Filter Extraction Process Used scissors to cut the lower portion of the disposable to expose the outside of the capture filter 36.

Used scissors to cut along the top weld, removed the capture filter 36, and cut along the length of the side welds.

Unfolded the capture filter 36 and used the 2⅞" hole punch to outline two sample areas at the middle crease of the filter.

Used the microtome blade to cut around the outlines to create the two samples, one for testing and one backup in case of shipping damage.

Sealed the samples into separate compartments of a TYVEK™ pouch and labeled with filter location, batch number, date of extraction, and test protocol number. Kept the remaining capture filter sections for posterity.

The 20 test articles, and their 20 backups, from the baffle filter and the capture filter of the disposable were sent for testing.

Testing

The samples prepared as described above were submitted for BFE testing by Nelson Laboratories of Salt Lake City Utah USA protocol modified to meet in use conditions for the filters.

The test procedure was performed to evaluate the BFE of test articles at an increased challenge level. A suspension of *Staphylococcus aureus*, ATCC #6538, was delivered at a challenge level of greater than $10^6$ colony forming units (CFU). The challenge was aerosolized using a nebulizer and delivered to the test article at a fixed air pressure and flow rate of 30 liters per minute (LPM). The aerosol droplets were generated in a glass aerosol chamber and drawn through the test article into all glass impingers (AGIs) for collection. The challenge was delivered for a three-minute interval and sampling through the AGIs was conducted for four minutes to clear the aerosol chamber. The mean particle size (MPS)

control was performed at a flow rate of 28.3 LPM using a six-stage, viable particle, ANDERSEN™ sampler for collection.

This test procedure was modified. Standard BFE procedure was modified in order to employ a more severe challenge than would be experienced in normal use. This method was adapted from ASTM F2101. All test method acceptance criteria were met. Testing was performed in compliance with US FDA good manufacturing practice (GMP) regulations 21 CFR Parts 210, 211 and 820.

Results

TABLE 18

BFE Results for Baffle filter

| Test Article Number | Total CFU Recovered | Filtration Efficiency | LRV Acceptance criteria (LRV ≥ 6.0) |
|---|---|---|---|
| 3364U | $1.8 \times 10^1$ | 99.99976 | 5.6 |
| 3365U | <1[a] | >99.999986 | 6.9 |
| 3366U | <1[a] | >99.999986 | 6.9 |
| 3367U | <1[a] | >99.999986 | 6.9 |
| 3368U | <1[a] | >99.999986 | 6.9 |
| 3369U | <1[a] | >99.999986 | 6.9 |
| 3370U | 1 | 99.999986 | 6.9 |
| 3371U | <1[a] | >99.999986 | 6.9 |
| 3373U | <1[a] | >99.999986 | 6.9 |
| 3374U | $5.3 \times 10^1$ | 99.99928 | 5.1 |
| 3375U | <1[a] | >99.9999901 | 7 |
| 3376U | <1[a] | >99.9999901 | 7 |
| 3377U | <1[a] | >99.9999901 | 7 |
| 3378U | $1.3 \times 10^2$ | 99.9988 | 4.9 |
| 3379U | <1[a] | >99.9999901 | 7 |
| 3380U | $1.9 \times 10^1$ | 99.99981 | 5.7 |
| 3381U | <1[a] | >99.9999901 | 7 |
| 3382U | <1[a] | >99.9999901 | 7 |
| 3383U | $9.5 \times 10^1$ | 99.99906 | 5 |
| 3395U | 1 | 99.9999901 | 7 |

LRV = Log Reduction Value
[a]There were no detected colonies on any of the assay plates for this test article.

Results from the capture filter samples are shown in Table 19. All 20 samples prepared from the crease of the capture filter (highest stress) had an LRV above 6.

TABLE 19

BFE Results for capture filter

| Test Article Number | Total CFU Recovered | Filtration Efficiency (%) | LRV Acceptance criteria (LRV ≥ 6.0) |
|---|---|---|---|
| 3364L | <1[a] | >99.999986 | 6.9 |
| 3365L | <1[a] | >99.999986 | 6.9 |
| 3366L | <1[a] | >99.999986 | 6.9 |
| 3367L | <1[a] | >99.999986 | 6.9 |
| 3368L | <1[a] | >99.999986 | 6.9 |
| 3369L | <1[a] | >99.999986 | 6.9 |
| 3370L | <1[a] | >99.999986 | 6.9 |
| 3371L | <1[a] | >99.999986 | 6.9 |
| 3373L | 5 | 99.999932 | 6.2 |
| 3374L | <1[a] | >99.999986 | 6.9 |
| 3375L | 1 | 99.9999901 | 7 |
| 3376L | <1[a] | >99.9999901 | 7 |
| 3377L | <1[a] | >99.9999901 | 7 |
| 3378L | 4 | 99.99996 | 6.4 |
| 3379L | <1[a] | >99.9999901 | 7 |
| 3380L | <1[a] | >99.9999901 | 7 |
| 3381L | <1[a] | >99.9999901 | 7 |

TABLE 19-continued

BFE Results for capture filter

| Test Article Number | Total CFU Recovered | Filtration Efficiency (%) | LRV Acceptance criteria (LRV ≥ 6.0) |
|---|---|---|---|
| 3382L | <1[a] | >99.9999901 | 7 |
| 3383L | 3 | 99.99997 | 6.5 |
| 3395L | <1[a] | >99.9999901 | 7 |

LRV = Log Reduction Value
[a]There were no detected colonies on any of the assay plates for this test article.

Of the 20 test samples prepared from the disposable baffle filter, 15 had an LRV greater than 6.0 meeting the acceptance criteria. Five (5) of the 20 samples had an LRV in the range of 4.9 to 5.7, meeting the acceptance criteria for ASTM 2101-14.

Capture filter samples were excised from the creased area where the most stress is expected to be applied. All 20 of the capture filter samples tested for a modified BFE test showed LRV greater than 6.0.

The Bacterial Filtration Efficiency (BFE) Study demonstrates that the baffle filters and capture filters in disposable maintain their integrity during and after exposure to the cumulative stresses of temperature and pressure of the spray drying process. Water was spray dried to expose the disposable to the temperatures and pressures of the spray drying process. The baffle filter and capture filter was tested per ASTM 2101-14 with an increased bacterial load of greater than $10^6$ to assess a log 6 reduction value (LRV) of colony forming units (CFU).

All of the test samples in this study were post-actual use and were heavily handled in test preparation as noted above. The filter material tested is delicate when handled. Without being bound to a particular theory applicant believes that the consistency and regularity of the 15 LRV>6 results for the baffle filter and the erratic, infrequent character of the 5 LRV<6 results in this study indicate that the 15 LRV>6 results are fairly representative of BFE of the baffle filter in actual use and that, in actual use, the LRV of the baffle filter in the system of the present invention is >6.

The baffle filter and capture filter in the disposable are used in a dry air environment and not specified as an aqueous sterilizing filter. The acceptance criterion for LRV of 6.0 and above is used to qualify sterilizing filters in an aqueous system per ASTM F838. ASTM F2101 for BFE testing (also used to demonstrate preservation of sterility of medical devices packaged in TYVEK™ film covers) requires that the test results demonstrate a log 3 reduction. All baffle filters and capture filters (minimum LRV of 4.9) exceed the ASTM F2101 LRV requirement of 3.0 and greater and demonstrates a margin of safety well beyond what is expected in production.

Example 13 ACD-A Comparability

The in vitro characterization data demonstrate that the manufacturing effects of the system are comparable between units spray dried with different starting materials. Units spray dried from apheresed plasma (ACD-A anti-coagulation treatment) showed similar percent change due to manufacturing effects on the starting material as compared to units spray dried from whole blood derived plasma (CPD anti-coagulation treatment). A statistical analysis (ANOVA) was performed on the percent change pre and post spray drying between the two starting materials across 20 assays including clotting times, coagulation function, and activation markers. Of the 20 assays, total protein concentration, PT, TT, and Factor VIII and XIII activities were determined to be statistically significantly different, however, the mean percent change is similar, and the mean values are all within the clinical reference range.

The manufacturing/spray drying effect of the system on the starting material was determined by calculating the change between the unit and its paired control plasma (CP) for each of the assay.

$$\text{Mean \% change} = \frac{1}{13}\sum_{i=1}^{13} \frac{FrontlineODP_i - \text{Control Plasma}_i}{\text{Control Plasma}_i} \times 100$$

Total protein concentration was 5.34 g/dL for apheresed plasma (−2% change) compared to 5.42 g/dL for whole blood plasma (−4% change). Although the ANOVA indicated a statistical significance, the total protein concentration is comparable and percent change for spray dried units spray dried from both starting materials are within 4%.

The percent change for clotting times PT and TT showed a statistically significant difference between units spray dried from apheresed plasma and whole blood plasma. However, the mean PT is similar for apheresed plasma (13.1 seconds) and whole blood plasma (12.5 seconds). These values are well within the normal reference range. The mean TT is similar for apheresed plasma (19.6 seconds) and whole blood plasma (17.2 seconds). Both values are within the normal reference range.

A statistically significant difference in percent change was observed for coagulation factors Factor VIII and Factor XIII activities. The percent change for Factor VIII activity was 24% and 18% for apheresed and whole blood plasma, respectively, and the mean values are within the normal reference range. The percent change for Factor XIII activity for apheresed plasma is 21% and 15% for whole blood plasma and mean values are also within the normal reference range.

In summary, the in vitro test results support the conclusion that the manufacturing/spray drying impact on both apheresed and whole blood plasma is comparable, and the coagulation profile is within ±20% of their paired control or within the normal reference range. The data also support the conclusion that manufacturing/spray drying impact on whole blood plasma treated with CP2D anti-coagulation treatment is comparable to that demonstrated for CPD treated whole blood plasma and apheresed plasma.

TABLE 20

Summary of characterization data for ACD-A and CPD plasma

| | | Unit Value (Mean ± 1 SD) | | Percent Change compared to Control (Mean ± 1 SD) | | |
|---|---|---|---|---|---|---|
| Assay | Clinical Reference Range | Apheresed ACD-A Plasma | Whole Blood CPD Plasma | Apheresed ACD-A Plasma | Whole Blood CPD Plasma | p-value |
| pH | (7.35-7.45) | 7.11 ± 0.18 | 7.04 ± 0.14 | NA | NA | NA |
| Total Protein (g/dl) | (6-8.3) | 5.34 ± 0.42 | 5.42 ± 0.38 | −2% ± 4% | −4% ± 4% | 0.026 |
| Osmolality (mOsm/kg) | (280-296) | 366 ± 13 | 377 ± 17 | 366 ± 13 | 377 ± 17 | NS |
| aPTT (s) | (22-35) | 29.1 ± 4.2 | 30.8 ± 4.0 | 2% ± 7% | 2% ± 8% | NS |
| Prothrombin Time (s) | (10-14) | 13.1 ± 0.6 | 12.5 ± 0.8 | 11% ± 3% | 7% ± 3% | 0.000 |
| Thrombin Time (s) | (14.5-20.5) | 19.6 ± 0.9 | 17.2 ± 1.3 | 25% ± 7% | 34% ± 9% | 0.003 |
| Factor V (%) | (50-200) | 102.9 ± 11.4 | 92.6 ± 15.9 | 6% ± 6% | −2% ± 7% | NS |
| Factor VII (%) | (50-200) | 84.8 ± 16.0 | 80.6 ± 16.2 | −14% ± 5% | −11% ± 6% | NS |
| Factor VIII (%) | (50-200) | 89.4 ± 26.9 | 78.1 ± 28.9 | −24% ± 5% | −18% ± 11% | 0.043 |
| Factor XIII Activity (%) | (57-192) | 84.3 ± 13.3 | 103.9 ± 20.9 | −21% ± 9% | −15% ± 8% | 0.014 |
| Factor XIII Antigen (%) | (75.2-154.8) | 87.5 ± 9.7 | 94.0 ± 17.1 | −12% ± 4% | −11% ± 6% | NS |
| Fibrinogen (mg/dL) | (150-400) | 233 ± 32 | 241 ± 48 | −12% ± 6% | −10% ± 8% | NS |
| Protein C (%) | (75-150) | 100 ± 14 | 100 ± 17 | −7% ± 5% | −9% ± 4% | NS |
| Protein S (%) | (57-155) | 86.3 ± 6.2 | 85.6 ± 14.7 | 13% ± 4% | −14% ± 6% | NS |
| Antithrombin III (%) | (80-120) | 93 ± 4 | 91 ± 10 | 7% ± 5% | −9% ± 5% | NS |
| von Willebrand Factor Antigen (%) | (50-200) | 120.4 ± 37.3 | 125.9 ± 35.4 | −4% ± 8% | −2% ± 8% | NS |
| VWF:RCo (%) | (50-200) | 42.4 ± 16.0 | 41.8 ± 14.5 | −58% ± 4% | 55% ± 7% | NS |

NS—not significant
NA—not applicable

Example 14 Rapid Spray Drying Time Duration 375 samples were spray dried using the methods and spray drying system described herein. Below is a summary of spray dry run times performed for 375 runs. n=375 runs

|  | Run duration [minutes] | Drying duration [minutes] | Total mass processed grams |
|---|---|---|---|
| Ave | 37.09 | 24.91 | 324 |
| Min | 32.64 | 22.61 | 298 |
| Max | 41.86 | 27.72 | 340 |
| Std Dev | 2.67 | 1.21 | 4.08 |
| Ave − 2SD | 31.75 | 22.48 | 316 |
| Ave + 2SD | 42.42 | 27.33 | 332 |

The average duration run is 37.09 minutes. As can be seen from the table above, liquid plasma can be rapidly dried using the methods and systems of the present invention.

Ranges of values include all values not specifically mentioned. For example, a range of "20% or greater" includes all values from 20% to 100% including 35%, 41.6%, 67.009%, etc., even though those values are not specifically mentioned. The range of 20% to 30% shall include, for example, the values of 21.0% and 28.009%, etc., even though those values are not specifically mentioned.

The terms about, approximately, substantially, and their equivalents may be understood to include their ordinary or customary meaning. In addition, if not defined throughout the specification for the specific usage, these terms can be generally understood to represent values about but not equal to a specified value. For example, 1%, 0.9%, 0.8%, 0.7%, 0.6%, 0.5%, 0.4%, 0.3%, 0.2%, 0.1%, 0.09% of a specified value.

The terms, comprise, include, and/or plural forms of each are open ended and include the listed items and can include additional items that are not listed. The phrase "And/or" is open ended and includes one or more of the listed items and combinations of the listed items.

The relevant teachings of all the references, patents and/or patent applications cited herein are incorporated herein by reference in their entirety. Citation of the above documents and studies is not intended as an admission that any of the foregoing is pertinent prior art. All statements as to the contents of these documents are based on the information available to the applicants and do not constitute any admission as to the correctness of the contents of these documents. The entire teachings of all applications, patents and references cited herein are incorporated herein by reference. Specifically, the entire teachings of U.S. Pat. Nos. 7,993,310, 8,469,202, 8,533,971, 8,407,912, 8,595,950, 8,601,712, 8,533,972, 8,434,242, 10,843,100, 9,561,184, 9,545,379, 11,052,045; US Patent Publication Nos. 2010/0108183, 2011/0142885, 2013/0000774, 2013/0126101, 2014/0083627, 2014/0083628, 2014/0088768, and U.S. patent application Ser. No. 14/670,127 are incorporated herein by reference and are instructive of what one of ordinary skill in the art would know and understand at the time of the present invention. Additionally, entire teachings of applications filed on even date herewith are hereby incorporated herein by reference: U.S. Application No. 63/406,747, entitled "Spray Dried Blood Plasma and Process That Reduces Pathogens"; U.S. application Ser. No. 17/945,132, entitled "Methods For Making Spray Dried Plasma"; U.S. application Ser. No. 17/945,130, entitled "Alignment of A Disposable For A Spray Drying Plasma System"; U.S. application Ser. No. 17/945,126, entitled "Pretreatment Of Plasma For Spray Drying And Storage"; U.S. application Ser. No. 17/945,129, entitled "Usability Of A Disposable For A Spray Drying Plasma System"; and U.S. application Ser. No. 17/945,125, entitled "Blood Plasma Product".

While this invention has been particularly shown and described with references to preferred embodiments thereof, it will be understood by those skilled in the art that various changes in form and details may be made therein without departing from the scope of the invention encompassed by the appended claims.

What is claimed is:

1. A drying chamber for use in a spray drying system that uses a spray drying disposable device having a spray drying head and the drying chamber, the drying chamber comprises:
   A) a first end in communication with the spray drying head, wherein the spray drying head provides atomized plasma droplets and drying gas to the drying chamber, wherein when in use the atomized plasma droplets are dried into dried plasma particles;
   B) a capture filter, residing in the drying chamber, wherein the capture filter captures the dried plasma particles and allows humid air to pass;
   C) a gas outlet, wherein said gas outlet is attached to an exhaust port of the spray drying system during operation, wherein the humid air flows through the gas outlet; and
   D) a section disposed between the first end and the gas outlet and configured to become a dried plasma unit after plasma is spray dried;
   wherein, when in use, the atomized plasma droplets evaporate in the drying chamber when coming into contact with the drying gas emitted from the spray drying head, to thereby obtain dried plasma particles and humid air.

2. The drying chamber of claim 1, wherein the section further comprises at least one injection port.

3. The drying chamber of claim 1, wherein the section further comprises a slot for hanging the dried plasma unit.

4. The drying chamber of claim 1, wherein the section further comprises a label.

5. The drying chamber of claim 1, further comprising cut and seal locations that, when sealed, form walls of the dried plasma unit.

6. The drying chamber of claim 5, wherein, once the plasma is dried, the section is sealed and separated at the cut and seal locations to become a dried plasma unit.

7. The drying chamber of claim 1, further including a separator at the capture filter, wherein the separator is disposed between the capture filter and the inner wall of the spray drying chamber.

8. The drying chamber of claim 1, wherein the capture filter comprises about a 0.2 micron filter.

9. A spray drying disposable device having a spray drying head and a plasma drying chamber, the spray drying disposable device comprises:
   A) the spray drying head that provides atomized plasma droplets and drying gas from a drying gas source to the drying chamber, wherein when in use the atomized plasma droplets are dried into dried plasma particles; and
   B) the drying chamber comprises:
      i) a first end in communication with the spray drying head;

ii) a capture filter, residing in the drying chamber, wherein the capture filter captures the dried plasma particles and allows humid air to pass;

iii) a gas outlet, wherein said gas outlet is attached to an exhaust port of the spray drying system during operation, wherein the humid air flows through the gas outlet; and iv) a section disposed between the first end and the gas outlet and configured to become a dried plasma unit after plasma is spray dried;

wherein, when in use, the atomized plasma droplets evaporate in the drying chamber when coming into contact with the drying gas emitted from the spray drying head, to thereby obtain dried plasma particles and humid air.

10. The spray drying disposable device of claim 9, wherein the section that becomes the dried plasma unit further comprises at least one injection port, a slot for hanging the dried plasma unit, a label, or a combination thereof.

11. The spray drying disposable device of claim 10, the drying chamber further comprising cut and seal locations that, when cut and sealed, form walls of the dried plasma unit.

12. The spray drying disposable device of claim 9, further including a separator at the capture filter, wherein the separator is disposed between the capture filter and an inner wall of the spray drying chamber.

13. The spray drying disposable device of claim 9, wherein the spray drying head further comprises a spray dry nozzle assembly in fluid communication with a plasma source that provides a plasma and a pressurized aerosol gas source that provides a pressurized aerosol gas, wherein spray drying nozzle comprises a vortex generator.

14. The spray drying disposable device of claim 13, wherein the spray dry nozzle assembly comprises a cannula having an outer surface.

15. The spray drying disposable device of claim 14, wherein the cannula has an inner diameter in a range between about 0.010 inches and about 0.040 inches and an outer diameter between about 0.030 inches and about 0.060 inches.

16. The spray drying disposable device of claim 13, wherein the vortex generator comprises a plurality of channels and a plurality of pads to create a vortex pattern of the pressurized aerosol gas.

17. The spray drying disposable device of claim 16, wherein the plurality of channels and the plurality of pads are curved.

18. The spray drying disposable device of claim 17, the plurality of channels are curved and the plurality of pads have one or more curved edges.

19. The spray drying disposable device of claim 14, the nozzle assembly comprises an opening having an inner surface and an opening diameter; wherein the cannula emits the plasma through said opening and said cannula having an inner diameter and an outer diameter, and said opening emits a vortex pattern of the pressurized aerosol gas.

20. The spray drying disposable device of claim 19, wherein the vortex pattern of the pressurized aerosol gas flows between the outer surface of the cannula and the inner surface of the opening.

21. The spray drying disposable device of claim 19, wherein a distance between the outer surface of the cannula and the inner surface of the opening is between about 0.015 inches and about 0.091 inches.

22. The spray drying disposable device of claim 13, wherein the nozzle assembly extends past a baffle plate into the plasma drying chamber.

23. The spray drying disposable device of claim 9, wherein the drying gas source provides uniform air pressure.

24. The spray drying disposable device of claim 23, further comprising a baffle plate having one or more ribs on which the filter rests.

25. The spray drying disposable device of claim 24, wherein the baffle plate comprises one or more channels of air flow communicating with one or more drying gas jets.

26. The spray drying disposable device of claim 25, wherein the one or more channels define one or more pie shaped air channel communicating with the one or more drying gas jet.

27. The spray drying disposable device of claim 9, further comprising a locating arrangement for aligning the spray drying disposable device with a spray drying apparatus.

* * * * *